US008775090B2

(12) United States Patent
Oganesyan et al.

(10) Patent No.: US 8,775,090 B2
(45) Date of Patent: Jul. 8, 2014

(54) CRYSTALS AND STRUCTURE OF A HUMAN IGG FC VARIANT WITH ENHANCED FCRN BINDING

(75) Inventors: Vaheh Oganesyan, North Potomac, MD (US); William F. Dall'Acqua, Gaithersburg, MD (US); Herren Wu, Boyds, MD (US)

(73) Assignee: MedImmune, LLC, Gaithersburg, MD (US)

( * ) Notice: Subject to any disclaimer, the term of this patent is extended or adjusted under 35 U.S.C. 154(b) by 180 days.

(21) Appl. No.: 13/133,845

(22) PCT Filed: Dec. 10, 2009

(86) PCT No.: PCT/US2009/067439
§ 371 (c)(1),
(2), (4) Date: Aug. 5, 2011

(87) PCT Pub. No.: WO2010/068722
PCT Pub. Date: Jun. 17, 2010

(65) Prior Publication Data
US 2011/0288276 A1    Nov. 24, 2011

Related U.S. Application Data

(60) Provisional application No. 61/201,665, filed on Dec. 12, 2008.

(51) Int. Cl.
*G01V 1/40* (2006.01)
*C12P 21/08* (2006.01)
*G01N 31/00* (2006.01)

(52) U.S. Cl.
USPC .................. 702/11; 530/387.9; 702/27

(58) Field of Classification Search
None
See application file for complete search history.

(56) References Cited

U.S. PATENT DOCUMENTS

| 4,703,039 A | 10/1987 | Hawiger et al. |
| 5,624,821 A | 4/1997 | Winter et al. |
| 5,648,260 A | 7/1997 | Winter et al. |
| 5,739,277 A | 4/1998 | Presta et al. |
| 5,747,035 A | 5/1998 | Presta et al. |
| 5,824,307 A | 10/1998 | Johnson |

(Continued)

FOREIGN PATENT DOCUMENTS

| EP | 0 368 684 | 5/1990 |
| EP | 0503648 | 9/1992 |

(Continued)

OTHER PUBLICATIONS

Sondermann et al., The 3.2-Å crystal structure of the human IgG1 Fc fragment—FcRIII complex, Nature (2000), vol. 406, pp. 267-273.*

(Continued)

*Primary Examiner* — Alexander Kim
(74) *Attorney, Agent, or Firm* — Mueting, Raasch & Gebhardt, P.A.

(57) ABSTRACT

Provided herein are crystalline forms of a human IgG Fc variant comprising triple-mutation M252Y/S254T/T256E that provides for increased binding affinity to human neonatal Fc receptor, methods of obtaining such crystals and high-resolution X-ray diffraction structures and atomic structure coordinates. Also provided are machine readable media embedded with the three-dimensional atomic structure coordinates of the human IgG Fc variant and methods of using them.

14 Claims, 8 Drawing Sheets

(56) References Cited

U.S. PATENT DOCUMENTS

Figure 1:
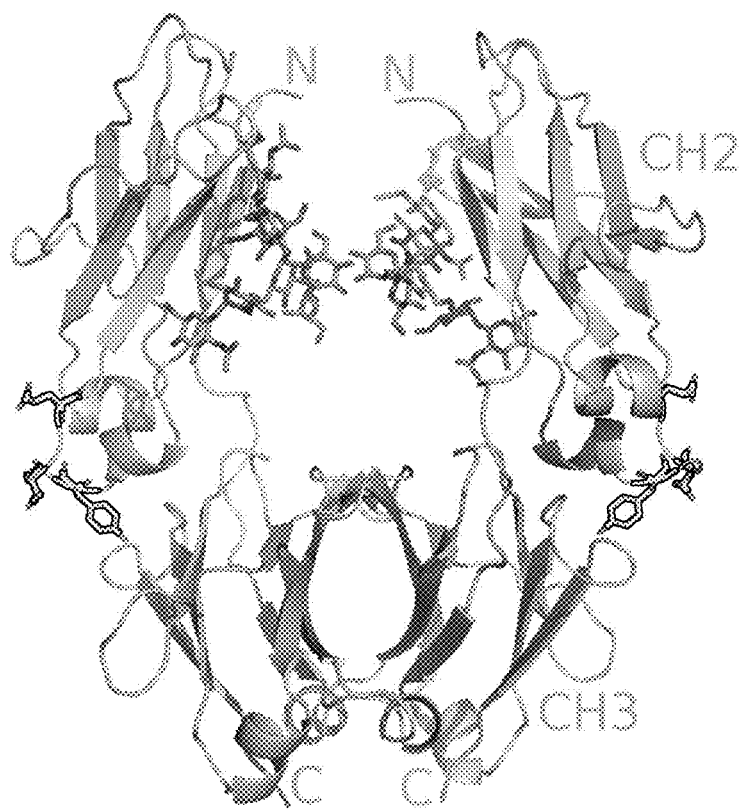

| | | | |
|---|---|---|---|
| 5,866,125 | A | 2/1999 | Brams et al. |
| 5,869,046 | A | 2/1999 | Presta et al. |
| 6,121,022 | A | 9/2000 | Presta et al. |
| 6,165,745 | A | 12/2000 | Ward et al. |
| 6,194,551 | B1 | 2/2001 | Idusogie et al. |
| 6,277,375 | B1 | 8/2001 | Ward |
| 6,528,624 | B1 | 3/2003 | Idusogie et al. |
| 6,538,124 | B1 | 3/2003 | Idusogie et al. |
| 6,572,856 | B1 | 6/2003 | Taylor et al. |
| 6,656,467 | B2 | 12/2003 | Young et al. |
| 6,737,056 | B1 | 5/2004 | Presta |
| 6,818,216 | B2 | 11/2004 | Young et al. |
| 6,855,493 | B2 | 2/2005 | Young et al. |
| 7,083,784 | B2 | 8/2006 | Dall'Acqua et al. |
| 7,132,100 | B2 | 11/2006 | Oliver et al. |
| 7,179,900 | B2 | 2/2007 | Young et al. |
| 7,217,797 | B2 | 5/2007 | Hinton |
| 7,217,798 | B2 | 5/2007 | Hinton et al. |
| 7,229,619 | B1 | 6/2007 | Young et al. |
| 7,294,336 | B2 | 11/2007 | Oliver et al. |
| 7,323,172 | B2 | 1/2008 | Young et al. |
| 7,361,740 | B2 | 4/2008 | Hinton |
| 7,365,168 | B2 | 4/2008 | Hinton et al. |
| 7,416,726 | B2 | 8/2008 | Ravetch |
| 7,425,618 | B2 | 9/2008 | Oliver et al. |
| 7,553,489 | B2 | 6/2009 | Young et al. |
| 7,635,568 | B2 | 12/2009 | Young et al. |
| 7,658,921 | B2 | 2/2010 | Dall'acqua et al. |
| 7,670,600 | B2 | 3/2010 | Dall'Acqua et al. |
| 7,700,735 | B2 | 4/2010 | Young et al. |
| 7,704,497 | B2 | 4/2010 | Dall'Acqua et al. |
| 7,740,851 | B2 | 6/2010 | Young et al. |
| 7,785,592 | B2 | 8/2010 | Oliver et al. |
| 7,847,082 | B2 | 12/2010 | Young et al. |
| 8,007,793 | B2 | 8/2011 | Oliver et al. |
| 8,012,476 | B2 | 9/2011 | Dall'Acqua et al. |
| 8,153,133 | B2 | 4/2012 | Young et al. |
| 8,323,962 | B2 | 12/2012 | Dall'Acqua et al. |
| 2002/0102257 | A1 | 8/2002 | Johnson |
| 2004/0002587 | A1 | 1/2004 | Watkins et al. |
| 2004/0137518 | A1* | 7/2004 | Lambert et al. ............ 435/7.1 |
| 2006/0115485 | A1 | 6/2006 | Losonsky et al. |
| 2009/0175883 | A1 | 7/2009 | Oliver et al. |
| 2010/0098708 | A1 | 4/2010 | Losonsky et al. |
| 2010/0239593 | A1 | 9/2010 | Spits |
| 2010/0266614 | A1 | 10/2010 | Young et al. |
| 2011/0158985 | A1 | 6/2011 | Losonsky et al. |
| 2012/0039876 | A1 | 2/2012 | Oliver et al. |
| 2012/0045456 | A1 | 2/2012 | Oliver et al. |
| 2012/0070446 | A1 | 3/2012 | Beaumont et al. |
| 2012/0070447 | A1 | 3/2012 | Young et al. |
| 2012/0135006 | A1 | 5/2012 | Young et al. |

FOREIGN PATENT DOCUMENTS

| | | | |
|---|---|---|---|
| EP | 0 327 378 | | 12/1996 |
| EP | 1265928 | | 12/2002 |
| WO | WO 89/07142 | | 8/1989 |
| WO | WO 91/14438 | | 10/1991 |
| WO | WO 93/22332 | | 11/1993 |
| WO | WO 94/29351 | | 12/1994 |
| WO | WO 96/32478 | | 10/1996 |
| WO | WO 97/34631 | | 9/1997 |
| WO | WO 97/43316 | | 11/1997 |
| WO | WO 98/23289 | | 6/1998 |
| WO | WO 98/50431 | | 11/1998 |
| WO | WO 99/01556 | | 1/1999 |
| WO | WO 99/43713 | | 9/1999 |
| WO | WO 99/51642 | | 10/1999 |
| WO | WO 00/09560 | | 2/2000 |
| WO | WO 00/42072 | | 7/2000 |
| WO | WO 01/58957 | | 8/2001 |
| WO | WO0260919 | * | 8/2002 |
| WO | WO 0286070 | * | 10/2002 |
| WO | WO 03/054213 | | 7/2003 |
| WO | WO 2004/016750 | | 2/2004 |
| WO | WO 2004/029207 | | 4/2004 |
| WO | WO 2004/035752 | | 4/2004 |
| WO | WO 2004/092219 | | 10/2004 |
| WO | WO 2010/068722 | | 6/2010 |

OTHER PUBLICATIONS

PDB (last viewed on May 17, 2013).*
Weber, Overview of Crystallization Methods. Methods in Enzymology, 1997, vol. 276, pp. 13-22.*
Drenth, "Principles of Protein X-Ray Crystallography", 2nd Edition, 1999, Springer-Verlag New York Inc., pp. 1-21.*
Klyushnichenko, Protein crystallization: From HTS to kilogram-scale, Curr. Op. Drug Discovery, 2003, vol. 6(6), pp. 848-854.*
Yang et al., Crystalline monoclonal antibodies for subcutaneous delivery, PNAS Jun. 10, 2003, vol. 100, pp. 6934-6939.*
Flower D.R. Drug Design Cutting Edge Approaches, The Royal Society of Chemistry, (2002), pp. 21-27.*
Hegyi et al., The Relationship between Protein Structure and Function: a Comprehensive Survey with Application to the Yeast Genome., J Mol Biol (1999), vol. 288, pp. 147-164.*
Bitoni et al.. 2004, "Pulmonary delivery of an erythropoietin Fc fusion protein in non-human primates through an immunoglobulin transport pathway", Proc Natl Acad Sci U S A. 101(26):9763-8.
Chaudhury et al.. 2003, "The major histocompatibility complex-related Fc receptor for IgG (FcRn) binds albumin and prolongs its lifespan". J. Exp. Med. 197:315-22.
Cochlovius et al., 2003, "Therapeutic Antibodies", Modern Drug Discovery. Oct. 2002. p. 33-38.
Datta-Mannan et al.. 2007, "Humanized IgG I variants with differential binding properties to the neonatal Fc receptor: relationship to pharmacokinetics in mice and primates", Drug Metab. Dispos. 35:86-94.
Datta-Mannan et al., 2007, "Monoconal antibody clearance Impact of modulating the interaction of IgG with the neonatal Fc receptor", J. Biol. Chem. 282:1709-17.
Feldman et al., 1998, "Anti-TNF alpha therapy is useful in rheumatoid arthritis and Crohn's disease: analysis of the mechanism of action predicts utility in other diseases". Transplant Proc., 30: 4126-4127.
Glennie et al., 2000, "Clinical trials of antibody therapy", Immunol Today. 2(8):403-10.
Gurbaxani et al., 2006, "Analysis of a family of antibodies with different half-lives in mice fails to find a correlation between affinity for FcRn and serum half-life", Mol. Immunol. 43(9):1462-73.
Haymann et al., 2000, "Characterization and localization of the neonatal Fc receptor in adult human kidney", J. Am. Soc. Nephrol. II: 632-639.
Hinton et al., 2004, "Engineered human IgG antibodies with longer serum half-lives in primates", J. Biol. Chem. 279:6213-16.
Hinton et al., 2005, "An engineered human IgG1 antibody with longer serum half-life", J Immunol. 176(1):346-56.
Humanizing Murine Monoclonal Antibodies—http://atlantis.unipv.it/abengin.html (website last accessed Nov. 7, 2000).
Isaacs et al., 1998, "Therapy with monoclonal antibodies. II. The contribution of Fc gamma receptor binding and the influence of C(H)1 and C(H)3 domains on in vivo effector function". J Immunol. 161(8):3862-9.
Israel et al., 1997, "Expression of the neonatal Fc receptor, FcRn, on human intestinal epithelial cells", Immunology. 92(1):69-74.
Johnson et al., 2000. "Kabat database and its applications: 30 years after the first variability plot", Nucleic Acids Res. 28(11):214-8.
Martin et al., 2001, "Crystal structure at 2.8 A of an FcRn/heterodimeric Fc complex: mechanism of pH-dependent binding", Mol. Cell. 7:867-77.
Martin, 2001, "Protein-Protein Recognition: The Neonatal Fc Receptor and Immunoglobulin G." Thesis in partial fulfillment of the requirements for the degree of Doctor of Philosophy. California Institute of Technology. Pasadena, California (submitted May 7, 2001).

(56) References Cited

OTHER PUBLICATIONS

Morrison et al., 2002, "Sequences in antibody molecules important for receptor-mediated transport into the chicken egg yolk", Mol. Immunol. 38:619-25.
Ober et al., 2001. Differences in promiscuity for antibody-FcRn interactions across species: implications for therapeutic antibodies. Int Immunol. 13(12):1551-9.
Physician's Desk Reference, 55th Ed., 2001, p. 1863 (Synagis®).
Physician's Desk Reference. 56th Ed., 2002. p. 2028 (Synagis®).
Physician's Desk Reference, 58th Ed., 2004, p. 1909 (Synagis®).
Spiekermann et al., 2002, "Receptor-mediated immunoglobulin G transport across mucosal barriers in adult life: functional expression of FcRn in the mammalian lung", J. Exp. Med. 196: 303-310. Erratum in: J. Exp. Med. (2003) 197, 1601.
Van Noort et al., 1998, "Cell Biology of a Autoimmune Diseases", International Review of Cytology, 178: 127-206.
Ward et al., 2003. "Evidence to support the cellular mechanism involved in serum IgG homeostasis in humans", Int. Immunol. 15:187-95.
Ward, et al. "Binding activities of a repertoire of single immunoglobulin variable domains secreted from *Escherichia coli*," Nature 341:544-546 (1989).
Wawrzynczak et al., 1992, "Recombinant mouse monoclonal antibodies with single amino acid substitutions affecting Clq and high affinity Fc receptor binding have identical serum half-lives in the BALB/c mouse", Mol. Immunol. 29:221-7.
Weng et al., 1998, "Computational determination of the structure of rat Fc bound to the neonatal Fc receptor", J. Mol. Biol. 282:217-25.
U.S. Appl. No. 09/724,396, published Nov. 28, 2000, Young et al. (Abandoned).
U.S. Appl. No. 13/413,609, published Mar. 6, 2012, Young et al.
U.S. Appl. No. 13/659,144, published Oct. 24, 2012, Dall'Acqua et al.
"Crystal Screen HT" User Guide, Jan. 1, 1992, pp. 1-8.
Ahouse et al. Mouse MHC class 1-like Fc receptor encoded outside the MHC. J Immunol. Dec. 1, 1993; 151(11):6076-88.
Borvak et al., 1998. Functional expression of the MHC class 1-related receptor, FcRn in endothelial cells of mice. *Intern. Immunol.* 10(9):1289-1298.
Burmeister et al. Crystal structure at 2.2 A resolution of the MHC-related neonatal Fc receptor. Nature. Nov. 24, 1994; 372(6504):336-43.
Burmeister et al. Crystal structure of the complex of rat neonatal Fc receptor with Fc. Nature. Nov. 24, 1994;372(6504):379-83.
Chintalacharuvu et al. Hybrid IgA2/IgG1 antibodies with tailor-made effector functions. Clin Immunol. Oct. 2001;101(1):21-31.
Cianga et al. Identification and function of neonatal Fc receptor in mammary gland of lactating mice. Eur J Immunol. Aug. 1999; 29(8):2515-23.
Dall'Acqua et al., Increasing the affinity of a human IgG1 for the neonatal Fc receptor: biological consequences. J Immunol. Nov. 1, 2002; 169(9):5171-80.
Dall'Acqua et al., Properties of human IgG1s engineered for enhanced binding to the neonatal Fc receptor (FcRn). J Biol Chem. Aug. 18, 2006;281(33):23514-24.
Dickinson et al. Bidirectional FcRn-dependent IgG transport in a polarized human intestinal epithelial cell line. J Clin Invest. Oct. 1999;104(7):903-11.
Fields et al., 1996, Crystal structure of the Vα domain of a T cell antigen receptor. *Immunotechnology* 2(4):270.
Firan et al., 2001, The MHC class I-related receptor, FcRn, plays an essential role in the maternofetal transfer of gamma-globulin in *Intern. Immunol.* 13:993-1002.
Ghetie et al. Multiple roles for the major histocompatibility complex class I- related receptor FcRn. Annu Rev Immunol. 2000;18:739-66. Review.
Ghetie et al., 1996, Abnormally short serum half-lives of IgG in beta 2-microglobulin-deficient mice. *Eur. J. Immunol.* 26:690-696.
Ghetie et al., 1997, Increasing the serum persistence of an IgG fragment by random mutagenesis. *Nature Biotech.* 15(7):637-640.

Ho et al., 1989, Site-directed mutagenesis by overlap extension using the polymerase chain reaction. *Gene* 15:51-59.
Israel et al., 1996, Increased clearance of IgG in mice that lack beta 2-microglobulin: possible protective role of FcRn. Immunology *Immunol.* 89:573-578.
Johnson et al., 1997, Development of a humanized monoclonal antibody (MEDI-493) with potent in vitro and in vivo activity against respiratory syncytial virus. *J. Infectious Disease* 176:1215-1224.
Junghans et al.,1996, The protection receptor for IgG catabolism is the beta2-microglobulin-containing neonatal intestinal transport receptor. *Proc. Natl. Acad. Sci. USA* 93:5512-5516.
Junghans, 1997, Finally! The Brambell receptor (fcRB). Mediator of transmission of immunity and protection from catabolism for IgG. *Immunologic Research* 16(1):29-57.
Junghans. 1997, IgG biosynthesis: no "immunoregulatory feedback". *Blood* 90(10):3815-3818.
Junghans, 1997. Next-generation Fc chimeric proteins: avoiding immune-system interactions. *Trends in Biotechnology* 5(15):155.
Kabat et al., 1991, Sequences of Proteins of Immunological Interest, U.S. Public Health Service, National Institutes of Health.
Kim et al., 1994. Catabolism of the murine IgG1 molecule: evidence that both CH2-CH3 domain interfaces are required for persistence of IgG1 in the circulation of mice. *Scandinavian J. Immunol.* 40(4):457-465.
Kim et al., 1994, Identifying amino acid residues that influence plasma clearance of murine IgG1 fragments by site-directed mutagenesis. *Eur. J. Immunol.* 24:542-548.
Kim et al., 1994, Localization of the site of the murine IgG1 molecule that is involved in binding to the murine intestinal Fc receptor. *Eur. J. Immunol* 24:2429-2439.
Kim et al., 1994, Mapping the site that controls the catabolism of the murine IgG1 molecule by site-directed mutagenesis. *FASEB J.* 8:pA467 (Abstract).
Kim et al., 1995, Evidence that the hinge region plays a role in maintaining serum levels of the murine IgG1 molecule. *Mol. Immunol.* 32(7):467-475.
Kim et al., 1995, Using recombinant techniques to localize the site of the murine IgG1 molecule that regulates serum persistence and neonatal transcytosis. *9th International Congress of Immunol.*, p. 469 (Abstract).
Kim et al., 1999. "Mapping the Site on Human IgG for Binding of the MHC Class 1-Related Receptor, FcRn," Eur. J. Immunol., 29:2819-2825.
Kristoffersen et al. Co-localization of the neonatal Fc gamma receptor and IgG in human placental term syncytiotrophoblasts. Eur J Immunol. Jul. 1996; 26(7):1668-71.
Kunkel et al., 1987, Rapid and efficient site-specific mutagenesis without phenotypic selection. Methods Enzymol. *Methods Enzymol.* 154:367-382.
Li et al., 1997, Dual conformations of a T cell receptor V alpha homodimer: implications for variability in V alpha V beta domain association. *J. Mol. Biol.* 269(3):385-394.
Martin et al. Characterization of the 2:1 complex between the class 1 MHC-related Fc receptor and its Fc ligand in solution. Biochemistry. Sep. 28, 1999;38(39):12639-47.
Medesan et al., 1996, Localization of the site of the IgG molecule that regulates maternofetal transmission in mice. *Eur. J. Immunol.* 26:2533-2536.
Medesan et al., 1997, Delineation of the amino acid residues involved in transcytosis and catabolism of mouse IgG1. *J. Immunol.* 158:2211-2217.
Medesan et al., 1998, Comparative studies of rat IgG to further delineate the Fc:FcRn interaction site. *Eur. J. Immunol.* 28(7):2092-2100.
Meng et al., Automated docking wtih grid-based energy evaluation. J. of Computational Chemistry, Jan. 1, 1992, pp. 505-524.
Oganesyan et al., Structural characterization of a human Fc fragment engineered for extended serum half-life. Mol Immunol. May 2009; 46(8-9):1750-5.
Popov et al., 1996 A novel and efficient route for the isolation of antibodies that recognise T cell receptor V alpha(s). *Mol. Immunol.* 33:493-502.

(56) References Cited

OTHER PUBLICATIONS

Popov et al., 1996, The stoichiometry and affinity of murine Fc fragments with the MHC class 1-related receptor, FcRn. *Mol. Immunol.* 33:521-530.

Raghavan et al. Analysis of the pH dependence of the neonatal Fc receptor/immunoglobulin G interaction using antibody and receptor variants. Biochemistry. Nov. 14, 1995;34(45):14649-57.

Raghavan et al. Investigation of the interaction beween the class 1 MHC-related Fc receptor and its immunoglobulin G ligand. Immunity. Jul. 1994;1(4):303-15.

Rodewald. pH-dependent binding of immunoglobulins to intestinal cells of the neonatal rat. J Cell Biol. Nov. 1976;71(2):666-9.

Sanchez et al. Stoichiometry of the interaction between the major histocompatibility complex-related Fc receptor and its Fc ligand. Biochemistry. Jul. 20, 1999;38(29):9471-6.

Sanger et al. 1977, DNA squencing with chain-terminating inhibitors. Proc Natl Aad Sci U S A. Dec. 1977; 74(12)5463-7. *Proc. Natl. Acad. Sci. USA* 74:5463-5467.

Schuck, et al., 1999, Sedimentation equilibrium analysis of recombinant mouse FcRn with murine IgG1. *Mol. Immunol.* 36:1117-1125.

Shields et al., 2001, High resolution mapping of the binding site on human IgG1 for Fc gamma RI, Fc gamma R11, Fc gamma RIII, and FcRn and design of IgG1 variants with improved binding to the Fc gamma R. *J. Biol. Chem.* 276:6591-6604.

Simister et al. An Fc receptor structurally related to MHC class 1 antigens. Nature. Jan. 12, 1989;337(6203):184-7.

Story et al., 1994, A major histocompatibility complex class 1-like Fc receptor cloned from human placenta: possible role in transfer of immunoglobulin G from mother to fetus. *J. Exp. Med.* 180:2377-2381.

Thatte et al., 1999, Molecular requirements for T cell recognition by a major histocompatibility complex class II-restricted T cell receptor: the involvement of the fourth hypervariable loop of the Valpha domain. *J. Exp. Med.* 189(3):509-520.

van der Merwe et al., 1993. Affinity and kinetic analysis of the interaction of the cell adhesion molecules rat CD2 and CD48. *EMBO J.* 12:4945-4594.

van der Merwe et al., 1994. Human cell-adhesion molecule CD2 binds CD58 (LFA-3) with a very low affinity and an extremely fast dissociation rate but does not bind CD48 or CD59. *Biochemistry* 33:10149-10160.

Vaughn et al. High-affinity binding of the neonatal Fc receptor to its IgG ligand requires receptor immobilization. Biochemistry. Aug. 5, 1997;36(31):9374-80.

Vaughn et al. Identification of critical IgG binding epitopes on the neonatal Fc receptor. J Mol Biol. Dec. 17, 1997;274(4):597-607.

Wallace et al. Studies on the immunoglobulin-G Fc-fragment receptor from neonatal rat small intestine. Biochem J. Apr. 15, 1980; 188(1):9-16.

Ward and Ghetie, 1995, The effector functions of immunoglobulins: implications for therapy. *Ther. Immunol.* 2:77-94.

Ward and Qadri, 1997, Biophysical and structural studies of TCRs and ligands: implications for T cell signaling. *Current Opinion Immunol.* 9(1):97-106.

West and Bjorkman, 2000, Crystal structure and immunoglobulin G binding properties of the human major histocompatibility complex-related Fc receptor(,). *Biochemistry* 39:9698-9708.

WO2010/068722 (PCT/US2009/067439)—International Preliminary Report on patentability datcd Jun. 14, 2011.

WO2010/068722 (PCT/US2009/067439)—International Preliminary Report on patentability dated Jun. 14, 2011—Written Opinion dated Dec. 6, 2011.

WO2010/068722 (PCT/US2009/067439)—International Search Report dated Jun. 17, 2010.

* cited by examiner

Figure 6

6A. Fc fragments

```
236
GGPSVFLFPPKPKDTLYITREPEVTCVVVDVSHEDPEVKFNWYVDGVEVHNAKTKPREEQ        Fc/YTE
VS-SVFIFPPKTKDVLTITLTPKVTCVVVDISQNDPEVRFSWFIDDVEVHTAQTHAPEKQ        Rat
237

YNSTYRVVSVLTVLHQDWLNGKEYKCKVSNKALPAPIEKTISKAKGQPREPQVYTLPPSR        Fc/YTE
SNSTLRSVSELPIVHRDWLNGKTFKCKVNSGAFPAPIEKSISKPEGTPRGPQVYTMAPPK        Rat

EEMTKNQVSLTCLVKGFYPSDIAVEWESNGQPENNYKTTPPVLDSDGSFFLYSKLTVDKS        Fc/YTE
EEMTQSQVSITCMVKGFYPPDIYTEWKMNGQPQENYKNTPPTMDTDGSYFLYSKLNVKKE        Rat

446
RWQQGNVFSCSVMHEALHNHYTQKSLSLSPGK                                    Fc/YTE
TWQQGNTFTCSVLHEGLHNHHTEKSLSHSPGK                                    Rat
                               446
```

6B. FcRn (β2 microglobulin chain)

```
1
IQRTPKIQVYSRHPAENGKSNFLNCYVSGFHPSDIEVDLLKNGERIEKVEHSDLSFSKDW        Human
IQKTPQIQVYSRHPPENGKPNFLNCYVSQFHPPQIEIELLKNGKKIPNIEMSDLSFSKDW        Rat
1
                                      99
SFYLLYYTEFTPTEKDEYACRVNHVTLSQPKIVKWDRDM                             Human
SFYILAHTEFTPTETDVYACRVKHVTLKEPKTVTWDRDM                             Rat
                                     99
```

6C. FcRn (α chain)

```
1
AESHLSLLYHLTAVSSPAPGTPAFWVSGWLGPQQYLSYNSLRGEAEPCGAWVWENQVSWY        Human
AEPRLPLMYHLAAVSDLSTGLPSFWATGWLGAQQYLTYNNLRQEADPCGAWIWENQVSWY        Rat
1

WEKETTDLRIKEKLFLEAFKALGG--KGPYTLQGLLGCELGPDNTSVPTAKFALNGEEFM        Human
WEKETTDLKSKEQLFLEAIRTLENQINGTFTLQGLLGCELAPDNSSLPTAVFALNGEEFM        Rat NFDLKQGTWGGDWPEALAISQRWQQQDKAANKELTFLLFSCPHRLREHLERGRGNLEWKE        Human
RFNPRTGNWSGEWPETDIVGNLWMKQPEAARKESEFLLTSCPERLLGHLERGRQNLEWKE        Rat PPSMRLKARPSSPGFSVLTCSAFSFYPPELQLRFLRNGLAAGTGQGDFGPNSDGSFHASS        Human
PPSMRLKARPGNSGSSVLTCAAFSFYPPELKFRFLRNGLASGSGNCSTGPNGDGSFHAWS        Rat 267
SLTVKSGDEHHYCCIVQHAGLAQPLRVEL                                       Human
LLEVKRGDEHHYQCQVEHEGLAQPLTVDL                                       Rat
                           269
```

Figure 7

SEQ ID NO: 7 Sequence of Fc/YTE Crystallized in Examples

236
    GGPSV FLFPPKPKDT L<u>YIT</u>R<u>E</u>PEVT
    261
    CVVVDVSHED PEVKFNWYVD GVEVHNAKTK PREEQYNSTY
    301
    RVVSVLTVLH QDWLNGKEYK CKVSNKALPA PIEKTISKAK
    341
    GQPREPQVYT LPPSREEMTK NQVSLTCLVK GFYPSDIAVE
    381
    WESNGQPENN YKTTPPVLDS DGSFFLYSKL TVDKSRWQQG
    421                                444
    NVFSCSVMHE ALHNHYTQKS LSLS

SEQ ID NO: 8 Sequence of Wild-type IgG Heavy Chain

223
    THTCPPCP APELLGGPSV FLFPPKPKDT LMISRTPEVT
    261
    CVVVDVSHED PEVKFNWYVD GVEVHNAKTK PREEQYNSTY
    301
    RVVSVLTVLH QDWLNGKEYK CKVSNKALPA PIEKTISKAK
    341
    GQPREPQVYT LPPSREEMTK NQVSLTCLVK GFYPSDIAVE
    381
    WESNGQPENN YKTTPPVLDS DGSFFLYSKL TVDKSRWQQG
    421                                447
    NVFSCSVMHE ALHNHYTQKS LSLSPGK

CRYSTALS AND STRUCTURE OF A HUMAN IGG FC VARIANT WITH ENHANCED FCRN BINDING

CROSS REFERENCE TO RELATED APPLICATION

This application is a national stage application of International Application No. PCT/2009/067439, filed on Dec. 10, 2009, which claims benefit of priority of U.S. Provisional Patent Application No. 61/201,665, filed on Dec. 12, 2008, each of which is hereby incorporated by reference in its entirety.

SEQUENCE LISTING

This application contains a Sequence Listing electronically submitted via EFS-Web to the United States Patent and Trademark Office as an ASCII text filed entitled "488-00020101_SubstituteSequenceListing_ST25.txt" having a size of 18 kilobytes and created on Feb. 3, 2014. The information contained in the Sequence Listing is incorporated by reference herein.

1. FIELD OF THE INVENTION

Provided herein are crystalline forms of a human IgG Fc variant comprising one or more amino acid residue mutations that provide for enhanced binding affinity with neonatal Fc receptor, methods of obtaining such crystals, high-resolution X-ray diffraction structures, and atomic structure coordinates. The one or more amino acid residue mutations are selected from the group consisting of 252Y, 254T and 256E. The crystals and the atomic structural information are useful for solving crystal and solution structures of related and unrelated proteins, and for screening for, identifying or designing compounds or antibodies that have altered, e.g., enhanced serum half-life.

2. BACKGROUND OF THE INVENTION

Antibodies are immunological proteins that bind a specific antigen. In most mammals, including humans and mice, antibodies are constructed from paired heavy and light polypeptide chains. Antibodies are made up of two distinct regions, referred to as the variable (Fv) and constant (Fc) regions. The light and heavy chain Fv regions contain the antigen binding determinants of the molecule and are responsible for binding the target antigen. The Fc regions define the class (or isotype) of antibody (IgG for example) and are responsible for binding a number of natural proteins to elicit important biochemical events.

The Fc region of an antibody interacts with a number of ligands including Fc receptors and other ligands, imparting an array of important functional capabilities referred to as effector functions. An important family of Fc receptors for the IgG class are the Fc gamma receptors. These receptors mediate communication between antibodies and the cellular atm of the immune system (Raghavan et al., 1996, *Annu Rev Cell Dev Biol* 12:181-220; Ravetch et al., 2001, *Annu Rev Immunol* 19:275-290). An important type of Fc gamma receptors for the IgG class is the neonatal Fc Receptor (FcRn). FcRn is a heterodimer, which comprises $\beta_2$-microglobulin and a membrane-anchored α chain that is related to the β chain of major histocompatibility complex class I molecules (Simister et al., 1989, *Nature* 337, 184-187; Burmeister et al., 1994, *Nature* 372, 336-343). FcRn recycles IgGs within endothelial cells and rescues them from a degradative pathway (Brambell et al., 1964, *Nature* 203, 1352-1354; Junghans et al., 1996, *Proc. Natl. Acad Sci.*, 93, 5512-5516; Ghetie and Ward, 2000, *Annu. Rev. Immunol.*, 18, 739-766; Roopenian & Akilesh, 2007, *Nat. Rev. Immunol.*, 7, 715-725). The most notable feature of the interaction between IgG Fc and FcRn is its pH dependency: the Fc portion of IgGs binds FcRn with a high affinity at pH 6.0 and is released at pH 7.2 (Rodewald, 1976, *J. Cell Biol.*, 71:666-669; Raghavan et al., 1995, *Biochemistry*, 34:14649-14657). This crucial characterstic is intricately linked to the IgG salvage mechanism, which involves recycling FcRn bound IgGs from within acidic lysosomes back to general circulation (Ghetie and Ward, 2000, *Annu. Rev. Immunol.*, 18, 739-766). As result, recycled IgGs exhibit a significantly prolonged serum half-life when compared with other serum proteins.

Several key features of antibodies including but not limited to, specificity for target, ability to mediate immune effector mechanisms, and long half-life in serum, make antibodies and related immunoglobulin molecules powerful therapeutics. Numerous monoclonal antibodies are currently in development or are being used therapeutically for the treatment of a variety of conditions including cancer. Examples of these include Vitaxin™ (MedImmune), a humanized Integrin αvβ3 antibody (e.g., PCT publication WO 2003/075957), Herceptin® (Genentech), a humanized anti-Her2/neu antibody approved to treat breast cancer (e.g., U.S. Pat. No. 5,677,171), CNTO 95 (Centocor), a human Integrin αv antibody (PCT publication WO 02/12501), Rituxan™ (IDEC/Genentech/Roche), a chimeric anti-CD20 antibody approved to treat Non-Hodgkin's lymphoma (e.g., U.S. Pat. No. 5,736,137) and Erbitux® (ImClone), a chimeric anti-EGFR antibody (e.g., U.S. Pat. No. 4,943,533).

There are a number of possible mechanisms by which antibodies destroy tumor cells, including anti-proliferation via blockage of needed growth pathways, intracellular signaling leading to apoptosis, enhanced down regulation and/or turnover of receptors, ADCC, CDC, and promotion of an adaptive immune response (Cragg et al., 1999, *Curr Opin Immunol.*, 11:541-547; Glennie et al., 2000, *Immunol Today* 21:403-410). However, despite widespread use, antibodies are not yet optimized for clinical use. Engineering IgGs for better binding to FcRn may represent a viable strategy for generation of therapeutic antibodies with increased serum persistence. Therapeutic antibodies that exhibited longer half-lives likely would be of benefit with increased efficacy because of sustained serum concentrations, decreased dosing frequency and/or lower cost of goods.

Various strategies have explored the effects of modulating the affinity of IgG molecules to FcRn on their serum persistence in vivo. In particular, several mutagenesis studies have targeted human Fc regions in an effort to decrease their binding affinity to human or murine FcRn at acidic pH. The serum half-lives of such engineered molecules were significantly reduced in mice expressing endogenous (Kim et al., 1999, *Eur. J. Immunol.*, 29, 2819-2825) or human (Petkova et al., 2006, *Int. Immunol.*, 18, 1759-1769) FcRn. Conversely, various Fc mutations have been described which resulted in significant increases in human or mouse IgG Fc binding to mouse (Ghetie et al., 1997, *Nat. Biotechnol.*, 15, 637-640), rhesus monkey (Hinton et al., 2004, *J. Biol. Chem.*, 279, 6213-6216; Hinton et al., 2005, *J. Immunol.*, 176, 346-356) and cynomolgus monkey (Dall' Acqua et al., 2006, *J. Biol. Chem.*, 281, 23514-23524) FcRn. These mutated IgG molecules were reported to have significantly improved serum half-life in the corresponding hosts.

One particular set of mutations, M252Y/S254T/T256E (referred to as 'YTE'), have been reported to result in an about 10-fold pH dependent increase in the binding of various humanized IgGs to both human and cynomolgus monkey FcRn at pH 6.0 (Dall' Acqua et al., 2002, *J. Immunol.*, 169, 5171-5180; Dall' Acqua et al., 2006, *J. Biol. Chem.*, 281, 23514-23524). When dosed in cynomolgus monkeys, the serum half-life of a YTE-modified humanized IgG was reported to be increased by nearly 4-fold when compared with its unmutated counterpart (Dall' Acqua et al., 2006, *J. Biol. Chem.*, 281, 23514-23524). The introduction of YTE into therapeutic IgGs could potentially provide many benefits such as reduced administration frequency and/or dosing requirements.

The three-dimensional structure coordinates of a crystalline Fc region with enhanced serum half-life, such as Fc/YTE, could enable one to elucidate a molecular mechanism of the enhanced interaction between Fc/YTE and FcRn. This three-dimentioanl structure coordinate could also be used to design and/or select Fc variants with altered (e.g., enhanced) FcRn binding affinity and serum half-life. Provided herein are the atomic structure coordinates of such Fc variants, particularly Fc/YTE.

3. SUMMARY OF THE INVENTION

In one aspect, provided here in are crystalline forms of a human IgG Fc variant, wherein the human Fc variant comprises one or more amino acid residue mutants and has an increased binding affinity for an FcRn as compared to a wild type human Fc not comprising the one or more amino acid residue mutants. In certain embodiments, the human IgG Fc variant comprises at least one amino acid residue mutation selected from the group consisting of 252Y, 254T, or 256E, as numbered by the EU index as set forth in Kabat. In certain embodiments, the human IgG Fc variant comprises each of the amino acid residue mutations 252Y, 254T, and 256E, as numbered by the EU index as set forth in Kabat. In particular embodiments, the Fc variant comprises the amino acid sequence SEQ ID NO:7. In some embodiments, the Fc variant consists of, or alternatively consists essentially of, the amino acid sequence SEQ ID NO:7.

The crystals provided herein include native crystals, in which the crystallized human IgG Fc variant is substantially pure; heavy-atom atom derivative crystals, in which the crystallized human IgG Fc variant is in association with one or more heavy-metal atoms; and co-crystals, in which the crystallized human IgG Fc variant is in association with one or more binding compounds, including but not limited to, an Fc receptor, a cofactor, a ligand, a substrate, a substrate analog, an inhibitor, an effector, etc. to form a crystalline complex. Preferably, such binding compounds bind an active site, such as the cleft formed by the $C_H2$ and $C_H3$ domains of the human IgG Fc variant. The co-crystals may be native poly-crystals, in which the complex is substantially pure, or they may be heavy-atom derivative co-crystals, in which the complex is in association with one or more heavy-metal atoms.

Figure 8:
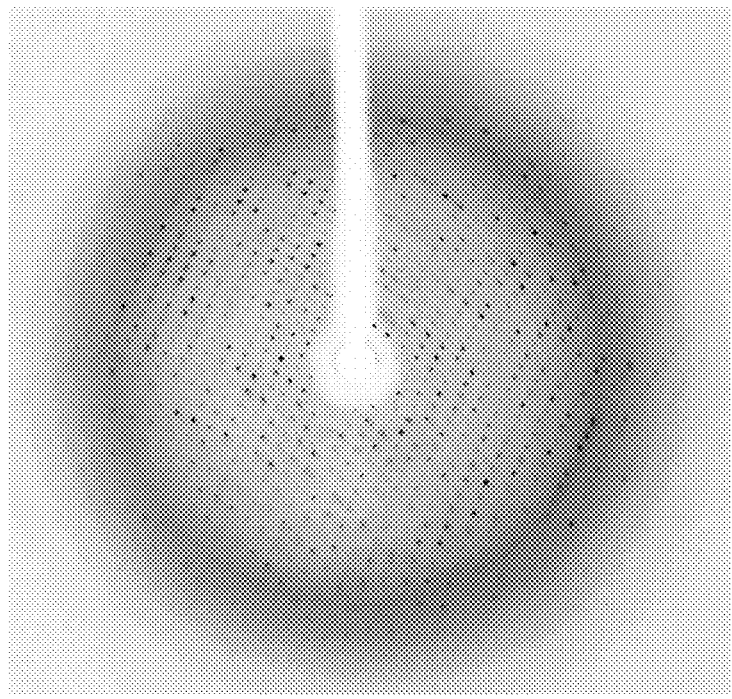

In certain embodiments, the crystals are generally characterized by an orthorhombic space group $P2_12_12_1$ with a unit cell of a=49.66 Å, b=79.54 Å, and c=145.53 Å, and are preferably of diffraction quality. A typical diffraction pattern is illustrated in FIG. 8. In more preferred embodiments, the crystals are of sufficient quality to permit the determination of the three-dimensional X-ray diffraction structure of a crystalline polypeptide(s) to high resolution, preferably to a resolution of greater than about 3 Å, typically in the range of about 2 Å to about 3 Å. The three-dimensional structural information may be used in a variety of methods to design and screen for compounds that bind a human IgG Fc region, as described in more detail below Also provided are methods of making the crystals. Generally, crystals are grown by dissolving substantially pure human IgG Fc variant in an aqueous buffer that includes a precipitant at a concentration just below that necessary to precipitate the polypeptide. Water is then removed by controlled evaporation to produce precipitating conditions, which are maintained until crystal growth ceases.

Co-crystals are prepared by soaking a native crystal prepared according to the above method in a liquor comprising the binding compound of the desired complexes. Alternatively, co-crystals may be prepared by co-crystallizing the complexes in the presence of the compound according to the method discussed above or by forming a complex comprising the polypeptide and the binding compound and crystallizing the complex.

Heavy-atom derivative crystals may be prepared by soaking native crystals or co-crystals prepared according to the above method in a liquor comprising a salt of a heavy atom or an organometallic compound. Alternatively, heavy-atom derivative crystals may be prepared by crystallizing a polypeptide comprising selenomethionine and/or selenocysteine residues according to the methods described previously for preparing native crystals.

In another aspect, provided herein is machine and/or computer-readable media embedded with the three-dimensional structural information obtained from the crystals, or portions or subsets thereof. Such three-dimensional structural information will typically include the atomic structure coordinates of the crystalline human IgG Fc variant, either alone or in a complex with a binding compound, or the atomic structure coordinates of a portion thereof such as, for example, the atomic structure coordinates of residues comprising an antigen binding site, but may include other structural information, such as vector representations of the atomic structures coordinates, etc. The types of machine- or computer-readable media into which the structural information is embedded typically include magnetic tape, floppy discs, hard disc storage media, optical discs, CD-ROM, or DVD-ROM, electrical storage media such as Flash memory, RAM, or ROM, and hybrids of any of these storage media. Such media further include paper on which is recorded the structural information that can be read by a scanning device and converted into a three-dimensional structure with an OCR and also include stereo diagrams of three-dimensional structures from which coordinates can be derived. The machine readable media may further comprise additional information that is useful for representing the three-dimensional structure, including, but not limited to, thermal parameters, chain identifiers, and connectivity information.

Provided here are illustrative working examples demonstrating the crystallization and characterization of crystals, the collection of diffraction data, and the determination and analysis of the three-dimensional structure of human IgG Fc variant.

The atomic structure coordinates and machine-readable media have a variety of uses. For example, the coordinates are useful for solving the three-dimensional X-ray diffraction and/or solution structures of other proteins, including, both alone or in complex with a binding compound. Structural information may also be used in a variety of molecular modeling and computer-based screening applications to, for example, intelligently screen or design human IgG Fc variants or antibody comprising Fc variant, or fragments thereof, that have altered biological activity, particularly altered binding affinity to a FcRn and/or altered serum half-life, to identify compounds that bind to a human IgG Fc region, or fragments thereof, for example, $C_H2$ or $C_H3$ domain of Fc region. Such compounds may be used to lead compounds in pharmaceutical efforts to identify compounds that mimic the human IgG Fc variant with enhanced FcRn binding affinity and/or serum half-life.

3.1 Abbreviations

The amino acid notations used herein for the twenty genetically encoded L-amino acids are conventional and are as follows:

| Amino Acid | One-Letter Symbol | Three-Letter Symbol |
|---|---|---|
| Alanine | A | Ala |
| Arginine | R | Arg |
| Asparagine | N | Asn |
| Aspartic acid | D | Asp |
| Cysteine | C | Cys |
| Glutamine | Q | Gln |
| Glutamic acid | E | Glu |
| Glycine | G | Gly |
| Histidine | H | His |
| Isoleucine | I | Ile |
| Leucine | L | Leu |
| Lysine | K | Lys |
| Methionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

As used herein, unless specifically delineated otherwise, the three-letter amino acid abbreviations designate amino acids in the L-configuration. Amino acids in the D-configuration are preceded with a "D-." For example, Arg designates L-arginine and D-Arg designates D-arginine. Likewise, the capital one-letter abbreviations refer to amino acids in the L-configuration. Lower-case one-letter abbreviations designate amino acids in the D-configuration. For example, "R" designates L-arginine and "r" designates D-arginine.

Unless noted otherwise, when polypeptide sequences are presented as a series of one-letter and/or three-letter abbreviations, the sequences are presented in the N C direction, in accordance with common practice.

3.2 Definitions

As used herein, the following terms shall have the following meanings:

"Genetically Encoded Amino Acid" refers to L-isomers of the twenty amino acids that are defined by genetic codons. The genetically encoded amino acids are the L-isomers of glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine.

"Genetically Non-Encoded Amino Acid" refers to amino acids that are not defined by genetic codons. Genetically non-encoded amino acids include derivatives or analogs of the genetically-encoded amino acids that are capable of being enzymatically incorporated into nascent polypeptides using conventional expression systems, such as selenomethionine (SeMet) and selenocysteine (SeCys); isomers of the genetically-encoded amino acids that are not capable of being enzymatically incorporated into nascent polypeptides using conventional expression systems, such as D-isomers of the genetically-encoded amino acids; L- and D-isomers of naturally occurring α-amino acids that are not defined by genetic codons, such as α-aminoisobutyric acid (Aib); L- and D-isomers of synthetic α-amino acids that are not defined by genetic codons; and other amino acids such as β-amino acids, γ-amino acids, etc. In addition to the D-isomers of the genetically-encoded amino acids, common genetically non-encoded amino acids include, but are not limited to norleucine (Nle), penicillamine (Pen), N-methylvaline (MeVal), homocysteine (hCys), homoserine (hSer), 2,3-diaminobutyric acid (Dab) and ornithine (Orn). Additional exemplary genetically non-encoded amino acids are found, for example, in *Practical Handbook of Biochemistry and Molecular Biology*, 1989, Fasman, Ed., CRC Press, Inc., Boca Raton, Fla., pp. 3-76 and the various references cited therein.

"Hydrophilic Amino Acid" refers to an amino acid having a side chain exhibiting a hydrophobicity of less than zero according to the normalized consensus hydrophobicity scale of Eisenberg et al., 1984, J. Mol. Biol. 179:125-142. Genetically encoded hydrophilic amino acids include Thr (T), Ser (S), His (H), Glu (E), Asn (N), Gln (Q), Asp (D), Lys (K) and Arg (R). Genetically non-encoded hydrophilic amino acids include the D-isomers of the above-listed genetically-encoded amino acids, ornithine (Orn), 2,3-diaminobutyric acid (Dab) and homoserine (hSer).

"Acidic Amino Acid" refers to a hydrophilic amino acid having a side chain pK value of less than 7 under physiological conditions. Acidic amino acids typically have negatively charged side chains at physiological pH due to loss of a hydrogen ion. Genetically encoded acidic amino acids include Glu (E) and Asp (D). Genetically non-encoded acidic amino acids include D-Glu (e) and D-Asp (d).

"Basic Amino Acid" refers to a hydrophilic amino acid having a side chain pK value of greater than 7 under physiological conditions. Basic amino acids typically have positively charged side chains at physiological pH due to association with hydronium ion. Genetically encoded basic amino acids include His (H), Arg (R) and Lys (K). Genetically non-encoded basic amino acids include the D-isomers of the above-listed genetically-encoded amino acids, ornithine (Orn) and 2,3-diaminobutyric acid (Dab).

"Polar Amino Acid" refers to a hydrophilic amino acid having a side chain that is uncharged at physiological pH, but which comprises at least one covalent bond in which the pair of electrons shared in common by two atoms is held more closely by one of the atoms. Genetically encoded polar amino acids include Asn (N), Gln (Q), Ser (S), and Thr (T). Genetically non-encoded polar amino acids include the D-isomers of the above-listed genetically-encoded amino acids and homoserine (hSer).

"Hydrophobic Amino Acid" refers to an amino acid having a side chain exhibiting a hydrophobicity of greater than zero according to the normalized consensus hydrophobicity scale of Eisenberg et al., 1984, J. Mol. Biol. 179:125-142. Genetically encoded hydrophobic amino acids include Pro (P), Ile (I), Phe (F), Val (V), Leu (L), Trp (W), Met (M), Ala (A), Gly (G) and Tyr (Y). Genetically non-encoded hydrophobic amino acids include the D-isomers of the above-listed genetically-encoded amino acids, norleucine (Nle) and N-methyl valine (MeVal).

"Aromatic Amino Acid" refers to a hydrophobic amino acid having a side chain comprising at least one aromatic or heteroaromatic ring. The aromatic or heteroaromatic ring may contain one or more substituents such as —OH, —SH, —CN, —F, —Cl, —Br, —I, —NO$_2$, —NO, —NH$_2$, —NHR, —NRR, —C(O)R, —C(O)OH, —C(O)OR, —C(O)NH$_2$, —C(O)NHR, —C(O)NRR and the like where each R is independently ($C_1$-$C_6$) alkyl, ($C_1$-$C_6$) alkenyl, or ($C_1$-$C_6$) alkynyl.

Genetically encoded aromatic amino acids include Phe (F), Tyr (Y), Trp (W) and His (H). Genetically non-encoded aromatic amino acids include the D-isomers of the above-listed genetically-encoded amino acids.

"Apolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G) and Ala (A). Genetically non-encoded apolar amino acids include the D-isomers of the above-listed genetically-encoded amino acids, norleucine (Nle) and N-methyl valine (MeVal).

"Aliphatic Amino Acid" refers to a hydrophobic amino acid having an aliphatic hydrocarbon side chain. Genetically encoded aliphatic amino acids include Ala (A), Val (V), Leu (L) and Ile (I). Genetically non-encoded aliphatic amino acids include the D-isomers of the above-listed genetically-encoded amino acids, norleucine (Nle) and N-methyl valine (MeVal).

"Helix-Breaking Amino Acid" refers to those amino acids that have a propensity to disrupt the structure of α-helices when contained at internal positions within the helix. Amino acid residues exhibiting helix-breaking properties are well-known in the art (see, e.g., Chou & Fasman, 1978, Ann. Rev. Biochem. 47:251-276) and include Pro (P), D-Pro (p), Gly (G) and potentially all D-amino acids (when contained in an L-polypeptide; conversely, L-amino acids disrupt helical structure when contained in a D-polypeptide).

"Cysteine-like Amino Acid" refers to an amino acid having a side chain capable of participating in a disulfide linkage. Thus, cysteine-like amino acids generally have a side chain containing at least one thiol (—SH) group. Cysteine-like amino acids are unusual in that they can form disulfide bridges with other cysteine-like amino acids. The ability of Cys (C) residues and other cysteine-like amino acids to exist in a polypeptide in either the reduced free —SH or oxidized disulfide-bridged form affects whether they contribute net hydrophobic or hydrophilic character to a polypeptide. Thus, while Cys (C) exhibits a hydrophobicity of 0.29 according to the consensus scale of Eisenberg (Eisenberg, 1984, supra), it is to be understood that for purposes of the present invention Cys (C) is categorized as a polar hydrophilic amino acid, notwithstanding the general classifications defined above. Other cysteine-like amino acids are similarly categorized as polar hydrophilic amino acids. Typical cysteine-like residues include, for example, penicillamine (Pen), homocysteine (hCys), etc.

As will be appreciated by those of skill in the art, the above-defined classes or categories are not mutually exclusive. Thus, amino acids having side chains exhibiting two or more physico-chemical properties can be included in multiple categories. For example, amino acid side chains having aromatic groups that are further substituted with polar substituents, such as Tyr (Y), may exhibit both aromatic hydrophobic properties and polar or hydrophilic properties, and could therefore be included in both the aromatic and polar categories. Typically, amino acids will be categorized in the class or classes that most closely define their net physicochemical properties. The appropriate categorization of any amino acid will be apparent to those of skill in the art.

The classifications of the genetically encoded and common non-encoded amino acids according to the categories defined above are summarized in Table 1, below. It is to be understood that Table 1 is for illustrative purposes only and does not purport to be an exhaustive list of the amino acid residues belonging to each class. Other amino acid residues not specifically mentioned herein can be readily categorized based on their observed physical and chemical properties in light of the definitions provided herein.

TABLE 1

CLASSIFICATIONS OF COMMONLY ENCOUNTERED AMINO ACIDS

| Classification | Genetically Encoded | Genetically Non-Encoded |
|---|---|---|
| Hydrophobic | | |
| Aromatic | F, Y, W, H | f, y, w, h |
| Apolar | L, V, I, M, G, A, P | l, v, i, m, a, p, Nle, MeVal |
| Aliphatic | A, V, L, I | a, v, l, I, Nle, MeVal |
| Hydrophilic | | |
| Acidic | D, E | d, e |
| Basic | H, K, R | h, k, r, Orn, Dab |
| Polar | C, Q, N, S, T | c, q, n, s, t, hSer |
| Helix-Breaking | P, G | P |

An "antibody" or "antibodies" refers to monoclonal antibodies, multispecific antibodies, human antibodies, humanized antibodies, synthetic antibodies, chimeric antibodies, camelized antibodies, single-chain Fvs (scFv), single chain antibodies, Fab fragments, F(ab') fragments, disulfide-linked Fvs (sdFv), intrabodies, and anti-idiotypic (anti-Id) antibodies (including, e.g., anti-Id and anti-anti-Id antibodies), bispecific, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass.

"Fc" "Fc region," or "Fc polypeptide," as used herein interchangeably, includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc may include the J chain. For IgG, Fc comprises immunoglobulin domains Cγ2 and Cγ3 (Cγ2 and Cγ3) and the hinge between Cγ1 (Cγ1) and Cγ2 (Cγ2). Although the boundaries of the Fc region may vary, the human IgG heavy chain Fc region is usually defined to comprise residues T223, or C226 or P230 to its carboxyl-terminus, wherein the numbering is according to the EU index as in Kabat et al. (1991, NIH Publication 91-3242, National Technical Information Service, Springfield, Va.).

The "EU index as set forth in Kabat" refers to the residue numbering of the human IgG1 EU antibody as described in Kabat et al. supra. Fc may refer to this region in isolation, or this region in the context of an antibody, antibody fragment, or Fc fusion protein. Note: Polymorphisms have been observed at a number of Fc positions, including but not limited to Kabat 270, 272, 312, 315, 356, and 358, and thus slight differences between the presented sequence and sequences in the prior art may exist.

"Human IgG Fc variant" or simply "Fc variant" refers to a human IgG Fc region comprises one or more amino acid substitution, deletion, insertion or modification (e.g., carbohydrate chemical modification) introduced at any position within the Fc region. In certain embodiments a human IgG Fc variant comprises one or more amino acid residue mutants and has an increased binding affinity for an FcRn as compared to the wild type Fc region not comprising the one or more amino acid residue mutants. Fc binding interactions are essential for hinging to neonatal receptor, but not limited to, increasing serum half-life of IgG. Accordingly, in certain embodiments, human IgG Fc variants exhibit altered binding affinity for at least one or more Fc ligands (e.g., FcRns) relative to an antibody having the same amino acid sequence but not comprising the one or more amino acid substitution, deletion, insertion or modification (referred to herein as a "comparable molecule") such as, for example, an unmodified Fc region containing naturally occurring amino acid residues at the corresponding position in the Fc region.

"Wild type human IgG Fc region" refers to a human IgG Fc region that comprises the amino acid sequence of SEQ ID NO: 2 or a fragment thereof (from residue T223 to residue K447 of human IgG heavy chain, wherein the numbering is according to the EU index as in Kabat).

"Amino acid residue mutations" refers to the substitution of an amino acid residue of a human IgG Fc region that confers enhanced binding to one or more Fc ligands (e.g., FcRns) relative to an antibody having the same amino acid sequence but not comprising the amino acid residue mutations. In certain embodiments, the human IgG Fc variant comprises a human IgG Fc region comprising at least one amino acid residue mutation selected from the group consisting of: 252Y, 254T, and 256E, wherein the numbering system is that of the EU index as set forth in Kabat et al. (1991, NIH Publication 91-3242, National Technical Information Service, Springfield, Va.).

"Conservative Mutant" refers to a mutant in which at least one amino acid residue from the wild-type sequence(s) is substituted with a different amino acid residue that has similar physical and chemical properties, i.e., an amino acid residue that is a member of the same class or category, as defined above. For example, a conservative mutant may be a polypeptide or combination of polypeptides that differs in amino acid sequence from the wild-type sequence(s) by the substitution of a specific aromatic Phe (F) residue with an aromatic Tyr (Y) or Trp (W) residue.

"Non-Conservative Mutant" refers to a mutant in which at least one amino acid residue from the wild-type sequence(s) is substituted with a different amino acid residue that has dissimilar physical and/or chemical properties, i.e., an amino acid residue that is a member of a different class or category, as defined above. For example, a non-conservative mutant may be a polypeptide or combination of polypeptides that differs in amino acid sequence from the wild-type sequence by the substitution of an acidic Glu (E) residue with a basic Arg (R), Lys (K) or Orn residue.

"Deletion Mutant" refers to a mutant having an amino acid sequence or sequences that differs from the wild-type sequence(s) by the deletion of one or more amino acid residues from the wild-type sequence(s). The residues may be deleted from internal regions of the wild-type sequence(s) and/or from one or both termini.

"Truncated Mutant" refers to a deletion mutant in which the deleted residues are from the N- and/or C-terminus of the wild-type sequence(s).

"Extended Mutant" refers to a mutant in which additional residues are added to the N- and/or C-terminus of the wild-type sequence(s).

"Methionine mutant" refers to (1) a mutant in which at least one methionine residue of the wild-type sequence(s) is replaced with another residue, preferably with an aliphatic residue, most preferably with a Leu (L) or Ile (I) residue; or (2) a mutant in which a non-methionine residue, preferably an aliphatic residue, most preferably a Leu (L) or Ile (I) residue, of the wild-type sequence(s) is replaced with a methionine residue.

"Selenomethionine mutant" refers to (1) a mutant which includes at least one selenomethionine (SeMet) residue, typically by substitution of a Met residue of the wild-type sequence(s) with a SeMet residue, or by addition of one or more SeMet residues at one or both termini, or (2) a methionine mutant in which at least one Met residue is substituted with a SeMet residue. Preferred SeMet mutants are those in which each Met residue is substituted with a SeMet residue.

"Cysteine mutant" refers to (1) a mutant in which at least one cysteine residue of the wild-type sequence(s) is replaced with another residue, preferably with a Ser (S) residue; or (2) a mutant in which a non-cysteine residue, preferably a Ser (S) residue, of the wild-type sequence(s) is replaced with a cysteine residue.

"Selenocysteine mutant" refers to (1) a mutant which includes at least one selenocysteine (SeCys) residue, typically by substitution of a Cys residue of the wild-type sequence(s) with a SeCys residue, or by addition of one or more SeCys residues at one or both termini, or (2) a cysteine mutant in which at least one Cys residue is substituted with a SeCys residue. Preferred SeCys mutants are those in which each Cys residue is substituted with a SeCys residue.

"Homologue" refers to a polypeptide having at least 80% amino acid sequence identity or having a BLAST score of $1 \times 10^{-6}$ over at least 100 amino acids (Altschul et al., 1997, *Nucleic Acids Res.* 25:3389-402) with human IgG Fc variant or any functional domain, e.g., $C_H2$ or $C_H3$, of Fc region.

"MEDI-524" refers to a wild type humanized anti-respiratory syncytial virus IgG1 antibody. A MEDI-524 is also known as Motavizumab, or NuMax.

"Association" refers to a condition of proximity between a chemical entity or compound, or portions or fragments thereof, and a polypeptide, or portions or fragments thereof. The association may be non-covalent, i.e., where the juxtaposition is energetically favored by, e.g., hydrogen-bonding, van der Waals, electrostatic or hydrophobic interactions, or it may be covalent.

"Complex" refers to a complex between a human IgG Fc variant and a binding compound, for example, a FcRn.

"Crystal" refers to a composition comprising a polypeptide complex in crystalline form. The term "crystal" includes native crystals, heavy-atom derivative crystals and poly-crystals, as defined herein.

"Crystallized human IgG Fc variant" refers to a human IgG Fc variant which is in the crystalline form.

"Native Crystal" refers to a crystal wherein the polypeptide complex is substantially pure. As used herein, native crystals do not include crystals of polypeptide complexes comprising amino acids that are modified with heavy atoms, such as crystals of selenomethionine mutants, selenocysteine mutants, etc.

"Heavy-atom Derivative Crystal" refers to a crystal wherein the polypeptide complex is in association with one or more heavy-metal atoms. As used herein, heavy-atom derivative crystals include native crystals into which a heavy metal atom is soaked, as well as crystals of selenomethionine mutants and selenocysteine mutants.

"Co-Crystal" refers to a composition comprising a complex, as defined above, in crystalline form. Co-crystals include native co-crystals and heavy-atom derivative co-crystals.

"Diffraction Quality Crystal" refers to a crystal that is well-ordered and of a sufficient size, i.e., at least 10 µm, preferably at least 50 µm, and most preferably at least 100 µm in its smallest dimension such that it produces measurable diffraction to at least 3 Å resolution, preferably to at least 2 Å resolution, and most preferably to at least 1.5 Å resolution or lower. Diffraction quality crystals include native crystals, heavy-atom derivative crystals, and poly-crystals.

"Unit Cell" refers to the smallest and simplest volume element (i.e., parallelpiped-shaped block) of a crystal that is completely representative of the unit or pattern of the crystal, such that the entire crystal can be generated by translation of the unit cell. The dimensions of the unit cell are defined by six numbers: dimensions a, b and c and angles $\alpha$, $\beta$ and $\gamma$ (Blundel et al., 1976, Protein Crystallography, Academic Press). A crystal is an efficiently packed array of many unit cells.

"Triclinic Unit Cell" refers to a unit cell in which a≠ b≠ c and $\alpha$≠ $\beta$≠ $\gamma$.

"Monoclinic Unit Cell" refers to a unit cell in which a≠ b≠ c; $\alpha$=$\gamma$=90°; and $\beta$≠ 90°, defined to be ≥90°.

"Orthorhombic Unit Cell" refers to a unit cell in which a≠ b≠ c; and $\alpha$=$\beta$=$\gamma$=90°.

"Tetragonal Unit Cell" refers to a unit cell in which a=b≠ c; and $\alpha$=$\beta$=$\gamma$=90°.

"Trigonal/Rhombohedral Unit Cell" refers to a unit cell in which a=b=c; and $\alpha$=$\beta$=$\gamma$≠ 90°.

"Trigonal/Hexagonal Unit Cell" refers to a unit cell in which a=b=c; $\alpha$=$\beta$=90°; and $\gamma$=120°.

"Cubic Unit Cell" refers to a unit cell in which a=b=c; and $\alpha$=$\beta$=$\gamma$90°.

"Crystal Lattice" refers to the array of points defined by the vertices of packed unit cells.

"Space Group" refers to the set of symmetry operations of a unit cell. In a space group designation (e.g., C2) the capital letter indicates the lattice type and the other symbols represent symmetry operations that can be carried out on the unit cell without changing its appearance.

"Asymmetric Unit" refers to the largest aggregate of molecules in the unit cell that possesses no symmetry elements that are part of the space group symmetry, but that can be juxtaposed on other identical entities by symmetry operations.

"Crystallographically-Related Dimer" refers to a dimer of two molecules wherein the symmetry axes or planes that relate the two molecules comprising the dimer coincide with the symmetry axes or planes of the crystal lattice.

"Non-Crystallographically-Related Dimer" refers to a dimer of two molecules wherein the symmetry axes or planes that relate the two molecules comprising the dimer do not coincide with the symmetry axes or planes of the crystal lattice.

"Isomorphous Replacement" refers to the method of using heavy-atom derivative crystals to obtain the phase information necessary to elucidate the three-dimensional structure of a crystallized polypeptide (Blundel et al., 1976, Protein Crystallography, Academic Press).

"Multi-Wavelength Anomalous Dispersion or MAD" refers to a crystallographic technique in which X-ray diffraction data are collected at several different wavelengths from a single heavy-atom derivative crystal, wherein the heavy atom has absorption edges near the energy of incoming X-ray radiation. The resonance between X-rays and electron orbitals leads to differences in X-ray scattering from absorption of the X-rays (known as anomalous scattering) and permits the locations of the heavy atoms to be identified, which in turn provides phase information for a crystal of a polypeptide. A detailed discussion of MAD analysis can be found in Hendrickson, 1985, Trans. Am. Crystallogr. Assoc., 21:11; Hendrickson et al., 1990, EMBO J. 9:1665; and Hendrickson, 1991, Science 4:91.

"Single Wavelength Anomalous Dispersion or SAD" refers to a crystallographic technique in which X-ray diffraction data are collected at a single wavelength from a single native or heavy-atom derivative crystal, and phase information is extracted using anomalous scattering information from atoms such as sulfur or chlorine in the native crystal or from the heavy atoms in the heavy-atom derivative crystal. The wavelength of X-rays used to collect data for this phasing technique need not be close to the absorption edge of the anomalous scatterer. A detailed discussion of SAD analysis can be found in Brodersen et al., 2000, Acta Cryst., D56:431-441.

"Single Isomorphous Replacement With Anomalous Scattering or SIRAS" refers to a crystallographic technique that combines isomorphous replacement and anomalous scattering techniques to provide phase information for a crystal of a polypeptide. X-ray diffraction data are collected at a single wavelength, usually from a single heavy-atom derivative crystal. Phase information obtained only from the location of the heavy atoms in a single heavy-atom derivative crystal leads to an ambiguity in the phase angle, which is resolved using anomalous scattering from the heavy atoms. Phase information is therefore extracted from both the location of the heavy atoms and from anomalous scattering of the heavy atoms. A detailed discussion of SIRAS analysis can be found in North, 1965, Acta Cryst. 18:212-216; Matthews, 1966, Acta Cryst. 20:82-86.

"Molecular Replacement" refers to the method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the polypeptides comprising the new crystal. (Jones et al., 1991, *Acta Crystallogr.* 47:753-70; Brunger et al., 1998, *Acta Crystallogr. D. Biol. Crystallogr.* 54:905-21)

"Having substantially the same three-dimensional structure" refers to a polypeptide that is characterized by a set of atomic structure coordinates that have a root mean square deviation (r.m.s.d.) of less than or equal to about 2 Å when superimposed onto the atomic structure coordinates of Table 5 when at least about 50% to 100% of the C$\alpha$ atoms of the coordinates are included in the superposition.

"C$\alpha$:" As used herein, "C$\alpha$" refers to the alpha carbon of an amino acid residue.

"Purified," when used in relation to an antibody, refers to a composition of antibodies that each have substantially similar specificities; e.g., the antibodies in the composition each bind essentially the same epitope. One method to obtain a purified antibody is to affinity purify the antibody from a polyclonal antibody preparation using a molecule that comprises the epitope of interest but not undesirable epitope(s). For example, a molecule comprising a neutralizing epitope but not an enhancing epitope can be used to obtain a purified antibody that binds the neutralizing epitope that is substantially free (e.g., antibodies of other specificity constitute less than about 0.1% of the total preparation) of antibodies that specifically bind the enhancing epitope.

4. BRIEF DESCRIPTION OF THE FIGURES

FIG. 1 provides a three-dimensional view of the asymmetric unit or an Fc/YTE crystal. The triple mutation comprising M252Y/S254T/T256E ('YTE') is shown in outlined sticks.

The carbohydrate residues attached to N297 on each polypeptide (shown as solid sticks) were modeled according to their electron density. This and subsequent illustrations were prepared using PyMOL (DeLano, 2002, The PyMOL Molecular Graphics System, DeLano Scientific, Palo Alto, Calif., USA. available on the World Wide Web at pymol.org).

Figure 2:
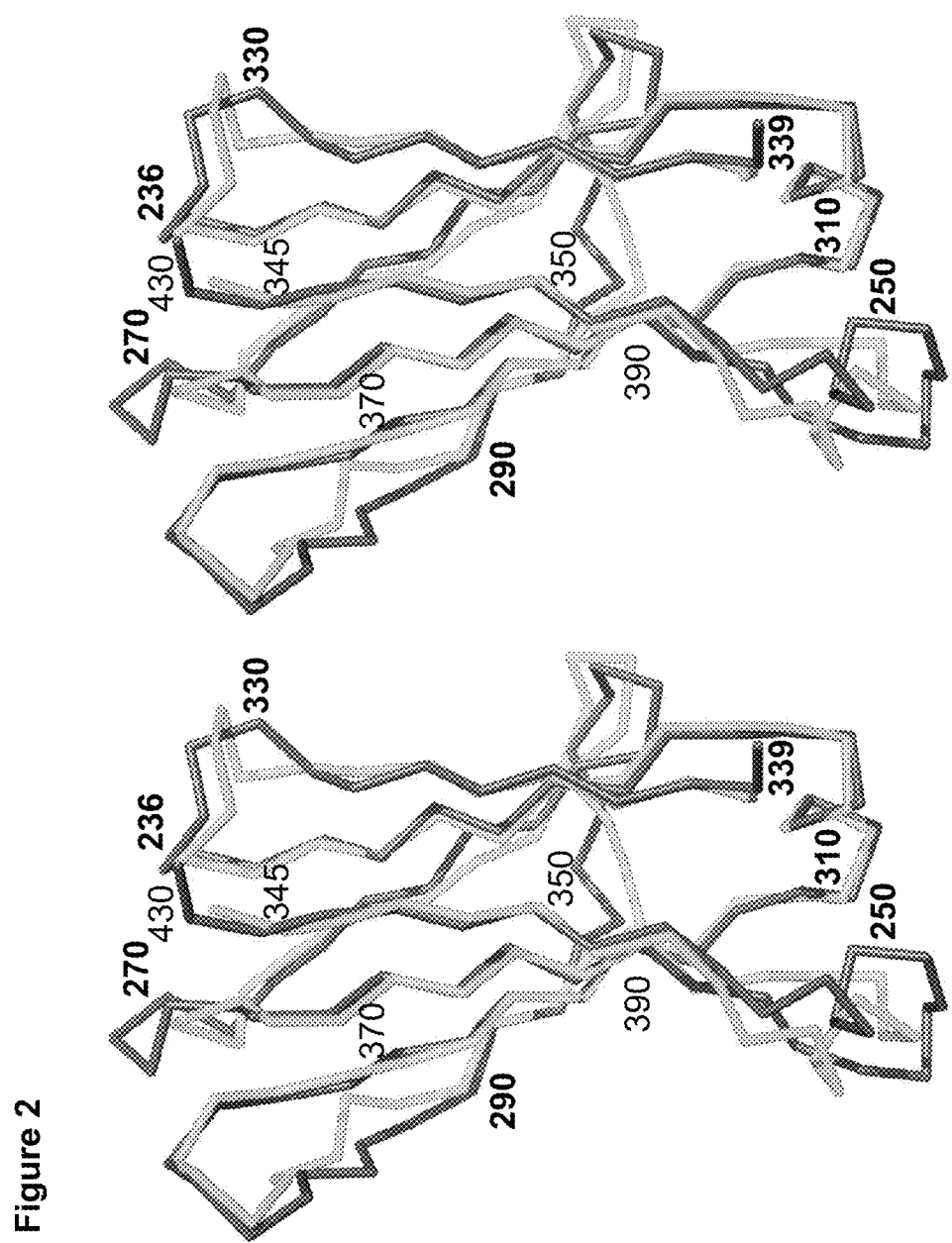

FIG. 2 provides a stereographic view of the superimposition of the $C_H2$ (in dark gray) and $C_H3$ (in light gray) domains of chain A of Fc/YTE. Superimposition of the Cα atoms was carried out using "Isqkab" (See Kabsch, W. 1976, *Acta Cryst.* A32, 922-923).

Figure 3:
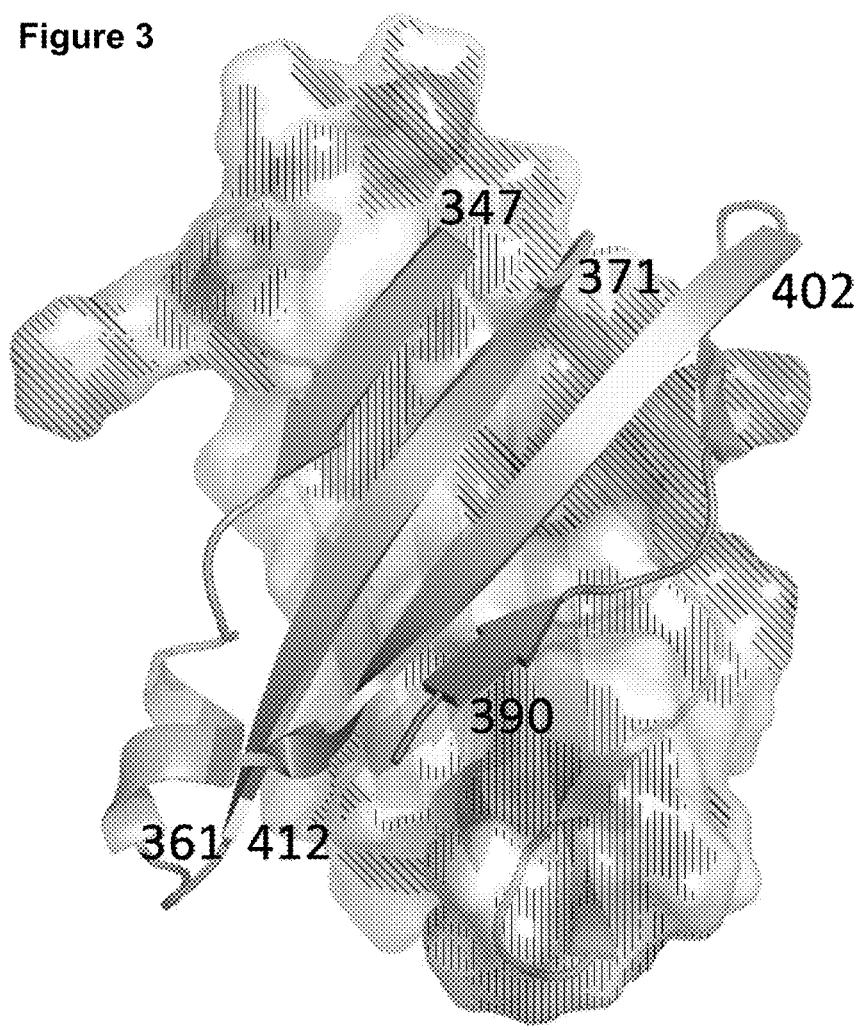

FIG. 3 provides a three-dimensional view of Fc/YTE $C_H3$ dimerization interface. The four-stranded antiparallel β-sheets comprising the major zone of intermolecular contacts is shown as a ribbon. Positive and negative electrostatic potentials are indicated in diagonal hatches and vertical hatches, respectively, and were calculated using APBS (Adaptive Poisson-Boltzmann Solver) plug-in in PyMOL.

Figure 4:

FIG. 4 shows a stereographic view of the final SigmaA weighted electron density map around the M252Y, S254T and T256E mutations (shown as thick sticks). The rest of polypeptide is shown in thin black sticks whereas the symmetry related molecule is shown in outlined thin white sticks. The map is contoured at 1.2σ.

Figure 5A:
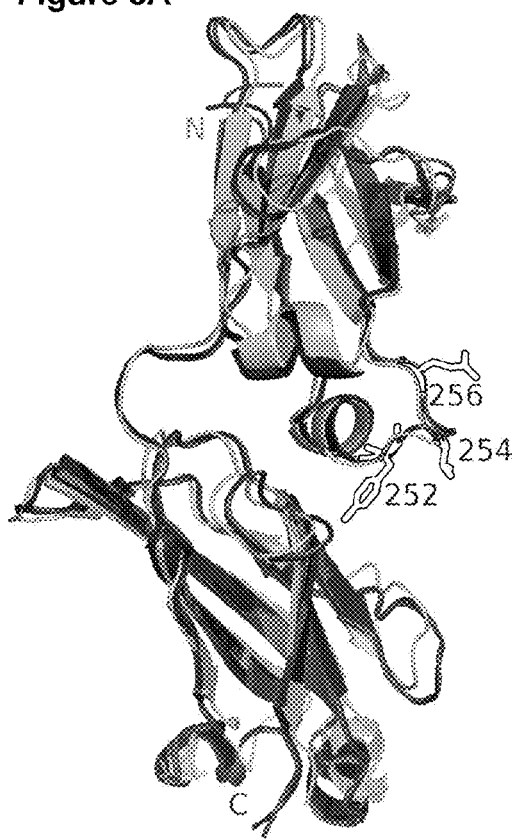

FIG. 5A provides a three-dimensional view of the superimposition of chain B of Fc/YTE (shown in black), chain B of human Fc (PDB Id. 2DTQ, shown in dark grey) and non-modified chain of rat Fc (PDB Id. 1I1A, shown in light grey). The triple mutation comprising M252Y/S254T/T256E is shown in outlined white sticks. Superimposition of the Cα atoms was carried out using "Isqkab" (Kabsch, W. 1976, *Acta Cryst.* A32, 922-923).

Figure 5B:
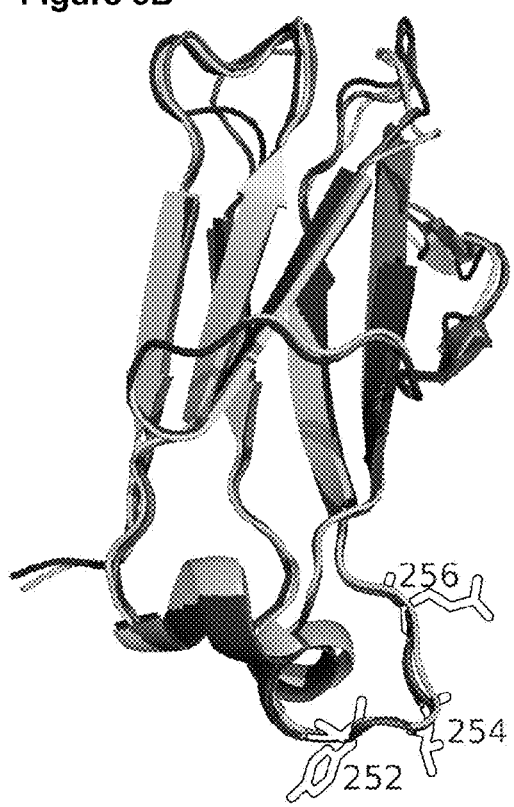

FIG. 5B provides a three-dimensional view of a superimposition of the $C_H2$ domain of chain B of Fc/YTE (shown in black), the $C_H2$ domain of chain B of human Fc (PDB Id. 2DTQ, shown in dark grey), and the $C_H2$ domain of the non-modified chain of rat (PDB Id. Fc 1I1A, shown in light grey). The triple mutation comprising M252Y/S254T/T256E is shown in outlined white sticks. Superimposition of the Cα atoms was carried out using "Isqkab" (Kabsch, W. 1976, *Acta Cryst.* A32, 922-923).

FIGS. 6A-6C provide sequence alignments of Fc/YTE (SEQ ID NO:1) with rat Fc (SEQ ID NO:2), of human FcRn β microglobulin chain (SEQ ID NO:3) with rat FcRn β microglobulin chain (SEQ ID NO:4), and of human FcRn α chain (SEQ ID NO: 5) with rat FcRn α chain (SEQ ID NO: 6). The full amino acid sequences are given using the standard one letter code. Shaded residues correspond to identity between human and rat sequences. The underlined positions correspond to the sites of the YTE substitutions in the human Fc.

FIG. 7 provides the amino acid sequences of Fc/YTE with M252Y, S254T, T256E amino acid substitution (SEQ ID NO:7) and wild type Human IgG Fc (SEQ ID NO:8).

FIG. 8 provides an example of diffraction pattern of the Fc/YTE crystal as described in the Examples.

4.1 Brief Description of the Tables

Table I provides classification of commonly encountered amino acids;

Table II summarizes the X-ray crystallographic data statictics and refinement results of the structure of crystalline Fc/YTE provided herein.

Table III summarizes the hydrogen bonds and salt bridges formed between the $C_{11}3$ doamins of Fc/YTE.

Table IV provides dissociation constants for the binding of unmutated human Fc and Fc/YTE to human FcRn.

Table V provides the atomic structure coordinates of native Fc/YTE crystal as determined by X-ray crystallography.

5. DETAILED DESCRIPTION OF THE INVENTION

5.1 Crystalline Fc Variant

Provided herein are crystalline forms of a human IgG Fc variant, wherein the human IgG Fc variant comprises one or more amino acid residue mutations and has an increased binding affinity for an FcRn as compared to a wild type human IgG Fc region not comprising the one or more amino acid residue mutants. In certain embodiments, the human IgG Fc variant comprises at least one amino acid residue mutation selected from the group consisting of 252Y, 254T, and 256E, as numbered by the EU index as set forth in Kabat. In certain embodiments, the human IgG Fc variant comprises each of the amino acid residue mutations 252Y, 254T, and 256E, as numbered by the EU index as set forth in Kabat. In particular embodiments, the Fc variant comprises the amino acid sequence of SEQ ID NO:7.

The crystals may be obtained include native crystals and heavy-atom crystals. Native crystals generally comprise substantially pure polypeptides corresponding to the human IgG Fc variant in crystalline form. In certain embodiments, the crystals are native crystals. In certain embodiments, the crystals are heavy-atom crystals. It is to be understood that the crystalline human IgG Fc variant may comprise one or more amino acid residue mutations other than 252Y, 254T, and 256E. Indeed, the crystals may comprise mutants of human IgG Fc variant. Mutants of human IgG Fc variant can be obtained by replacing at least one amino acid residue in the sequence of human IgG Fc variant with a different amino acid residue, or by adding or deleting one or more amino acid residues within the wild-type sequence and/or at the N- and/or C-terminus of the wild-type Fc region. Preferably, such mutants will crystallize under crystallization conditions that are substantially similar to those used to crystallize the corresponding human IgG Fc variant.

The types of mutants contemplated include conservative mutants, non-conservative mutants, deletion mutants, truncated mutants, extended mutants, methionine mutants, selenomethionine mutants, cysteine mutants and selenocysteine mutants. Preferably, a mutant displays biological activity that is substantially similar to that of the corresponding human IgG Fc variant. Methionine, selenomethionine, cysteine, and selenocysteine mutants are particularly useful for producing heavy-atom derivative crystals, as described in detail, below.

It will be recognized by one of skill in the art that the types of mutants contemplated herein are not mutually exclusive; that is, for example, a polypeptide having a conservative mutation in one amino acid may in addition have a truncation of residues at the N-terminus, and several Leu or Ile→Met mutations.

Sequence alignments of polypeptides in a protein family or of homologous polypeptide domains can be used to identify potential amino acid residues in the polypeptide sequence that are candidates for mutation. Identifying mutations that do not significantly interfere with the three-dimensional structure of the human IgG Fc variant and/or that do not deleteriously affect, and that may even enhance, the activity of the human IgG Fc variant will depend, in part, on the region where the mutation occurs. In framework regions, or regions containing significant secondary structure, such as those regions shown in FIG. 5A, conservative amino acid substitutions are preferred.

Conservative amino acid substitutions are well-known in the art, and include substitutions made on the basis of a similarity in polarity, charge, solubility, hydrophobicity and/or the hydrophilicity of the amino acid residues involved.

Typical conservative substitutions are those in which the amino acid is substituted with a different amino acid that is a member of the same class or category, as those classes are defined herein. Thus, typical conservative substitutions include aromatic to aromatic, apolar to apolar, aliphatic to aliphatic, acidic to acidic, basic to basic, polar to polar, etc. Other conservative amino acid substitutions are well known in the art. It will be recognized by those of skill in the art that generally, a total of about 20% or fewer, typically about 10% or fewer, most usually about 5% or fewer, of the amino acids in the wild-type polypeptide sequence can be conservatively substituted with other amino acids without deleteriously affecting the biological activity and/or three-dimensional structure of the molecule, provided that such substitutions do not involve residues that are critical for activity, as discussed above.

In some embodiments, it may be desirable to make mutations in the active site of a protein, e.g., to reduce or completely eliminate protein activity. Mutations that will reduce or completely eliminate the activity of a particular protein will be apparent to those of skill in the art.

The amino acid residue Cys (C) is unusual in that it can form disulfide bridges with other Cys (C) residues or other sulfhydryl-containing amino acids ("cysteine-like amino acids"). The ability of Cys (C) residues and other cysteine-like amino acids to exist in a polypeptide in either the reduced free —SH or oxidized disulfide-bridged form affects whether Cys (C) residues contribute net hydrophobic or hydrophilic character to a polypeptide. While Cys (C) exhibits a hydrophobicity of 0.29 according to the consensus scale of Eisenberg (Eisenberg, 1984, supra), it is to be understood that for purposes of the present invention Cys (C) is categorized as a polar hydrophilic amino acid, notwithstanding the general classifications defined above. Preferably, Cys residues that are known to participate in disulfide bridges, such as those linking the heavy chain to the light chain of an antibody, or a portion thereof, are not substituted or are conservatively substituted with other cysteine-like amino acids so that the residue can participate in a disulfide bridge. Typical cysteine-like residues include, for example, Pen, hCys, etc. Substitutions for Cys residues that interfere with crystallization are discussed infra.

While in most instances the amino acids of human IgG Fc variant will be substituted with genetically-encoded amino acids, in certain circumstances mutants may include genetically non-encoded amino acids. For example, non-encoded derivatives of certain encoded amino acids, such as SeMet and/or SeCys, may be incorporated into the polypeptide chain using biological expression systems (such SeMet and SeCys mutants are described in more detail, infra).

Alternatively, in instances where the mutant will be prepared in whole or in part by chemical synthesis, virtually any non-encoded amino acids may be used, ranging from D-isomers of the genetically encoded amino acids to non-encoded naturally-occurring natural and synthetic amino acids.

Conservative amino acid substitutions for many of the commonly known non-genetically encoded amino acids are well known in the art. Conservative substitutions for other non-encoded amino acids can be determined based on their physical properties as compared to the properties of the genetically encoded amino acids.

In some instances, it may be particularly advantageous or convenient to substitute, delete from and/or add amino acid residues to human IgG Fc variant in order to provide convenient cloning sites in cDNA encoding the polypeptide, to aid in purification of the polypeptide, etc. Such substitutions, deletions and/or additions that do not substantially alter the three dimensional structure of the wile type human IgG Fc region will be apparent to those having skills in the art. These substitutions, deletions and/or additions include, but are not limited to, His tags, BirA tags, intein-containing self-cleaving tags, maltose binding protein fusions, glutathione S-transferase protein fusions, antibody fusions, green fluorescent protein fusions, signal peptide fusions, biotin accepting peptide fusions, and the like. In certain embodiments, the human IgG Fc variant comprises a His tag. In other embodiments, the human IgG Fc variant comprises a BirA tag. In a preferred embodiment, the human IgG Fc variant comprises a His tag and a BirA tag.

Mutations may also be introduced into a polypeptide sequence where there are residues, e.g., cysteine residues, that interfere with crystallization. Such cysteine residues can be substituted with an appropriate amino acid that does not readily form covalent bonds with other amino acid residues under crystallization conditions; e.g., by substituting the cysteine with Ala, Ser or Gly. Any cysteine located in a non-helical or non-n-stranded segment, based on secondary structure assignments, are good candidates for replacement.

The heavy-atom derivative crystals from which the atomic structure coordinates can be obtained generally comprise a crystalline human IgG Fc variant. There are at least two types of heavy-atom derivatives of polypeptides: heavy-atom derivatives resulting from exposure of the protein to a heavy metal in solution, wherein crystals are grown in medium comprising the heavy metal, or in crystalline form, wherein the heavy metal diffuses into the crystal, and heavy-atom derivatives wherein the polypeptide comprises heavy-atom containing amino acids, e.g., selenomethionine and/or selenocysteine mutants.

In practice, heavy-atom derivatives of the first type can be formed by soaking a native crystal in a solution comprising heavy metal atom salts, or organometallic compounds, e.g., lead chloride, gold thiomalate, ethylmercurithiosalicylic acid-sodium salt (thimerosal), uranyl acetate, platinum tetrachloride, osmium tetraoxide, zinc sulfate, and cobalt hexamine, which can diffuse through the crystal and bind to the crystalline polypeptide complex.

Heavy-atom derivatives of this type can also be formed by adding to a crystallization solution comprising the polypeptide complex to be crystallized an amount of a heavy metal atom salt, which may associate with the protein complex and be incorporated into the crystal. The location(s) of the bound heavy metal atom(s) can be determined by X-ray diffraction analysis of the crystal. This information, in turn, is used to generate the phase information needed to construct the three-dimensional structure of the protein.

Heavy-atom derivative crystals may also be prepared from human IgG Fc variant. Such selenocysteine or selenomethionine mutants may be made from human IgG Fc variant or a mutant by expression of human IgG Fc variant in auxotrophic E. coli strains. Hendrickson et al., 1990, *EMBO J.* 9:1665-1672. In this method, the human IgG Fc variant or its mutant may be expressed in a host organism on a growth medium depleted of either natural cysteine or methionine (or both) but enriched in selenocysteine or selenomethionine (or both). Alternatively, a selenocysteine or selenomethionine mutant may be made using nonauxotrophic E. coli strains, e.g., by inhibiting methionine biosynthesis in these strains with high concentrations of Ile, Lys, Phe, Leu, Val or Thr and then providing selenomethionine in the medium (Doublié, 1997, *Methods in Enzymology* 276:523-530). Furthermore, selenocysteine can be selectively incorporated into polypeptides by exploiting the prokaryotic and eukaryotic mechanisms for selenocysteine incorporation into certain classes of proteins in vivo, as described in U.S. Pat. No. 5,700,660 to Leonard et al. (filed Jun. 7, 1995). One of skill in the art will recognize that selenocysteine is preferably not incorporated in place of cysteine residues that form disulfide bridges, as these may be important for maintaining the three-dimensional structure of the protein and are preferably not to be eliminated. One of skill in the art will further recognize that, in order to obtain accurate phase information, approximately one selenium atom should be incorporated for every 140 amino acid residues of the polypeptide chain. The number of selenium atoms incorporated into the polypeptide chain can be conveniently controlled by designing a Met or Cys mutant having an appropriate number of Met and/or Cys residues, as described more fully below.

In some instances, a polypeptide to be crystallized may not contain cysteine or methionine residues. Therefore, if selenomethionine and/or selenocysteine mutants are to be used to obtain heavy-atom derivative crystals, methionine and/or cysteine residues must be introduced into the polypeptide chain. Likewise, Cys residues may be introduced into the polypeptide chain if the use of a cysteine-binding heavy metal, such as mercury, is contemplated for production of a heavy-atom derivative crystal.

Such mutations are preferably introduced into the polypeptide sequence at sites that will not disturb the overall protein fold. For example, a residue that is conserved among many members of the protein family or that is thought to be involved in maintaining its activity or structural integrity, as determined by, e.g., sequence alignments, should not be mutated to a Met or Cys. In addition, conservative mutations, such as Ser to Cys, or Leu or Ile to Met, are preferably introduced. One additional consideration is that, in order for a heavy-atom derivative crystal to provide phase information for structure determination, the location of the heavy atom(s) in the crystal unit cell should be determinable and provide phase information. Therefore, a mutation is preferably not introduced into a portion of the protein that is likely to be mobile, e.g., at, or within about 1-5 residues of, the N- and C-termini.

Conversely, if there are too many methionine and/or cysteine residues in a polypeptide sequence, over-incorporation of the selenium-containing side chains can lead to the inability of the polypeptide to fold and/or crystallize, and may potentially lead to complications in solving the crystal structure. In this case, methionine and/or cysteine mutants are prepared by substituting one or more of these Met and/or Cys residues with another residue. The considerations for these substitutions are the same as those discussed above for mutations that introduce methionine and/or cysteine residues into the polypeptide. Specifically, the Met and/or Cys residues are preferably conservatively substituted with Leu/Ile and Ser, respectively.

As DNA encoding cysteine and methionine mutants can be used in the methods described above for obtaining SeCys and SeMet heavy-atom derivative crystals, the preferred Cys or Met mutant will have one Cys or Met residue for every 140 amino acids.

5.2 Production of Polypeptides

The human IgG Fc variants or mutants thereof may be chemically synthesized in whole or part using techniques that are well-known in the art (see, e.g., Creighton, 1983, Proteins: Structures and Molecular Principles, W.H. Freeman & Co., NY.). Alternatively, methods that are well known to those skilled in the art can be used to construct expression vectors containing the human IgG Fc variant polypeptide coding sequence and appropriate transcriptional/translational control signals. These methods include in vitro recombinant DNA techniques, synthetic techniques and in vivo recombination/genetic recombination. See, for example, the techniques described in the current editions of Sambrook et al., 2001, *Molecular Cloning: A Laboratory Manual*, 3d Ed., Cold Spring Harbor Laboratory, NY and Ausubel et al., 2004, *Current Protocols in Molecular Biology*, Greene Publishing Associates and Wiley Interscience, NY. The human IgG Fc variant may also be produced by digesting an IgG with papain.

A variety of host-expression vector systems may be utilized to express the human IgG Fc variant coding sequences. These include but are not limited to microorganisms such as bacteria transformed with recombinant bacteriophage DNA, plasmid DNA or cosmid DNA expression vectors containing the human IgG Fc region coding sequences; yeast transformed with recombinant yeast expression vectors containing the Fc coding sequences; insect cell systems infected with recombinant virus expression vectors (e.g., baculovirus) containing the Fc coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the Fc coding sequences; or animal cell systems. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

Depending on the host/vector system utilized, any of a number of suitable transcription and translation elements, including constitutive and inducible promoters, may be used in the expression vector. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the tyrosine kinase domain DNA, SV40-, BPV- and EBV-based vectors may be used with an appropriate selectable marker.

The expression vector may be introduced into host cells via any one of a number of techniques including but not limited to transformation, transfection, infection, protoplast fusion, and electroporation. The expression vector-containing cells are clonally propagated and individually analyzed to determine whether they produce human IgG Fc variant. Identification of human IgG Fc variant-expressing host cell clones may be done by several means, including but not limited to immunological reactivity with anti-human IgG Fc variant or antiimmunoglobulin antibodies, and the presence of host cell-associated Fc biological activity.

Expression of human IgG Fc variant may also be performed using in vitro produced synthetic mRNA. Synthetic mRNA can be efficiently translated in various cell-free systems, including but not limited to wheat germ extracts and reticulocyte extracts, as well as efficiently translated in cell based systems, including but not limited to microinjection into frog oocytes. Further, nucleic acids expressing human IgG Fc variant can be constructed and expressed by gene synthesis using oligonucleotides. See Hoover & Lubkowski, 2002, *Nucleic Acids Res* 30:e43.

To determine the human IgG Fc variant DNA sequences that yields optimal levels of Fc biological activity, modified Fc variant molecules are constructed. Host cells are transformed with the cDNA molecules and the levels of Fc RNA and/or protein are measured.

Levels of Fc protein in host cells are quantitated by a variety of methods such as immunoaffinity and/or ligand affinity techniques, Fc specific beads or Fc specific antibodies are used to isolate $^{35}$S-methionine labeled or unlabeled Fc. Labeled or unlabeled Fc is analyzed by SDS-PAGE. Unlabeled Fc is detected by Western blotting, ELISA or RIA employing Fc-specific antibodies.

Following expression of human IgG Fc variant in a recombinant host cell, Fc may be recovered to provide human IgG Fc variant in active form. Several human IgG Fc variant purification procedures are available and suitable for use. Recombinant Fc may be purified from cell lysates or from conditioned culture media, by various combinations of or individual application of, fractionation, or chromatography steps that are known in the art.

In addition, recombinant human IgG Fc variant can be separated from other cellular proteins by use of an immunoaffinity column made with monoclonal or polyclonal antibodies specific for full length nascent Fc or polypeptide fragments thereof.

Alternatively, human IgG Fc variant may be recovered from a host cell in an unfolded, inactive form, e.g., from inclusion bodies of bacteria. Proteins recovered in this form may be solublized using a denaturant, e.g., guanidinium hydrochloride, and then refolded into an active form using methods known to those skilled in the art, such as dialysis. See, for example, the techniques described in Sambrook et al., 2001, *Molecular Cloning: A Laboratory Manual*, 3d Ed., Cold Spring Harbor Laboratory, NY and Ausubel et al., 2004, *Current Protocols in Molecular Biology*, Greene Publishing Associates and Wiley Interscience, NY.

Still further, human IgG Fc variant can be prepared from an antibody according to any known method without limitation. Generally, Fc fragments can be prepared by Papain digestion of an antibody; however, any technique that cleaves an antibody heavy chain at or near the hinge region can be used to prepare the Fc fragments. Useful protocols for making Fc fragments from antibodies, including monoclonal antibodies, are described in, e.g., Harlow et al., 1988, *Antibodies: A Laboratory Manual*, Cold Spring Harbor Laboratory Press, 2nd ed. These techniques can be used to prepare Fc variants from an antibody according to any of the methods described herein.

5.3 Crystallization of Polypeptides and Characterization of Crystal

The native, heavy-atom derivative, and/or co-crystals from which the atomic structure coordinates can be obtained are well-known in the art of protein crystallography, including batch, liquid bridge, dialysis, and vapor diffusion methods (see, e.g., McPherson, 1998, *Crystallization of Biological Macromolecules*, Cold Spring Harbor Press, New York; McPherson, 1990, *Eur. J. Biochem.* 189:1-23; Weber, 1991, *Adv. Protein Chem.* 41:1-36).

Generally, native crystals are grown by dissolving substantially pure human IgG Fc variant in an aqueous buffer containing a precipitant at a concentration just below that necessary to precipitate the protein. Examples of precipitants include, but are not limited to, polyethylene glycol, ammonium sulfate, 2-methyl-2,4-pentanediol, sodium citrate, sodium chloride, glycerol, isopropanol, lithium sulfate, sodium acetate, sodium formate, potassium sodium tartrate, ethanol, hexanediol, ethylene glycol, dioxane, t-butanol and combinations thereof Water is removed by controlled evaporation to produce precipitating conditions, which are maintained until crystal growth ceases.

In a preferred embodiment, native crystals are grown by vapor diffusion in sitting drops (McPherson, 1982, *Preparation and Analysis of Protein Crystals*, John Wiley, New York; McPherson, 1990, *Eur. J. Biochem.* 189:1-23). In this method, the polypeptide/precipitant solution is allowed to equilibrate in a closed container with a larger aqueous reservoir having a precipitant concentration optimal for producing crystals. Generally, less than about 25 µL of substantially pure polypeptide solution is mixed with an equal volume of reservoir solution, giving a precipitant concentration about half that required for crystallization. The sealed container is allowed to stand, usually for about 2-6 weeks, until crystals grow.

In certain embodiments, the crystals are produced by a method comprising the steps of (a) mixing a volume of a solution comprising a human IgG Fc variant with a volume of a reservoir solution comprising a precipitant; and (b) incubating the mixture obtained in step (a) over the reservoir solution in a closed container, under conditions suitable for crystallization until the crystal forms. The mixture comprising the Fc variant and reservoir solution can be incubated at a temperature between 0° C.-100° C., between 5° C.-50° C., 5° C.-40° C., preferably between 20° C.-30° C.

For native crystals from which the atomic structure coordinates can be obtained, it has been found that hanging drops of about 2 µL containing about 1 µL of 1.8 mg/ml human IgG Fc variant in 100 mM 2-(N-morpholino)ethanesulfonic acid (MES) at pH 6.5, 15% polyethylene glycol (PEG) 6000, 5% 2-methyl-2,4-pentaediol (MPD) suspended over 300 µl reservoir solution for about 5 days at about 20-30° C. provide diffraction quality crystals.

Of course, those having skill in the art will recognize that the above-described crystallization conditions can be varied. Such variations may be used alone or in combination, and include polypeptide solutions containing polypeptide concentrations between 0.01 mg/mL and 100 mg/mL, preferably, between 0.1 mg/ml and 10 mg/ml; MES concentrations between 1 mM and 1000 mM, preferably, between 10 mM and 200 mM; MPD concentrations between 1% and 20%, preferably, between 3% and 7%; glycerol concentration between 0.1% to 50% (w/v), preferably, between 1% and 10% (w/v); pH ranges between 4.0 and 10.0, preferably, between 6.0 and 7.0; and reservoir solutions containing PEG molecular weights of 100 to 20000, at concentrations between about 0.1% and 50% (w/v), preferably, between 5% and 25% (w/v). Other buffer solutions may be used such as HEPES, CAPS, CAPSO, BIS TRIS, MES, MOPS, MOPSO, PIPES, TRIS, and the like, so long as the desired pH range is maintained.

Heavy-atom derivative crystals can be obtained by soaking native crystals in mother liquor containing salts of heavy metal atoms.

Heavy-atom derivative crystals can also be obtained from SeMet and/or SeCys mutants, as described above for native crystals.

Mutant proteins may crystallize under slightly different crystallization conditions than wild-type protein, or under very different crystallization conditions, depending on the nature of the mutation, and its location in the protein. For example, a non-conservative mutation may result in alteration of the hydrophilicity of the mutant, which may in turn make the mutant protein either more soluble or less soluble than the wild-type protein. Typically, if a protein becomes more hydrophilic as a result of a mutation, it will be more soluble than the wild-type protein in an aqueous solution and a higher precipitant concentration will be needed to cause it to crystallize. Conversely, if a protein becomes less hydrophilic as a result of a mutation, it will be less soluble in an aqueous solution and a lower precipitant concentration will be needed to cause it to crystallize. If the mutation happens to be in a region of the protein involved in crystal lattice contacts, crystallization conditions may be affected in more unpredictable ways.

Co-crystals can be obtained by soaking a native crystal in mother liquor containing compound that binds human IgG Fc such as an FcRn, or by co-crystallizing human IgG Fc variant in the presence of one or more binding compounds 5.4 Characterization of Crystals The dimensions of a unit cell of a crystal are defined by six numbers, the lengths of three unique edges, a, b, and c, and three unique angles, $\alpha$, $\beta$, and $\gamma$. The type of unit cell that comprises a crystal is dependent on the values of these variables, as discussed above.

When a crystal is placed in an X-ray beam, the incident X-rays interact with the electron cloud of the molecules that make up the crystal, resulting in X-ray scatter. The combination of X-ray scatter with the lattice of the crystal gives rise to nonuniformity of the scatter; areas of high intensity are called diffracted X-rays. The angle at which diffracted beams emerge from the crystal can be computed by treating diffraction as if it were reflection from sets of equivalent, parallel planes of atoms in a crystal (Bragg's Law). The most obvious sets of planes in a crystal lattice are those that are parallel to the faces of the unit cell. These and other sets of planes can be drawn through the lattice points. Each set of planes is identified by three indices, hkl. The h index gives the number of parts into which the a edge of the unit cell is cut, the k index gives the number of parts into which the b edge of the unit cell is cut, and the l index gives the number of parts into which the c edge of the unit cell is cut by the set of hkl planes. Thus, for example, the 235 planes cut the a edge of each unit cell into halves, the b edge of each unit cell into thirds, and the c edge of each unit cell into fifths. Planes that are parallel to the be face of the unit cell are the 100 planes; planes that are parallel to the ac face of the unit cell are the 010 planes; and planes that are parallel to the ab face of the unit cell are the 001 planes.

When a detector is placed in the path of the diffracted X-rays, in effect cutting into the sphere of diffraction, a series of spots, or reflections, are recorded to produce a "still" diffraction pattern. Each reflection is the result of X-rays reflecting off one set of parallel planes, and is characterized by an intensity, which is related to the distribution of molecules in the unit cell, and hkl indices, which correspond to the parallel planes from which the beam producing that spot was reflected. If the crystal is rotated about an axis perpendicular to the X-ray beam, a large number of reflections is recorded on the detector, resulting in a diffraction pattern as shown, for example, in FIG. 8.

The unit cell dimensions and space group of a crystal can be determined from its diffraction pattern. First, the spacing of reflections is inversely proportional to the lengths of the edges of the unit cell. Therefore, if a diffraction pattern is recorded when the X-ray beam is perpendicular to a face of the unit cell, two of the unit cell dimensions may be deduced from the spacing of the reflections in the x and y directions of the detector, the crystal-to-detector distance, and the wavelength of the X-rays. Those of skill in the art will appreciate that, in order to obtain all three unit cell dimensions, the crystal can be rotated such that the X-ray beam is perpendicular to another face of the unit cell. Second, the angles of a unit cell can be determined by the angles between lines of spots on the diffraction pattern. Third, the absence of certain reflections and the repetitive nature of the diffraction pattern, which may be evident by visual inspection, indicate the internal symmetry, or space group, of the crystal. Therefore, a crystal may be characterized by its unit cell and space group, as well as by its diffraction pattern.

Once the dimensions of the unit cell are determined, the likely number of polypeptides in the asymmetric unit can be deduced from the size of the polypeptide, the density of the average protein, and the typical solvent content of a protein crystal, which is usually in the range of 30-70% of the unit cell volume (Matthews, 1968, J. Mol. Biol. 33(2):491-497).

The human IgG Fc variant crystals are generally characterized by a diffraction pattern that is substantially similar to the diffractin pattern as shown in FIG. 8. The crystals are further characterized by unit cell dimensions and space group symmetry information obtained from the diffraction patterns, as described above. The crystals, which may be native crystals, heavy-atom derivative crystals or poly-crystals, have an orthorhombic unit cell (i.e., unit cells wherein a$\ne$b$\ne$c and $\alpha=\beta=\gamma=90°$) and space group symmetry $P2_12_12_1$.

One form of crystalline human IgG Fc variant was obtained. In this form (designated "$P2_12_12_1$ form"), the unit cell has dimensions of a=49.66 Å, b=79.54 Å, and c=145.53 Å. In this form, there is one human IgG Fc variant in the asymmetric unit.

5.5 Collection of Data and Determination of Structure Solutions

The diffraction pattern is related to the three-dimensional shape of the molecule by a Fourier transform. The process of determining the solution is in essence a re-focusing of the diffracted X-rays to produce a three-dimensional image of the molecule in the crystal. Since re-focusing of X-rays cannot be done with a lens at this time, it is done via mathematical operations.

The sphere of diffraction has symmetry that depends on the internal symmetry of the crystal, which means that certain orientations of the crystal will produce the same set of reflections. Thus, a crystal with high symmetry has a more repetitive diffraction pattern, and there are fewer unique reflections that need to be recorded in order to have a complete representation of the diffraction. The goal of data collection, a dataset, is a set of consistently measured, indexed intensities for as many reflections as possible. A complete dataset is collected if at least 80%, preferably at least 90%, most preferably at least 95% of unique reflections are recorded. In one embodiment, a complete dataset is collected using one crystal. In another embodiment, a complete dataset is collected using more than one crystal of the same type.

Sources of X-rays include, but are not limited to, a rotating anode X-ray generator such as a Rigaku MicroMax™-007 or a beamline at a synchrotron light source, such as the Advanced Photon Source at Argonne National Laboratory. Suitable detectors for recording diffraction patterns include, but are not limited to, X-ray sensitive film, multiwire area detectors, image plates coated with phosphorus, and CCD cameras. Typically, the detector and the X-ray beam remain stationary, so that, in order to record diffraction from different parts of the crystal's sphere of diffraction, the crystal itself is moved via an automated system of moveable circles called a goniostat.

One of the biggest problems in data collection, particularly from macromolecular crystals having a high solvent content, is the rapid degradation of the crystal in the X-ray beam. In order to slow the degradation, data is often collected from a crystal at liquid nitrogen temperatures. In order for a crystal to survive the initial exposure to liquid nitrogen, the formation of ice within the crystal can be prevented by the use of a cryoprotectant. Suitable cryoprotectants include, but are not limited to, low molecular weight polyethylene glycols, ethylene glycol, sucrose, glycerol, xylitol, and combinations thereof. Crystals may be soaked in a solution comprising the one or more cryoprotectants prior to exposure to liquid nitrogen, or the one or more cryoprotectants may be added to the crystallization solution. Data collection at liquid nitrogen temperatures may allow the collection of an entire dataset from one crystal.

Once a dataset is collected, the information is used to determine the three-dimensional structure of the molecule in the crystal. However, this cannot be done from a single measurement of reflection intensities because certain information, known as phase information, is lost between the three-dimensional shape of the molecule and its Fourier transform, the diffraction pattern. This phase information can be acquired by methods described below in order to perform a Fourier transform on the diffraction pattern to obtain the three-dimensional structure of the molecule in the crystal. It is the determination of phase information that in effect refocuses X-rays to produce the image of the molecule.

One method of obtaining phase information is by isomorphous replacement, in which heavy-atom derivative crystals are used. In this method, the positions of heavy atoms bound to the molecules in the heavy-atom derivative crystal are determined, and this information is then used to obtain the phase information necessary to elucidate the three-dimensional structure of a native crystal. (Blundel et al., 1976, Protein Crystallography, Academic Press.)

Another method of obtaining phase information is by molecular replacement, which is a method of calculating initial phases for a new crystal of a polypeptide whose structure coordinates are unknown by orienting and positioning a polypeptide whose structure coordinates are known within the unit cell of the new crystal so as to best account for the observed diffraction pattern of the new crystal. Phases are then calculated from the oriented and positioned polypeptide and combined with observed amplitudes to provide an approximate Fourier synthesis of the structure of the molecules comprising the new crystal. (Lattman, 1985, *Methods in Enzymology* 115:55-77; Rossmann, 1972, "The Molecular Replacement Method," *Int. Sci. Rev. Ser. No.* 13, Gordon & Breach, New York.)

A third method of phase determination is multi-wavelength anomalous diffraction or MAD. In this method, X-ray diffraction data are collected at several different wavelengths from a single crystal containing at least one heavy atom with absorption edges near the energy of incoming X-ray radiation. The resonance between X-rays and electron orbitals leads to differences in X-ray scattering that permits the locations of the heavy atoms to be identified, which in turn provides phase information for a crystal of a polypeptide. A detailed discussion of MAD analysis can be found in Hendrickson, 1985, *Trans. Am. Crystallogr. Assoc.* 21:11; Hendrickson et al., 1990, *EMBO J.* 9:1665; and Hendrickson, 1991, *Science* 4:91.

A fourth method of determining phase information is single wavelength anomalous dispersion or SAD. In this technique, X-ray diffraction data are collected at a single wavelength from a single native or heavy-atom derivative crystal, and phase information is extracted using anomalous scattering information from atoms such as sulfur or chlorine in the native crystal or from the heavy atoms in the heavy-atom derivative crystal. The wavelength of X-rays used to collect data for this phasing technique need not be close to the absorption edge of the anomalous scatterer. A detailed discussion of SAD analysis can be found in Brodersen et al., 2000, *Acta Cryst.* D56:431-441.

A fifth method of determining phase information is single isomorphous replacement with anomalous scattering or SIRAS. This technique combines isomorphous replacement and anomalous scattering techniques to provide phase information for a crystal of a polypeptide. X-ray diffraction data are collected at a single wavelength, usually from a single heavy-atom derivative crystal. Phase information obtained only from the location of the heavy atoms in a single heavy-atom derivative crystal leads to an ambiguity in the phase angle, which is resolved using anomalous scattering from the heavy atoms. Phase information is therefore extracted from both the location of the heavy atoms and from anomalous scattering of the heavy atoms. A detailed discussion of SIRAS analysis can be found in North, 1965, *Acta Cryst.* 18:212-216; Matthews, 1966, *Acta Cryst.* 20:82-86.

Provided herein are the high-resolution three-dimensional structures and atomic structure coordinates of a crystalline human IgG Fc variant, particularly Fc/YTE, determined by X-ray crystallography. The specific methods used to obtain the structure coordinates are provided in the examples, infra. The atomic structure coordinates of crystalline Fc/YTE, obtained from the $P2_12_12_1$ form of the crystal to 2.5 Å resolution, are listed in Table V.

After a model is generated, a structure is refined. Refinement is the process of minimizing the function $$R_{factor} = \frac{\Sigma_{hkl}||F_{obs}(hkl)|-|F_{calc}(hkl)||}{\Sigma_{hkl}|F_{obs}(hkl)|}$$

which is the difference between observed and calculated intensity values (measured by an R-factor), and which is a function of the position, temperature factor, and occupancy of each non-hydrogen atom in the model. This usually involves alternate cycles of real space refinement, i.e., calculation of electron density maps and model building, and reciprocal space refinement, i.e., computational attempts to improve the agreement between the original intensity data and intensity data generated from each successive model. Refinement ends when the function $\Phi$ converges on a minimum wherein the model fits the electron density map and is stereochemically and conformationally reasonable. During refinement, ordered solvent molecules are added to the structure.

5.5.1 Structures of Human IgG Fc Variant

Provided herein are the high-resolution three-dimensional structures and atomic structure coordinates of a crystalline human IgG Fc variant, particularly Fc/YTE, determined by X-ray crystallography. The specific methods used to obtain the structure coordinates are provided in the examples, infra.

The atomic structure coordinates of crystalline Fc/YTE, obtained from the P2₁2₁2₁ form of the crystal to 2.5 Å resolution, are listed in Table IV.

Those skilled in the art will recognize that atomic structure coordinates as determined by X-ray crystallography are not without error. Thus, it is to be understood that any set of structure coordinates obtained for crystals of human IgG Fc variant, whether native crystals, heavy-atom derivative crystals or poly-crystals, that have a root mean square deviation ("r.m.s.d.") of less than or equal to about 2 Å when superimposed, using backbone atoms (N, Cα, C and O), on the structure coordinates listed in Table V are considered to be identical with the structure coordinates listed in the Table when at least about 50% to 100% of the backbone atoms of the constituents of the human IgG Fc variant are included in the superposition.

The overall three-dimensional structure of Fc/YTE is very similar to previously reported structures of human Fc regions. See Deisenhofer et al. 1981, *Biochemistry* 20: 2361-2370; Sondermann et al. 2000, *Nature* 406, 267-273; Krapp et al. 2003, *J. Mol. Biol.* 325: 979-989, Matsumiya et al. 2007, *J. Mol. Biol.* 368, 767-779.

In particular, the structure of the unmutated human Fc described by Matsumiya et al. 2007, *J. Mol. Biol.* 368, 767-779, with PDB ID number 2DTQ, exhibited the most similarity in cell parameters, space group and packing when compared with Fc/YTE. All $C_H2$ and $C_H3$ domains showed considerable structural conservation and rigidity when considered together. Indeed, superimposition of $C_H2$ and $C_H3$ domains from 2DTQ showed RMS deviations ranging from 0.37 Å (chain B of Fc/YTE over chain B of 2DTQ; FIG. 5A) to 0.86 Å (chain A of Fc/YTE over chain B of 2DTQ). However, Fc/YTE mutations introduce several additional hydrogen bonds and change in surface of contact between Fc/YTE and FnRn.

An additional hydrogen bond was identified between Y252/O$_n$ in the mutated Fc and E133/Oε1 or E133/Oε2 in human FcRn α chain. No such hydrogen bond exists between M252 in the wild type IgG Fc amd E133 in human FcRn α chain.

Similarly to Fc/YTE, rat Fc harbors a threonine at position 254. The Oγ1 atom of this residue potentially forms a hydrogen bond with E133/Oε1 or E133/Oε2 in human FcRn α, chain, though a similar bond might already exist with S254 in an unmutated human Fc.

Additionally, an additional hydrogen bond was introduced between E256/Oε1 or E256/Oε2 in the mutated Fc and Q2/Oε1 or Q2/Nε2 in human β2 microglobulin, which is likely due to an increase in length of the side chain at amino acid position 256.

Further, the introduction of YTE in IgG Fc region casued an increase in the surface of contact between the mutated IgG Fc and human FcRn α chain, with an increased area of about 30 Å². In addition, an additional 20 Å² increase in the surface of contact was identified between the mutated Fc and human FcRn β2 microglobulin. All together, the mutations at M252Y, S254T, and T256E significantly increase the surface of contact between mutated IgG Fc and human FcRn for about 50 Å². Thus, Fc/YTE significantly increases the number of contact points at the Fc/FcRn interface when compared with an unmutated human Fc.

5.6 Structure Coordinates

The atomic structure coordinates can be used in molecular modeling and design, as described more fully below. Encompassed herein are the structure coordinates and other information, e.g., amino acid sequence, connectivity tables, vector-based representations, temperature factors, etc., used to generate the three-dimensional structure of the polypeptide for use in the software programs described below and other software programs.

The machine-readable media is embedded with information that corresponds to a three-dimensional structural representation of a crystal comprising a human IgG Fc variant in crystalline form or with portions thereof describedherein. In certain embodiments, the crytal is diffraction quality. In certain embodiments, the crystal is a native crystal. In certain embodiments, the crystal is a heavy-atom derivative crytal. In certain embodiments, the information comprises the atomic structure coordinates of a human IgG Fc variant, or a subset thereof. In certain embodiments, the information comprises the atomic structure coordinates of Table V or a subset thereof.

As used herein, "machine-readable medium" refers to any medium that can be read and accessed directly by a computer or scanner. Such media include, but are not limited to: magnetic storage media, such as floppy discs, hard disc storage medium and magnetic tape; optical storage media such as optical discs, CD-ROM, or DVD-ROM; electrical storage media such as Flash memory, RAM, or ROM; and hybrids of these categories such as magnetic/optical storage media. Such media further include paper on which is recorded a representation of the atomic structure coordinates, e.g., Cartesian coordinates, that can be read by a scanning device and converted into a three-dimensional structure with an OCR.

A variety of data storage structures are available to a skilled artisan for creating a computer readable medium having recorded thereon the atomic structure coordinates or portions thereof and/or X-ray diffraction data. The choice of the data storage structure will generally be based on the means chosen to access the stored information. In addition, a variety of data processor programs and formats can be used to store the sequence and X-ray data information on a computer readable medium. Such formats include, but are not limited to, Protein Data Bank ("PDB") format (Research Collaboratory for Structural Bioinformatics; Cambridge Crystallographic Data Centre format; Structure-data ("SD") file format (MDL Information Systems, Inc.; Dalby et al., 1992, J. Chem. Inf. Comp. Sci. 32:244-255), and line-notation, e.g., as used in SMILES (Weininger, 1988, J. Chem. Inf. Comp. Sci. 28:31-36). Methods of converting between various formats read by different computer software will be readily apparent to those of skill in the art, e.g., BABEL (v. 1.06, Walters & Stahl, ©1992, 1993, 1994). All format representations of the polypeptide coordinates described herein, or portions thereof, are contemplated by the present invention. By providing computer readable medium having stored thereon the atomic coordinates, one of skill in the art can routinely access the atomic coordinates, or portions thereof, and related information for use in modeling and design programs, described in detail below.

While Cartesian coordinates are important and convenient representations of the three-dimensional structure of a polypeptide, those of skill in the art will readily recognize that other representations of the structure are also useful. Therefore, the three-dimensional structure of a polypeptide, as discussed herein, includes not only the Cartesian coordinate representation, but also all alternative representations of the three-dimensional distribution of atoms. For example, atomic coordinates may be represented as a Z-matrix, wherein a first atom of the protein is chosen, a second atom is placed at a defined distance from the first atom, a third atom is placed at a defined distance from the second atom so that it makes a defined angle with the first atom. Each subsequent atom is placed at a defined distance from a previously placed atom with a specified angle with respect to the third atom, and at a specified torsion angle with respect to a fourth atom. Atomic coordinates may also be represented as a Patterson function, wherein all interatomic vectors are drawn and are then placed with their tails at the origin. This representation is particularly useful for locating heavy atoms in a unit cell. In addition, atomic coordinates may be represented as a series of vectors having magnitude and direction and drawn from a chosen origin to each atom in the polypeptide structure. Furthermore, the positions of atoms in a three-dimensional structure may be represented as fractions of the unit cell (fractional coordinates), or in spherical polar coordinates.

Additional information, such as thermal parameters, which measure the motion of each atom in the structure, chain identifiers, which identify the particular chain of a multi-chain protein in which an atom is located, and connectivity information, which indicates to which atoms a particular atom is bonded, is also useful for representing a three-dimensional molecular structure.

5.7 Uses of the Atomic Structure Coordinates

Structure information, typically in the form of the atomic structure coordinates, can be used in a variety of computational or computer-based methods to, for example, design, screen for and/or identify compounds that bind the crystallized polypeptide or a portion or fragment thereof, to intelligently design mutants that have altered biological properties, to intelligently design and/or modify antibodies that have desirable binding characteristics, and the like. The three-dimensional structural representation of the human IgG Fc variant can be visually inspected or compared with a three-dimensional structural representation of a wild type human IgG Fc region.

In one embodiment, the crystals and structure coordinates obtained therefrom are useful for identifying and/or designing compounds that bind human IgG Fc region as an approach towards developing new therapeutic agents. For example, a high resolution X-ray structure will often show the locations of ordered solvent molecules around the protein, and in particular at or near putative binding sites on the protein. This information can then be used to design molecules that bind these sites, the compounds synthesized and tested for binding in biological assays. See Travis, 1993, *Science* 262:1374.

In another embodiment, the structure is probed with a plurality of molecules to determine their ability to bind to human IgG Fc region at various sites. Such compounds can be used as targets or leads in medicinal chemistry efforts to identify, for example, inhibitors of potential therapeutic importance.

In yet another embodiment, the structure can be used to computationally screen small molecule data bases for chemical entities or compounds that can bind in whole, or in part, to human IgG Fc region, particularly, bind in the cleft formed between the Fc $C_H2$ and $C_H3$ domain of Fc region. In this screening, the quality of fit of such entities or compounds to the binding site may be judged either by shape complementarity or by estimated interaction energy. See Meng et al., 1992, *J. Comp. Chem.* 13:505-524.

The design of compounds that bind to or inhibit human IgG Fc region, according to this invention generally involves consideration of two factors. First, the compound should be capable of physically and structurally associating with human IgG Fc region. This association can be covalent or non-covalent. For example, covalent interactions may be important for designing irreversible inhibitors of a protein. Non-covalent molecular interactions important in the association of human IgG Fc region with its ligand include hydrogen bonding, ionic interactions and van der Waals and hydrophobic interactions. Second, the compound should be able to assume a conformation that allows it to associate with human IgG Fc region. Although certain portions of the compound will not directly participate in this association with IgG Fc region, those portions may still influence the overall conformation of the molecule. This, in turn, may impact potency. Such conformational requirements include the overall three-dimensional structure and orientation of the chemical group or compound in relation to all or a portion of the binding site, or the spacing between functional groups of a compound comprising several chemical groups that directly interact with human IgG Fc region.

The potential inhibitory or binding effect of a chemical compound on human IgG Fc region may be analyzed prior to its actual synthesis and testing by the use of computer modeling techniques. If the theoretical structure of the given compound suggests insufficient interaction and association between it and human IgG Fc region, synthesis and testing of the compound is unnecessary. However, if computer modeling indicates a strong interaction, the molecule may then be synthesized and tested for its ability to bind to human IgG Fc region and inhibit its binding activity. In this manner, synthesis of ineffective compounds may be avoided.

An inhibitory or other binding compound of human IgG Fc region may be computationally evaluated and designed by means of a series of steps in which chemical groups or fragments are screened and selected for their ability to associate with the cleft formed between the Fc $C_H2$ and $C_H3$ domain of Fc region or other areas of human IgG Fc region. One skilled in the art may use one of several methods to screen chemical groups or fragments for their ability to associate with human IgG Fc region. This process may begin by visual inspection of, for example, the binding site on the computer screen based on the cleft formed between the Fc $C_H2$ and $C_H3$ domain of Fc variant coordinates. Selected fragments or chemical groups may then be positioned in a variety of orientations, or docked, within the cleft formed between the Fc $C_H2$ and $C_H3$ domain of Fc region. Docking may be accomplished using software such as QUANTA and SYBYL, followed by energy minimization and molecular dynamics with standard molecular mechanics force fields, such as CHARMM and AMBER.

These principles may also be used to design and evaluate compounds that can mimic human IgG Fc variant with one or more amino acid residue mutations and have an increased binding affinity for an FcRn compared to a wild type human IgG Fc region not comprising the amino acid residue mutations, or to design and evaluate a modification of a human IgG Fc region that would result in an increased binding affinity for a FcRn or an increased serum half-life compared to the comparable human IgG Fc region not comprising the modification. These principles may also be used to design and evaluate a modification of a human IgG Fc region that would result in decreased binding affinity for a FcRn or a reduced serum half-life compared to the comparable human IgG Fc region not comprising the modification. Such modifications include and are not limited to amino acid substitution with a natural or a non-natural amino acid residue, or a carbohydrate chemical modification.

In certain embodiments, the modifications would result in additional hydrogen bonds between Y252/$O_\eta$ in the mutated Fc and E133/O$\epsilon$1 or E133/O$\epsilon$2 in human FcRn $\alpha$ chain.

In certain embodiments, the modifications would result in additional hydrogen bonds between T254/O$\gamma$1 in the mutated Fc and E133/O$\epsilon$1 or E133/O$\epsilon$2 in human FcRn $\alpha$ chain.

In certain embodiments, the modifications would result in additional hydrogen bonds between E256/O$\epsilon$1 or E256/O$\epsilon$2 in the mutated Fc and Q2/O$\epsilon$1 or Q2/N$\epsilon$2 in human $\beta$2 microglobulin.

In certain embodiments, the modifications would result in an about 30 Å² increase in the surface of contact between the human IgG Fc variant and human FcRn α chain.

In certain embodiments, the modifications would result in an about 20 Å$^2$ increase in the surface of contact between the human IgG Fc variant and human FcRn β chain.

Specialized computer programs may also assist in the process of selecting fragments or chemical groups. These include:

1. GRID (Goodford, 1985, *J. Med. Chem,* 28:849-857). GRID is available from Oxford University, Oxford, UK;

2. MCSS (Miranker & Karplus, 1991, *Proteins: Structure, Function and Genetics* 11:29-34). MCSS is available from Molecular Simulations, Burlington, Mass.;

3. AUTODOCK (Goodsell & Olsen, 1990, *Proteins: Structure, Function, and Genetics* 8:195-202). AUTODOCK is available from Scripps Research Institute, La Jolla, Calif.; and 4. DOCK (Kuntz et al., 1982, *J. Mol. Biol.* 161:269-288). DOCK is available from University of California, San Francisco, Calif.

Once suitable chemical groups or fragments have been selected, they can be assembled into a single compound or inhibitor. Assembly may proceed by visual inspection of the relationship of the fragments to each other in the three-dimensional image displayed on a computer screen in relation to the structure coordinates of human IgG Fc variant. This would be followed by manual model building using software such as QUANTA or SYBYL. Useful programs to aid one of skill in the art in connecting the individual chemical groups or fragments include:

1. CAVEAT (Bartlett et al., 1989, "CAVEAT: A Program to Facilitate the Structure-Derived Design of Biologically Active Molecules," In Molecular Recognition in Chemical and Biological Problems', Special Pub., Royal Chem. Soc. 78:182-196). CAVEAT is available from the University of California, Berkeley, Calif.;

2. 3D Database systems such as MACCS-3D (MDL Information Systems, San Leandro, Calif.). This area is reviewed in Martin, 1992, J. Med. Chem. 35:2145-2154); and 3. HOOK (available from Molecular Simulations, Burlington, Mass.). Instead of proceeding to build a human IgG Fc binding compound in a step-wise fashion one fragment or chemical group at a time, as described above, Fc region binding compounds may be designed as a whole or "de novo" using either an empty Fc region binding site or optionally including some portion(s) of a known inhibitor(s). These methods include:

1. LUDI (Bohm, 1992, *J. Comp. Aid. Molec. Design* 6:61-78). LUDI is available from Molecular Simulations, Inc., San Diego, Calif.;

2. LEGEND (Nishibata & Itai, 1991, *Tetrahedron* 47:8985). LEGEND is available from Molecular Simulations, Burlington, Mass.; and 3. LeapFrog (available from Tripos, Inc., St. Louis, Mo.).

Other molecular modeling techniques may also be employed in accordance with this invention. See, e.g., Cohen et al., 1990, *J. Med. Chem.* 33:883-894. See also Navia & Murcko, 1992, Cur. Op. Struct. Biol. 2:202-210.

Once a compound or a modification has been designed or selected by the above methods, the efficiency with which that compound may bind to Fc region or a ligand of a Fc region may be tested and optimized by computational evaluation. For example, a compound that has been designed or selected to function as a Fc region binding compound should also preferably occupy a volume not overlapping the volume occupied by the binding site residues when the native receptor is bound. An effective Fc region compound preferably demonstrates a relatively small difference in energy between its bound and free states (i.e., it should have a small deformation energy of binding). Thus, the most efficient Fc region binding compounds should preferably be designed with a deformation energy of binding of not greater than about 10 kcal/mol, preferably, not greater than 7 kcal/mol. Fc region binding compounds may interact with the protein in more than one conformation that is similar in overall binding energy. In those cases, the deformation energy of binding is taken to be the difference between the energy of the free compound and the average energy of the conformations observed when the inhibitor binds to the enzyme.

A compound selected or designed for binding to human IgG Fc region may be further computationally optimized so that in its bound state it would preferably lack repulsive electrostatic interaction with the target protein. Such non-complementary electrostatic interactions include repulsive charge-charge, dipole-dipole and charge-dipole interactions. Specifically, the sum of all electrostatic interactions between the inhibitor and the protein when the inhibitor is bound to it preferably make a neutral or favorable contribution to the enthalpy of binding.

Specific computer software is available in the art to evaluate compound defoiination energy and electrostatic interaction. Examples of programs designed for such uses include: Gaussian 92, revision C (Frisch, Gaussian, Inc., Pittsburgh, Pa. ©1992); AMBER, version 4.0 (Kollman, University of California at San Francisco, ©1994); QUANTA/CHARMM (Molecular Simulations, Inc., Burlington, Mass., ©1994); and Insight II/Discover (Biosym Technologies Inc., San Diego, Calif., ©1994). These programs may be implemented, for instance, using a computer workstation, as are well-known in the art. Other hardware systems and software packages will be known to those skilled in the art. Once a compound has been optimally selected or designed, as described above, substitutions may then be made in some of its atoms or chemical groups in order to improve or modify its binding properties. Generally, initial substitutions are conservative, i.e the replacement group will have approximately the same size, shape, hydrophobicity and charge as the original group. One of skill in the art will understand that substitutions known in the art to alter conformation should be avoided. Such altered chemical compounds may then be analyzed for efficiency of binding to Fc region by the same computer methods described in detail above.

Specific computer software is available in the art to evaluate compound deformation energy and electrostatic interaction. Examples of programs designed for such uses include: Gaussian 92, revision C (Frisch, Gaussian, Inc., Pittsburgh, Pa. ©1992); AMBER, version 4.0 (Kollman, University of California at San Francisco, ©1994); QUANTA/CHARMM (Molecular Simulations, Inc., Burlington, Mass., ©1994); and Insight II/Discover (Biosym Technologies Inc., San Diego, Calif., ©1994). These programs may be implemented, for instance, using a computer workstation, as are well-known in the art. Other hardware systems and software packages will be known to those skilled in the art. Once a Fc region-binding compound has been optimally selected or designed, as described above, substitutions may then be made in some of its atoms or chemical groups in order to improve or modify its binding properties. Generally, initial substitutions are conservative, i.e., the replacement group will have approximately the same size, shape, hydrophobicity and charge as the original group. One of skill in the art will understand that substitutions known in the art to alter conformation should be avoided. Such altered chemical compounds may then be analyzed for efficiency of binding to human IgG Fc region by the same computer methods described in detail above.

The structure coordinates of human IgG Fc variant, or portions thereof, are particularly useful to solve the structure of those other crystal forms of human IgG Fc region or fragments. They may also be used to solve the structure of human IgG Fc variant mutants, IgG Fc-complexes, fragments thereof, or of the crystalline form of any other protein that shares significant amino acid sequence homology with a structural domain of IgG Fc region.

One method that may be employed for this purpose is molecular replacement. In this method, the unknown crystal structure, whether it is another crystal form of human IgG Fc variant, or its mutant or complex, or the crystal of some other protein with significant amino acid sequence homology to any functional domain of human IgG Fc region, may be determined using phase information from the human IgG Fc variant structure coordinates. The phase information may also be used to determine the crystal structure of human IgG Fc variant mutants or complexes thereof, and other proteins with significant homology to human IgG Fc variant or a fragment thereof. This method will provide an accurate three-dimensional structure for the unknown protein in the new crystal more quickly and efficiently than attempting to determine such information ab initio. In addition, in accordance with this invention, human IgG Fc variant may be crystallized in complex with known Fc binding compound, such as FcRn. The crystal structures of a series of such complexes may then be solved by molecular replacement and compared with that of human IgG Fc variant. Potential sites for modification within the various binding sites of the protein may thus be identified. This information provides an additional tool for determining the most efficient binding interactions, for example, increased hydrophobic interactions, between human IgG Fc region and a chemical group or compound.

If an unknown crystal form has the same space group as and similar cell dimensions to the known human IgG Fc variant crystal form, then the phases derived from the known crystal form can be directly applied to the unknown crystal form, and in turn, an electron density map for the unknown crystal form can be calculated. Difference electron density maps can then be used to examine the differences between the unknown crystal form and the known crystal form. A difference electron density map is a subtraction of one electron density map, e.g., that derived from the known crystal form, from another electron density map, e.g., that derived from the unknown crystal form. Therefore, all similar features of the two electron density maps are eliminated in the subtraction and only the differences between the two structures remain. For example, if the unknown crystal form is of a human IgG Fc variant complex, then a difference electron density map between this map and the map derived from the native, uncomplexed crystal will ideally show only the electron density of the ligand. Similarly, if amino acid side chains have different conformations in the two crystal forms, then those differences will be highlighted by peaks (positive electron density) and valleys (negative electron density) in the difference electron density map, making the differences between the two crystal forms easy to detect. However, if the space groups and/or cell dimensions of the two crystal forms are different, then this approach will not work and molecular replacement must be used in order to derive phases for the unknown crystal All of the complexes referred to above may be studied using well-known X-ray diffraction techniques and may be refined versus 5 Å to 1.5 Å, or greater resolution X-ray data to an R value of about 0.20 or less using computer software, such as X-PLOR (Yale University, (c) 1992, distributed by Molecular Simulations, Inc.). See, e.g., Blundel et al., 1976, *Protein Crystallography*, Academic Press.; Methods in Enzymology, vol. 114 & 115, Wyckoff et al., eds., Academic Press, 1985. This information may thus be used to optimize known classes of human IgG Fc binding compounds, and more importantly, to design and synthesize novel classes of IgG Fc binding compounds.

The structure coordinates of human IgG Fc variant will also facilitate the identification of related proteins or enzymes analogous to human IgG Fc in function, structure or both, thereby further leading to novel therapeutic modes for treating or preventing human IgG Fc mediated diseases.

Subsets of the atomic structure coordinates can be used in any of the above methods. Particularly useful subsets of the coordinates include, but are not limited to, coordinates of single domains, coordinates of residues lining an antigen binding site, coordinates of residues of a CDR, coordinates of residues that participate in important protein-protein contacts at an interface, and Cα coordinates. For example, the coordinates of a fragment of an antibody that contains the antigen binding site may be used to design inhibitors that bind to that site, even though the antibody is fully described by a larger set of atomic coordinates. Therefore, a set of atomic coordinates that define the entire polypeptide chain, although useful for many applications, do not necessarily need to be used for the methods described herein.

Exemplary molecular screening or designing methods by using the three-dimensional structural representation of a human IgG Fc variant comprising one or more amino acid residue mutants and has an increased binding affinity for a FcRn compared to a wild type human IgG Fc region not comprising the amino acid residue mutants or portion thereof, particularly that of the human IgG Fc variant comprise may comprise at least one amino acid residue mutant selected from the group consisting of 252Y, 254T, and 256E, as numbered by the EU index as set forth in Kabat, and preferably that of the human IgG Fc variant comprises the amino acid sequence of SEQ ID NO:7, are descrbied below.

In one aspect, provided herein are methods of identifying or designing compounds that binds a human IgG or a human IgG Fc region, comprising using a three-dimensional structural representation of a human IgG Fc variant.

In certain embodiments, provided herein is a method of identifying a compound that binds a human IgG or a human IgG Fc region, comprising using a three-dimensional structural representation of a human IgG Fc variant comprising one or more amino acid residue mutants and has an increased binding affinity for a FcRn compared to a wild type human IgG Fc region not comprising the amino acid residue mutants, or portion thereof, to computationally screen a candidate compound for an ability to bind the human IgG or the human IgG Fc region. The computational screen may comprise the steps of synthesizing the candidate compound; and screening the candidate compound for an ability to bind a human IgG or a human IgG Fc. In such methods, the three-dimensional structural representation of the human IgG Fc variant may be visually inspected to identify a candidate compound. The method may further comprise comparing a three-dimensional structural representation of a wild type human IgG Fc region with that of the human IgG Fc variant.

In certain embodiments, provided herein is a method of designing a compound that binds a human IgG or a human IgG Fc region, comprising using a three-dimensional structural representation of a human IgG Fc variant comprising one or more amino acid residue mutants and has an increased binding affinity for a FcRn compared to a wild type human IgG Fc region not comprising the amino acid residue mutants, or portion thereof, to computationally design a synthesizable candidate compound for an ability to bind the human IgG or the human IgG Fc region. The computational design may comprise the steps of synthesizing the candidate compound; and screening the candidate compound for an ability to bind a human IgG or a human IgG Fc. In such methods, the three-dimensional structural representation of the human IgG Fc variant may be visually inspected to identify a candidate compound. The method may further comprise comparing a three-dimensional structural representation of a wild type human IgG Fc region with that of the human IgG Fc variant.

In another aspects, provided herein are methods of identifying or designing a modification of a human IgG Fc region that would result in an altered binding affinity for a FcRn or an altered serum half-life compared to the comparable human IgG Fc region not comprising the modification, by using a three-dimensional structural representation of a human IgG Fc variant. In some embodiments, the the human IgG Fc variant comprises at least one amino acid residue mutation selected from the group consisting of 252Y, 254T and 256E, as numbered by the EU index as set forth in Kabat. In some embodiments, the human IgG Fc variant comprises each of the amino acid residue mutations 252Y, 254T and 256E, as numbered by the EU index as set forth in Kabat. In some embodiments, the human IgG Fc variant comprises the amino acid sequence of SEQ ID NO:7.

In another aspects, provided herein are methods of identifying or designing a modification of a human IgG Fc region that would result in additional hydrogen bonds, increase in surface of contact, or both, with FcRn compared to the comparable human IgG Fc region not comprising the modification, by using a three-dimensional structural representation of a human IgG Fc variant. In certain embodiments, the modification may result in an altered, e.g., increased, binding affinity for a FcRn or an altered, e.g., increased serum half-life compared to the comparable human IgG Fc region not comprising the modification. In some embodiments, the human IgG Fc variant comprises each of the amino acid residue mutations 252Y, 254T and 256E, as numbered by the EU index as set forth in Kabat. In some embodiments, the human IgG Fc variant comprises the amino acid sequence of SEQ ID NO:7.

In another aspects, provided herein are methods of identifying or designing a modification of a human IgG Fc region that would result in fewer hydrogen bonds, decrease in surface of contact, or both, with FcRn compared to the comparable human IgG Fc region not comprising the modification, by using a three-dimensional structural representation of a human IgG Fc variant. In certain embodiments, the modification may result in an altered, e.g., reduced, binding affinity for a FcRn or an altered, e.g., reduced serum half-life compared to the comparable human IgG Fc region not comprising the modification.

Such modification includes but is not limited to an amino acid insertion, an amino acid deletion, an amino acid substitution by a natural or an unnatural amino acid residue, and a carbohydrate chemical modification.

In certain embodiments, provided herein is a method of identifying a modification of a human IgG Fc region that would result in an altered binding affinity for a FcRn or an altered serum half-life compared to the comparable human IgG Fc region not comprising the modification, comprising using a three-dimensional structural representation of a human IgG Fc variant comprising one or more amino acid residue mutants, wherein said human IgG Fc variant has an increased binding affinity for a FcRn compared to a wild type human IgG Fc region not comprising the amino acid residue mutants, or portion thereof, to computationally screen a modification that result in an altered binding affinity for a FcRn or an altered serum half-life. In such methods, the three-dimensional structural representation of the human IgG Fc variant may be visually inspected to identify a candidate compound. The method may further comprise comparing a three-dimensional structural representation of a wild type human IgG Fc region with that of the human IgG Fc variant.

In certain embodiments, provided herein is a method of identifying a modification of a human IgG Fc region that would result in a reduced binding affinity for a FcRn or a reduced serum half-life compared to the comparable human IgG Fc region not comprising the modification, comprising using a three-dimensional structural representation of a human IgG Fc variant comprising one or more amino acid residue mutants, wherein said human IgG Fc variant has an increased binding affinity for a FcRn compared to a wild type human IgG Fc region not comprising the amino acid residue mutants or portion thereof, to computationally screen a modification that result in a reduced binding affinity for a FcRn or a reduced serum half-life. In some embodiments, the modification may result in fewer hydrogen bonds between the amino acid residue Y252 in the human IgG Fc variant and the relevant amino acids in the human FcRn $\alpha$ chain. In some embodiments, the modification may result in an fewer hydrogen bonds between the amino acid residue T254 in the human IgG Fc variant and the relevant amino acids in the human FcRn $\alpha$ chain. In some embodiments, the modification may result in fewer hydrogen bond between the the amino acid E256 in the human IgG Fc variant and the relevant amino acids in human FcRn $\beta$2 microglobulin. In some embodiments, the modification may result in reduction in the surface of contact between the human IgG Fc variant and human FcRn $\alpha$ chain. In some embodiments, the modification may result in a reduction in the surface of contact between the human IgG Fc variant and human FcRn $\beta$2 microglobulin.

In certain embodiments, provided herein is a method of identifying a modification of a human IgG Fc region that would result in an increased binding affinity for a FcRn or an increased serum half-life compared to the comparable human IgG Fc region not comprising the modification, comprising using a three-dimensional structural representation of a human IgG Fc variant comprising one or more amino acid residue mutants, wherein said human IgG Fc variant has an increased binding affinity for a FcRn compared to a wild type human IgG Fc region not comprising the amino acid residue mutants, or portion thereof, to computationally screen a modification that result in an increased binding affinity for a FcRn or an increased serum half-life. In some embodiments, the modification may result in additional hydrogen bond between the $O_n$ atom of Y252 in the human IgG Fc variant and O$\epsilon$1 or O$\epsilon$2 atom of E133 in the human FcRn $\alpha$ chain. In some embodiments, the modification may result in an additional hydrogen bond between the O$\gamma$1 atom of T254 in the human IgG Fc variant and O$\epsilon$1 or O$\epsilon$2 atom of E133 in the human FcRn $\alpha$ chain. In some embodiments, the modification may result in additional hydrogen bond between the O$\epsilon$1 or O$\epsilon$2 atom of E256 in the human IgG Fc variant and Q2/O$\epsilon$1 or Q2/N$\epsilon$2 in human FcRn $\beta$2 microglobulin. In some embodiments, the modification may result in an about 30 Å$^2$ increase in the surface of contact between the human IgG Fc variant and human FcRn $\alpha$ chain. In some embodiments, the modification may result in an about 20 Å$^2$ increase in the surface of contact between the human IgG Fc variant and human FcRn $\beta$2 microglobulin.

In certain embodiments, provided herein is a method of designing a modification of a human IgG Fc region that would result in an altered binding affinity for a FcRn or an altered serum half-life compared to the comparable human IgG Fc region not comprising the modification, comprising using a three-dimensional structural representation of a human IgG Fc variant comprising one or more amino acid residue mutants, wherein said human IgG Fc variant has an increased binding affinity for a FcRn compared to a wild type human IgG Fc region not comprising the amino acid residue mutants, or portion thereof, to computationally design a modification that result in an altered binding affinity for a FcRn or an altered serum half-life. In such methods, the three-dimensional structural representation of the human IgG Fc variant may be visually inspected to identify a candidate compound. The method may further comprise comparing a three-dimensional structural representation of a wild type human IgG Fc region with that of the human IgG Fc variant.

In certain embodiments, provided herein is a method of designing a modification of a human IgG Fc region that would result in a reduced binding affinity for a FcRn or a reduced serum half-life compared to the comparable human IgG Fc region not comprising the modification, comprising using a three-dimensional structural representation of a human IgG Fc variant comprising one or more amino acid residue mutants, wherein said human IgG Fc variant has an increased binding affinity for a FcRn compared to a wild type human IgG Fc region not comprising the amino acid residue mutants, or portion thereof, to computationally design a modification that result in a reduced binding affinity for a FcRn or a reduced serum half-life. In some embodiments, the modification may result in fewer hydrogen bonds between the amino acid residue Y252 in the human IgG Fc variant and the relevant amino acids in the human FcRn α chain. In some embodiments, the modification may result in an fewer hydrogen bonds between the amino acid residue T254 in the human IgG Fc variant and the relevant amino acids in the human FcRn α chain. In some embodiments, the modification may result in fewer hydrogen bond between the the amino acid E256 in the human IgG Fc variant and the relevant amino acids in human FcRn β2 microglobulin. In some embodiments, the modification may result in reduction in the surface of contact between the human IgG Fc variant and human FcRn α chain. In some embodiments, the modification may result in a reduction in the surface of contact between the human IgG Fc variant and human FcRn β2 microglobulin.

In certain embodiments, provided herein is a method of designing a modification of a human IgG Fc region that would result in an increased binding affinity for a FcRn or an increased serum half-life compared to the comparable human IgG Fc region not comprising the modification, comprising using a three-dimensional structural representation of a human IgG Fc variant comprising one or more amino acid residue mutants, wherein said human IgG Fc variant hasan increased binding affinity for a FcRn compared to a wild type human IgG Fc region not comprising the amino acid residue mutants, or portion thereof, to computationally design a modification that result in an increased binding affinity for a FcRn or an increased serum half-life. In some embodiments, the modification may result in additional hydrogen bond between the $O_n$ atom of Y252 in the human IgG Fc variant and Oε1 or Oε2 atom of E133 in the human FcRn α chain. In some embodiments, the modification may result in an additional hydrogen bond between the Oγ1 atom of T254 in the human IgG Fc variant and Oε1 or Oε2 atom of E133 in the human FcRn α chain. In some embodiments, the modification may result in additional hydrogen bond between the Oε1 or Oε2 atom of E256 in the human IgG Fc variant and Q2/Oε1 or Q2/Nε2 in human FcRn β2 microglobulin. In some embodiments, the modification may result in an about 30 Å$^2$ increase in the surface of contact between the human IgG Fc variant and human FcRn α chain. In some embodiments, the modification may result in an about 20 Å$^2$ increase in the surface of contact between the human IgG Fc variant and human FcRn β2 microglobulin.

The following examples are provided to illustrate aspects of the invention, and are not intended to limit the scope of the invention in any way.

6. EXAMPLES

The subsections below describe the production of a human IgG Fc variant Fc/YTE, and the preparation and characterization of diffraction quality Fc/YTE crystals.

6.1 Production and Purification of Fc/YTE

6.1.1 Generation, Expression and Purification of Unmuated Human Fc

An unmutated Fc fragment was obtained direcgtly from the enzymatic cleavage of a humanized anti-respiratory syncytial virus IgG1, κ (MED1524, Wu et al., 2007, *J. Mol. Biol.* 368, 652-665). Digestion was carried out using immobilized papain according to the manufacturer's instructions (Thermo Scientific, Rockford, Ill.). Purification was first performed on HiTrap protein A columns according to the manufacturer's instructions (GE Healthcare, Piscataway, N.J.). After overnight dialysis in 50 mM NaOAc, pH 5.2 at 4° C., the purified protein solution was further applied to a HiTrap SP HP column (GE Healthcare) and collected in the flow through.

This procedure yielded a homogenous Fc preparation, as judged by reducing and non-reducing SDS-polyacrylamide gel electrophoresis (PAGE). In particular, the SDS-PAGE profile of this unmutated human Fc only revealed the presence of one band around 25 or 50 kDa under reducing or non-reducing conditions, respectively.

6.1.2 Generation, Expression and Purification of Fc/YTE

The heavy chain of MEDI-524 (see section above) cloned into a previously described mammalian expression vector (Oganesyan et al., 2008, *Mol. Immunol.* 45, 1872-1882) was used as an initial template for polymerase chain reaction (PCR) amplification. More precisely, an expression cassette encoding the Fc portion (heavy chain residues 223-447) was PCR-generated directly from the MEDI-524 construct and cloned as an XbaI/EcoRI fragment into the same vector. The YTE combination of mutations (M252Y/S254T/T256E) was introduced into the heavy chain of MEDI-524. Generation of these mutations was carried out by site-directed mutagenesis using a Quick Change XL Mutagenesis Kit according to the manufacturer's instructions (Stratagene, La Jolla, Calif.), and the primers: 5'-GCATGTGACCTCAGGTTCCCGAGT-GATATAGAGGGTGTCCTTGGG-3' (SEQ ID NO: 9) and 5'-CCCAAGGACACCCTCTATATCACTCGG-GAACCTGAGGTCACATGC-3' (SEQ ID NO:10). This generated MEDI-524-YTE.

The construct were then transiently transfected into Human Embryonic Kidney (HEK) 293 cells using Lipofectamine (Invitrogen, Inc.) and standard protocols. Fc/YTE was typically harvested at 72, 144 and 216 hours post-transfection and purified from the conditioned media directly on HiTrap protein A columns according to the manufacturer's instructions (GE Healthcare). Purified Fc/YTE (typically >95% homogeneity, as judged by reducing and non-reducing SDS-PAGE) was then dialyzed against 50 mM NaOAc, pH 5.2 overnight at 4° C. Similar to the unmutated human Fc descrived in the previous section, the SDS-PAGE profile of Fc/YTE showed the presence of only one band around 25 or 50 kDa under reducing or non-reducing conditions, respectively. Thus, at least one interchain disulfide bond at positions C226 and/or C229 was formed in the middle hinge of Fc/YTE.

6.1.3 Crystallization of Fc/YTE

Purified Fc/YTE was concentrated to about 13 mg/ml using a Vivaspin concentrator (30 kDa cut-off; Sartorius AG, Edgewood, NY). The initial crystallization conditions were identified using the following commercial screens: Index and Crystal Screen I/II (Hampton Research, Aliso Viejo, Calif.), Wizard ½ (Emerald BioSystems, Inc., Bainbridge Island, Wash.), Proplex and PACT (Molecular Dimensions, Apopka, Fla.). Each of these screens pointed to various potential crystallization conditions. Further optimization in hanging drops where 1 ml of 0.1 M MES, pH 6.5, 15% polyethylene glycol (PEG) 6000, 5% 2-methyl-2,4-pentanediol (MPD) was mixed with 1 ml of a 1.8 mg/ml Fc/YTE solution led to the growth of diffraction-quality crystals. Their sizes ranged from 150 to 250 mm. Prior to data collection, the crystal was soaked in the mother liquor supplemented with 10, 15, 20 and 25% glycerol, consecutively.

6.2 Analysis and Characterization of Fc/YTE Crystals

This example describes the methods used to generate and collect diffraction data from Fc/YTE crystals and determine the structure of the Fc/YTE from such data.

6.2.1 Diffraction Data Collection

Diffraction data were collected at the Center for Advanced Research in Biotechnology (CARB, University of Maryland Biotechnology Institute, Rockville, Md.) using a Rigaku MicroMax™-007 rotating anode generator with an R-AXIS IV++ area detector (Rigaku/MSC, The Woodlands, Tex.). The crystal was cooled to 105 K with an X-stream™2000 Cryogenic cooler (Rigaku/MSC). The initial diffraction pattern extended up to 2.8 Å. For annealing purposes, the crystal was taken from the goniometer head and placed into a fresh drop of mother liquor containing 25% glycerol. This procedure slightly improved its diffraction properties. During data collection, 214 consecutive images with an oscillation range of 0.5° and an exposure time of 600 seconds were measured. Data collected from a single crystal yielded a nearly complete set at resolution of 2.5 Å. Data were processed with HKL 2000 (Otwinowski and Minor, 1997, *Mode. Methods in Enzymology* 276A, 307-326). Data reduction, molecular replacement, refinement, and electron density calculation were carried out using the CCP4 (Collaborative Computational Project) program suite.

6.2.2 Structure Determination

The crystal structure of a human IgG1 Fc fragment containing the M252Y/S254T/T256E triple substitution (Fc/YTE) was determined by molecular replacement and refined at a 2.5 Å resolution. More precisely, various human Fc regions deposited with the Protein Data Bank (PDB; Berman et al. 2000, *Nuci. Acids Res.* 28, 235-242) were evaluated as potential models for molecular replacement. The space group and cell parameters of the Fc/YTE crystal matches best those of PDB ID number 2DTQ (Matsumiya et al. 2007, *J. Mol. Biol.* 368, 767-779). 2DTQ was used as the replacement model in the present study because of its high resolution and unliganded state.

The $C_H2$ and $C_H3$ domains were used separately in order to minimize and potential bias in terms of the domain relative orientation. The three amino acid substitutions which comprised YTE were first modeled as alanine residues and then incorporated as such (M252Y, S254T, T256E) when allowed by the corresponding electron densities After several rounds of refinement using "Refmac 5" (Murshudov et al. 1997, *Acta Cryst.* D53, 240-255) and manual re-building using the "O" software (Jones et al. 1991, *Acta Cryst.* A47, 110-119), the model was analyzed using the TLS Motion Determination (TLSMD) program running on its web Server (Painter et al. 2006, *Acta Cryst.* D62, 439-450). Further refinement was then carried out with Refinac 5 in TLSMD mode using two distinct groups of residues (238-340 and 341-444). Both of these groups, as expected, corresponded to the $C_H2$ and $C_H3$ domains of Fc/YTE. The tight and medium non-crystallographic symmetry restraints were imposed throughout the refinement process for the main chain and side chain atoms of $C_H2$ and $C_H3$ domains, respectively. Amino acids corresponding to positions 223-235 and 445-447 were excluded from the final model due to the absence of corresponding electron density. Thus, although present in the crystal, the middle hinge of Fc/YTE could not be visualized. This is a likely consequence of this region's dynamic nature. Most atoms of the side chains at mutated positions 252, 254 and 256 in both polypeptides were well-defined. The N-linked glycan chains were modeled in accordance with their electron density.

Thus, in summary, the resulting model contained (i) two polypeptides (chains A and B) with the amino acids corresponding to positions 236 to 444, (ii) one branched carbohydrate chain attached to N297 in each polypeptide, (iii) nine sugar moieties per glycan chain (essentially as described in the context of other mutated human Fc structures, namely PDB ID number 2QL1 and 3C2S; Oganesyan et al., 2008, *Mol. Immunol.* 45, 1872-1882, and Oganesyan et al., 2008, *Acta Cryst.* D64, 700-704), and (iv) 68 water molecules. Data collection and refinement statistics for the data set and model are shown in Table II. The asymmetric unit contents of the Fc/YTE crystal is shown in FIG. 1.

6.2.3 Structural Analysis

The Fc/YTE fragment consisted of two chemically identical polypeptides forming a typical horseshoe shape (FIG. 1). Both chains could be divided into structurally similar $C_H2$ and $C_H3$ domains as seen in other human Fc structures. In particular, for each Fc/YTE chain A and B, these domains superimposed with an RMS displacement of 1.9 Å (FIG. 2). Dimerization of the Fc occurred almost exclusively through the $C_H3$ domain's curved four-stranded antiparallel β-sheets (FIG. 3), thus forming an 8-stranded β-barrel with a calculated free enthalpy gain of approximately −5 kcal/mol (AG; European Bioinformatics Institute (EBI) PISA server). The contact interface included thirty-four amino acids from each of these domains and formed a surface area of 1140 Å$^2$. More precisely, it contained two intermolecular hydrogen bonds and nine intermolecular salt bridges (as defined by bonds between atoms bearing opposite charges at a distance of at least 4 Å; see details in Table III). Eleven residues on each $C_H3$ domain contributed to intermolecular hydrophobic interaction (V348, L351, P352, P353, V363, L368, P395, P396, V397, L398 and F405). The N-linked glycan chains interacted through one intermolecular hydrogen bond at a distance of 2.8 Å between the O4 atoms of each Man4 residue. The YTE substitutions were clearly visible into the $C_H2$ domains (FIG. 4).

6.2.3.1 Comparison of Fc/YTE with Other Human Fc Fragments

The overall three-dimensional structure of Fc/YTE is very similar to previously reported structures of human Fc regions (Deisenhofer et al. 1981, *Biochemistry* 20, 2361-2370; Sondermann et al. 2000, *Nature* 406, 267-273; Krapp et al. 2003, *J. Mol. Biol.* 325, 979-989; Matsumiya et al. 2007, *J. Mol. Biol.* 368, 767-779; Oganesyan et al., 2008, *Acta Cryst.* D64, 700-704). In particular, the structure of the unmutated human Fc described by Matsumiya et al. 2007, *J. Mol. Biol.* 368, 767-779, with PDB ID number 2DTQ, exhibited the most similarity in cell parameters, space group and packing when compared with Fc/YTE. Superimposition of Fc/YTE polypeptides with those of 2DTQ through their Cα atoms confirmed this great similarity. When both $C_H2$ and $C_H3$ domains were considered together, the polypeptide chains superimposed with RMS displacements ranging from 0.37 Å (chain B of Fc/YTE over chain B of 2DTQ; FIG. 5A) to 0.86 Å (chain A of Fc/YTE over chain B of 2DTQ). For comparison purposes, the superimposition of non-crystallography related chains A and B of Fc/YTE resulted in an RMS displacement of 0.65 Å. A similar range was seen when the $C_H2$ and $C_H3$ domains were considered separately. In this situation, $C_H2$ RMS displacements ranging from 0.42 Å (CH2/B of Fc/YTE over $C_H2$/B of 2DTQ; FIG. 5B) to 0.70 Å ($C_H2$/A of Fc/YTE over $C_H2$/B of 2DTQ) were observed. The greatest difference between Cα atoms (1.1 Å) occurred for residues at position 254. Differences between Cα atoms were less than 0.10 Å between 2DTQ and Fc/YTE at the other major putative interaction sites with human FcRn such as at positions 309-311 and 433-436 (Dall' Acqua et al., 2002, *J. Immunol.* 169, 5171-5180). Thus, the effect of YTE in terms of increased IgG binding to FcRn is unlikely to be due to long-range conformational rearrangements at the complex interface.

6.2.3.2 Comparison of Fc/YTE with Rat Fc

Molecular modeling suggested that potential favorable hydrogen bonds between Fc/YTE and FcRn and increase in the surface of contact between the two partners may account in part for the corresponding increase of Fc/YTE binding affinity to human FcRn.

Molecular modeling was conducted on the three-dimensional structure of the complex between rat Fc and rat FcRn, which was previously solved by Martin et al., *Mol. Cell.* 7, 867-877. Fc/YTE and rat Fc (defined thereafter as the non-modified chain of PDB ID number 1I1A) exhibited significant similarities in their amino acid sequence (65% identity; FIG. 6) and structure (FIGS. 5A-B). As shown in FIG. 5A, the corresponding RMS displacements over $C_\alpha$ atoms for the Fc polypeptides ranged from 1.1 Å (chain B of Fc/YTE over rat Fc) to 1.44 Å (chain A of Fc/YTE over rat Fc). In the mutated region spanning residues 252-256, the $C_\alpha$ atoms of residues 252, 253 and 254 exhibited the largest differences (1.2, 1.7 and 1.3 Å, respectively, when comparing $C_H2$/A of Fc/YTE with $C_H2$ of rat Fc). Likewise, human and rat FcRn (PDB ID numbers 1EXU and 1I1A, respectively) also exhibited significant similarities in their amino acid sequence (over 67 and 74% identity for a and β2 microglobulin chains, respectively; see FIG. 6) and structure (RMS displacement of 1.5 Å when α and β2 microglobulin chains were considered together). The YTE mutations were introduced onto the rat Fc structure in silico and rat FcRn structure was also replaced with human FcRn. The extent of between Fc/YTE and FcRn was assessed by (i) the hydrogen bonds between select positions of the polypeptide chain of Fc/YTE and the polypeptide chain FcRn, and (ii) the change in the surface of contact between Fc/YTE and FcRn α chain, and between Fc/YTE and FcRn β2 microglobulin.

The the introduction of M252Y resulted in a plausible additional hydrogen bond between Y252/$O_\eta$ in the mutated Fc and E133/Oε1 or E133/Oε2 in human FcRn (α chain).

Similarly to Fc/YTE, rat Fc harbors a threonine at position 254. The Oγ1 atom of this residue potentially forms a hydrogen bond with E133/Oε1 or E133/Oε2 in human FcRn (α chain), though a similar bond might already exist with S254 in an unmutated human Fc.

Additionally, the introduction of T256E resulted in a possible additional hydrogen bond between E256/Oε1 or E256/Oε2 in the mutated Fc and Q2/Oε1 or Q2/Nε2 in human β2 microglobulin due to an increase in length of the side chain at this position. In macromolecular terms, the introduction of YTE also seemed to result in an about 30 Å$^2$ increase in the surface of contact between the mutated Fc and human FcRn α chain. In addition, about 20 Å$^2$ increase in the surface of contact was identified between the mutated Fc and human FcRn β2 microglobulin. All together, the mutations at M252Y, S254T, and T256E could significantly increase the number of contact points at the Fc/FcRn interface when compared with an unmutated human Fc.

The above analyses should only be considered as tentative due to the complexity of making predictions using models. These predictions may be improved once the Fc/YTE-human FcRn complex is crystallized and its three-dimensional structure solved.

Table V, following below, provides the atomic structure coordinates of Fc/YTE. In the Table, coordinates for Fc/YTE are provided.

The following abbreviations are used in Table V:

"Atom Type" refers to the element whose coordinates are provided. The first letter in the column defines the element.

"A.A." refers to amino acid.

"X, Y and Z" provide the Cartesian coordinates of the element.

"B" is a thermal factor that measures movement of the atom around its atomic center.

"OCC" refers to occupancy, and represents the percentage of time the atom type occupies the particular coordinate. OCC values range from 0 to 1, with 1 being 100%.

6.2.4 Interaction with Human FcRn

Generation of Human FcRn

Human FcRn used in BIAcore measurements was cloned, expressed, and purified as described in Dall' Acqua et al., 2002, J. Immunol., 169, 5171-5180.

BIAcore Measurements

The interaction of soluble human FcRn with immobilized unmutated human Fc and Fc/YTE was monitored by surface plasmon resonance detection using a BIAcore 3000 instrument (GE Healthcare, Piscataway, N.J.). Unmutated human Fc and Fc/YTE were first coupled to the dextran matrix of a CM5 sensor chip (GE Healthcare) using an Amine Coupling Kit at a surface density of between 4139 and 4291 RU according to the manufacturer's instructions. Human FcRn was used in equilibrium binding experiments at concentrations ranging from 1.46 nM to 3 uM at a flow rate of 5 uL/min. Dilutions and binding experiments were carried out at 25° C. in phosphate buffered saline (PBS), pH 6.0 containing 0.05% Tween 20. Steady-state binding data were collected for 50 min. Both Fc surfaces were regenerated with six 1-min injection of PBS, pH 7.4 containing 0.05% Tween 20. Human FcRn was also allowed to flow over an uncoated cell. The sensorgrams from these blank runs were then subtracted from those obtained with Fc-coupled chips. Dissociation constants ($K_d$s) were determined by fitting the corresponding binding isotherms.

Interaction with Human FcRn

As shown in Table IV, the dissociation constant for mutant Fc/YTE is 72±5, and the dissociation constant for unmutated human Fc is 550±147. Therefore, the Fc/YTE has nearly eight-fold high binding affinity to FcRn than the unmutated human Fc The three-dimensional structure of the Fc/YTE-human FcRn complex would likely provide a robust molecular explanation for the increased binding affinity between YTE-modified human Fc and human FcRn. By using the publicly available structure of a rat Fc-rat FcRn complex and assuming a similar interaction interface for human Fc/YTE and human FcRn, some important clues may be obtained. As described in the previous section, a model of the complex between human Fc/YTE and human FcRn was constructed. The three mutations M252Y/S254T/T256E are likely to establish three additional hydrogen bonds with the side chain of human FcRn. In addition, the introduction of M252Y/S254T/T256E also seemed to result in about 30 Å$^2$ increase in the surface of contact between the mutated Fc and human FcRn α chain and about 20 Å$^2$ increase in the surface of contact between the mutated Fc and human FcRn β2 microglobulin. The end result is an increased binding affinity between human IgG variant Fc/YTE and human FcRn.

The present invention is not to be limited in scope by the exemplified embodiments, which are intended as illustrations of single aspects of the invention. Indeed, various modifications of the invention in addition to those described herein will become apparent to those having skill in the art from the foregoing description and accompanying drawings. Such modifications are intended to fall with in the scope of the appended claims. All documents referenced in this application, whether patents, published or unpublished patent applications, either U.S. or foreign, literature references, nucleotide or amino acid sequences identified by Accession No. or otherwise, are hereby incorporated by reference in their entireties for any and all purposes.

TABLE II

X-Ray data collection and model refinement statistics.

| | |
|---|---|
| Wavelength, Å | 1.54 |
| Resolution, Å | 19.90-2.50 (2.58-2.50)$^a$ |
| Space group | P2$_1$2$_1$2$_1$ |
| Cell parameters, Å | 49.66, 79.54, 145.53 |
| Total reflections | 44,985 |
| Rejections | 564 |
| Unique reflections | 19,236 |
| Average redundancy | 3.87 (3.73)$^a$ |
| Completeness, % | 92.4 (93.2)$^a$ |
| R$_{merge}$ | 0.103 (0.435)$^a$ |
| I/σ(I) | 7.4 (2.7)$^a$ |
| R factor/Free R factor | 0.227/0.290 |
| RMSD bonds, Å | 0.012 |
| RMSD angles, ° | 1.41 |
| Residues in most favored region of {ϕ, ψ} space$^b$, % | 88.5 |

TABLE II-continued

X-Ray data collection and model refinement statistics.

| | |
|---|---|
| Residues in additionally allowed region of {ϕ, ψ} space, % | 10.5 |
| Number of protein atoms | 3616 |
| Number of non-protein atoms | 133 |
| B factor (Model/Wilson), Å$^2$ | 53/66 |

$^a$ Values in parentheses correspond to the highest resolution shell.
$^b$ Ramachandran plot was produced using PROCHECK (Laskowski et al., 1993).

TABLE III

Summary of hydrogen bonds and salt bridges formed between the C$_H$3 domains of Fc/YTE.

| C$_H$3, Chain B | Distance (Å) | C$_H$3, Chain A |
|---|---|---|
| | Hydrogen bonds | |
| Thr 366 [Oγ1]$^a$ | 2.75 | Tyr 407 [Oη] |
| Tyr 407 [Oη] | 2.56 | Thr 366 [Oγ1] |
| | Salt bridges | |
| Asp 356 [Oδ1] | 2.96 | Lys 439 [Nζ] |
| Glu 357 [Oε2] | 3.67 | Lys 370 [Nζ] |
| Ser 364 [Oγ] | 3.86 | Lys 370 [Nζ] |
| Lys 370 [Nζ] | 3.64 | Glu 357 [Oε2] |
| Asn 390 [Nδ2] | 3.57 | Ser 400 [Oγ] |
| Asp 399 [Oδ1] | 3.78 | Lys 409 [Nζ] |
| Asp 399 [Oδ2] | 2.63 | Lys 409 [Nζ] |
| Lys 409 [Nζ] | 3.81 | Asp 399 [Oδ1] |
| Ser 444 [Oγ] | 2.77 | Arg 355 [Nη] |

$^a$ Letters in bracket refer to the corresponding interacting atoms.

TABLE IV

Dissociation constants for the binding of unmutated human Fc and Fc/YTE to human FcRn$^a$.

| Molecule | K$_d$-Human FcRn (nM) |
|---|---|
| Unmutated human Fc | 550 ± 147 |
| Fc/YTE | 72 ± 5 |

$^a$ Affinity measurements were carried out by BIAcore as described in Materials and Methods. Errors were estimated as the standard deviations of 2 independent experiments for each interacting pair.

TABLE V

Atomic Structure Coordinates of Fc/YTE (SEQ ID NO: 11)

| | | Atom A.A. Type | | | X | Y | Z | Occ | B | |
|---|---|---|---|---|---|---|---|---|---|---|
| ATOM | 1 | N | GLY | A | 236 | 15.912 | −4.606 | 0.974 | 1 | 81.39 N |
| ATOM | 2 | CA | GLY | A | 236 | 17.26 | −4.684 | 1.622 | 1 | 81.31 C |
| ATOM | 3 | C | GLY | A | 236 | 17.773 | −6.115 | 1.715 | 1 | 81.33 C |
| ATOM | 4 | O | GLY | A | 236 | 18.987 | −6.371 | 1.629 | 1 | 81.47 O |
| ATOM | 5 | N | GLY | A | 237 | 16.84 | −7.044 | 1.914 | 1 | 80.63 N |
| ATOM | 6 | CA | GLY | A | 237 | 17.122 | −8.458 | 1.788 | 1 | 79.65 C |
| ATOM | 7 | C | GLY | A | 237 | 16.915 | −8.857 | 0.342 | 1 | 79.01 C |
| ATOM | 8 | O | GLY | A | 237 | 17.703 | −8.474 | −0.537 | 1 | 79 O |
| ATOM | 9 | N | PRO | A | 238 | 15.84 | −9.608 | 0.069 | 1 | 77.79 N |
| ATOM | 10 | CA | PRO | A | 238 | 15.706 | −10.202 | −1.257 | 1 | 76.74 C |
| ATOM | 11 | CB | PRO | A | 238 | 14.634 | −11.27 | −1.051 | 1 | 76.91 C |
| ATOM | 12 | CG | PRO | A | 238 | 13.795 | −10.742 | 0.051 | 1 | 77.45 C |
| ATOM | 13 | CD | PRO | A | 238 | 14.709 | −9.949 | 0.946 | 1 | 77.86 C |
| ATOM | 14 | C | PRO | A | 238 | 15.297 | −9.202 | −2.338 | 1 | 75.63 C |
| ATOM | 15 | O | PRO | A | 238 | 14.579 | −8.231 | −2.061 | 1 | 75.68 O |
| ATOM | 16 | N | SER | A | 239 | 15.771 | −9.45 | −3.554 | 1 | 73.97 N |
| ATOM | 17 | CA | SER | A | 239 | 15.447 | −8.613 | −4.708 | 1 | 72.7 C |
| ATOM | 18 | CB | SER | A | 239 | 16.665 | −7.792 | −5.115 | 1 | 72.74 C |

TABLE V-continued

Atomic Structure Coordinates of Fc/YTE (SEQ ID NO: 11)

| | | Atom | A.A. | Type | | X | Y | Z | Occ | B | |
|---|---|---|---|---|---|---|---|---|---|---|---|
| ATOM | 19 | OG | SER | A | 239 | 17.027 | −6.933 | −4.051 | 1 | 72.49 | O |
| ATOM | 20 | C | SER | A | 239 | 14.939 | −9.456 | −5.881 | 1 | 71.37 | C |
| ATOM | 21 | O | SER | A | 239 | 15.284 | −10.631 | −6.01 | 1 | 71.37 | O |
| ATOM | 22 | N | VAL | A | 240 | 14.098 | −8.844 | −6.71 | 1 | 69.59 | N |
| ATOM | 23 | CA | VAL | A | 240 | 13.389 | −9.534 | −7.773 | 1 | 68.08 | C |
| ATOM | 24 | CB | VAL | A | 240 | 11.863 | −9.368 | −7.618 | 1 | 68.16 | C |
| ATOM | 25 | CG1 | VAL | A | 240 | 11.128 | −10.303 | −8.563 | 1 | 68.06 | C |
| ATOM | 26 | CG2 | VAL | A | 240 | 11.433 | −9.616 | −6.173 | 1 | 67.87 | C |
| ATOM | 27 | C | VAL | A | 240 | 13.8 | −8.956 | −9.119 | 1 | 66.66 | C |
| ATOM | 28 | O | VAL | A | 240 | 14.116 | −7.779 | −9.224 | 1 | 66.3 | O |
| ATOM | 29 | N | PHE | A | 241 | 13.809 | −9.809 | −10.138 | 1 | 65.2 | N |
| ATOM | 30 | CA | PHE | A | 241 | 14.028 | −9.403 | −11.524 | 1 | 63.79 | C |
| ATOM | 31 | CB | PHE | A | 241 | 15.459 | −9.692 | −11.949 | 1 | 63.93 | C |
| ATOM | 32 | CG | PHE | A | 241 | 16.468 | −8.85 | −11.24 | 1 | 64.1 | C |
| ATOM | 33 | CD1 | PHE | A | 241 | 17.226 | −9.37 | −10.201 | 1 | 64.69 | C |
| ATOM | 34 | CE1 | PHE | A | 241 | 18.156 | −8.592 | −9.542 | 1 | 64.29 | C |
| ATOM | 35 | CZ | PHE | A | 241 | 18.327 | −7.286 | −9.904 | 1 | 64.14 | C |
| ATOM | 36 | CE2 | PHE | A | 241 | 17.567 | −6.753 | −10.932 | 1 | 64.22 | C |
| ATOM | 37 | CD2 | PHE | A | 241 | 16.649 | −7.533 | −11.594 | 1 | 63.56 | C |
| ATOM | 38 | C | PHE | A | 241 | 13.062 | −10.17 | −12.409 | 1 | 62.52 | C |
| ATOM | 39 | O | PHE | A | 241 | 12.836 | −11.357 | −12.19 | 1 | 62.2 | O |
| ATOM | 40 | N | LEU | A | 242 | 12.495 | −9.48 | −13.399 | 1 | 60.97 | N |
| ATOM | 41 | CA | LEU | A | 242 | 11.442 | −10.034 | −14.25 | 1 | 59.8 | C |
| ATOM | 42 | CB | LEU | A | 242 | 10.127 | −9.264 | −14.033 | 1 | 59.76 | C |
| ATOM | 43 | CG | LEU | A | 242 | 8.818 | −9.805 | −14.658 | 1 | 59.96 | C |
| ATOM | 44 | CD1 | LEU | A | 242 | 8.637 | −11.309 | −14.462 | 1 | 58.63 | C |
| ATOM | 45 | CD2 | LEU | A | 242 | 7.609 | −9.058 | −14.109 | 1 | 58.98 | C |
| ATOM | 46 | C | LEU | A | 242 | 11.9 | −9.93 | −15.691 | 1 | 58.63 | C |
| ATOM | 47 | O | LEU | A | 242 | 12.061 | −8.837 | −16.221 | 1 | 58.75 | O |
| ATOM | 48 | N | PHE | A | 243 | 12.127 | −11.066 | −16.326 | 1 | 57.37 | N |
| ATOM | 49 | CA | PHE | A | 243 | 12.683 | −11.063 | −17.67 | 1 | 56.41 | C |
| ATOM | 50 | CB | PHE | A | 243 | 13.82 | −12.062 | −17.766 | 1 | 57.38 | C |
| ATOM | 51 | CG | PHE | A | 243 | 14.924 | −11.797 | −16.805 | 1 | 57.89 | C |
| ATOM | 52 | CD1 | PHE | A | 243 | 15.889 | −10.847 | −17.091 | 1 | 58.24 | C |
| ATOM | 53 | CE1 | PHE | A | 243 | 16.921 | −10.586 | −16.199 | 1 | 57.99 | C |
| ATOM | 54 | CZ | PHE | A | 243 | 16.999 | −11.284 | −14.997 | 1 | 59.15 | C |
| ATOM | 55 | CE2 | PHE | A | 243 | 16.037 | −12.243 | −14.697 | 1 | 59.9 | C |
| ATOM | 56 | CD2 | PHE | A | 243 | 14.999 | −12.493 | −15.606 | 1 | 59.98 | C |
| ATOM | 57 | C | PHE | A | 243 | 11.601 | −11.428 | −18.658 | 1 | 54.93 | C |
| ATOM | 58 | O | PHE | A | 243 | 10.747 | −12.253 | −18.351 | 1 | 54.58 | O |
| ATOM | 59 | N | PRO | A | 244 | 11.633 | −10.819 | −19.853 | 1 | 53.21 | N |
| ATOM | 60 | CA | PRO | A | 244 | 10.567 | −11.049 | −20.814 | 1 | 52.76 | C |
| ATOM | 61 | CB | PRO | A | 244 | 10.657 | −9.82 | −21.711 | 1 | 52.66 | C |
| ATOM | 62 | CG | PRO | A | 244 | 12.123 | −9.505 | −21.729 | 1 | 52.62 | C |
| ATOM | 63 | CD | PRO | A | 244 | 12.656 | −9.905 | −20.386 | 1 | 52.8 | C |
| ATOM | 64 | C | PRO | A | 244 | 10.848 | −12.304 | −21.607 | 1 | 51.61 | C |
| ATOM | 65 | O | PRO | A | 244 | 11.889 | −12.896 | −21.452 | 1 | 51.47 | O |
| ATOM | 66 | N | PRO | A | 245 | 9.919 | −12.726 | −22.445 | 1 | 50.98 | N |
| ATOM | 67 | CA | PRO | A | 245 | 10.24 | −13.819 | −23.36 | 1 | 50.91 | C |
| ATOM | 68 | CB | PRO | A | 245 | 8.873 | −14.204 | −23.919 | 1 | 50.72 | C |
| ATOM | 69 | CG | PRO | A | 245 | 8.096 | −12.972 | −23.868 | 1 | 50.83 | C |
| ATOM | 70 | CD | PRO | A | 245 | 8.532 | −12.275 | −22.605 | 1 | 51.08 | C |
| ATOM | 71 | C | PRO | A | 245 | 11.188 | −13.41 | −24.495 | 1 | 50.33 | C |
| ATOM | 72 | O | PRO | A | 245 | 11.453 | −12.237 | −24.7 | 1 | 50.8 | O |
| ATOM | 73 | N | LYS | A | 246 | 11.697 | −14.383 | −25.222 | 1 | 49.96 | N |
| ATOM | 74 | CA | LYS | A | 246 | 12.604 | −14.093 | −26.322 | 1 | 49.83 | C |
| ATOM | 75 | CB | LYS | A | 246 | 13.454 | −15.321 | −26.716 | 1 | 50.67 | C |
| ATOM | 76 | CG | LYS | A | 246 | 14.257 | −15.931 | −25.577 | 1 | 51.51 | C |
| ATOM | 77 | CD | LYS | A | 246 | 15.497 | −15.122 | −25.306 | 1 | 53.03 | C |
| ATOM | 78 | CE | LYS | A | 246 | 16.16 | −15.512 | −23.979 | 1 | 53.95 | C |
| ATOM | 79 | NZ | LYS | A | 246 | 15.507 | −14.87 | −22.766 | 1 | 55.68 | N |
| ATOM | 80 | C | LYS | A | 246 | 11.744 | −13.684 | −27.488 | 1 | 48.55 | C |
| ATOM | 81 | O | LYS | A | 246 | 10.74 | −14.288 | −27.741 | 1 | 47.83 | O |
| ATOM | 82 | N | PRO | A | 247 | 12.142 | −12.642 | −28.19 | 1 | 48.21 | N |
| ATOM | 83 | CA | PRO | A | 247 | 11.411 | −12.198 | −29.352 | 1 | 48.2 | C |
| ATOM | 84 | CB | PRO | A | 247 | 12.421 | −11.26 | −30.04 | 1 | 48.54 | C |
| ATOM | 85 | CG | PRO | A | 247 | 13.185 | −10.659 | −28.91 | 1 | 48.41 | C |
| ATOM | 86 | CD | PRO | A | 247 | 13.301 | −11.772 | −27.898 | 1 | 48.66 | C |
| ATOM | 87 | C | PRO | A | 247 | 10.988 | −13.323 | −30.293 | 1 | 47.63 | C |
| ATOM | 88 | O | PRO | A | 247 | 9.886 | −13.307 | −30.809 | 1 | 47.25 | O |
| ATOM | 89 | N | LYS | A | 248 | 11.871 | −14.292 | −30.49 | 1 | 47.5 | N |
| ATOM | 90 | CA | LYS | A | 248 | 11.633 | −15.374 | −31.42 | 1 | 47.25 | C |
| ATOM | 91 | CB | LYS | A | 248 | 12.911 | −16.206 | −31.583 | 1 | 47.38 | C |
| ATOM | 92 | CG | LYS | A | 248 | 12.984 | −16.991 | −32.871 | 1 | 47.85 | C |
| ATOM | 93 | CD | LYS | A | 248 | 14.344 | −17.732 | −32.995 | 1 | 48.44 | C |
| ATOM | 94 | CE | LYS | A | 248 | 14.405 | −18.691 | −34.201 | 1 | 48.7 | C |

TABLE V-continued

Atomic Structure Coordinates of Fc/YTE (SEQ ID NO: 11)

| | Atom | A.A. | Type | | | X | Y | Z | Occ | B | |
|---|---|---|---|---|---|---|---|---|---|---|---|
| ATOM | 95 | NZ | LYS | A | 248 | 15.781 | −19.296 | −34.404 | 1 | 48.87 | N |
| ATOM | 96 | C | LYS | A | 248 | 10.468 | −16.232 | −30.939 | 1 | 46.63 | C |
| ATOM | 97 | O | LYS | A | 248 | 9.638 | −16.712 | −31.758 | 1 | 46.26 | O |
| ATOM | 98 | N | ASP | A | 249 | 10.399 | −16.38 | −29.615 | 1 | 45.9 | N |
| ATOM | 99 | CA | ASP | A | 249 | 9.485 | −17.311 | −28.969 | 1 | 45.99 | C |
| ATOM | 100 | CB | ASP | A | 249 | 9.856 | −17.505 | −27.493 | 1 | 46.09 | C |
| ATOM | 101 | CG | ASP | A | 249 | 11.153 | −18.263 | −27.295 | 1 | 46.51 | C |
| ATOM | 102 | OD1 | ASP | A | 249 | 11.632 | −18.942 | −28.233 | 1 | 45.92 | O |
| ATOM | 103 | OD2 | ASP | A | 249 | 11.694 | −18.181 | −26.17 | 1 | 48.4 | O |
| ATOM | 104 | C | ASP | A | 249 | 8.022 | −16.906 | −29.018 | 1 | 45.47 | C |
| ATOM | 105 | O | ASP | A | 249 | 7.151 | −17.747 | −28.817 | 1 | 45.62 | O |
| ATOM | 106 | N | THR | A | 250 | 7.744 | −15.635 | −29.265 | 1 | 45.13 | N |
| ATOM | 107 | CA | THR | A | 250 | 6.366 | −15.121 | −29.21 | 1 | 45.19 | C |
| ATOM | 108 | CB | THR | A | 250 | 6.33 | −13.679 | −28.617 | 1 | 44.95 | C |
| ATOM | 109 | OG1 | THR | A | 250 | 7.044 | −12.798 | −29.481 | 1 | 43.29 | O |
| ATOM | 110 | CG2 | THR | A | 250 | 6.986 | −13.616 | −27.192 | 1 | 44 | C |
| ATOM | 111 | C | THR | A | 250 | 5.722 | −15.109 | −30.588 | 1 | 45.08 | C |
| ATOM | 112 | O | THR | A | 250 | 4.521 | −14.93 | −30.7 | 1 | 45.23 | O |
| ATOM | 113 | N | LEU | A | 251 | 6.515 | −15.344 | −31.625 | 1 | 45.49 | N |
| ATOM | 114 | CA | LEU | A | 251 | 6.095 | −15.145 | −33 | 1 | 46.04 | C |
| ATOM | 115 | CB | LEU | A | 251 | 7.212 | −14.441 | −33.753 | 1 | 46.46 | C |
| ATOM | 116 | CG | LEU | A | 251 | 7.841 | −13.162 | −33.162 | 1 | 46.52 | C |
| ATOM | 117 | CD1 | LEU | A | 251 | 9.197 | −12.886 | −33.814 | 1 | 46.04 | C |
| ATOM | 118 | CD2 | LEU | A | 251 | 6.905 | −11.978 | −33.341 | 1 | 46.44 | C |
| ATOM | 119 | C | LEU | A | 251 | 5.795 | −16.464 | −33.715 | 1 | 46.77 | C |
| ATOM | 120 | O | LEU | A | 251 | 5.44 | −16.478 | −34.893 | 1 | 46.39 | O |
| ATOM | 121 | N | TYR | A | 252 | 5.957 | −17.582 | −33.005 | 1 | 47.85 | N |
| ATOM | 122 | CA | TYR | A | 252 | 5.805 | −18.891 | −33.609 | 1 | 48.18 | C |
| ATOM | 123 | CB | TYR | A | 252 | 7.182 | −19.399 | −34.051 | 1 | 48.5 | C |
| ATOM | 124 | CG | TYR | A | 252 | 7.877 | −18.468 | −35.002 | 1 | 47.94 | C |
| ATOM | 125 | CD1 | TYR | A | 252 | 9.082 | −17.805 | −34.713 | 1 | 48.14 | C |
| ATOM | 126 | CE1 | TYR | A | 252 | 9.637 | −16.943 | −35.643 | 1 | 48.23 | C |
| ATOM | 127 | CZ | TYR | A | 252 | 9.016 | −16.745 | −36.85 | 1 | 48.35 | C |
| ATOM | 128 | OH | TYR | A | 252 | 9.597 | −15.893 | −37.764 | 1 | 48.63 | O |
| ATOM | 129 | CE2 | TYR | A | 252 | 7.834 | −17.378 | −37.139 | 1 | 48.51 | C |
| ATOM | 130 | CD2 | TYR | A | 252 | 7.281 | −18.235 | −36.226 | 1 | 48.31 | C |
| ATOM | 131 | C | TYR | A | 252 | 5.148 | −19.866 | −32.64 | 1 | 49.16 | C |
| ATOM | 132 | O | TYR | A | 252 | 5.551 | −19.911 | −31.481 | 1 | 49.69 | O |
| ATOM | 133 | N | ILE | A | 253 | 4.122 | −20.645 | −33.069 | 1 | 50.2 | N |
| ATOM | 134 | CA | ILE | A | 253 | 3.451 | −21.593 | −32.153 | 1 | 50.51 | C |
| ATOM | 135 | CB | ILE | A | 253 | 2.154 | −22.206 | −32.763 | 1 | 50.58 | C |
| ATOM | 136 | CG1 | ILE | A | 253 | 2.036 | −21.885 | −34.239 | 1 | 51.05 | C |
| ATOM | 137 | CD1 | ILE | A | 253 | 2.847 | −22.802 | −35.126 | 1 | 51.02 | C |
| ATOM | 138 | CG2 | ILE | A | 253 | 0.934 | −21.695 | −32.024 | 1 | 50.29 | C |
| ATOM | 139 | C | ILE | A | 253 | 4.466 | −22.639 | −31.791 | 1 | 51.11 | C |
| ATOM | 140 | O | ILE | A | 253 | 4.521 | −23.169 | −30.68 | 1 | 51.73 | O |
| ATOM | 141 | N | THR | A | 254 | 5.27 | −22.868 | −32.784 | 1 | 51.68 | N |
| ATOM | 142 | CA | THR | A | 254 | 6.398 | −23.754 | −32.724 | 1 | 51.41 | C |
| ATOM | 143 | CB | THR | A | 254 | 7.245 | −23.522 | −33.987 | 1 | 51.77 | C |
| ATOM | 144 | OG1 | THR | A | 254 | 6.574 | −24.065 | −35.134 | 1 | 53.28 | O |
| ATOM | 145 | CG2 | THR | A | 254 | 8.622 | −24.156 | −33.816 | 1 | 52.12 | C |
| ATOM | 146 | C | THR | A | 254 | 7.23 | −23.518 | −31.482 | 1 | 51.35 | C |
| ATOM | 147 | O | THR | A | 254 | 7.913 | −24.423 | −31.006 | 1 | 51.7 | O |
| ATOM | 148 | N | ARG | A | 255 | 7.208 | −22.32 | −30.947 | 1 | 51.02 | N |
| ATOM | 149 | CA | ARG | A | 255 | 8.094 | −22.064 | −29.81 | 1 | 51.11 | C |
| ATOM | 150 | CB | ARG | A | 255 | 9.051 | −20.938 | −30.193 | 1 | 51.2 | C |
| ATOM | 151 | CG | ARG | A | 255 | 9.674 | −21.152 | −31.556 | 1 | 51.83 | C |
| ATOM | 152 | CD | ARG | A | 255 | 10.713 | −20.102 | −31.881 | 1 | 52.58 | C |
| ATOM | 153 | NE | ARG | A | 255 | 11.761 | −20.024 | −30.864 | 1 | 54.14 | N |
| ATOM | 154 | CZ | ARG | A | 255 | 12.856 | −20.796 | −30.843 | 1 | 55.39 | C |
| ATOM | 155 | NH1 | ARG | A | 255 | 13.054 | −21.703 | −31.803 | 1 | 56.99 | N |
| ATOM | 156 | NH2 | ARG | A | 255 | 13.745 | −20.652 | −29.863 | 1 | 54.08 | N |
| ATOM | 157 | C | ARG | A | 255 | 7.308 | −21.83 | −28.524 | 1 | 50.58 | C |
| ATOM | 158 | O | ARG | A | 255 | 6.1 | −21.627 | −28.55 | 1 | 50.99 | O |
| ATOM | 159 | N | GLU | A | 256 | 8.017 | −21.865 | −27.402 | 1 | 50.06 | N |
| ATOM | 160 | CA | GLU | A | 256 | 7.394 | −21.738 | −26.078 | 1 | 50.32 | C |
| ATOM | 161 | CB | GLU | A | 256 | 7.644 | −22.999 | −25.23 | 1 | 50.59 | C |
| ATOM | 162 | CG | GLU | A | 256 | 7.184 | −24.321 | −25.852 | 1 | 52.18 | C |
| ATOM | 163 | CD | GLU | A | 256 | 8.016 | −25.532 | −25.417 | 1 | 53.3 | C |
| ATOM | 164 | OE1 | GLU | A | 256 | 8.408 | −25.605 | −24.246 | 1 | 57.8 | O |
| ATOM | 165 | OE2 | GLU | A | 256 | 8.279 | −26.415 | −26.276 | 1 | 55.55 | O |
| ATOM | 166 | C | GLU | A | 256 | 7.893 | −20.52 | −25.307 | 1 | 49.4 | C |
| ATOM | 167 | O | GLU | A | 256 | 8.888 | −20.614 | −24.582 | 1 | 49.03 | O |
| ATOM | 168 | N | PRO | A | 257 | 7.216 | −19.37 | −25.466 | 1 | 48.79 | N |
| ATOM | 169 | CA | PRO | A | 257 | 7.659 | −18.179 | −24.769 | 1 | 48.92 | C |
| ATOM | 170 | CB | PRO | A | 257 | 6.897 | −17.078 | −25.473 | 1 | 48.32 | C |

TABLE V-continued

Atomic Structure Coordinates of Fc/YTE (SEQ ID NO: 11)

| | | Atom | A.A. | Type | | X | Y | Z | Occ | B | |
|---|---|---|---|---|---|---|---|---|---|---|---|
| ATOM | 171 | CG | PRO | A | 257 | 5.695 | −17.73 | −25.986 | 1 | 48.27 | C |
| ATOM | 172 | CD | PRO | A | 257 | 5.99 | −19.134 | −26.242 | 1 | 48.29 | C |
| ATOM | 173 | C | PRO | A | 257 | 7.297 | −18.243 | −23.294 | 1 | 48.73 | C |
| ATOM | 174 | O | PRO | A | 257 | 6.237 | −18.718 | −22.957 | 1 | 48.81 | O |
| ATOM | 175 | N | GLU | A | 258 | 8.179 | −17.777 | −22.429 | 1 | 49.43 | N |
| ATOM | 176 | CA | GLU | A | 258 | 7.928 | −17.781 | −20.988 | 1 | 50.38 | C |
| ATOM | 177 | CB | GLU | A | 258 | 8.781 | −18.857 | −20.301 | 1 | 50.56 | C |
| ATOM | 178 | CG | GLU | A | 258 | 8.802 | −20.25 | −20.952 | 1 | 50.75 | C |
| ATOM | 179 | CD | GLU | A | 258 | 9.718 | −21.222 | −20.197 | 1 | 51.13 | C |
| ATOM | 180 | OE1 | GLU | A | 258 | 9.24 | −22.308 | −19.838 | 1 | 54.13 | O |
| ATOM | 181 | OE2 | GLU | A | 258 | 10.902 | −20.911 | −19.938 | 1 | 50.77 | O |
| ATOM | 182 | C | GLU | A | 258 | 8.317 | −16.413 | −20.408 | 1 | 50.6 | C |
| ATOM | 183 | O | GLU | A | 258 | 9.107 | −15.707 | −21.002 | 1 | 50.6 | O |
| ATOM | 184 | N | VAL | A | 259 | 7.764 | −16.064 | −19.254 | 1 | 51.37 | N |
| ATOM | 185 | CA | VAL | A | 259 | 8.174 | −14.897 | −18.481 | 1 | 52.66 | C |
| ATOM | 186 | CB | VAL | A | 259 | 6.958 | −14.006 | −18.105 | 1 | 52.38 | C |
| ATOM | 187 | CG1 | VAL | A | 259 | 7.33 | −12.995 | −17.039 | 1 | 52 | C |
| ATOM | 188 | CG2 | VAL | A | 259 | 6.405 | −13.293 | −19.326 | 1 | 53.16 | C |
| ATOM | 189 | C | VAL | A | 259 | 8.801 | −15.445 | −17.195 | 1 | 53.73 | C |
| ATOM | 190 | O | VAL | A | 259 | 8.193 | −16.29 | −16.529 | 1 | 53.25 | O |
| ATOM | 191 | N | THR | A | 260 | 9.99 | −14.957 | −16.831 | 1 | 55.5 | N |
| ATOM | 192 | CA | THR | A | 260 | 10.77 | −15.57 | −15.751 | 1 | 57.02 | C |
| ATOM | 193 | CB | THR | A | 260 | 12.128 | −16.137 | −16.254 | 1 | 56.7 | C |
| ATOM | 194 | OG1 | THR | A | 260 | 11.949 | −16.857 | −17.476 | 1 | 56.92 | O |
| ATOM | 195 | CG2 | THR | A | 260 | 12.708 | −17.063 | −15.232 | 1 | 56.25 | C |
| ATOM | 196 | C | THR | A | 260 | 11.074 | −14.602 | −14.629 | 1 | 58.54 | C |
| ATOM | 197 | O | THR | A | 260 | 11.879 | −13.694 | −14.798 | 1 | 59 | O |
| ATOM | 198 | N | CYS | A | 261 | 10.457 | −14.822 | −13.476 | 1 | 60.75 | N |
| ATOM | 199 | CA | CYS | A | 261 | 10.71 | −14.009 | −12.294 | 1 | 62.55 | C |
| ATOM | 200 | CB | CYS | A | 261 | 9.421 | −13.876 | −11.477 | 1 | 62.52 | C |
| ATOM | 201 | SG | CYS | A | 261 | 9.445 | −12.667 | −10.119 | 1 | 61.43 | S |
| ATOM | 202 | C | CYS | A | 261 | 11.831 | −14.634 | −11.447 | 1 | 64.5 | C |
| ATOM | 203 | O | CYS | A | 261 | 11.716 | −15.768 | −10.979 | 1 | 64.7 | O |
| ATOM | 204 | N | VAL | A | 262 | 12.904 | −13.879 | −11.247 | 1 | 66.89 | N |
| ATOM | 205 | CA | VAL | A | 262 | 14.056 | −14.326 | −10.468 | 1 | 68.87 | C |
| ATOM | 206 | CB | VAL | A | 262 | 15.34 | −14.15 | −11.276 | 1 | 68.77 | C |
| ATOM | 207 | CG1 | VAL | A | 262 | 16.542 | −14.599 | −10.463 | 1 | 69.29 | C |
| ATOM | 208 | CG2 | VAL | A | 262 | 15.247 | −14.932 | −12.589 | 1 | 68.71 | C |
| ATOM | 209 | C | VAL | A | 262 | 14.186 | −13.536 | −9.159 | 1 | 70.89 | C |
| ATOM | 210 | O | VAL | A | 262 | 14.367 | −12.326 | −9.184 | 1 | 71.09 | O |
| ATOM | 211 | N | VAL | A | 263 | 14.076 | −14.228 | −8.026 | 1 | 73.28 | N |
| ATOM | 212 | CA | VAL | A | 263 | 14.321 | −13.632 | −6.706 | 1 | 75.14 | C |
| ATOM | 213 | CB | VAL | A | 263 | 13.255 | −14.091 | −5.688 | 1 | 75.44 | C |
| ATOM | 214 | CG1 | VAL | A | 263 | 13.477 | −13.428 | −4.324 | 1 | 75.38 | C |
| ATOM | 215 | CG2 | VAL | A | 263 | 11.847 | −13.785 | −6.22 | 1 | 75.84 | C |
| ATOM | 216 | C | VAL | A | 263 | 15.719 | −14.016 | −6.178 | 1 | 77.05 | C |
| ATOM | 217 | O | VAL | A | 263 | 16.067 | −15.198 | −6.127 | 1 | 77.35 | O |
| ATOM | 218 | N | VAL | A | 264 | 16.511 | −13.02 | −5.779 | 1 | 79 | N |
| ATOM | 219 | CA | VAL | A | 264 | 17.848 | −13.259 | −5.21 | 1 | 80.23 | C |
| ATOM | 220 | CB | VAL | A | 264 | 18.943 | −12.809 | −6.168 | 1 | 80.1 | C |
| ATOM | 221 | CG1 | VAL | A | 264 | 18.874 | −13.628 | −7.449 | 1 | 79.94 | C |
| ATOM | 222 | CG2 | VAL | A | 264 | 18.815 | −11.325 | −6.445 | 1 | 79.99 | C |
| ATOM | 223 | C | VAL | A | 264 | 18.042 | −12.553 | −3.864 | 1 | 81.86 | C |
| ATOM | 224 | O | VAL | A | 264 | 17.209 | −11.732 | −3.465 | 1 | 81.97 | O |
| ATOM | 225 | N | ASP | A | 265 | 19.143 | −12.897 | −3.182 | 1 | 83.57 | N |
| ATOM | 226 | CA | ASP | A | 265 | 19.492 | −12.39 | −1.843 | 1 | 84.74 | C |
| ATOM | 227 | CB | ASP | A | 265 | 19.665 | −10.851 | −1.819 | 1 | 84.86 | C |
| ATOM | 228 | CG | ASP | A | 265 | 20.725 | −10.345 | −2.799 | 1 | 84.74 | C |
| ATOM | 229 | OD1 | ASP | A | 265 | 20.644 | −9.159 | −3.189 | 1 | 85.04 | O |
| ATOM | 230 | OD2 | ASP | A | 265 | 21.632 | −11.111 | −3.175 | 1 | 84.15 | O |
| ATOM | 231 | C | ASP | A | 265 | 18.458 | −12.808 | −0.794 | 1 | 86.05 | C |
| ATOM | 232 | O | ASP | A | 265 | 18.022 | −11.988 | 0.019 | 1 | 86.24 | O |
| ATOM | 233 | N | VAL | A | 266 | 18.086 | −14.083 | −0.795 | 1 | 87.39 | N |
| ATOM | 234 | CA | VAL | A | 266 | 17.046 | −14.569 | 0.122 | 1 | 88.48 | C |
| ATOM | 235 | CB | VAL | A | 266 | 16.273 | −15.747 | −0.49 | 1 | 88.56 | C |
| ATOM | 236 | CG1 | VAL | A | 266 | 14.935 | −15.922 | 0.213 | 1 | 88.38 | C |
| ATOM | 237 | CG2 | VAL | A | 266 | 16.073 | −15.529 | −1.987 | 1 | 88.96 | C |
| ATOM | 238 | C | VAL | A | 266 | 17.622 | −14.999 | 1.487 | 1 | 89.58 | C |
| ATOM | 239 | O | VAL | A | 266 | 18.414 | −15.945 | 1.563 | 1 | 89.8 | O |
| ATOM | 240 | N | SER | A | 267 | 17.208 | −14.296 | 2.546 | 1 | 90.79 | N |
| ATOM | 241 | CA | SER | A | 267 | 17.63 | −14.553 | 3.943 | 1 | 91.53 | C |
| ATOM | 242 | CB | SER | A | 267 | 16.536 | −14.068 | 4.927 | 1 | 91.58 | C |
| ATOM | 243 | OG | SER | A | 267 | 16.887 | −14.212 | 6.301 | 1 | 90.99 | O |
| ATOM | 244 | C | SER | A | 267 | 17.928 | −16.025 | 4.182 | 1 | 92.43 | C |
| ATOM | 245 | O | SER | A | 267 | 17.053 | −16.88 | 4.011 | 1 | 92.31 | O |
| ATOM | 246 | N | HIS | A | 268 | 19.164 | −16.317 | 4.581 | 1 | 93.63 | N |

TABLE V-continued

Atomic Structure Coordinates of Fc/YTE (SEQ ID NO: 11)

| | | Atom | A.A. | Type | | X | Y | Z | Occ | B | |
|---|---|---|---|---|---|---|---|---|---|---|---|
| ATOM | 247 | CA | HIS | A | 268 | 19.598 | −17.705 | 4.789 | 1 | 94.54 | C |
| ATOM | 248 | CB | HIS | A | 268 | 21.098 | −17.781 | 5.103 | 1 | 95.04 | C |
| ATOM | 249 | CG | HIS | A | 268 | 21.77 | −18.969 | 4.49 | 1 | 95.57 | C |
| ATOM | 250 | ND1 | HIS | A | 268 | 22.887 | −18.861 | 3.689 | 1 | 96.17 | N |
| ATOM | 251 | CE1 | HIS | A | 268 | 23.248 | −20.062 | 3.275 | 1 | 96.61 | C |
| ATOM | 252 | NE2 | HIS | A | 268 | 22.395 | −20.945 | 3.763 | 1 | 96.34 | N |
| ATOM | 253 | CD2 | HIS | A | 268 | 21.457 | −20.287 | 4.523 | 1 | 95.74 | C |
| ATOM | 254 | C | HIS | A | 268 | 18.796 | −18.401 | 5.893 | 1 | 95.18 | C |
| ATOM | 255 | O | HIS | A | 268 | 18.614 | −19.629 | 5.864 | 1 | 95.04 | O |
| ATOM | 256 | N | GLU | A | 269 | 18.33 | −17.594 | 6.849 | 1 | 95.81 | N |
| ATOM | 257 | CA | GLU | A | 269 | 17.447 | −18.04 | 7.919 | 1 | 96.3 | C |
| ATOM | 258 | CB | GLU | A | 269 | 17.123 | −16.879 | 8.885 | 1 | 96.58 | C |
| ATOM | 259 | CG | GLU | A | 269 | 18.26 | −16.484 | 9.856 | 1 | 96.72 | C |
| ATOM | 260 | CD | GLU | A | 269 | 19.406 | −15.739 | 9.182 | 1 | 96.79 | C |
| ATOM | 261 | OE1 | GLU | A | 269 | 19.223 | −15.273 | 8.04 | 1 | 97.3 | O |
| ATOM | 262 | OE2 | GLU | A | 269 | 20.492 | −15.62 | 9.788 | 1 | 96.5 | O |
| ATOM | 263 | C | GLU | A | 269 | 16.151 | −18.609 | 7.339 | 1 | 96.72 | C |
| ATOM | 264 | O | GLU | A | 269 | 15.916 | −19.822 | 7.395 | 1 | 96.79 | O |
| ATOM | 265 | N | ASP | A | 270 | 15.339 | −17.719 | 6.762 | 1 | 97.09 | N |
| ATOM | 266 | CA | ASP | A | 270 | 14.008 | −18.058 | 6.235 | 1 | 97.09 | C |
| ATOM | 267 | CB | ASP | A | 270 | 13.01 | −16.925 | 6.541 | 1 | 97.47 | C |
| ATOM | 268 | CG | ASP | A | 270 | 13.091 | −16.428 | 7.989 | 1 | 98.07 | C |
| ATOM | 269 | OD1 | ASP | A | 270 | 13.542 | −17.195 | 8.873 | 1 | 98.5 | O |
| ATOM | 270 | OD2 | ASP | A | 270 | 12.701 | −15.261 | 8.238 | 1 | 98.56 | O |
| ATOM | 271 | C | ASP | A | 270 | 14.08 | −18.296 | 4.712 | 1 | 97.14 | C |
| ATOM | 272 | O | ASP | A | 270 | 14.265 | −17.352 | 3.941 | 1 | 97.3 | O |
| ATOM | 273 | N | PRO | A | 271 | 13.918 | −19.557 | 4.267 | 1 | 96.82 | N |
| ATOM | 274 | CA | PRO | A | 271 | 14.194 | −19.86 | 2.857 | 1 | 96.04 | C |
| ATOM | 275 | CB | PRO | A | 271 | 14.589 | −21.338 | 2.91 | 1 | 96.4 | C |
| ATOM | 276 | CG | PRO | A | 271 | 13.752 | −21.902 | 4.041 | 1 | 96.86 | C |
| ATOM | 278 | C | PRO | A | 271 | 12.982 | −19.688 | 1.939 | 1 | 95.28 | C |
| ATOM | 279 | O | PRO | A | 271 | 13.093 | −19.891 | 0.731 | 1 | 95.26 | O |
| ATOM | 280 | N | GLU | A | 272 | 11.848 | −19.298 | 2.508 | 1 | 94.1 | N |
| ATOM | 281 | CA | GLU | A | 272 | 10.564 | −19.508 | 1.864 | 1 | 93.15 | C |
| ATOM | 282 | CB | GLU | A | 272 | 9.572 | −20.04 | 2.897 | 1 | 93.37 | C |
| ATOM | 283 | CG | GLU | A | 272 | 9.818 | −21.516 | 3.231 | 1 | 93.81 | C |
| ATOM | 284 | CD | GLU | A | 272 | 9.642 | −21.848 | 4.703 | 1 | 93.91 | C |
| ATOM | 285 | OE1 | GLU | A | 272 | 9.576 | −23.063 | 5.025 | 1 | 94.32 | O |
| ATOM | 286 | OE2 | GLU | A | 272 | 9.58 | −20.9 | 5.529 | 1 | 94.26 | O |
| ATOM | 287 | C | GLU | A | 272 | 10 | −18.275 | 1.173 | 1 | 92 | C |
| ATOM | 288 | O | GLU | A | 272 | 9.491 | −17.364 | 1.837 | 1 | 91.96 | O |
| ATOM | 289 | N | VAL | A | 273 | 10.086 | −18.284 | −0.163 | 1 | 90.48 | N |
| ATOM | 290 | CA | VAL | A | 273 | 9.498 | −17.26 | −1.044 | 1 | 89.13 | C |
| ATOM | 291 | CB | VAL | A | 273 | 10.408 | −16.979 | −2.243 | 1 | 89.08 | C |
| ATOM | 292 | CG1 | VAL | A | 273 | 9.852 | −15.833 | −3.034 | 1 | 89.41 | C |
| ATOM | 293 | CG2 | VAL | A | 273 | 11.832 | −16.696 | −1.796 | 1 | 89.21 | C |
| ATOM | 294 | C | VAL | A | 273 | 8.157 | −17.71 | −1.642 | 1 | 87.84 | C |
| ATOM | 295 | O | VAL | A | 273 | 8.056 | −18.814 | −2.197 | 1 | 87.75 | O |
| ATOM | 296 | N | LYS | A | 274 | 7.141 | −16.85 | −1.564 | 1 | 86 | N |
| ATOM | 297 | CA | LYS | A | 274 | 5.823 | −17.171 | −2.125 | 1 | 84.84 | C |
| ATOM | 298 | CB | LYS | A | 274 | 4.746 | −16.999 | −1.053 | 1 | 84.99 | C |
| ATOM | 299 | CG | LYS | A | 274 | 3.432 | −17.717 | −1.33 | 1 | 85.29 | C |
| ATOM | 300 | CD | LYS | A | 274 | 2.322 | −17.153 | −0.441 | 1 | 84.97 | C |
| ATOM | 301 | CE | LYS | A | 274 | 1.712 | −15.893 | −1.032 | 1 | 84.92 | C |
| ATOM | 302 | NZ | LYS | A | 274 | 1.104 | −14.99 | −0.023 | 1 | 85.1 | N |
| ATOM | 303 | C | LYS | A | 274 | 5.503 | −16.309 | −3.357 | 1 | 83.41 | C |
| ATOM | 304 | O | LYS | A | 274 | 5.332 | −15.09 | −3.252 | 1 | 83.45 | O |
| ATOM | 305 | N | PHE | A | 275 | 5.425 | −16.953 | −4.52 | 1 | 81.56 | N |
| ATOM | 306 | CA | PHE | A | 275 | 5.081 | −16.271 | −5.773 | 1 | 80.12 | C |
| ATOM | 307 | CB | PHE | A | 275 | 5.716 | −17.003 | −6.969 | 1 | 79.71 | C |
| ATOM | 308 | CG | PHE | A | 275 | 7.223 | −16.914 | −7.014 | 1 | 79.42 | C |
| ATOM | 309 | CD1 | PHE | A | 275 | 8.008 | −17.705 | −6.186 | 1 | 79.74 | C |
| ATOM | 310 | CE1 | PHE | A | 275 | 9.4 | −17.619 | −6.231 | 1 | 79.53 | C |
| ATOM | 311 | CZ | PHE | A | 275 | 10.014 | −16.741 | −7.112 | 1 | 78.92 | C |
| ATOM | 312 | CE2 | PHE | A | 275 | 9.243 | −15.952 | −7.941 | 1 | 78.54 | C |
| ATOM | 313 | CD2 | PHE | A | 275 | 7.857 | −16.04 | −7.892 | 1 | 78.47 | C |
| ATOM | 314 | C | PHE | A | 275 | 3.559 | −16.187 | −5.988 | 1 | 78.72 | C |
| ATOM | 315 | O | PHE | A | 275 | 2.847 | −17.171 | −5.793 | 1 | 78.54 | O |
| ATOM | 316 | N | ASN | A | 276 | 3.066 | −15.006 | −6.369 | 1 | 77.17 | N |
| ATOM | 317 | CA | ASN | A | 276 | 1.751 | −14.874 | −7.032 | 1 | 75.81 | C |
| ATOM | 318 | CB | ASN | A | 276 | 0.79 | −13.972 | −6.244 | 1 | 75.76 | C |
| ATOM | 319 | CG | ASN | A | 276 | 0.613 | −14.398 | −4.793 | 1 | 74.98 | C |
| ATOM | 320 | OD1 | ASN | A | 276 | −0.488 | −14.713 | −4.371 | 1 | 73.42 | O |
| ATOM | 321 | ND2 | ASN | A | 276 | 1.695 | −14.384 | −4.024 | 1 | 75.04 | N |
| ATOM | 322 | C | ASN | A | 276 | 1.97 | −14.266 | −8.418 | 1 | 74.46 | C |
| ATOM | 323 | O | ASN | A | 276 | 2.779 | −13.352 | −8.561 | 1 | 74.39 | O |

TABLE V-continued

Atomic Structure Coordinates of Fc/YTE (SEQ ID NO: 11)

| | Atom | A.A. | Type | | | X | Y | Z | Occ | B | |
|---|---|---|---|---|---|---|---|---|---|---|---|
| ATOM | 324 | N | TRP | A | 277 | 1.269 | −14.772 | −9.43 | 1 | 73.05 | N |
| ATOM | 325 | CA | TRP | A | 277 | 1.35 | −14.216 | −10.785 | 1 | 72.25 | C |
| ATOM | 326 | CB | TRP | A | 277 | 1.719 | −15.291 | −11.807 | 1 | 69.26 | C |
| ATOM | 327 | CG | TRP | A | 277 | 3.156 | −15.71 | −11.81 | 1 | 67 | C |
| ATOM | 328 | CD1 | TRP | A | 277 | 3.699 | −16.725 | −11.089 | 1 | 65.11 | C |
| ATOM | 329 | NE1 | TRP | A | 277 | 5.041 | −16.837 | −11.356 | 1 | 65.65 | N |
| ATOM | 330 | CE2 | TRP | A | 277 | 5.395 | −15.885 | −12.273 | 1 | 72.06 | C |
| ATOM | 331 | CD2 | TRP | A | 277 | 4.229 | −15.153 | −12.587 | 1 | 70.5 | C |
| ATOM | 332 | CE3 | TRP | A | 277 | 4.318 | −14.114 | −13.514 | 1 | 70.54 | C |
| ATOM | 333 | CZ3 | TRP | A | 277 | 5.55 | −13.838 | −14.084 | 1 | 76.45 | C |
| ATOM | 334 | CH2 | TRP | A | 277 | 6.694 | −14.59 | −13.754 | 1 | 76.09 | C |
| ATOM | 335 | CZ2 | TRP | A | 277 | 6.637 | −15.613 | −12.855 | 1 | 70.74 | C |
| ATOM | 336 | C | TRP | A | 277 | 0.023 | −13.598 | −11.204 | 1 | 71.84 | C |
| ATOM | 337 | O | TRP | A | 277 | −1.036 | −14.073 | −10.795 | 1 | 71.93 | O |
| ATOM | 338 | N | TYR | A | 278 | 0.085 | −12.552 | −12.037 | 1 | 71.35 | N |
| ATOM | 339 | CA | TYR | A | 278 | −1.117 | −11.885 | −12.552 | 1 | 70.86 | C |
| ATOM | 340 | CB | TYR | A | 278 | −1.422 | −10.607 | −11.767 | 1 | 71.01 | C |
| ATOM | 341 | CG | TYR | A | 278 | −1.504 | −10.788 | −10.267 | 1 | 71.07 | C |
| ATOM | 342 | CD1 | TYR | A | 278 | −0.356 | −10.801 | −9.487 | 1 | 70.57 | C |
| ATOM | 343 | CE1 | TYR | A | 278 | −0.422 | −10.963 | −8.12 | 1 | 70.92 | C |
| ATOM | 344 | CZ | TYR | A | 278 | −1.656 | −11.097 | −7.505 | 1 | 71.62 | C |
| ATOM | 345 | OH | TYR | A | 278 | −1.733 | −11.248 | −6.141 | 1 | 71.92 | O |
| ATOM | 346 | CE2 | TYR | A | 278 | −2.815 | −11.088 | −8.257 | 1 | 71.58 | C |
| ATOM | 347 | CD2 | TYR | A | 278 | −2.731 | −10.935 | −9.633 | 1 | 71.67 | C |
| ATOM | 348 | C | TYR | A | 278 | −0.985 | −11.526 | −14.028 | 1 | 70.51 | C |
| ATOM | 349 | O | TYR | A | 278 | 0.056 | −11.032 | −14.472 | 1 | 70.03 | O |
| ATOM | 350 | N | VAL | A | 279 | −2.063 | −11.773 | −14.768 | 1 | 70.01 | N |
| ATOM | 351 | CA | VAL | A | 279 | −2.174 | −11.396 | −16.158 | 1 | 69.76 | C |
| ATOM | 352 | CB | VAL | A | 279 | −2.478 | −12.62 | −17.028 | 1 | 69.4 | C |
| ATOM | 353 | CG1 | VAL | A | 279 | −2.518 | −12.242 | −18.484 | 1 | 69.06 | C |
| ATOM | 354 | CG2 | VAL | A | 279 | −1.433 | −13.686 | −16.799 | 1 | 68.99 | C |
| ATOM | 355 | C | VAL | A | 279 | −3.289 | −10.364 | −16.255 | 1 | 69.83 | C |
| ATOM | 356 | O | VAL | A | 279 | −4.469 | −10.692 | −16.12 | 1 | 70.34 | O |
| ATOM | 357 | N | ASP | A | 280 | −2.901 | −9.109 | −16.458 | 1 | 69.96 | N |
| ATOM | 358 | CA | ASP | A | 280 | −3.831 | −7.975 | −16.536 | 1 | 70.06 | C |
| ATOM | 359 | CB | ASP | A | 280 | −4.78 | −8.12 | −17.746 | 1 | 69.77 | C |
| ATOM | 360 | CG | ASP | A | 280 | −4.131 | −7.717 | −19.066 | 1 | 68.61 | C |
| ATOM | 361 | OD1 | ASP | A | 280 | −3.072 | −7.049 | −19.078 | 1 | 67.5 | O |
| ATOM | 362 | OD2 | ASP | A | 280 | −4.713 | −8.058 | −20.101 | 1 | 67.15 | O |
| ATOM | 363 | C | ASP | A | 280 | −4.623 | −7.791 | −15.239 | 1 | 70.43 | C |
| ATOM | 364 | O | ASP | A | 280 | −5.817 | −7.509 | −15.27 | 1 | 70.78 | O |
| ATOM | 365 | N | GLY | A | 281 | −3.946 | −7.936 | −14.103 | 1 | 70.7 | N |
| ATOM | 366 | CA | GLY | A | 281 | −4.584 | −7.842 | −12.79 | 1 | 70.89 | C |
| ATOM | 367 | C | GLY | A | 281 | −5.18 | −9.152 | −12.28 | 1 | 71.27 | C |
| ATOM | 368 | O | GLY | A | 281 | −5.265 | −9.363 | −11.072 | 1 | 71.6 | O |
| ATOM | 369 | N | VAL | A | 282 | −5.587 | −10.035 | −13.189 | 1 | 71.43 | N |
| ATOM | 370 | CA | VAL | A | 282 | −6.3 | −11.252 | −12.814 | 1 | 71.62 | C |
| ATOM | 371 | CB | VAL | A | 282 | −7.196 | −11.754 | −13.963 | 1 | 71.53 | C |
| ATOM | 372 | CG1 | VAL | A | 282 | −8.126 | −12.828 | −13.46 | 1 | 71.22 | C |
| ATOM | 373 | CG2 | VAL | A | 282 | −7.982 | −10.615 | −14.58 | 1 | 71.65 | C |
| ATOM | 374 | C | VAL | A | 282 | −5.316 | −12.365 | −12.469 | 1 | 71.94 | C |
| ATOM | 375 | O | VAL | A | 282 | −4.474 | −12.724 | −13.288 | 1 | 72.24 | O |
| ATOM | 376 | N | GLU | A | 283 | −5.434 | −12.938 | −11.277 | 1 | 72.12 | N |
| ATOM | 377 | CA | GLU | A | 283 | −4.469 | −13.954 | −10.831 | 1 | 72.14 | C |
| ATOM | 378 | CB | GLU | A | 283 | −4.667 | −14.312 | −9.347 | 1 | 72.03 | C |
| ATOM | 379 | CG | GLU | A | 283 | −3.434 | −14.937 | −8.716 | 1 | 72.08 | C |
| ATOM | 380 | CD | GLU | A | 283 | −3.574 | −15.213 | −7.22 | 1 | 71.94 | C |
| ATOM | 381 | OE1 | GLU | A | 283 | −4.708 | −15.185 | −6.706 | 1 | 71.84 | O |
| ATOM | 382 | OE2 | GLU | A | 283 | −2.542 | −15.473 | −6.562 | 1 | 70.7 | O |
| ATOM | 383 | C | GLU | A | 283 | −4.53 | −15.211 | −11.705 | 1 | 72.12 | C |
| ATOM | 384 | O | GLU | A | 283 | −5.601 | −15.61 | −12.147 | 1 | 71.99 | O |
| ATOM | 385 | N | VAL | A | 284 | −3.365 | −15.795 | −11.978 | 1 | 72.24 | N |
| ATOM | 386 | CA | VAL | A | 284 | −3.264 | −17.065 | −12.715 | 1 | 72.41 | C |
| ATOM | 387 | CB | VAL | A | 284 | −2.635 | −16.917 | −14.146 | 1 | 72.22 | C |
| ATOM | 388 | CG1 | VAL | A | 284 | −3.589 | −16.189 | −15.073 | 1 | 71.65 | C |
| ATOM | 389 | CG2 | VAL | A | 284 | −1.264 | −16.233 | −14.095 | 1 | 71.52 | C |
| ATOM | 390 | C | VAL | A | 284 | −2.422 | −18.003 | −11.883 | 1 | 72.48 | C |
| ATOM | 391 | O | VAL | A | 284 | −1.677 | −17.551 | −11.01 | 1 | 72.61 | O |
| ATOM | 392 | N | HIS | A | 285 | −2.545 | −19.301 | −12.142 | 1 | 72.86 | N |
| ATOM | 393 | CA | HIS | A | 285 | −1.936 | −20.306 | −11.263 | 1 | 73.5 | C |
| ATOM | 394 | CB | HIS | A | 285 | −3.014 | −20.943 | −10.368 | 1 | 73.7 | C |
| ATOM | 395 | CG | HIS | A | 285 | −3.742 | −19.95 | −9.512 | 1 | 73.91 | C |
| ATOM | 396 | ND1 | HIS | A | 285 | −3.254 | −19.516 | −8.298 | 1 | 74.71 | N |
| ATOM | 397 | CE1 | HIS | A | 285 | −4.088 | −18.627 | −7.783 | 1 | 75.22 | C |
| ATOM | 398 | NE2 | HIS | A | 285 | −5.094 | −18.462 | −8.623 | 1 | 75.02 | N |
| ATOM | 399 | CD2 | HIS | A | 285 | −4.902 | −19.28 | −9.711 | 1 | 74.34 | C |

TABLE V-continued

Atomic Structure Coordinates of Fc/YTE (SEQ ID NO: 11)

| | Atom | A.A. | Type | | X | Y | Z | Occ | B | |
|---|---|---|---|---|---|---|---|---|---|---|
| ATOM | 400 | C | HIS | A | 285 | −1.129 | −21.385 | −11.965 | 1 | 73.83 C |
| ATOM | 401 | O | HIS | A | 285 | −0.54 | −22.23 | −11.288 | 1 | 73.95 O |
| ATOM | 402 | N | ASN | A | 286 | −1.063 | −21.337 | −13.298 | 1 | 74.38 N |
| ATOM | 403 | CA | ASN | A | 286 | −0.285 | −22.305 | −14.074 | 1 | 75.05 C |
| ATOM | 404 | CB | ASN | A | 286 | −0.762 | −22.392 | −15.539 | 1 | 74.59 C |
| ATOM | 405 | CG | ASN | A | 286 | −0.542 | −21.1 | −16.334 | 1 | 74.45 C |
| ATOM | 406 | OD1 | ASN | A | 286 | −0.868 | −20.007 | −15.881 | 1 | 74.07 O |
| ATOM | 407 | ND2 | ASN | A | 286 | −0.019 | −21.236 | −17.542 | 1 | 74.3 N |
| ATOM | 408 | C | ASN | A | 286 | 1.216 | −22.052 | −14.007 | 1 | 75.79 C |
| ATOM | 409 | O | ASN | A | 286 | 1.985 | −22.704 | −14.704 | 1 | 75.88 O |
| ATOM | 410 | N | ALA | A | 287 | 1.638 | −21.126 | −13.154 | 1 | 77.14 N |
| ATOM | 411 | CA | ALA | A | 287 | 3.055 | −20.851 | −12.962 | 1 | 78.59 C |
| ATOM | 412 | CB | ALA | A | 287 | 3.234 | −19.734 | −11.949 | 1 | 78.51 C |
| ATOM | 413 | C | ALA | A | 287 | 3.794 | −22.099 | −12.501 | 1 | 79.89 C |
| ATOM | 414 | O | ALA | A | 287 | 3.202 | −22.969 | −11.863 | 1 | 80.26 O |
| ATOM | 415 | N | LYS | A | 288 | 5.084 | −22.171 | −12.812 | 1 | 81.56 N |
| ATOM | 416 | CA | LYS | A | 288 | 5.905 | −23.33 | −12.48 | 1 | 83.04 C |
| ATOM | 417 | CB | LYS | A | 288 | 6.214 | −24.123 | −13.753 | 1 | 83.16 C |
| ATOM | 418 | CG | LYS | A | 288 | 4.954 | −24.679 | −14.42 | 1 | 83.45 C |
| ATOM | 419 | CD | LYS | A | 288 | 5.199 | −26.035 | −15.066 | 1 | 83.8 C |
| ATOM | 420 | CE | LYS | A | 288 | 3.87 | −26.728 | −15.354 | 1 | 84.17 C |
| ATOM | 421 | NZ | LYS | A | 288 | 4.039 | −28.186 | −15.601 | 1 | 84.09 N |
| ATOM | 422 | C | LYS | A | 288 | 7.191 | −22.923 | −11.753 | 1 | 84.19 C |
| ATOM | 423 | O | LYS | A | 288 | 8.161 | −22.505 | −12.376 | 1 | 84 O |
| ATOM | 424 | N | THR | A | 289 | 7.187 | −23.029 | −10.43 | 1 | 85.89 N |
| ATOM | 425 | CA | THR | A | 289 | 8.302 | −22.618 | −9.601 | 1 | 87.35 C |
| ATOM | 426 | CB | THR | A | 289 | 7.793 | −22.048 | −8.271 | 1 | 87.17 C |
| ATOM | 427 | CG1 | THR | A | 289 | 6.671 | −21.191 | −8.504 | 1 | 86.73 O |
| ATOM | 428 | CG2 | THR | A | 289 | 8.904 | −21.265 | −7.583 | 1 | 86.46 C |
| ATOM | 429 | C | THR | A | 289 | 9.318 | −23.74 | −9.34 | 1 | 89.02 C |
| ATOM | 430 | O | THR | A | 289 | 8.949 | −24.868 | −8.988 | 1 | 88.84 O |
| ATOM | 431 | N | LYS | A | 290 | 10.597 | −23.405 | −9.529 | 1 | 91.09 N |
| ATOM | 432 | CA | LYS | A | 290 | 11.708 | −24.338 | −9.322 | 1 | 92.71 C |
| ATOM | 433 | CB | LYS | A | 290 | 12.814 | −24.107 | −10.375 | 1 | 92.78 C |
| ATOM | 434 | CG | LYS | A | 290 | 12.302 | −23.892 | −11.807 | 1 | 92.98 C |
| ATOM | 435 | CD | LYS | A | 290 | 13.429 | −23.818 | −12.843 | 1 | 92.65 C |
| ATOM | 436 | CE | LYS | A | 290 | 12.924 | −23.315 | −14.196 | 1 | 92.33 C |
| ATOM | 437 | NZ | LYS | A | 290 | 11.648 | −23.964 | −14.609 | 1 | 91.82 N |
| ATOM | 438 | C | LYS | A | 290 | 12.295 | −24.225 | −7.932 | 1 | 94.46 C |
| ATOM | 439 | O | LYS | A | 290 | 11.919 | −23.378 | −7.124 | 1 | 94.6 O |
| ATOM | 440 | N | PRO | A | 291 | 13.238 | −25.132 | −7.722 | 1 | 96.58 N |
| ATOM | 441 | CA | PRO | A | 291 | 13.917 | −25.221 | −6.439 | 1 | 97.74 C |
| ATOM | 442 | CB | PRO | A | 291 | 13.585 | −26.616 | −5.91 | 1 | 97.72 C |
| ATOM | 443 | CG | PRO | A | 291 | 12.994 | −27.344 | −7.062 | 1 | 97.26 C |
| ATOM | 444 | CD | PRO | A | 291 | 13.238 | −26.488 | −8.278 | 1 | 96.7 C |
| ATOM | 445 | C | PRO | A | 291 | 15.439 | −25.021 | −6.463 | 1 | 99.18 C |
| ATOM | 446 | O | PRO | A | 291 | 16.179 | −25.504 | −7.315 | 1 | 99.19 O |
| ATOM | 447 | N | ARG | A | 292 | 15.787 | −24.255 | −5.415 | 1 | 100.87 N |
| ATOM | 448 | CA | ARG | A | 292 | 17.096 | −23.855 | −4.883 | 1 | 102.18 C |
| ATOM | 449 | CB | ARG | A | 292 | 17.446 | −24.889 | −3.803 | 1 | 102.28 C |
| ATOM | 450 | CG | ARG | A | 292 | 16.286 | −25.34 | −2.972 | 1 | 102.39 C |
| ATOM | 451 | CD | ARG | A | 292 | 15.742 | −24.125 | −2.246 | 1 | 102.57 C |
| ATOM | 452 | NE | ARG | A | 292 | 14.629 | −24.453 | −1.38 | 1 | 102.78 N |
| ATOM | 453 | CZ | ARG | A | 292 | 14.17 | −23.616 | −0.458 | 1 | 103.3 C |
| ATOM | 454 | NH1 | ARG | A | 292 | 14.728 | −22.424 | −0.308 | 1 | 103.42 N |
| ATOM | 455 | NH2 | ARG | A | 292 | 13.152 | −23.972 | 0.313 | 1 | 103.44 N |
| ATOM | 456 | C | ARG | A | 292 | 18.309 | −23.731 | −5.765 | 1 | 103.4 C |
| ATOM | 457 | O | ARG | A | 292 | 18.867 | −24.753 | −6.154 | 1 | 103.43 O |
| ATOM | 458 | N | GLU | A | 293 | 18.748 | −22.526 | −6.087 | 1 | 104.94 N |
| ATOM | 459 | CA | GLU | A | 293 | 19.989 | −22.347 | −6.865 | 1 | 106.2 C |
| ATOM | 460 | CB | GLU | A | 293 | 19.665 | −21.815 | −8.253 | 1 | 106.4 C |
| ATOM | 461 | CG | GLU | A | 293 | 18.777 | −22.729 | −9.088 | 1 | 106.81 C |
| ATOM | 462 | CD | GLU | A | 293 | 17.905 | −21.942 | −10.057 | 1 | 106.67 C |
| ATOM | 463 | OE1 | GLU | A | 293 | 17.648 | −20.741 | −9.78 | 1 | 106.83 O |
| ATOM | 464 | OE2 | GLU | A | 293 | 17.478 | −22.517 | −11.088 | 1 | 106.88 O |
| ATOM | 465 | C | GLU | A | 293 | 20.958 | −21.459 | −6.056 | 1 | 107.34 C |
| ATOM | 466 | O | GLU | A | 293 | 21.557 | −20.515 | −6.577 | 1 | 107.25 O |
| ATOM | 467 | N | GLU | A | 294 | 21.087 | −21.81 | −4.759 | 1 | 108.68 N |
| ATOM | 468 | CA | GLU | A | 294 | 21.942 | −21.067 | −3.839 | 1 | 109.28 C |
| ATOM | 469 | CB | GLU | A | 294 | 22.027 | −21.778 | −2.48 | 1 | 109.33 C |
| ATOM | 470 | CG | GLU | A | 294 | 22.884 | −21.081 | −1.422 | 1 | 109.12 C |
| ATOM | 471 | CD | GLU | A | 294 | 22.836 | −21.792 | −0.069 | 1 | 109.38 C |
| ATOM | 472 | OE1 | GLU | A | 294 | 23.849 | −21.744 | 0.668 | 1 | 109.25 O |
| ATOM | 473 | OE2 | GLU | A | 294 | 21.789 | −22.402 | 0.256 | 1 | 109.34 O |
| ATOM | 474 | C | GLU | A | 294 | 23.345 | −20.816 | −4.402 | 1 | 110.1 C |
| ATOM | 475 | O | GLU | A | 294 | 24.25 | −21.641 | −4.249 | 1 | 109.98 O |

TABLE V-continued

Atomic Structure Coordinates of Fc/YTE (SEQ ID NO: 11)

| | Atom | A.A. | Type | | X | Y | Z | Occ | B | |
|---|---|---|---|---|---|---|---|---|---|---|
| ATOM | 476 | N | GLN | A | 295 | 23.502 | −19.666 | −5.063 | 1 | 110.96 N |
| ATOM | 477 | CA | GLN | A | 295 | 24.793 | −19.251 | −5.621 | 1 | 111.4 C |
| ATOM | 478 | CB | GLN | A | 295 | 24.638 | −18.026 | −6.543 | 1 | 111.73 C |
| ATOM | 479 | CG | GLN | A | 295 | 24.058 | −18.335 | −7.93 | 1 | 112.05 C |
| ATOM | 480 | CD | GLN | A | 295 | 25.05 | −18.853 | −8.945 | 1 | 112.31 C |
| ATOM | 481 | OE1 | GLN | A | 295 | 26.072 | −18.211 | −9.204 | 1 | 112.63 O |
| ATOM | 482 | NE2 | GLN | A | 295 | 24.766 | −20.012 | −9.532 | 1 | 112.2 N |
| ATOM | 483 | C | GLN | A | 295 | 25.767 | −18.979 | −4.488 | 1 | 111.85 C |
| ATOM | 484 | O | GLN | A | 295 | 25.383 | −18.686 | −3.354 | 1 | 111.99 O |
| ATOM | 485 | N | TYR | A | 296 | 27.058 | −19.093 | −4.804 | 1 | 112.07 N |
| ATOM | 486 | CA | TYR | A | 296 | 28.108 | −18.928 | −3.789 | 1 | 112.03 C |
| ATOM | 487 | CB | TYR | A | 296 | 29.461 | −19.405 | −4.339 | 1 | 112.44 C |
| ATOM | 488 | CG | TYR | A | 296 | 29.665 | −20.907 | −4.219 | 1 | 112.86 C |
| ATOM | 489 | CD1 | TYR | A | 296 | 28.669 | −21.809 | −4.61 | 1 | 112.22 C |
| ATOM | 490 | CE1 | TYR | A | 296 | 28.857 | −23.181 | −4.502 | 1 | 112.2 C |
| ATOM | 491 | CZ | TYR | A | 296 | 30.051 | −23.671 | −4 | 1 | 112.97 C |
| ATOM | 492 | OH | TYR | A | 296 | 30.255 | −25.026 | −3.887 | 1 | 112.69 O |
| ATOM | 493 | CE2 | TYR | A | 296 | 31.053 | −22.802 | −3.606 | 1 | 113.67 C |
| ATOM | 494 | CD2 | TYR | A | 296 | 30.858 | −21.427 | −3.72 | 1 | 113.59 C |
| ATOM | 495 | C | TYR | A | 296 | 28.231 | −17.516 | −3.215 | 1 | 112.01 C |
| ATOM | 496 | O | TYR | A | 296 | 28.958 | −16.649 | −3.723 | 1 | 112.11 O |
| ATOM | 497 | N | ASN | A | 297 | 27.523 | −17.336 | −2.115 | 1 | 111.61 N |
| ATOM | 498 | CA | ASN | A | 297 | 27.508 | −16.112 | −1.295 | 1 | 111.13 C |
| ATOM | 499 | CB | ASN | A | 297 | 26.778 | −14.952 | −1.976 | 1 | 111.47 C |
| ATOM | 500 | CG | ASN | A | 297 | 25.471 | −15.322 | −2.617 | 1 | 112.51 C |
| ATOM | 501 | OD1 | ASN | A | 297 | 24.641 | −15.99 | −1.995 | 1 | 112.88 O |
| ATOM | 502 | ND2 | ASN | A | 297 | 25.267 | −14.899 | −3.843 | 1 | 113.86 N |
| ATOM | 503 | C | ASN | A | 297 | 26.873 | −16.381 | 0.059 | 1 | 110.56 C |
| ATOM | 504 | O | ASN | A | 297 | 27.062 | −15.606 | 0.992 | 1 | 110.48 O |
| ATOM | 505 | N | SER | A | 298 | 26.108 | −17.476 | 0.213 | 1 | 109.73 N |
| ATOM | 506 | CA | SER | A | 298 | 25.382 | −17.734 | 1.422 | 1 | 108.98 C |
| ATOM | 507 | CB | SER | A | 298 | 26.212 | −17.296 | 2.643 | 1 | 109.15 C |
| ATOM | 508 | OG | SER | A | 298 | 27.229 | −18.238 | 2.937 | 1 | 109.46 O |
| ATOM | 509 | C | SER | A | 298 | 24.014 | −17.061 | 1.355 | 1 | 108.26 C |
| ATOM | 510 | O | SER | A | 298 | 23.536 | −16.506 | 2.338 | 1 | 108.33 O |
| ATOM | 511 | N | THR | A | 299 | 23.394 | −17.134 | 0.17 | 1 | 107.11 N |
| ATOM | 512 | CA | THR | A | 299 | 22.005 | −16.667 | −0.059 | 1 | 105.78 C |
| ATOM | 513 | CB | THR | A | 299 | 21.941 | −15.164 | −0.439 | 1 | 105.92 C |
| ATOM | 514 | OG1 | THR | A | 299 | 23.128 | −14.793 | −1.151 | 1 | 105.73 O |
| ATOM | 515 | CG2 | THR | A | 299 | 21.792 | −14.285 | 0.8 | 1 | 105.97 C |
| ATOM | 516 | C | THR | A | 299 | 21.327 | −17.47 | −1.178 | 1 | 104.73 C |
| ATOM | 517 | O | THR | A | 299 | 21.978 | −17.829 | −2.172 | 1 | 104.86 O |
| ATOM | 518 | N | TYR | A | 300 | 20.023 | −17.73 | −1.027 | 1 | 103.03 N |
| ATOM | 519 | CA | TYR | A | 300 | 19.262 | −18.524 | −2.017 | 1 | 101.23 C |
| ATOM | 520 | CB | TYR | A | 300 | 17.976 | −19.091 | −1.404 | 1 | 102.28 C |
| ATOM | 521 | CG | TYR | A | 300 | 18.143 | −20.07 | −0.258 | 1 | 102.87 C |
| ATOM | 522 | CD1 | TYR | A | 300 | 17.922 | −19.666 | 1.066 | 1 | 103.49 C |
| ATOM | 523 | CE1 | TYR | A | 300 | 18.049 | −20.561 | 2.13 | 1 | 103.3 C |
| ATOM | 524 | CZ | TYR | A | 300 | 18.386 | −21.883 | 1.874 | 1 | 103.47 C |
| ATOM | 525 | OH | TYR | A | 300 | 18.512 | −22.764 | 2.93 | 1 | 103.32 O |
| ATOM | 526 | CE2 | TYR | A | 300 | 18.595 | −22.316 | 0.563 | 1 | 103.37 C |
| ATOM | 527 | CD2 | TYR | A | 300 | 18.466 | −21.41 | −0.494 | 1 | 103.22 C |
| ATOM | 528 | C | TYR | A | 300 | 18.855 | −17.738 | −3.283 | 1 | 99.21 C |
| ATOM | 529 | O | TYR | A | 300 | 18.673 | −16.514 | −3.244 | 1 | 99.06 O |
| ATOM | 530 | N | ARG | A | 301 | 18.696 | −18.479 | −4.383 | 1 | 96.08 N |
| ATOM | 531 | CA | ARG | A | 301 | 18.121 | −17.977 | −5.627 | 1 | 94.02 C |
| ATOM | 532 | CB | ARG | A | 301 | 19.179 | −17.981 | −6.727 | 1 | 94.12 C |
| ATOM | 533 | CG | ARG | A | 301 | 18.662 | −17.67 | −8.129 | 1 | 94.77 C |
| ATOM | 534 | CD | ARG | A | 301 | 19.797 | −17.733 | −9.136 | 1 | 94.24 C |
| ATOM | 535 | NE | ARG | A | 301 | 19.464 | −17.056 | −10.392 | 1 | 94.4 N |
| ATOM | 536 | CZ | ARG | A | 301 | 19.127 | −17.657 | −11.535 | 1 | 94.17 C |
| ATOM | 537 | NH1 | ARG | A | 301 | 19.047 | −18.979 | −11.625 | 1 | 94.1 N |
| ATOM | 538 | NH2 | ARG | A | 301 | 18.861 | −16.917 | −12.607 | 1 | 94.1 N |
| ATOM | 539 | C | ARG | A | 301 | 16.963 | −18.887 | −6.037 | 1 | 91.77 C |
| ATOM | 540 | O | ARG | A | 301 | 17.154 | −20.1 | −6.152 | 1 | 91.76 O |
| ATOM | 541 | N | VAL | A | 302 | 15.778 | −18.309 | −6.267 | 1 | 88.74 N |
| ATOM | 542 | CA | VAL | A | 302 | 14.602 | −19.08 | −6.709 | 1 | 86.24 C |
| ATOM | 543 | CB | VAL | A | 302 | 13.525 | −19.151 | −5.625 | 1 | 86.3 C |
| ATOM | 544 | CG1 | VAL | A | 302 | 12.653 | −20.397 | −5.833 | 1 | 86.11 C |
| ATOM | 545 | CG2 | VAL | A | 302 | 14.165 | −19.142 | −4.249 | 1 | 86.32 C |
| ATOM | 546 | C | VAL | A | 302 | 13.956 | −18.484 | −7.961 | 1 | 83.91 C |
| ATOM | 547 | O | VAL | A | 302 | 13.747 | −17.267 | −8.044 | 1 | 84.15 O |
| ATOM | 548 | N | VAL | A | 303 | 13.617 | −19.349 | −8.916 | 1 | 80.73 N |
| ATOM | 549 | CA | VAL | A | 303 | 13.117 | −18.926 | −10.228 | 1 | 77.99 C |
| ATOM | 550 | CB | VAL | A | 303 | 14.088 | −19.378 | −11.344 | 1 | 77.81 C |
| ATOM | 551 | CG1 | VAL | A | 303 | 13.551 | −19.042 | −12.717 | 1 | 77.44 C |

TABLE V-continued

Atomic Structure Coordinates of Fc/YTE (SEQ ID NO: 11)

| | | Atom | A.A. | Type | | X | Y | Z | Occ | B | |
|---|---|---|---|---|---|---|---|---|---|---|---|
| ATOM | 552 | CG2 | VAL | A | 303 | 15.437 | −18.726 | −11.142 | 1 | 78.19 | C |
| ATOM | 553 | C | VAL | A | 303 | 11.716 | −19.483 | −10.492 | 1 | 75.48 | C |
| ATOM | 554 | O | VAL | A | 303 | 11.487 | −20.699 | −10.413 | 1 | 75.23 | O |
| ATOM | 555 | N | SER | A | 304 | 10.776 | −18.588 | −10.79 | 1 | 72.39 | N |
| ATOM | 556 | CA | SER | A | 304 | 9.457 | −18.996 | −11.26 | 1 | 70.04 | C |
| ATOM | 557 | CB | SER | A | 304 | 8.364 | −18.386 | −10.396 | 1 | 69.85 | C |
| ATOM | 558 | OG | SER | A | 304 | 7.125 | −19.038 | −10.622 | 1 | 69.78 | O |
| ATOM | 559 | C | SER | A | 304 | 9.254 | −18.615 | −12.731 | 1 | 67.72 | C |
| ATOM | 560 | O | SER | A | 304 | 9.638 | −17.529 | −13.163 | 1 | 67.17 | O |
| ATOM | 561 | N | VAL | A | 305 | 8.647 | −19.535 | −13.479 | 1 | 65.36 | N |
| ATOM | 562 | CA | VAL | A | 305 | 8.446 | −19.413 | −14.913 | 1 | 63.45 | C |
| ATOM | 563 | CB | VAL | A | 305 | 9.119 | −20.559 | −15.654 | 1 | 63.06 | C |
| ATOM | 564 | CG1 | VAL | A | 305 | 8.959 | −20.395 | −17.16 | 1 | 62.17 | C |
| ATOM | 565 | CG2 | VAL | A | 305 | 10.569 | −20.62 | −15.273 | 1 | 63.31 | C |
| ATOM | 566 | C | VAL | A | 305 | 6.969 | −19.503 | −15.202 | 1 | 61.79 | C |
| ATOM | 567 | O | VAL | A | 305 | 6.322 | −20.489 | −14.838 | 1 | 61.45 | O |
| ATOM | 568 | N | LEU | A | 306 | 6.44 | −18.458 | −15.839 | 1 | 60.06 | N |
| ATOM | 569 | CA | LEU | A | 306 | 5.051 | −18.425 | −16.281 | 1 | 58.8 | C |
| ATOM | 570 | CB | LEU | A | 306 | 4.363 | −17.112 | −15.89 | 1 | 58.87 | C |
| ATOM | 571 | CG | LEU | A | 306 | 2.927 | −16.919 | −16.401 | 1 | 59.29 | C |
| ATOM | 572 | CD1 | LEU | A | 306 | 2.078 | −18.1 | −15.979 | 1 | 59.79 | C |
| ATOM | 573 | CD2 | LEU | A | 306 | 2.314 | −15.621 | −15.916 | 1 | 58.1 | C |
| ATOM | 574 | C | LEU | A | 306 | 5.059 | −18.611 | −17.782 | 1 | 57.47 | C |
| ATOM | 575 | O | LEU | A | 306 | 5.743 | −17.91 | −18.509 | 1 | 57.7 | O |
| ATOM | 576 | N | THR | A | 307 | 4.332 | −19.612 | −18.228 | 1 | 56.22 | N |
| ATOM | 577 | CA | THR | A | 307 | 4.198 | −19.916 | −19.635 | 1 | 55.43 | C |
| ATOM | 578 | CB | THR | A | 307 | 3.681 | −21.343 | −19.832 | 1 | 55.3 | C |
| ATOM | 579 | OG1 | THR | A | 307 | 4.797 | −22.258 | −19.84 | 1 | 55.4 | O |
| ATOM | 580 | CG2 | THR | A | 307 | 2.898 | −21.438 | −21.135 | 1 | 55.44 | C |
| ATOM | 581 | C | THR | A | 307 | 3.18 | −18.957 | −20.188 | 1 | 54.38 | C |
| ATOM | 582 | O | THR | A | 307 | 2.115 | −18.823 | −19.604 | 1 | 54.76 | O |
| ATOM | 583 | N | VAL | A | 308 | 3.5 | −18.278 | −21.282 | 1 | 52.88 | N |
| ATOM | 584 | CA | VAL | A | 308 | 2.578 | −17.305 | −21.844 | 1 | 52.43 | C |
| ATOM | 585 | CB | VAL | A | 308 | 3.225 | −15.899 | −22.001 | 1 | 52.57 | C |
| ATOM | 586 | CG1 | VAL | A | 308 | 3.829 | −15.406 | −20.638 | 1 | 51.57 | C |
| ATOM | 587 | CG2 | VAL | A | 308 | 4.257 | −15.915 | −23.157 | 1 | 51.87 | C |
| ATOM | 588 | C | VAL | A | 308 | 2.048 | −17.732 | −23.2 | 1 | 50.88 | C |
| ATOM | 589 | O | VAL | A | 308 | 2.709 | −18.403 | −23.983 | 1 | 50.26 | O |
| ATOM | 590 | N | LEU | A | 309 | 0.842 | −17.297 | −23.486 | 1 | 49.78 | N |
| ATOM | 591 | CA | LEU | A | 309 | 0.274 | −17.522 | −24.797 | 1 | 49.04 | C |
| ATOM | 592 | CB | LEU | A | 309 | −1.248 | −17.503 | −24.722 | 1 | 49.14 | C |
| ATOM | 593 | CG | LEU | A | 309 | −1.798 | −18.751 | −24.038 | 1 | 49.35 | C |
| ATOM | 594 | CD1 | LEU | A | 309 | −3.231 | −18.47 | −23.463 | 1 | 49.8 | C |
| ATOM | 595 | CD2 | LEU | A | 309 | −1.761 | −19.906 | −25.03 | 1 | 48.85 | C |
| ATOM | 596 | C | LEU | A | 309 | 0.772 | −16.456 | −25.75 | 1 | 48.59 | C |
| ATOM | 597 | O | LEU | A | 309 | 0.848 | −15.261 | −25.401 | 1 | 48.66 | O |
| ATOM | 598 | N | HIS | A | 310 | 1.07 | −16.891 | −26.965 | 1 | 47.9 | N |
| ATOM | 599 | CA | HIS | A | 310 | 1.675 | −16.034 | −27.97 | 1 | 47.68 | C |
| ATOM | 600 | CB | HIS | A | 310 | 1.864 | −16.805 | −29.279 | 1 | 47.48 | C |
| ATOM | 601 | CG | HIS | A | 310 | 2.721 | −18.03 | −29.152 | 1 | 47.69 | C |
| ATOM | 602 | ND1 | HIS | A | 310 | .2.273 | −19.207 | −28.584 | 1 | 48.37 | N |
| ATOM | 603 | CE1 | HIS | A | 310 | 3.239 | −20.103 | −28.605 | 1 | 47.1 | C |
| ATOM | 604 | NE2 | HIS | A | 310 | 4.293 | −19.556 | −29.182 | 1 | 47.36 | N |
| ATOM | 605 | CD2 | HIS | A | 310 | 3.996 | −18.263 | −29.53 | 1 | 47.29 | C |
| ATOM | 606 | C | HIS | A | 310 | 0.833 | −14.759 | −28.172 | 1 | 47.39 | C |
| ATOM | 607 | O | HIS | A | 310 | 1.358 | −13.651 | −28.029 | 1 | 46.83 | O |
| ATOM | 608 | N | GLN | A | 311 | −0.465 | −14.924 | −28.451 | 1 | 47.34 | N |
| ATOM | 609 | CA | GLN | A | 311 | −1.394 | −13.774 | −28.675 | 1 | 47.53 | C |
| ATOM | 610 | CB | GLN | A | 311 | −2.829 | −14.233 | −29.022 | 1 | 47.62 | C |
| ATOM | 611 | CG | GLN | A | 311 | −3.068 | −14.569 | −30.481 | 1 | 50.67 | C |
| ATOM | 612 | CD | GLN | A | 311 | −4.5 | −15.123 | −30.771 | 1 | 52.84 | C |
| ATOM | 613 | OE1 | GLN | A | 311 | −5.477 | −14.824 | −30.051 | 1 | 59.19 | O |
| ATOM | 614 | NE2 | GLN | A | 311 | −4.617 | −15.926 | −31.843 | 1 | 58.3 | N |
| ATOM | 615 | C | GLN | A | 311 | −1.494 | −12.837 | −27.481 | 1 | 45.98 | C |
| ATOM | 616 | O | GLN | A | 311 | −1.657 | −11.639 | −27.66 | 1 | 46.03 | O |
| ATOM | 617 | N | ASP | A | 312 | −1.441 | −13.372 | −26.269 | 1 | 44.87 | N |
| ATOM | 618 | CA | ASP | A | 312 | −1.553 | −12.524 | −25.075 | 1 | 44.26 | C |
| ATOM | 619 | CB | ASP | A | 312 | −1.556 | −13.342 | −23.775 | 1 | 44.42 | C |
| ATOM | 620 | CG | ASP | A | 312 | −2.845 | −14.133 | −23.541 | 1 | 44.76 | C |
| ATOM | 621 | OD1 | ASP | A | 312 | −3.891 | −13.828 | −24.141 | 1 | 45.72 | O |
| ATOM | 622 | OD2 | ASP | A | 312 | −2.804 | −15.075 | −22.721 | 1 | 45.22 | O |
| ATOM | 623 | C | ASP | A | 312 | −0.397 | −11.553 | −25.022 | 1 | 43.37 | C |
| ATOM | 624 | O | ASP | A | 312 | −0.565 | −10.367 | −24.767 | 1 | 44.25 | O |
| ATOM | 625 | N | TRP | A | 313 | 0.806 | −12.049 | −25.234 | 1 | 42.51 | N |
| ATOM | 626 | CA | TRP | A | 313 | 1.969 | −11.162 | −25.236 | 1 | 41.61 | C |
| ATOM | 627 | CB | TRP | A | 313 | 3.27 | −11.947 | −25.425 | 1 | 39.94 | C |

TABLE V-continued

Atomic Structure Coordinates of Fc/YTE (SEQ ID NO: 11)

| | | Atom | A.A. | Type | | X | Y | Z | Occ | B | |
|---|---|---|---|---|---|---|---|---|---|---|---|
| ATOM | 628 | CG | TRP | A | 313 | 4.412 | −11.064 | −25.497 | 1 | 39.14 | C |
| ATOM | 629 | CD1 | TRP | A | 313 | 4.961 | −10.537 | −26.626 | 1 | 38.27 | C |
| ATOM | 630 | NE1 | TRP | A | 313 | 6.013 | −9.724 | −26.292 | 1 | 38.53 | N |
| ATOM | 631 | CE2 | TRP | A | 313 | 6.14 | −9.681 | −24.928 | 1 | 37.52 | C |
| ATOM | 632 | CD2 | TRP | A | 313 | 5.139 | −10.514 | −24.391 | 1 | 38.38 | C |
| ATOM | 633 | CE3 | TRP | A | 313 | 5.043 | −10.648 | −23.005 | 1 | 38.28 | C |
| ATOM | 634 | CZ3 | TRP | A | 313 | 5.957 | −9.95 | −22.201 | 1 | 39.09 | C |
| ATOM | 635 | CH2 | TRP | A | 313 | 6.95 | −9.147 | −22.772 | 1 | 38.94 | C |
| ATOM | 636 | CZ2 | TRP | A | 313 | 7.059 | −9.01 | −24.139 | 1 | 38.29 | C |
| ATOM | 637 | C | TRP | A | 313 | 1.828 | −10.099 | −26.321 | 1 | 40.81 | C |
| ATOM | 638 | O | TRP | A | 313 | 2.007 | −8.938 | −26.062 | 1 | 39.84 | O |
| ATOM | 639 | N | LEU | A | 314 | 1.485 | −10.508 | −27.532 | 1 | 41.5 | N |
| ATOM | 640 | CA | LEU | A | 314 | 1.416 | −9.566 | −28.647 | 1 | 42.24 | C |
| ATOM | 641 | CB | LEU | A | 314 | 1.326 | −10.297 | −29.979 | 1 | 41.78 | C |
| ATOM | 642 | CG | LEU | A | 314 | 2.557 | −11.14 | −30.317 | 1 | 42.42 | C |
| ATOM | 643 | CD1 | LEU | A | 314 | 2.333 | −11.953 | −31.588 | 1 | 41.08 | C |
| ATOM | 644 | CD2 | LEU | A | 314 | 3.848 | −10.26 | −30.432 | 1 | 42.93 | C |
| ATOM | 645 | C | LEU | A | 314 | 0.258 | −8.594 | −28.483 | 1 | 42.89 | C |
| ATOM | 646 | O | LEU | A | 314 | 0.317 | −7.489 | −28.98 | 1 | 43.96 | O |
| ATOM | 647 | N | ASN | A | 315 | −0.792 | −9.001 | −27.796 | 1 | 43.32 | N |
| ATOM | 648 | CA | ASN | A | 315 | −1.853 | −8.079 | −27.426 | 1 | 44.24 | C |
| ATOM | 649 | CB | ASN | A | 315 | −3.121 | −8.84 | −27.007 | 1 | 44.68 | C |
| ATOM | 650 | CG | ASN | A | 315 | −3.822 | −9.482 | −28.173 | 1 | 46.04 | C |
| ATOM | 651 | OD1 | ASN | A | 315 | −3.465 | −9.259 | −29.328 | 1 | 48.09 | O |
| ATOM | 652 | ND2 | ASN | A | 315 | −4.837 | −10.281 | −27.881 | 1 | 48.35 | N |
| ATOM | 653 | C | ASN | A | 315 | −1.458 | −7.164 | −26.281 | 1 | 44.84 | C |
| ATOM | 654 | O | ASN | A | 315 | −2.255 | −6.321 | −25.877 | 1 | 45.12 | O |
| ATOM | 655 | N | GLY | A | 316 | −0.262 | −7.329 | −25.729 | 1 | 45.24 | N |
| ATOM | 656 | CA | GLY | A | 316 | 0.247 | −6.362 | −24.776 | 1 | 45.93 | C |
| ATOM | 657 | C | GLY | A | 316 | −0.241 | −6.607 | −23.367 | 1 | 46.62 | C |
| ATOM | 658 | O | GLY | A | 316 | −0.227 | −5.719 | −22.557 | 1 | 46.4 | O |
| ATOM | 659 | N | LYS | A | 317 | −0.648 | −7.827 | −23.056 | 1 | 48.11 | N |
| ATOM | 660 | CA | LYS | A | 317 | −1.068 | −8.133 | −21.699 | 1 | 49.41 | C |
| ATOM | 661 | CB | LYS | A | 317 | −1.65 | −9.544 | −21.611 | 1 | 49.44 | C |
| ATOM | 662 | CG | LYS | A | 317 | −2.802 | −9.769 | −22.586 | 1 | 49.51 | C |
| ATOM | 663 | CD | LYS | A | 317 | −3.888 | −10.66 | −22.03 | 1 | 50.65 | C |
| ATOM | 664 | CE | LYS | A | 317 | −4.902 | −11.082 | −23.129 | 1 | 51.98 | C |
| ATOM | 665 | NZ | LYS | A | 317 | −5.682 | −9.954 | −23.765 | 1 | 54.44 | N |
| ATOM | 666 | C | LYS | A | 317 | 0.08 | −7.917 | −20.701 | 1 | 50.38 | C |
| ATOM | 667 | O | LYS | A | 317 | 1.263 | −8.125 | −21.004 | 1 | 50.09 | O |
| ATOM | 668 | N | GLU | A | 318 | −0.277 | −7.444 | −19.517 | 1 | 51.77 | N |
| ATOM | 669 | CA | GLU | A | 318 | 0.731 | −7.121 | −18.516 | 1 | 53.09 | C |
| ATOM | 670 | CB | GLU | A | 318 | 0.278 | −5.956 | −17.629 | 1 | 53.43 | C |
| ATOM | 671 | CG | GLU | A | 318 | 1.24 | −4.775 | −17.652 | 1 | 55.17 | C |
| ATOM | 672 | CD | GLU | A | 318 | 0.735 | −3.587 | −16.829 | 1 | 56.07 | C |
| ATOM | 673 | OE1 | GLU | A | 318 | −0.355 | −3.037 | −17.152 | 1 | 58.91 | O |
| ATOM | 674 | OE2 | GLU | A | 318 | 1.441 | −3.209 | −15.86 | 1 | 59.64 | O |
| ATOM | 675 | C | GLU | A | 318 | 0.946 | −8.367 | −17.683 | 1 | 53.36 | C |
| ATOM | 676 | O | GLU | A | 318 | −0.021 | −9.023 | −17.33 | 1 | 53.3 | O |
| ATOM | 677 | N | TYR | A | 319 | 2.203 | −8.71 | −17.411 | 1 | 53.76 | N |
| ATOM | 678 | CA | TYR | A | 319 | 2.509 | −9.805 | −16.526 | 1 | 54.43 | C |
| ATOM | 679 | CB | TYR | A | 319 | 3.392 | −10.812 | −17.243 | 1 | 53.24 | C |
| ATOM | 680 | CG | TYR | A | 319 | 2.708 | −11.459 | −18.422 | 1 | 52.45 | C |
| ATOM | 681 | CD1 | TYR | A | 319 | 2.707 | −10.843 | −19.667 | 1 | 52.57 | C |
| ATOM | 682 | CE1 | TYR | A | 319 | 2.062 | −11.421 | −20.75 | 1 | 52.4 | C |
| ATOM | 683 | CZ | TYR | A | 319 | 1.415 | −12.638 | −20.598 | 1 | 51.88 | C |
| ATOM | 684 | OH | TYR | A | 319 | 0.801 | −13.19 | −21.673 | 1 | 51.8 | O |
| ATOM | 685 | CE2 | TYR | A | 319 | 1.414 | −13.285 | −19.376 | 1 | 52.11 | C |
| ATOM | 686 | CD2 | TYR | A | 319 | 2.055 | −12.686 | −18.292 | 1 | 52.03 | C |
| ATOM | 687 | C | TYR | A | 319 | 3.171 | −9.277 | −15.252 | 1 | 55.47 | C |
| ATOM | 688 | O | TYR | A | 319 | 4.148 | −8.541 | −15.312 | 1 | 55.28 | O |
| ATOM | 689 | N | LYS | A | 320 | 2.63 | −9.666 | −14.101 | 1 | 57.51 | N |
| ATOM | 690 | CA | LYS | A | 320 | 3.115 | −9.207 | −12.812 | 1 | 58.96 | C |
| ATOM | 691 | CB | LYS | A | 320 | 2.041 | −8.343 | −12.171 | 1 | 58.89 | C |
| ATOM | 692 | CG | LYS | A | 320 | 2.305 | −7.993 | −10.718 | 1 | 58.84 | C |
| ATOM | 693 | CD | LYS | A | 320 | 1.544 | −6.739 | −10.315 | 1 | 59.21 | C |
| ATOM | 694 | CE | LYS | A | 320 | 0.081 | −7.023 | −10.048 | 1 | 59.52 | C |
| ATOM | 695 | NZ | LYS | A | 320 | −0.533 | −5.921 | −9.238 | 1 | 59.62 | N |
| ATOM | 696 | C | LYS | A | 320 | 3.514 | −10.366 | −11.875 | 1 | 60.61 | C |
| ATOM | 697 | O | LYS | A | 320 | 2.779 | −11.33 | −11.702 | 1 | 60.35 | O |
| ATOM | 698 | N | CYS | A | 321 | 4.695 | −10.246 | −11.275 | 1 | 63.1 | N |
| ATOM | 699 | CA | CYS | A | 321 | 5.234 | −11.226 | −10.339 | 1 | 64.56 | C |
| ATOM | 700 | CB | CYS | A | 321 | 6.66 | −11.611 | −10.754 | 1 | 64.44 | C |
| ATOM | 701 | SG | CYS | A | 321 | 7.52 | −12.65 | −9.53 | 1 | 64.32 | S |
| ATOM | 702 | C | CYS | A | 321 | 5.268 | −10.601 | −8.946 | 1 | 66.35 | C |
| ATOM | 703 | O | CYS | A | 321 | 5.984 | −9.625 | −8.734 | 1 | 65.97 | O |

TABLE V-continued

Atomic Structure Coordinates of Fc/YTE (SEQ ID NO: 11)

| | | Atom | A.A. | Type | | X | Y | Z | Occ | B | |
|---|---|---|---|---|---|---|---|---|---|---|---|
| ATOM | 704 | N | LYS | A | 322 | 4.484 | −11.15 | −8.011 | 1 | 69.02 | N |
| ATOM | 705 | CA | LYS | A | 322 | 4.555 | −10.747 | −6.596 | 1 | 70.61 | C |
| ATOM | 706 | CB | LYS | A | 322 | 3.166 | −10.619 | −5.959 | 1 | 70.58 | C |
| ATOM | 707 | CG | LYS | A | 322 | 3.155 | −9.688 | −4.727 | 1 | 70.15 | C |
| ATOM | 708 | CD | LYS | A | 322 | 2.184 | −10.131 | −3.619 | 1 | 70.91 | C |
| ATOM | 709 | CE | LYS | A | 322 | 0.717 | −9.77 | −3.917 | 1 | 71.63 | C |
| ATOM | 710 | NZ | LYS | A | 322 | −0.214 | −10.159 | −2.797 | 1 | 71.3 | N |
| ATOM | 711 | C | LYS | A | 322 | 5.373 | −11.762 | −5.815 | 1 | 72.36 | C |
| ATOM | 712 | O | LYS | A | 322 | 5.009 | −12.934 | −5.742 | 1 | 72.57 | O |
| ATOM | 713 | N | VAL | A | 323 | 6.487 | −11.315 | −5.251 | 1 | 74.57 | N |
| ATOM | 714 | CA | VAL | A | 323 | 7.31 | −12.165 | −4.397 | 1 | 76.38 | C |
| ATOM | 715 | CB | VAL | A | 323 | 8.798 | −12.046 | −4.772 | 1 | 76.47 | C |
| ATOM | 716 | CG1 | VAL | A | 323 | 9.65 | −12.883 | −3.831 | 1 | 76.23 | C |
| ATOM | 717 | CG2 | VAL | A | 323 | 9.014 | −12.471 | −6.232 | 1 | 76.18 | C |
| ATOM | 718 | C | VAL | A | 323 | 7.102 | −11.8 | −2.92 | 1 | 78.08 | C |
| ATOM | 719 | O | VAL | A | 323 | 7.425 | −10.696 | −2.483 | 1 | 77.74 | O |
| ATOM | 720 | N | SER | A | 324 | 6.55 | −12.74 | −2.162 | 1 | 80.38 | N |
| ATOM | 721 | CA | SER | A | 324 | 6.265 | −12.523 | −0.739 | 1 | 82.21 | C |
| ATOM | 722 | CB | SER | A | 324 | 4.889 | −13.108 | −0.381 | 1 | 82.42 | C |
| ATOM | 723 | OG | SER | A | 324 | 3.906 | −12.748 | −1.345 | 1 | 83.07 | O |
| ATOM | 724 | C | SER | A | 324 | 7.353 | −13.121 | 0.175 | 1 | 83.93 | C |
| ATOM | 725 | O | SER | A | 324 | 7.91 | −14.196 | −0.112 | 1 | 84.08 | O |
| ATOM | 726 | N | ASN | A | 325 | 7.648 | −12.419 | 1.273 | 1 | 85.81 | N |
| ATOM | 727 | CA | ASN | A | 325 | 8.625 | −12.896 | 2.263 | 1 | 86.72 | C |
| ATOM | 728 | CB | ASN | A | 325 | 10.047 | −12.711 | 1.724 | 1 | 86.89 | C |
| ATOM | 729 | CG | ASN | A | 325 | 11.067 | −13.529 | 2.485 | 1 | 86.9 | C |
| ATOM | 730 | OD1 | ASN | A | 325 | 11.391 | −13.222 | 3.636 | 1 | 88.16 | O |
| ATOM | 731 | ND2 | ASN | A | 325 | 11.584 | −14.58 | 1.846 | 1 | 87.35 | N |
| ATOM | 732 | C | ASN | A | 325 | 8.486 | −12.211 | 3.641 | 1 | 87.89 | C |
| ATOM | 733 | O | ASN | A | 325 | 8.21 | −11.013 | 3.726 | 1 | 88.18 | O |
| ATOM | 734 | N | LYS | A | 326 | 8.686 | −12.979 | 4.711 | 1 | 88.95 | N |
| ATOM | 735 | CA | LYS | A | 326 | 8.617 | −12.445 | 6.085 | 1 | 89.46 | C |
| ATOM | 736 | CB | LYS | A | 326 | 8.607 | −13.583 | 7.11 | 1 | 89.88 | C |
| ATOM | 737 | CG | LYS | A | 326 | 7.338 | −14.431 | 7.089 | 1 | 90.4 | C |
| ATOM | 738 | CD | LYS | A | 326 | 7.426 | −15.577 | 8.097 | 1 | 90.45 | C |
| ATOM | 739 | CE | LYS | A | 326 | 6.069 | −16.241 | 8.355 | 1 | 90.94 | C |
| ATOM | 740 | NZ | LYS | A | 326 | 6.069 | −17.029 | 9.635 | 1 | 91.2 | N |
| ATOM | 741 | C | LYS | A | 326 | 9.755 | −11.471 | 6.41 | 1 | 89.78 | C |
| ATOM | 742 | O | LYS | A | 326 | 9.616 | −10.653 | 7.323 | 1 | 89.95 | O |
| ATOM | 743 | N | ALA | A | 327 | 10.87 | −11.567 | 5.676 | 1 | 89.85 | N |
| ATOM | 744 | CA | ALA | A | 327 | 11.963 | −10.593 | 5.773 | 1 | 89.74 | C |
| ATOM | 745 | CB | ALA | A | 327 | 13.161 | −11.029 | 4.921 | 1 | 89.79 | C |
| ATOM | 746 | C | ALA | A | 327 | 11.474 | −9.206 | 5.345 | 1 | 89.84 | C |
| ATOM | 747 | O | ALA | A | 327 | 11.555 | −8.246 | 6.119 | 1 | 89.84 | O |
| ATOM | 748 | N | LEU | A | 328 | 10.947 | −9.119 | 4.123 | 1 | 89.63 | N |
| ATOM | 749 | CA | LEU | A | 328 | 10.401 | −7.866 | 3.583 | 1 | 89.29 | C |
| ATOM | 750 | CB | LEU | A | 328 | 10.088 | −8.023 | 2.088 | 1 | 89.52 | C |
| ATOM | 751 | CG | LEU | A | 328 | 11.199 | −8.467 | 1.123 | 1 | 89.78 | C |
| ATOM | 752 | CD1 | LEU | A | 328 | 10.585 | −8.99 | −0.175 | 1 | 89.86 | C |
| ATOM | 753 | CD2 | LEU | A | 328 | 12.207 | −7.341 | 0.832 | 1 | 89.88 | C |
| ATOM | 754 | C | LEU | A | 328 | 9.108 | −7.465 | 4.326 | 1 | 89.07 | C |
| ATOM | 755 | O | LEU | A | 328 | 8.349 | −8.345 | 4.744 | 1 | 89.36 | O |
| ATOM | 756 | N | PRO | A | 329 | 8.838 | −6.143 | 4.48 | 1 | 88.33 | N |
| ATOM | 757 | CA | PRO | A | 329 | 7.564 | −5.778 | 5.121 | 1 | 87.46 | C |
| ATOM | 758 | CB | PRO | A | 329 | 7.769 | −4.316 | 5.549 | 1 | 87.69 | C |
| ATOM | 759 | CG | PRO | A | 329 | 8.953 | −3.807 | 4.749 | 1 | 88.06 | C |
| ATOM | 760 | CD | PRO | A | 329 | 9.623 | −4.962 | 4.061 | 1 | 88.3 | C |
| ATOM | 761 | C | PRO | A | 329 | 6.425 | −5.927 | 4.113 | 1 | 86.77 | C |
| ATOM | 762 | O | PRO | A | 329 | 5.52 | −6.758 | 4.303 | 1 | 86.8 | O |
| ATOM | 763 | N | ALA | A | 330 | 6.502 | −5.138 | 3.04 | 1 | 85.54 | N |
| ATOM | 764 | CA | ALA | A | 330 | 5.649 | −5.309 | 1.874 | 1 | 84.19 | C |
| ATOM | 765 | CB | ALA | A | 330 | 5.434 | −3.966 | 1.176 | 1 | 84.24 | C |
| ATOM | 766 | C | ALA | A | 330 | 6.304 | −6.308 | 0.911 | 1 | 83.11 | C |
| ATOM | 767 | O | ALA | A | 330 | 7.526 | −6.252 | 0.685 | 1 | 82.89 | O |
| ATOM | 768 | N | PRO | A | 331 | 5.497 | −7.235 | 0.347 | 1 | 81.52 | N |
| ATOM | 769 | CA | PRO | A | 331 | 5.954 | −8.048 | −0.786 | 1 | 80.07 | C |
| ATOM | 770 | CB | PRO | A | 331 | 4.716 | −8.865 | −1.163 | 1 | 80.32 | C |
| ATOM | 771 | CG | PRO | A | 331 | 3.828 | −8.823 | 0.004 | 1 | 80.98 | C |
| ATOM | 772 | CD | PRO | A | 331 | 4.115 | −7.561 | 0.743 | 1 | 81.45 | C |
| ATOM | 773 | C | PRO | A | 331 | 6.378 | −7.172 | −1.972 | 1 | 78.58 | C |
| ATOM | 774 | O | PRO | A | 331 | 5.855 | −6.062 | −2.141 | 1 | 78.35 | O |
| ATOM | 775 | N | ILE | A | 332 | 7.317 | −7.67 | −2.775 | 1 | 76.58 | N |
| ATOM | 776 | CA | ILE | A | 332 | 7.827 | −6.934 | −3.933 | 1 | 75.21 | C |
| ATOM | 777 | CB | ILE | A | 332 | 9.295 | −7.293 | −4.238 | 1 | 75.31 | C |
| ATOM | 778 | CG1 | ILE | A | 332 | 10.209 | −6.789 | −3.118 | 1 | 75.32 | C |
| ATOM | 779 | CD1 | ILE | A | 332 | 11.679 | −7.086 | −3.342 | 1 | 75.35 | C |

TABLE V-continued

Atomic Structure Coordinates of Fc/YTE (SEQ ID NO: 11)

| | | Atom | A.A. | Type | | X | Y | Z | Occ | B | |
|---|---|---|---|---|---|---|---|---|---|---|---|
| ATOM | 780 | CG2 | ILE | A | 332 | 9.724 | −6.711 | −5.579 | 1 | 75.64 | C |
| ATOM | 781 | C | ILE | A | 332 | 6.989 | −7.248 | −5.162 | 1 | 73.74 | C |
| ATOM | 782 | O | ILE | A | 332 | 6.549 | −8.385 | −5.354 | 1 | 74.08 | O |
| ATOM | 783 | N | GLU | A | 333 | 6.773 | −6.235 | −5.993 | 1 | 71.58 | N |
| ATOM | 784 | CA | GLU | A | 333 | 6.073 | −6.404 | −T256 | 1 | 69.76 | C |
| ATOM | 785 | CB | GLU | A | 333 | 4.728 | −5.661 | −7.214 | 1 | 69.88 | C |
| ATOM | 786 | CG | GLU | A | 333 | 3.621 | −6.456 | −6.551 | 1 | 70.18 | C |
| ATOM | 787 | CD | GLU | A | 333 | 2.266 | −5.768 | −6.626 | 1 | 70.27 | C |
| ATOM | 788 | OE1 | GLU | A | 333 | 2.085 | −4.707 | −6 | 1 | 71.1 | O |
| ATOM | 789 | OE2 | GLU | A | 333 | 1.369 | −6.305 | −7.297 | 1 | 71 | O |
| ATOM | 790 | C | GLU | A | 333 | 6.928 | −5.915 | −8.432 | 1 | 67.69 | C |
| ATOM | 791 | O | GLU | A | 333 | 7.591 | −4.878 | −8.345 | 1 | 67.07 | O |
| ATOM | 792 | N | LYS | A | 334 | 6.912 | −6.686 | −9.52 | 1 | 65.44 | N |
| ATOM | 793 | CA | LYS | A | 334 | 7.527 | −6.282 | −10.788 | 1 | 63.7 | C |
| ATOM | 794 | CB | LYS | A | 334 | 8.832 | −7.036 | −11.015 | 1 | 63.61 | C |
| ATOM | 795 | CG | LYS | A | 334 | 9.982 | −6.543 | −10.154 | 1 | 63.86 | C |
| ATOM | 796 | CD | LYS | A | 334 | 10.614 | −5.28 | −10.711 | 1 | 63.42 | C |
| ATOM | 797 | CE | LYS | A | 334 | 11.749 | −4.795 | −9.827 | 1 | 63.3 | C |
| ATOM | 798 | NZ | LYS | A | 334 | 12.72 | −3.952 | −10.578 | 1 | 63.84 | N |
| ATOM | 799 | C | LYS | A | 334 | 6.572 | −6.584 | −11.923 | 1 | 61.92 | C |
| ATOM | 800 | O | LYS | A | 334 | 5.885 | −7.603 | −11.905 | 1 | 61.92 | O |
| ATOM | 801 | N | THR | A | 335 | 6.534 | −5.702 | −12.919 | 1 | 59.86 | N |
| ATOM | 802 | CA | THR | A | 335 | 5.659 | −5.893 | −14.076 | 1 | 58.45 | C |
| ATOM | 803 | CB | THR | A | 335 | 4.487 | −4.901 | −14.042 | 1 | 58.39 | C |
| ATOM | 804 | OG1 | THR | A | 335 | 4.042 | −4.749 | −12.695 | 1 | 58.4 | O |
| ATOM | 805 | CG2 | THR | A | 335 | 3.324 | −5.396 | −14.885 | 1 | 58.97 | C |
| ATOM | 806 | C | THR | A | 335 | 6.441 | −5.772 | −15.386 | 1 | 56.64 | C |
| ATOM | 807 | O | THR | A | 335 | 7.409 | −5.027 | −15.487 | 1 | 56.16 | O |
| ATOM | 808 | N | ILE | A | 336 | 6.027 | −6.546 | −16.377 | 1 | 55.05 | N |
| ATOM | 809 | CA | ILE | A | 336 | 6.686 | −6.569 | −17.673 | 1 | 54.08 | C |
| ATOM | 810 | CB | ILE | A | 336 | 7.751 | −7.711 | −17.762 | 1 | 54.14 | C |
| ATOM | 811 | CG1 | ILE | A | 336 | 8.888 | −7.318 | −18.713 | 1 | 54.57 | C |
| ATOM | 812 | CD1 | ILE | A | 336 | 10.182 | −8.014 | −18.408 | 1 | 54.85 | C |
| ATOM | 813 | CG2 | ILE | A | 336 | 7.127 | −9.036 | −18.205 | 1 | 53.44 | C |
| ATOM | 814 | C | ILE | A | 336 | 5.629 | −6.754 | −18.751 | 1 | 52.71 | C |
| ATOM | 815 | O | ILE | A | 336 | 4.596 | −7.4 | −18.516 | 1 | 52.59 | O |
| ATOM | 816 | N | SER | A | 337 | 5.869 | −6.156 | −19.91 | 1 | 51.03 | N |
| ATOM | 817 | CA | SER | A | 337 | 4.979 | −6.318 | −21.049 | 1 | 50.26 | C |
| ATOM | 818 | CB | SER | A | 337 | 3.731 | −5.459 | −20.873 | 1 | 50.13 | C |
| ATOM | 819 | OG | SER | A | 337 | 4.077 | −4.094 | −20.88 | 1 | 50.03 | O |
| ATOM | 820 | C | SER | A | 337 | 5.689 | −5.912 | −22.332 | 1 | 49.26 | C |
| ATOM | 821 | O | SER | A | 337 | 6.837 | −5.5 | −22.3 | 1 | 49.48 | O |
| ATOM | 822 | N | LYS | A | 338 | 4.999 | −6.046 | −23.459 | 1 | 47.87 | N |
| ATOM | 823 | CA | LYS | A | 338 | 5.52 | −5.583 | −24.719 | 1 | 47.3 | C |
| ATOM | 824 | CB | LYS | A | 338 | 4.736 | −6.205 | −25.869 | 1 | 47.05 | C |
| ATOM | 825 | CG | LYS | A | 338 | 5.21 | −5.783 | −27.226 | 1 | 46.44 | C |
| ATOM | 826 | CD | LYS | A | 338 | 4.313 | −6.328 | −28.325 | 1 | 46.14 | C |
| ATOM | 827 | CE | LYS | A | 338 | 3.338 | −5.301 | −28.84 | 1 | 44.69 | C |
| ATOM | 828 | NZ | LYS | A | 338 | 2.318 | −5.891 | −29.703 | 1 | 44.54 | N |
| ATOM | 829 | C | LYS | A | 338 | 5.362 | −4.072 | −24.73 | 1 | 47.09 | C |
| ATOM | 830 | O | LYS | A | 338 | 4.291 | −3.529 | −24.387 | 1 | 47.23 | O |
| ATOM | 831 | N | ALA | A | 339 | 6.431 | −3.387 | −25.106 | 1 | 46.91 | N |
| ATOM | 832 | CA | ALA | A | 339 | 6.39 | −1.948 | −25.225 | 1 | 46.93 | C |
| ATOM | 833 | CB | ALA | A | 339 | 7.68 | −1.43 | −25.809 | 1 | 46.02 | C |
| ATOM | 834 | C | ALA | A | 339 | 5.153 | −1.472 | −26.036 | 1 | 47.01 | C |
| ATOM | 835 | O | ALA | A | 339 | 4.726 | −2.078 | −27.032 | 1 | 46.65 | O |
| ATOM | 836 | N | LYS | A | 340 | 4.562 | −0.388 | −25.56 | 1 | 47.37 | N |
| ATOM | 837 | CA | LYS | A | 340 | 3.342 | 0.128 | −26.129 | 1 | 47.45 | C |
| ATOM | 838 | CB | LYS | A | 340 | 2.644 | 1.009 | −25.103 | 1 | 47.91 | C |
| ATOM | 839 | CG | LYS | A | 340 | 2.262 | 0.289 | −23.832 | 1 | 48.04 | C |
| ATOM | 840 | CD | LYS | A | 340 | 1.517 | 1.212 | −22.897 | 1 | 48.5 | C |
| ATOM | 841 | CE | LYS | A | 340 | 0.716 | 0.441 | −21.871 | 1 | 48.97 | C |
| ATOM | 842 | NZ | LYS | A | 340 | 0.433 | 1.289 | −20.679 | 1 | 50.1 | N |
| ATOM | 843 | C | LYS | A | 340 | 3.696 | 0.955 | −27.328 | 1 | 47.43 | C |
| ATOM | 844 | O | LYS | A | 340 | 4.813 | 1.469 | −27.425 | 1 | 48.21 | O |
| ATOM | 845 | N | GLY | A | 341 | 2.738 | 1.129 | −28.219 | 1 | 46.85 | N |
| ATOM | 846 | CA | GLY | A | 341 | 2.959 | 1.878 | −29.438 | 1 | 46.83 | C |
| ATOM | 847 | C | GLY | A | 341 | 2.332 | 1.065 | −30.526 | 1 | 46.83 | C |
| ATOM | 848 | O | GLY | A | 341 | 1.878 | −0.045 | −30.271 | 1 | 47.3 | O |
| ATOM | 849 | N | GLN | A | 342 | 2.266 | 1.605 | −31.731 | 1 | 46.86 | N |
| ATOM | 850 | CA | GLN | A | 342 | 1.691 | 0.861 | −32.833 | 1 | 46.85 | C |
| ATOM | 851 | CB | GLN | A | 342 | 0.873 | 1.764 | −33.752 | 1 | 46.77 | C |
| ATOM | 852 | CG | GLN | A | 342 | −0.44 | 2.19 | −33.156 | 1 | 47.01 | C |
| ATOM | 853 | CD | GLN | A | 342 | −1.37 | 1.021 | −32.93 | 1 | 47.62 | C |
| ATOM | 854 | OE1 | GLN | A | 342 | −1.91 | 0.443 | −33.885 | 1 | 47.76 | O |
| ATOM | 855 | NE2 | GLN | A | 342 | −1.571 | 0.665 | −31.655 | 1 | 47.36 | N |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 856 | C | GLN | A | 342 | 2.831 | 0.229 | −33.583 | 1 | 46.78 C |
| ATOM | 857 | O | GLN | A | 342 | 3.765 | 0.937 | −33.943 | 1 | 46.76 O |
| ATOM | 858 | N | PRO | A | 343 | 2.761 | −1.099 | −33.819 | 1 | 47.18 N |
| ATOM | 859 | CA | PRO | A | 343 | 3.846 | −1.846 | −34.408 | 1 | 47.99 C |
| ATOM | 860 | CB | PRO | A | 343 | 3.324 | −3.281 | −34.391 | 1 | 47.67 C |
| ATOM | 861 | CG | PRO | A | 343 | 2.246 | −3.288 | −33.429 | 1 | 47.36 C |
| ATOM | 862 | CD | PRO | A | 343 | 1.609 | −1.982 | −33.574 | 1 | 47.32 C |
| ATOM | 863 | C | PRO | A | 343 | 4.1 | −1.406 | −35.843 | 1 | 48.78 C |
| ATOM | 864 | O | PRO | A | 343 | 3.177 | −0.979 | −36.513 | 1 | 49.01 O |
| ATOM | 865 | N | ARG | A | 344 | 5.341 | −1.505 | −36.297 | 1 | 49.92 N |
| ATOM | 866 | CA | ARG | A | 344 | 5.728 | −0.934 | −37.573 | 1 | 51.29 C |
| ATOM | 867 | CB | ARG | A | 344 | 6.462 | 0.396 | −37.382 | 1 | 51.55 C |
| ATOM | 868 | CG | ARG | A | 344 | 5.52 | 1.54 | −37.095 | 1 | 54.21 C |
| ATOM | 869 | CD | ARG | A | 344 | 6.271 | 2.81 | −36.712 | 1 | 56.48 C |
| ATOM | 870 | NE | ARG | A | 344 | 6.91 | 3.412 | −37.876 | 1 | 60.58 N |
| ATOM | 871 | CZ | ARG | A | 344 | 7.428 | 4.64 | −37.913 | 1 | 62.87 C |
| ATOM | 872 | NH1 | ARG | A | 344 | 7.406 | 5.434 | −36.829 | 1 | 63.85 N |
| ATOM | 873 | NH2 | ARG | A | 344 | 7.966 | 5.08 | −39.049 | 1 | 62.8 N |
| ATOM | 874 | C | ARG | A | 344 | 6.602 | −1.909 | −38.318 | 1 | 50.54 C |
| ATOM | 875 | O | ARG | A | 344 | 7.496 | −2.516 | −37.747 | 1 | 49.71 O |
| ATOM | 876 | N | GLU | A | 345 | 6.317 | −2.038 | −39.602 | 1 | 50.58 N |
| ATOM | 877 | CA | GLU | A | 345 | 6.894 | −3.072 | −40.397 | 1 | 51.06 C |
| ATOM | 878 | CB | GLU | A | 345 | 6.092 | −3.278 | −41.675 | 1 | 50.96 C |
| ATOM | 879 | CG | GLU | A | 345 | 6.58 | −4.467 | −42.482 | 1 | 51.52 C |
| ATOM | 880 | CD | GLU | A | 345 | 5.995 | −4.546 | −43.873 | 1 | 51.93 C |
| ATOM | 881 | OE1 | GLU | A | 345 | 5.871 | −5.674 | −44.358 | 1 | 54.41 O |
| ATOM | 882 | OE2 | GLU | A | 345 | 5.696 | −3.511 | −44.492 | 1 | 52.6 O |
| ATOM | 883 | C | GLU | A | 345 | 8.342 | −2.738 | −40.727 | 1 | 51.05 C |
| ATOM | 884 | O | GLU | A | 345 | 8.614 | −1.655 | −41.236 | 1 | 51.42 O |
| ATOM | 885 | N | PRO | A | 346 | 9.268 | −3.676 | −40.451 | 1 | 51.08 N |
| ATOM | 886 | CA | PRO | A | 346 | 10.676 | −3.492 | −40.745 | 1 | 51.19 C |
| ATOM | 887 | CB | PRO | A | 346 | 11.335 | −4.727 | −40.139 | 1 | 51.22 C |
| ATOM | 888 | CG | PRO | A | 346 | 10.313 | −5.367 | −39.27 | 1 | 51.72 C |
| ATOM | 889 | CD | PRO | A | 346 | 9.009 | −4.987 | −39.835 | 1 | 51.35 C |
| ATOM | 890 | C | PRO | A | 346 | 10.941 | −3.497 | −42.227 | 1 | 51.72 C |
| ATOM | 891 | O | PRO | A | 346 | 10.421 | −4.358 | −42.933 | 1 | 51.77 O |
| ATOM | 892 | N | GLN | A | 347 | 11.744 | −2.56 | −42.712 | 1 | 52.03 N |
| ATOM | 893 | CA | GLN | A | 347 | 12.232 | −2.686 | −44.065 | 1 | 52.3 C |
| ATOM | 894 | CB | GLN | A | 347 | 12.26 | −1.338 | −44.775 | 1 | 53 C |
| ATOM | 895 | CG | GLN | A | 347 | 11.043 | −0.399 | −44.496 | 1 | 55.01 C |
| ATOM | 896 | CD | GLN | A | 347 | 9.672 | −1.024 | −44.791 | 1 | 57.88 C |
| ATOM | 897 | OE1 | GLN | A | 347 | 9.499 | −1.78 | −45.757 | 1 | 60.17 O |
| ATOM | 898 | NE2 | GLN | A | 347 | 8.68 | −0.682 | −43.964 | 1 | 58.69 N |
| ATOM | 899 | C | GLN | A | 347 | 13.61 | −3.37 | −43.948 | 1 | 52.13 C |
| ATOM | 900 | O | GLN | A | 347 | 14.369 | −3.109 | −43.032 | 1 | 52.48 O |
| ATOM | 901 | N | VAL | A | 348 | 13.901 | −4.286 | −44.858 | 1 | 51.76 N |
| ATOM | 902 | CA | VAL | A | 348 | 15.058 | −5.15 | −44.744 | 1 | 51.5 C |
| ATOM | 903 | CB | VAL | A | 348 | 14.604 | −6.624 | −44.553 | 1 | 51.75 C |
| ATOM | 904 | CG1 | VAL | A | 348 | 15.803 | −7.602 | −44.569 | 1 | 51.7 C |
| ATOM | 905 | CG2 | VAL | A | 348 | 13.767 | −6.759 | −43.268 | 1 | 51.56 C |
| ATOM | 906 | C | VAL | A | 348 | 15.869 | −5.005 | −46.017 | 1 | 51.4 C |
| ATOM | 907 | O | VAL | A | 348 | 15.349 | −5.245 | −47.109 | 1 | 51.73 O |
| ATOM | 908 | N | TYR | A | 349 | 17.128 | −4.599 | −45.876 | 1 | 51.04 N |
| ATOM | 909 | CA | TYR | A | 349 | 17.995 | −4.286 | −47.012 | 1 | 50.83 C |
| ATOM | 910 | CB | TYR | A | 349 | 18.171 | −2.769 | −47.177 | 1 | 50.89 C |
| ATOM | 911 | CG | TYR | A | 349 | 16.906 | −1.977 | −47.279 | 1 | 51.13 C |
| ATOM | 912 | CD1 | TYR | A | 349 | 16.051 | −2.126 | −48.365 | 1 | 50.23 C |
| ATOM | 913 | CE1 | TYR | A | 349 | 14.853 | −1.378 | −48.46 | 1 | 50.33 C |
| ATOM | 914 | CZ | TYR | A | 349 | 14.533 | −0.478 | −47.449 | 1 | 51.29 C |
| ATOM | 915 | OH | TYR | A | 349 | 13.377 | 0.266 | −47.514 | 1 | 50.34 O |
| ATOM | 916 | CE2 | TYR | A | 349 | 15.385 | −0.316 | −46.36 | 1 | 51.85 C |
| ATOM | 917 | CD2 | TYR | A | 349 | 16.562 | −1.057 | −46.287 | 1 | 51.85 C |
| ATOM | 918 | C | TYR | A | 349 | 19.38 | −4.895 | −46.816 | 1 | 50.64 C |
| ATOM | 919 | O | TYR | A | 349 | 20.05 | −4.662 | −45.806 | 1 | 50.24 O |
| ATOM | 920 | N | THR | A | 350 | 19.823 | −5.644 | −47.808 | 1 | 50.76 N |
| ATOM | 921 | CA | THR | A | 350 | 21.126 | −6.298 | −47.755 | 1 | 50.86 C |
| ATOM | 922 | CB | THR | A | 350 | 21.025 | −7.666 | −48.384 | 1 | 50.55 C |
| ATOM | 923 | OG1 | THR | A | 350 | 20.443 | −7.524 | −49.68 | 1 | 49.66 O |
| ATOM | 924 | CG2 | THR | A | 350 | 20.128 | −8.527 | −47.541 | 1 | 50.48 C |
| ATOM | 925 | C | THR | A | 350 | 22.129 | −5.454 | −48.52 | 1 | 50.95 C |
| ATOM | 926 | O | THR | A | 350 | 21.804 | −4.944 | −49.584 | 1 | 51.24 O |
| ATOM | 927 | N | LEU | A | 351 | 23.33 | −5.291 | −47.97 | 1 | 51.23 N |
| ATOM | 928 | CA | LEU | A | 351 | 24.348 | −4.42 | −48.577 | 1 | 51.4 C |
| ATOM | 929 | CB | LEU | A | 351 | 24.611 | −3.189 | −47.689 | 1 | 51.14 C |
| ATOM | 930 | CG | LEU | A | 351 | 23.412 | −2.45 | −47.061 | 1 | 50.64 C |
| ATOM | 931 | CD1 | LEU | A | 351 | 23.817 | −1.44 | −45.945 | 1 | 48.94 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 932 | CD2 | LEU | A | 351 | 22.605 | −1.768 | −48.117 | 1 | 49.95 C |
| ATOM | 933 | C | LEU | A | 351 | 25.651 | −5.207 | −48.786 | 1 | 51.72 C |
| ATOM | 934 | O | LEU | A | 351 | 26.223 | −5.73 | −47.816 | 1 | 51.82 O |
| ATOM | 935 | N | PRO | A | 352 | 26.15 | −5.273 | −50.04 | 1 | 52.09 N |
| ATOM | 936 | CA | PRO | A | 352 | 27.311 | −6.122 | −50.284 | 1 | 52.58 C |
| ATOM | 937 | CB | PRO | A | 352 | 27.432 | −6.131 | −51.818 | 1 | 52.09 C |
| ATOM | 938 | CG | PRO | A | 352 | 26.839 | −4.886 | −52.244 | 1 | 51.37 C |
| ATOM | 939 | CD | PRO | A | 352 | 25.734 | −4.57 | −51.267 | 1 | 51.94 C |
| ATOM | 940 | C | PRO | A | 352 | 28.55 | −5.519 | −49.669 | 1 | 53.12 C |
| ATOM | 941 | O | PRO | A | 352 | 28.534 | −4.35 | −49.298 | 1 | 52.78 O |
| ATOM | 942 | N | PRO | A | 353 | 29.643 | −6.291 | −49.617 | 1 | 54.44 N |
| ATOM | 943 | CA | PRO | A | 353 | 30.849 | −5.739 | −49.036 | 1 | 55.64 C |
| ATOM | 944 | CB | PRO | A | 353 | 31.846 | −6.912 | −49.055 | 1 | 55.26 C |
| ATOM | 945 | CG | PRO | A | 353 | 31.109 | −8.095 | −49.467 | 1 | 54.98 C |
| ATOM | 946 | CD | PRO | A | 353 | 29.847 | −7.647 | −50.145 | 1 | 54.53 C |
| ATOM | 947 | C | PRO | A | 353 | 31.368 | −4.561 | −49.869 | 1 | 56.8 C |
| ATOM | 948 | O | PRO | A | 353 | 31.246 | −4.567 | −51.092 | 1 | 56.33 O |
| ATOM | 949 | N | SER | A | 354 | 31.905 | −3.549 | −49.192 | 1 | 58.44 N |
| ATOM | 950 | CA | SER | A | 354 | 32.592 | −2.457 | −49.867 | 1 | 59.75 C |
| ATOM | 951 | CB | SER | A | 354 | 33.303 | −1.584 | −48.838 | 1 | 59.65 C |
| ATOM | 952 | OG | SER | A | 354 | 34.38 | −0.837 | −49.387 | 1 | 59.17 O |
| ATOM | 953 | C | SER | A | 354 | 33.616 | −2.982 | −50.862 | 1 | 61.14 C |
| ATOM | 954 | O | SER | A | 354 | 34.231 | −4.035 | −50.646 | 1 | 61.64 O |
| ATOM | 955 | N | ARG | A | 355 | 33.795 | −2.238 | −51.949 | 1 | 62.75 N |
| ATOM | 956 | CA | ARG | A | 355 | 34.884 | −2.502 | −52.912 | 1 | 64.18 C |
| ATOM | 957 | CB | ARG | A | 355 | 34.939 | −1.413 | −54.007 | 1 | 65.1 C |
| ATOM | 958 | CG | ARG | A | 355 | 33.562 | −0.861 | −54.481 | 1 | 67.91 C |
| ATOM | 959 | CD | ARG | A | 355 | 33.725 | 0.07 | −55.72 | 1 | 68.57 C |
| ATOM | 960 | NE | ARG | A | 355 | 32.457 | 0.551 | −56.281 | 1 | 69.61 N |
| ATOM | 961 | CZ | ARG | A | 355 | 32.367 | 1.385 | −57.322 | 1 | 72.02 C |
| ATOM | 962 | NH1 | ARG | A | 355 | 33.463 | 1.846 | −57.923 | 1 | 73.99 N |
| ATOM | 963 | NH2 | ARG | A | 355 | 31.175 | 1.774 | −57.78 | 1 | 73.51 N |
| ATOM | 964 | C | ARG | A | 355 | 36.248 | −2.573 | −52.193 | 1 | 63.71 C |
| ATOM | 965 | O | ARG | A | 355 | 37.066 | −3.425 | −52.501 | 1 | 63.38 O |
| ATOM | 966 | N | ASP | A | 356 | 36.467 | −1.678 | −51.232 | 1 | 63.49 N |
| ATOM | 967 | CA | ASP | A | 356 | 37.742 | −1.592 | −50.52 | 1 | 63.77 C |
| ATOM | 968 | CB | ASP | A | 356 | 37.857 | −0.268 | −49.736 | 1 | 64.16 C |
| ATOM | 969 | CG | ASP | A | 356 | 37.586 | 0.989 | −50.607 | 1 | 66.07 C |
| ATOM | 970 | OD1 | ASP | A | 356 | 38.189 | 2.056 | −50.324 | 1 | 67.37 O |
| ATOM | 971 | OD2 | ASP | A | 356 | 36.759 | 0.919 | −51.556 | 1 | 68.39 O |
| ATOM | 972 | C | ASP | A | 356 | 37.989 | −2.759 | −49.555 | 1 | 63.58 C |
| ATOM | 973 | O | ASP | A | 356 | 39.118 | −2.981 | −49.169 | 1 | 64.02 O |
| ATOM | 974 | N | GLU | A | 357 | 36.947 | −3.481 | −49.138 | 1 | 63.25 N |
| ATOM | 975 | CA | GLU | A | 357 | 37.12 | −4.609 | −48.212 | 1 | 63.07 C |
| ATOM | 976 | CB | GLU | A | 357 | 35.816 | −4.946 | −47.453 | 1 | 62.91 C |
| ATOM | 977 | CG | GLU | A | 357 | 36.026 | −5.899 | −46.249 | 1 | 62.56 C |
| ATOM | 978 | CD | GLU | A | 357 | 34.74 | −6.237 | −45.48 | 1 | 61.56 C |
| ATOM | 979 | OE1 | GLU | A | 357 | 33.666 | −6.263 | −46.105 | 1 | 60.46 O |
| ATOM | 980 | OE2 | GLU | A | 357 | 34.807 | −6.488 | −44.256 | 1 | 57.28 O |
| ATOM | 981 | C | GLU | A | 357 | 37.602 | −5.843 | −48.959 | 1 | 63.08 C |
| ATOM | 982 | O | GLU | A | 357 | 38.3 | −6.687 | −48.383 | 1 | 62.39 O |
| ATOM | 983 | N | LEU | A | 358 | 37.244 | −5.937 | −50.241 | 1 | 63.33 N |
| ATOM | 984 | CA | LEU | A | 358 | 37.491 | −7.161 | −51.016 | 1 | 63.84 C |
| ATOM | 985 | CB | LEU | A | 358 | 36.695 | −7.158 | −52.346 | 1 | 63.39 C |
| ATOM | 986 | CG | LEU | A | 358 | 35.197 | −7.555 | −52.151 | 1 | 62.65 C |
| ATOM | 987 | CD1 | LEU | A | 358 | 34.227 | −6.89 | −53.133 | 1 | 61.9 C |
| ATOM | 988 | CD2 | LEU | A | 358 | 34.998 | −9.058 | −52.161 | 1 | 60.24 C |
| ATOM | 989 | C | LEU | A | 358 | 38.995 | −7.482 | −51.178 | 1 | 64.31 C |
| ATOM | 990 | O | LEU | A | 358 | 39.358 | −8.57 | −51.582 | 1 | 64.27 O |
| ATOM | 991 | N | THR | A | 359 | 39.869 | −6.561 | −50.783 | 1 | 65.1 N |
| ATOM | 992 | CA | THR | A | 359 | 41.295 | −6.882 | −50.654 | 1 | 65.41 C |
| ATOM | 993 | CB | THR | A | 359 | 42.169 | −5.587 | −50.534 | 1 | 65.78 C |
| ATOM | 994 | OG1 | THR | A | 359 | 41.462 | −4.449 | −51.052 | 1 | 65.98 C |
| ATOM | 995 | CG2 | THR | A | 359 | 43.461 | −5.75 | −51.32 | 1 | 65.93 C |
| ATOM | 996 | C | THR | A | 359 | 41.629 | −7.854 | −49.486 | 1 | 65.88 C |
| ATOM | 997 | O | THR | A | 359 | 42.674 | −8.517 | −49.532 | 1 | 66.26 O |
| ATOM | 998 | N | LYS | A | 360 | 40.772 | −7.943 | −48.455 | 1 | 65.87 N |
| ATOM | 999 | CA | LYS | A | 360 | 41.022 | −8.848 | −47.298 | 1 | 65.52 C |
| ATOM | 1000 | CB | LYS | A | 360 | 40.286 | −8.381 | −46.025 | 1 | 65.72 C |
| ATOM | 1001 | CG | LYS | A | 360 | 40.441 | −6.915 | −45.658 | 1 | 65.78 C |
| ATOM | 1002 | CD | LYS | A | 360 | 41.603 | −6.656 | −44.728 | 1 | 66.52 C |
| ATOM | 1003 | CE | LYS | A | 360 | 42.12 | −5.205 | −44.889 | 1 | 66.63 C |
| ATOM | 1004 | NZ | LYS | A | 360 | 42.895 | −4.673 | −43.701 | 1 | 65.99 N |
| ATOM | 1005 | C | LYS | A | 360 | 40.562 | −10.269 | −47.668 | 1 | 65.44 C |
| ATOM | 1006 | O | LYS | A | 360 | 39.966 | −10.439 | −48.729 | 1 | 65.49 O |
| ATOM | 1007 | N | ASN | A | 361 | 40.806 | −11.271 | −46.806 | 1 | 64.94 N |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 1008 | CA | ASN | A | 361 | 40.38 | −12.659 | −47.105 | 1 | 64.76 | C |
| ATOM | 1009 | CB | ASN | A | 361 | 41.356 | −13.727 | −46.566 | 1 | 65.25 | C |
| ATOM | 1010 | CG | ASN | A | 361 | 42.768 | −13.192 | −46.366 | 1 | 67.11 | C |
| ATOM | 1011 | OD1 | ASN | A | 361 | 43.288 | −13.193 | −45.236 | 1 | 69.72 | O |
| ATOM | 1012 | ND2 | ASN | A | 361 | 43.4 | −12.729 | −47.456 | 1 | 67.81 | N |
| ATOM | 1013 | C | ASN | A | 361 | 38.98 | −12.967 | −46.569 | 1 | 64.3 | C |
| ATOM | 1014 | O | ASN | A | 361 | 38.289 | −13.857 | −47.084 | 1 | 64.07 | O |
| ATOM | 1015 | N | GLN | A | 362 | 38.593 | −12.255 | −45.511 | 1 | 63.52 | N |
| ATOM | 1016 | CA | GLN | A | 362 | 37.243 | −12.324 | −44.953 | 1 | 62.54 | C |
| ATOM | 1017 | CB | GLN | A | 362 | 37.321 | −12.299 | −43.425 | 1 | 63 | C |
| ATOM | 1018 | CG | GLN | A | 362 | 38.201 | −13.37 | −42.808 | 1 | 64.3 | C |
| ATOM | 1019 | CD | GLN | A | 362 | 37.422 | −14.57 | −42.296 | 1 | 66.19 | C |
| ATOM | 1020 | OE1 | GLN | A | 362 | 37.945 | −15.385 | −41.535 | 1 | 68.19 | O |
| ATOM | 1021 | NE2 | GLN | A | 362 | 36.175 | −14.687 | −42.71 | 1 | 67.33 | N |
| ATOM | 1022 | C | GLN | A | 362 | 36.506 | −11.084 | −45.428 | 1 | 61.37 | C |
| ATOM | 1023 | O | GLN | A | 362 | 37.114 | −10.015 | −45.478 | 1 | 61.5 | O |
| ATOM | 1024 | N | VAL | A | 363 | 35.224 | −11.206 | −45.78 | 1 | 59.86 | N |
| ATOM | 1025 | CA | VAL | A | 363 | 34.416 | −10.035 | −46.163 | 1 | 58.94 | C |
| ATOM | 1026 | CB | VAL | A | 363 | 34.061 | −10.017 | −47.674 | 1 | 58.87 | C |
| ATOM | 1027 | CG1 | VAL | A | 363 | 35.28 | −10.306 | −48.534 | 1 | 58.54 | C |
| ATOM | 1028 | CG2 | VAL | A | 363 | 32.948 | −10.988 | −47.982 | 1 | 58.69 | C |
| ATOM | 1029 | C | VAL | A | 363 | 33.114 | −9.928 | −45.343 | 1 | 58.37 | C |
| ATOM | 1030 | O | VAL | A | 363 | 32.71 | −10.868 | −44.63 | 1 | 58.55 | O |
| ATOM | 1031 | N | SER | A | 364 | 32.462 | −8.772 | −45.438 | 1 | 57.03 | N |
| ATOM | 1032 | CA | SER | A | 364 | 31.308 | −8.483 | −44.6 | 1 | 55.8 | C |
| ATOM | 1033 | CB | SER | A | 364 | 31.544 | −7.227 | −43.737 | 1 | 55.95 | C |
| ATOM | 1034 | OG | SER | A | 364 | 32.653 | −7.4 | −42.85 | 1 | 55.67 | O |
| ATOM | 1035 | C | SER | A | 364 | 30.064 | −8.336 | −45.459 | 1 | 54.59 | C |
| ATOM | 1036 | O | SER | A | 364 | 30.001 | −7.476 | −46.338 | 1 | 54.4 | O |
| ATOM | 1037 | N | LEU | A | 365 | 29.099 | −9.222 | −45.219 | 1 | 52.98 | N |
| ATOM | 1038 | CA | LEU | A | 365 | 27.77 | −9.066 | −45.753 | 1 | 52.21 | C |
| ATOM | 1039 | CB | LEU | A | 365 | 27.185 | −10.418 | −46.173 | 1 | 52.5 | C |
| ATOM | 1040 | CG | LEU | A | 365 | 27.98 | −11.243 | −47.198 | 1 | 53.65 | C |
| ATOM | 1041 | CD1 | LEU | A | 365 | 27.137 | −12.437 | −47.67 | 1 | 54.6 | C |
| ATOM | 1042 | CD2 | LEU | A | 365 | 28.457 | −10.422 | −48.394 | 1 | 53.52 | C |
| ATOM | 1043 | C | LEU | A | 365 | 26.916 | −8.39 | −44.676 | 1 | 50.99 | C |
| ATOM | 1044 | O | LEU | A | 365 | 26.88 | −8.847 | −43.523 | 1 | 51.28 | O |
| ATOM | 1045 | N | THR | A | 366 | 26.249 | −7.306 | −45.069 | 1 | 49.06 | N |
| ATOM | 1046 | CA | THR | A | 366 | 25.506 | −6.45 | −44.171 | 1 | 48.25 | C |
| ATOM | 1047 | CB | THR | A | 366 | 25.892 | −4.982 | −44.365 | 1 | 47.82 | C |
| ATOM | 1048 | OG1 | THR | A | 366 | 27.236 | −4.799 | −43.931 | 1 | 48.09 | O |
| ATOM | 1049 | CG2 | THR | A | 366 | 24.979 | −4.044 | −43.559 | 1 | 47.87 | C |
| ATOM | 1050 | C | THR | A | 366 | 24.014 | −6.542 | −44.418 | 1 | 47.53 | C |
| ATOM | 1051 | O | THR | A | 366 | 23.552 | −6.587 | −45.587 | 1 | 47.04 | O |
| ATOM | 1052 | N | CYS | A | 367 | 23.262 | −6.511 | −43.315 | 1 | 46.24 | N |
| ATOM | 1053 | CA | CYS | A | 367 | 21.823 | −6.519 | −43.405 | 1 | 45.38 | C |
| ATOM | 1054 | CB | CYS | A | 367 | 21.317 | −7.838 | −42.882 | 1 | 45.41 | C |
| ATOM | 1055 | SG | CYS | A | 367 | 19.603 | −8.072 | −43.15 | 1 | 46.71 | S |
| ATOM | 1056 | C | CYS | A | 367 | 21.231 | −5.37 | −42.619 | 1 | 44.24 | C |
| ATOM | 1057 | O | CYS | A | 367 | 21.35 | −5.312 | −41.407 | 1 | 44.65 | O |
| ATOM | 1058 | N | LEU | A | 368 | 20.585 | −4.45 | −43.308 | 1 | 43.27 | N |
| ATOM | 1059 | CA | LEU | A | 368 | 20.008 | −3.288 | −42.651 | 1 | 42.94 | C |
| ATOM | 1060 | CB | LEU | A | 368 | 20.284 | −2.012 | −43.454 | 1 | 42.37 | C |
| ATOM | 1061 | CG | LEU | A | 368 | 19.541 | −0.759 | −42.99 | 1 | 42.55 | C |
| ATOM | 1062 | CD1 | LEU | A | 368 | 19.76 | −0.515 | −41.486 | 1 | 42.92 | C |
| ATOM | 1063 | CD2 | LEU | A | 368 | 19.931 | 0.473 | −43.811 | 1 | 42.31 | C |
| ATOM | 1064 | C | LEU | A | 368 | 18.504 | −3.478 | −42.439 | 1 | 42.53 | C |
| ATOM | 1065 | O | LEU | A | 368 | 17.729 | −3.573 | −43.405 | 1 | 42.36 | O |
| ATOM | 1066 | N | VAL | A | 369 | 18.113 | −3.493 | −41.165 | 1 | 41.9 | N |
| ATOM | 1067 | CA | VAL | A | 369 | 16.736 | −3.644 | −40.766 | 1 | 41.64 | C |
| ATOM | 1068 | CB | VAL | A | 369 | 16.551 | −4.787 | −39.741 | 1 | 41.64 | C |
| ATOM | 1069 | CG1 | VAL | A | 369 | 15.059 | −5.057 | −39.529 | 1 | 40.98 | C |
| ATOM | 1070 | CG2 | VAL | A | 369 | 17.313 | −6.056 | −40.174 | 1 | 41.1 | C |
| ATOM | 1071 | C | VAL | A | 369 | 16.376 | −2.352 | −40.097 | 1 | 41.47 | C |
| ATOM | 1072 | O | VAL | A | 369 | 17.011 | −1.97 | −39.112 | 1 | 40.83 | O |
| ATOM | 1073 | N | LYS | A | 370 | 15.374 | −1.667 | −40.63 | 1 | 41.5 | N |
| ATOM | 1074 | CA | LYS | A | 370 | 14.98 | −0.371 | −40.09 | 1 | 41.93 | C |
| ATOM | 1075 | CB | LYS | A | 370 | 15.639 | 0.728 | −40.907 | 1 | 41.91 | C |
| ATOM | 1076 | CG | LYS | A | 370 | 15.193 | 0.764 | −42.342 | 1 | 42.56 | C |
| ATOM | 1077 | CD | LYS | A | 370 | 15.629 | 2.068 | −43.037 | 1 | 42.24 | C |
| ATOM | 1078 | CE | LYS | A | 370 | 14.78 | 3.22 | −42.607 | 1 | 42.17 | C |
| ATOM | 1079 | NZ | LYS | A | 370 | 15.12 | 4.428 | −43.371 | 1 | 43.9 | N |
| ATOM | 1080 | C | LYS | A | 370 | 13.462 | −0.188 | −40.067 | 1 | 42.08 | C |
| ATOM | 1081 | O | LYS | A | 370 | 12.71 | −1.045 | −40.526 | 1 | 43.91 | O |
| ATOM | 1082 | N | GLY | A | 371 | 13.002 | 0.923 | −39.536 | 1 | 41.39 | N |
| ATOM | 1083 | CA | GLY | A | 371 | 11.572 | 1.24 | −39.58 | 1 | 41.33 | C |

TABLE V-continued

Atomic Structure Coordinates of Fc/YTE (SEQ ID NO: 11)

| Atom |  |  | A.A. | Type |  | X | Y | Z | Occ | B |  |
|---|---|---|---|---|---|---|---|---|---|---|---|
| ATOM | 1084 | C | GLY | A | 371 | 10.659 | 0.434 | −38.67 | 1 | 41.44 | C |
| ATOM | 1085 | O | GLY | A | 371 | 9.439 | 0.511 | −38.789 | 1 | 42.95 | O |
| ATOM | 1086 | N | PHE | A | 372 | 11.23 | −0.294 | −37.726 | 1 | 40.93 | N |
| ATOM | 1087 | CA | PHE | A | 372 | 10.476 | −1.257 | −36.936 | 1 | 39.92 | C |
| ATOM | 1088 | CB | PHE | A | 372 | 11.146 | −2.633 | −37.004 | 1 | 39.01 | C |
| ATOM | 1089 | CG | PHE | A | 372 | 12.466 | −2.747 | −36.276 | 1 | 38.13 | C |
| ATOM | 1090 | CD1 | PHE | A | 372 | 12.51 | −3.073 | −34.931 | 1 | 39.24 | C |
| ATOM | 1091 | CE1 | PHE | A | 372 | 13.729 | −3.251 | −34.263 | 1 | 39.15 | C |
| ATOM | 1092 | CZ | PHE | A | 372 | 14.923 | −3.133 | −34.983 | 1 | 38.42 | C |
| ATOM | 1093 | CE2 | PHE | A | 372 | 14.876 | −2.829 | −36.321 | 1 | 37.19 | C |
| ATOM | 1094 | CD2 | PHE | A | 372 | 13.651 | −2.658 | −36.963 | 1 | 37.42 | C |
| ATOM | 1095 | C | PHE | A | 372 | 10.192 | −0.859 | −35.491 | 1 | 39.82 | C |
| ATOM | 1096 | O | PHE | A | 372 | 11.012 | −0.23 | −34.83 | 1 | 40.57 | O |
| ATOM | 1097 | N | TYR | A | 373 | 8.997 | −1.215 | −35.031 | 1 | 39.64 | N |
| ATOM | 1098 | CA | TYR | A | 373 | 8.557 | −0.975 | −33.658 | 1 | 39.35 | C |
| ATOM | 1099 | CB | TYR | A | 373 | 7.826 | 0.382 | −33.501 | 1 | 39.36 | C |
| ATOM | 1100 | CG | TYR | A | 373 | 7.624 | 0.77 | −32.042 | 1 | 39.28 | C |
| ATOM | 1101 | CD1 | TYR | A | 373 | 8.55 | 1.523 | −31.379 | 1 | 38.86 | C |
| ATOM | 1102 | CE1 | TYR | A | 373 | 8.405 | 1.834 | −30.029 | 1 | 38.64 | C |
| ATOM | 1103 | CZ | TYR | A | 373 | 7.318 | 1.413 | −29.345 | 1 | 39.1 | C |
| ATOM | 1104 | OH | TYR | A | 373 | 7.201 | 1.763 | −28.023 | 1 | 39.95 | O |
| ATOM | 1105 | CE2 | TYR | A | 373 | 6.355 | 0.676 | −29.975 | 1 | 39.93 | C |
| ATOM | 1106 | CD2 | TYR | A | 373 | 6.512 | 0.349 | −31.327 | 1 | 40.92 | C |
| ATOM | 1107 | C | TYR | A | 373 | 7.631 | −2.125 | −33.328 | 1 | 38.59 | C |
| ATOM | 1108 | O | TYR | A | 373 | 6.921 | −2.579 | −34.23 | 1 | 38.68 | O |
| ATOM | 1109 | N | PRO | A | 374 | 7.664 | −2.636 | −32.076 | 1 | 37.94 | N |
| ATOM | 1110 | CA | PRO | A | 374 | 8.593 | −2.367 | −30.974 | 1 | 37.55 | C |
| ATOM | 1111 | CB | PRO | A | 374 | 7.918 | −3.017 | −29.778 | 1 | 38 | C |
| ATOM | 1112 | CG | PRO | A | 374 | 7.032 | −4.093 | −30.372 | 1 | 37.59 | C |
| ATOM | 1113 | CD | PRO | A | 374 | 6.619 | −3.609 | −31.688 | 1 | 37.98 | C |
| ATOM | 1114 | C | PRO | A | 374 | 9.965 | −2.981 | −31.255 | 1 | 37.55 | C |
| ATOM | 1115 | O | PRO | A | 374 | 10.181 | −3.494 | −32.351 | 1 | 37.99 | O |
| ATOM | 1116 | N | SER | A | 375 | 10.887 | −2.907 | −30.296 | 1 | 37.44 | N |
| ATOM | 1117 | CA | SER | A | 375 | 12.301 | −3.198 | −30.554 | 1 | 37.27 | C |
| ATOM | 1118 | CB | SER | A | 375 | 13.203 | −2.492 | −29.538 | 1 | 36.95 | C |
| ATOM | 1119 | OG | SER | A | 375 | 13.355 | −3.229 | −28.332 | 1 | 37.12 | O |
| ATOM | 1120 | C | SER | A | 375 | 12.568 | −4.684 | −30.581 | 1 | 37.35 | C |
| ATOM | 1121 | O | SER | A | 375 | 13.622 | −5.127 | −31.052 | 1 | 37.69 | O |
| ATOM | 1122 | N | ASP | A | 376 | 11.611 | −5.459 | −30.089 | 1 | 37.77 | N |
| ATOM | 1123 | CA | ASP | A | 376 | 11.734 | −6.908 | −30.087 | 1 | 38.03 | C |
| ATOM | 1124 | CB | ASP | A | 376 | 10.541 | −7.532 | −29.382 | 1 | 37.7 | C |
| ATOM | 1125 | CG | ASP | A | 376 | 10.32 | −6.963 | −27.992 | 1 | 39.88 | C |
| ATOM | 1126 | OD1 | ASP | A | 376 | 9.16 | −6.681 | −27.656 | 1 | 44.56 | O |
| ATOM | 1127 | OD2 | ASP | A | 376 | 11.277 | −6.78 | −27.214 | 1 | 40.71 | O |
| ATOM | 1128 | C | ASP | A | 376 | 11.838 | −7.403 | −31.543 | 1 | 38.34 | C |
| ATOM | 1129 | O | ASP | A | 376 | 10.933 | −7.158 | −32.38 | 1 | 37.82 | O |
| ATOM | 1130 | N | ILE | A | 377 | 12.95 | −8.079 | −31.835 | 1 | 38.45 | N |
| ATOM | 1131 | CA | ILE | A | 377 | 13.233 | −8.593 | −33.183 | 1 | 38.48 | C |
| ATOM | 1132 | CB | ILE | A | 377 | 13.689 | −7.461 | −34.13 | 1 | 38.23 | C |
| ATOM | 1133 | CG1 | ILE | A | 377 | 13.537 | −7.876 | −35.615 | 1 | 39.52 | C |
| ATOM | 1134 | CD1 | ILE | A | 377 | 13.851 | −6.731 | −36.637 | 1 | 38.68 | C |
| ATOM | 1135 | CG2 | ILE | A | 377 | 15.101 | −7.023 | −33.824 | 1 | 35.64 | C |
| ATOM | 1136 | C | ILE | A | 377 | 14.321 | −9.668 | −33.093 | 1 | 39.17 | C |
| ATOM | 1137 | O | ILE | A | 377 | 15.061 | −9.774 | −32.069 | 1 | 39.62 | O |
| ATOM | 1138 | N | ALA | A | 378 | 14.399 | −10.484 | −34.135 | 1 | 39.33 | N |
| ATOM | 1139 | CA | ALA | A | 378 | 15.469 | −11.465 | −34.278 | 1 | 39.92 | C |
| ATOM | 1140 | CB | ALA | A | 378 | 15.011 | −12.852 | −33.786 | 1 | 40.38 | C |
| ATOM | 1141 | C | ALA | A | 378 | 15.954 | −11.551 | −35.72 | 1 | 40.36 | C |
| ATOM | 1142 | O | ALA | A | 378 | 15.193 | −11.38 | −36.693 | 1 | 39.95 | O |
| ATOM | 1143 | N | VAL | A | 379 | 17.242 | −11.835 | −35.841 | 1 | 40.88 | N |
| ATOM | 1144 | CA | VAL | A | 379 | 17.912 | −11.797 | −37.123 | 1 | 41.17 | C |
| ATOM | 1145 | CB | VAL | A | 379 | 18.647 | −10.459 | −37.338 | 1 | 40.47 | C |
| ATOM | 1146 | CG1 | VAL | A | 379 | 19.348 | −10.457 | −38.68 | 1 | 40.4 | C |
| ATOM | 1147 | CG2 | VAL | A | 379 | 17.674 | −9.299 | −37.24 | 1 | 38.37 | C |
| ATOM | 1148 | C | VAL | A | 379 | 18.9 | −12.941 | −37.155 | 1 | 41.98 | C |
| ATOM | 1149 | O | VAL | A | 379 | 19.606 | −13.203 | −36.165 | 1 | 41.6 | O |
| ATOM | 1150 | N | GLU | A | 380 | 18.939 | −13.598 | −38.308 | 1 | 42.85 | N |
| ATOM | 1151 | CA | GLU | A | 380 | 19.699 | −14.816 | −38.518 | 1 | 44 | C |
| ATOM | 1152 | CB | GLU | A | 380 | 18.869 | −16.057 | −38.131 | 1 | 44.03 | C |
| ATOM | 1153 | CG | GLU | A | 380 | 18.812 | −16.317 | −36.615 | 1 | 45.59 | C |
| ATOM | 1154 | CD | GLU | A | 380 | 17.751 | −17.32 | −36.18 | 1 | 45.61 | C |
| ATOM | 1155 | OE1 | GLU | A | 380 | 17.4 | −18.223 | −36.944 | 1 | 49.21 | O |
| ATOM | 1156 | OE2 | GLU | A | 380 | 17.256 | −17.202 | −35.051 | 1 | 48.35 | O |
| ATOM | 1157 | C | GLU | A | 380 | 20.103 | −14.878 | −39.998 | 1 | 44.44 | C |
| ATOM | 1158 | O | GLU | A | 380 | 19.472 | −14.266 | −40.87 | 1 | 43.74 | O |
| ATOM | 1159 | N | TRP | A | 381 | 21.198 | −15.59 | −40.219 | 1 | 45.3 | N |

TABLE V-continued

Atomic Structure Coordinates of Fc/YTE (SEQ ID NO: 11)

| | Atom | A.A. | Type | | X | Y | Z | Occ | B | |
|---|---|---|---|---|---|---|---|---|---|---|
| ATOM | 1160 | CA | TRP | A | 381 | 21.74 | −15.737 | −41.551 | 1 | 46.71 | C |
| ATOM | 1161 | CB | TRP | A | 381 | 23.149 | −15.198 | −41.599 | 1 | 46.55 | C |
| ATOM | 1162 | CG | TRP | A | 381 | 23.253 | −13.735 | −41.503 | 1 | 46.22 | C |
| ATOM | 1163 | CD1 | TRP | A | 381 | 23.34 | −12.997 | −40.365 | 1 | 46.42 | C |
| ATOM | 1164 | NE1 | TRP | A | 381 | 23.454 | −11.664 | −40.697 | 1 | 46.71 | N |
| ATOM | 1165 | CE2 | TRP | A | 381 | 23.427 | −11.538 | −42.056 | 1 | 45.18 | C |
| ATOM | 1166 | CD2 | TRP | A | 381 | 23.306 | −12.822 | −42.582 | 1 | 44.93 | C |
| ATOM | 1167 | CE3 | TRP | A | 381 | 23.257 | −12.974 | −43.961 | 1 | 46.08 | C |
| ATOM | 1168 | CZ3 | TRP | A | 381 | 23.326 | −11.839 | −44.765 | 1 | 45.44 | C |
| ATOM | 1169 | CH2 | TRP | A | 381 | 23.452 | −10.577 | −44.211 | 1 | 45.2 | C |
| ATOM | 1170 | CZ2 | TRP | A | 381 | 23.509 | −10.401 | −42.859 | 1 | 45.93 | C |
| ATOM | 1171 | C | TRP | A | 381 | 21.802 | −17.197 | −41.919 | 1 | 47.94 | C |
| ATOM | 1172 | O | TRP | A | 381 | 21.941 | −18.05 | −41.059 | 1 | 47.84 | O |
| ATOM | 1173 | N | GLU | A | 382 | 21.723 | −17.466 | −43.205 | 1 | 49.94 | N |
| ATOM | 1174 | CA | GLU | A | 382 | 21.833 | −18.798 | −43.752 | 1 | 51.96 | C |
| ATOM | 1175 | CB | GLU | A | 382 | 20.48 | −19.542 | −43.654 | 1 | 51.84 | C |
| ATOM | 1176 | CG | GLU | A | 382 | 19.448 | −19.124 | −44.707 | 1 | 52.61 | C |
| ATOM | 1177 | CD | GLU | A | 382 | 18.131 | −19.869 | −44.608 | 1 | 53.26 | C |
| ATOM | 1178 | OE1 | GLU | A | 382 | 17.531 | −19.849 | −43.519 | 1 | 53.57 | O |
| ATOM | 1179 | OE2 | GLU | A | 382 | 17.699 | −20.463 | −45.627 | 1 | 55.32 | O |
| ATOM | 1180 | C | GLU | A | 382 | 22.257 | −18.735 | −45.224 | 1 | 53.24 | C |
| ATOM | 1181 | O | GLU | A | 382 | 22.132 | −17.713 | −45.892 | 1 | 53.42 | O |
| ATOM | 1182 | N | SER | A | 383 | 22.764 | −19.874 | −45.698 | 1 | 55.24 | N |
| ATOM | 1183 | CA | SER | A | 383 | 23.161 | −20.08 | −47.105 | 1 | 56.59 | C |
| ATOM | 1184 | CB | SER | A | 383 | 24.633 | −19.76 | −47.41 | 1 | 56.67 | C |
| ATOM | 1185 | OG | SER | A | 383 | 24.853 | −19.666 | −48.812 | 1 | 56.97 | O |
| ATOM | 1186 | C | SER | A | 383 | 22.869 | −21.534 | −47.497 | 1 | 58.04 | C |
| ATOM | 1187 | O | SER | A | 383 | 23.033 | −22.424 | −46.673 | 1 | 58.09 | O |
| ATOM | 1188 | N | ASN | A | 384 | 22.423 | −21.763 | −48.728 | 1 | 59.8 | N |
| ATOM | 1189 | CA | ASN | A | 384 | 21.955 | −23.069 | −49.314 | 1 | 60.15 | C |
| ATOM | 1190 | CB | ASN | A | 384 | 23.069 | −23.917 | −49.972 | 1 | 60.72 | C |
| ATOM | 1191 | CG | ASN | A | 384 | 22.533 | −24.981 | −50.922 | 1 | 61.49 | C |
| ATOM | 1192 | OD1 | ASN | A | 384 | 21.328 | −25.154 | −51.045 | 1 | 65.18 | O |
| ATOM | 1193 | ND2 | ASN | A | 384 | 23.42 | −25.693 | −51.598 | 1 | 61.34 | N |
| ATOM | 1194 | C | ASN | A | 384 | 21.226 | −23.903 | −48.264 | 1 | 60.45 | C |
| ATOM | 1195 | O | ASN | A | 384 | 21.511 | −25.073 | −48.072 | 1 | 60.7 | O |
| ATOM | 1196 | N | GLY | A | 385 | 20.278 | −23.233 | −47.594 | 1 | 60.84 | N |
| ATOM | 1197 | CA | GLY | A | 385 | 19.441 | −23.838 | −46.571 | 1 | 60.78 | C |
| ATOM | 1198 | C | GLY | A | 385 | 20.07 | −24.122 | −45.203 | 1 | 60.98 | C |
| ATOM | 1199 | O | GLY | A | 385 | 19.413 | −24.739 | −44.367 | 1 | 61.03 | O |
| ATOM | 1200 | N | GLN | A | 386 | 21.304 | −23.661 | −44.951 | 1 | 61.07 | N |
| ATOM | 1201 | CA | GLN | A | 386 | 22.012 | −23.965 | −43.695 | 1 | 61.1 | C |
| ATOM | 1202 | CB | GLN | A | 386 | 23.313 | −24.739 | −43.994 | 1 | 61.47 | C |
| ATOM | 1203 | CG | GLN | A | 386 | 23.764 | −25.673 | −42.878 | 1 | 62.21 | C |
| ATOM | 1204 | CD | GLN | A | 386 | 23.561 | −27.12 | −43.221 | 1 | 64.63 | C |
| ATOM | 1205 | OE1 | GLN | A | 386 | 22.437 | −27.602 | −43.343 | 1 | 66.03 | O |
| ATOM | 1206 | NE2 | GLN | A | 386 | 24.663 | −27.847 | −43.391 | 1 | 64.22 | N |
| ATOM | 1207 | C | GLN | A | 386 | 22.362 | −22.734 | −42.848 | 1 | 60.87 | C |
| ATOM | 1208 | O | GLN | A | 386 | 22.938 | −21.78 | −43.367 | 1 | 60.67 | O |
| ATOM | 1209 | N | PRO | A | 387 | 21.999 | −22.744 | −41.542 | 1 | 60.96 | N |
| ATOM | 1210 | CA | PRO | A | 387 | 22.328 | −21.626 | −40.671 | 1 | 60.75 | C |
| ATOM | 1211 | CB | PRO | A | 387 | 21.962 | −22.16 | −39.296 | 1 | 60.86 | C |
| ATOM | 1212 | CG | PRO | A | 387 | 20.812 | −23.08 | −39.534 | 1 | 61.09 | C |
| ATOM | 1213 | CD | PRO | A | 387 | 21.009 | −23.657 | −40.912 | 1 | 61.04 | C |
| ATOM | 1214 | C | PRO | A | 387 | 23.8 | −21.259 | −40.78 | 1 | 60.51 | C |
| ATOM | 1215 | O | PRO | A | 387 | 24.68 | −22.122 | −40.697 | 1 | 60.87 | O |
| ATOM | 1216 | N | GLU | A | 388 | 24.08 | −19.966 | −41.015 | 1 | 60.01 | N |
| ATOM | 1217 | CA | GLU | A | 388 | 25.457 | −19.427 | −41.125 | 1 | 59.54 | C |
| ATOM | 1218 | CB | GLU | A | 388 | 25.493 | −18.163 | −41.998 | 1 | 59.6 | C |
| ATOM | 1219 | CG | GLU | A | 388 | 25.727 | −18.382 | −43.484 | 1 | 59.65 | C |
| ATOM | 1220 | CD | GLU | A | 388 | 26.985 | −19.179 | −43.815 | 1 | 59.72 | C |
| ATOM | 1221 | OE1 | GLU | A | 388 | 28.067 | −18.894 | −43.262 | 1 | 59.3 | O |
| ATOM | 1222 | OE2 | GLU | A | 388 | 26.872 | −20.097 | −44.64 | 1 | 60.98 | O |
| ATOM | 1223 | C | GLU | A | 388 | 26.03 | −19.161 | −39.724 | 1 | 59.03 | C |
| ATOM | 1224 | O | GLU | A | 388 | 25.354 | −18.677 | −38.807 | 1 | 59.18 | O |
| ATOM | 1225 | N | ASN | A | 389 | 27.278 | −19.516 | −39.566 | 1 | 58.67 | N |
| ATOM | 1226 | CA | ASN | A | 389 | 27.975 | −19.459 | −38.298 | 1 | 58.05 | C |
| ATOM | 1227 | CB | ASN | A | 389 | 29.258 | −20.273 | −38.429 | 1 | 58.63 | C |
| ATOM | 1228 | CG | ASN | A | 389 | 29.055 | −21.75 | −38.754 | 1 | 59.65 | C |
| ATOM | 1229 | OD1 | ASN | A | 389 | 28.09 | −22.118 | −39.437 | 1 | 61.76 | O |
| ATOM | 1230 | ND2 | ASN | A | 389 | 29.943 | −22.601 | −38.258 | 1 | 60.15 | N |
| ATOM | 1231 | C | ASN | A | 389 | 28.351 | −18.074 | −37.742 | 1 | 57.15 | C |
| ATOM | 1232 | O | ASN | A | 389 | 28.101 | −17.763 | −36.565 | 1 | 57.44 | O |
| ATOM | 1233 | N | ASN | A | 390 | 28.94 | −17.252 | −38.588 | 1 | 55.93 | N |
| ATOM | 1234 | CA | ASN | A | 390 | 29.8 | −16.131 | −38.166 | 1 | 54.89 | C |
| ATOM | 1235 | CB | ASN | A | 390 | 31.144 | −16.237 | −38.935 | 1 | 55.23 | C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 1236 | CG | ASN | A | 390 | 32.358 | −15.763 | −38.136 | 1 | 55.49 | C |
| ATOM | 1237 | OD1 | ASN | A | 390 | 33.489 | −15.908 | −38.599 | 1 | 56.19 | O |
| ATOM | 1238 | ND2 | ASN | A | 390 | 32.139 | −15.211 | −36.955 | 1 | 56.16 | N |
| ATOM | 1239 | C | ASN | A | 390 | 29.149 | −14.782 | −38.445 | 1 | 53.51 | C |
| ATOM | 1240 | O | ASN | A | 390 | 29.56 | −14.067 | −39.353 | 1 | 53.42 | O |
| ATOM | 1241 | N | TYR | A | 391 | 28.109 | −14.458 | −37.687 | 1 | 52.09 | N |
| ATOM | 1242 | CA | TYR | A | 391 | 27.5 | −13.138 | −37.746 | 1 | 51.28 | C |
| ATOM | 1243 | CB | TYR | A | 391 | 26.118 | −13.198 | −38.409 | 1 | 51.8 | C |
| ATOM | 1244 | CG | TYR | A | 391 | 25.081 | −14.009 | −37.643 | 1 | 52.96 | C |
| ATOM | 1245 | CD1 | TYR | A | 391 | 24.824 | −15.347 | −37.955 | 1 | 51.26 | C |
| ATOM | 1246 | CE1 | TYR | A | 391 | 23.893 | −16.068 | −37.247 | 1 | 51.79 | C |
| ATOM | 1247 | CZ | TYR | A | 391 | 23.201 | −15.456 | −36.226 | 1 | 52.78 | C |
| ATOM | 1248 | OH | TYR | A | 391 | 22.256 | −16.14 | −35.498 | 1 | 51.67 | O |
| ATOM | 1249 | CE2 | TYR | A | 391 | 23.431 | −14.148 | −35.911 | 1 | 52.48 | C |
| ATOM | 1250 | CD2 | TYR | A | 391 | 24.362 | −13.437 | −36.603 | 1 | 52.64 | C |
| ATOM | 1251 | C | TYR | A | 391 | 27.417 | −12.507 | −36.345 | 1 | 50.37 | C |
| ATOM | 1252 | O | TYR | A | 391 | 27.494 | −13.196 | −35.332 | 1 | 50.68 | O |
| ATOM | 1253 | N | LYS | A | 392 | 27.296 | −11.186 | −36.293 | 1 | 49.15 | N |
| ATOM | 1254 | CA | LYS | A | 392 | 26.953 | −10.496 | −35.055 | 1 | 47.72 | C |
| ATOM | 1255 | CB | LYS | A | 392 | 28.177 | −9.865 | −34.42 | 1 | 47.91 | C |
| ATOM | 1256 | CG | LYS | A | 392 | 29.196 | −10.87 | −33.894 | 1 | 47.96 | C |
| ATOM | 1257 | CD | LYS | A | 392 | 28.753 | −11.533 | −32.615 | 1 | 48.17 | C |
| ATOM | 1258 | CE | LYS | A | 392 | 29.916 | −12.273 | −31.949 | 1 | 48.1 | C |
| ATOM | 1259 | NZ | LYS | A | 392 | 29.585 | −12.7 | −30.566 | 1 | 47.47 | N |
| ATOM | 1260 | C | LYS | A | 392 | 25.96 | −9.429 | −35.415 | 1 | 46.16 | C |
| ATOM | 1261 | O | LYS | A | 392 | 26.041 | −8.86 | −36.482 | 1 | 44.99 | O |
| ATOM | 1262 | N | THR | A | 393 | 25.004 | −9.186 | −34.527 | 1 | 45.07 | N |
| ATOM | 1263 | CA | THR | A | 393 | 23.951 | −8.209 | −34.791 | 1 | 44.98 | C |
| ATOM | 1264 | CB | THR | A | 393 | 22.531 | −8.878 | −34.894 | 1 | 44.46 | C |
| ATOM | 1265 | OG1 | THR | A | 393 | 22.603 | −10.035 | −35.724 | 1 | 43.36 | O |
| ATOM | 1266 | CG2 | THR | A | 393 | 21.521 | −7.932 | −35.488 | 1 | 43.87 | C |
| ATOM | 1267 | C | THR | A | 393 | 24.003 | −7.105 | −33.724 | 1 | 44.27 | C |
| ATOM | 1268 | O | THR | A | 393 | 24.096 | −7.378 | −32.545 | 1 | 44.64 | O |
| ATOM | 1269 | N | THR | A | 394 | 23.972 | −5.853 | −34.16 | 1 | 43.79 | N |
| ATOM | 1270 | CA | THR | A | 394 | 23.968 | −4.729 | −33.233 | 1 | 43.28 | C |
| ATOM | 1271 | CB | THR | A | 394 | 24.013 | −3.378 | −33.978 | 1 | 43.17 | C |
| ATOM | 1272 | OG1 | THR | A | 394 | 22.756 | −3.164 | −34.642 | 1 | 44.55 | O |
| ATOM | 1273 | CG2 | THR | A | 394 | 25.133 | −3.36 | −35.006 | 1 | 42.39 | C |
| ATOM | 1274 | C | THR | A | 394 | 22.681 | −4.775 | −32.429 | 1 | 42.53 | C |
| ATOM | 1275 | O | THR | A | 394 | 21.685 | −5.326 | −32.893 | 1 | 42.68 | O |
| ATOM | 1276 | N | PRO | A | 395 | 22.688 | −4.194 | −31.221 | 1 | 42.13 | N |
| ATOM | 1277 | CA | PRO | A | 395 | 21.418 | −3.943 | −30.538 | 1 | 42.13 | C |
| ATOM | 1278 | CB | PRO | A | 395 | 21.842 | −3.205 | −29.265 | 1 | 42.14 | C |
| ATOM | 1279 | CG | PRO | A | 395 | 23.244 | −3.666 | −29.021 | 1 | 41.52 | C |
| ATOM | 1280 | CD | PRO | A | 395 | 23.835 | −3.767 | −30.4 | 1 | 41.9 | C |
| ATOM | 1281 | C | PRO | A | 395 | 20.518 | −3.054 | −31.376 | 1 | 42.01 | C |
| ATOM | 1282 | O | PRO | A | 395 | 21.001 | −2.433 | −32.33 | 1 | 42.31 | O |
| ATOM | 1283 | N | PRO | A | 396 | 19.21 | −3.016 | −31.063 | 1 | 41.74 | N |
| ATOM | 1284 | CA | PRO | A | 396 | 18.349 | −2.063 | −31.736 | 1 | 41.91 | C |
| ATOM | 1285 | CB | PRO | A | 396 | 16.946 | −2.467 | −31.272 | 1 | 41.29 | C |
| ATOM | 1286 | CG | PRO | A | 396 | 17.101 | −3.874 | −30.772 | 1 | 41 | C |
| ATOM | 1287 | CD | PRO | A | 396 | 18.443 | −3.884 | −30.156 | 1 | 41.39 | C |
| ATOM | 1288 | C | PRO | A | 396 | 18.671 | −0.647 | −31.314 | 1 | 42.29 | C |
| ATOM | 1289 | O | PRO | A | 396 | 19.071 | −0.417 | −30.178 | 1 | 42.46 | O |
| ATOM | 1290 | N | VAL | A | 397 | 18.49 | 0.293 | −32.228 | 1 | 42.83 | N |
| ATOM | 1291 | CA | VAL | A | 397 | 18.799 | 1.688 | −31.959 | 1 | 43.54 | C |
| ATOM | 1292 | CB | VAL | A | 397 | 19.966 | 2.162 | −32.846 | 1 | 43.44 | C |
| ATOM | 1293 | CG1 | VAL | A | 397 | 20.328 | 3.598 | −32.514 | 1 | 42.5 | C |
| ATOM | 1294 | CG2 | VAL | A | 397 | 21.171 | 1.226 | −32.682 | 1 | 42.82 | C |
| ATOM | 1295 | C | VAL | A | 397 | 17.572 | 2.546 | −32.242 | 1 | 44.44 | C |
| ATOM | 1296 | O | VAL | A | 397 | 16.943 | 2.42 | −33.29 | 1 | 45.53 | O |
| ATOM | 1297 | N | LEU | A | 398 | 17.204 | 3.406 | −31.306 | 1 | 45.39 | N |
| ATOM | 1298 | CA | LEU | A | 398 | 16.086 | 4.31 | −31.533 | 1 | 45.69 | C |
| ATOM | 1299 | CB | LEU | A | 398 | 15.683 | 5.028 | −30.229 | 1 | 46.22 | C |
| ATOM | 1300 | CG | LEU | A | 398 | 14.532 | 6.057 | −30.277 | 1 | 46.12 | C |
| ATOM | 1301 | CD1 | LEU | A | 398 | 13.225 | 5.485 | −30.898 | 1 | 45.7 | C |
| ATOM | 1302 | CD2 | LEU | A | 398 | 14.285 | 6.558 | −28.869 | 1 | 45.69 | C |
| ATOM | 1303 | C | LEU | A | 398 | 16.486 | 5.3 | −32.632 | 1 | 46.24 | C |
| ATOM | 1304 | O | LEU | A | 398 | 17.438 | 6.054 | −32.471 | 1 | 46.63 | O |
| ATOM | 1305 | N | ASP | A | 399 | 15.78 | 5.248 | −33.762 | 1 | 46.5 | N |
| ATOM | 1306 | CA | ASP | A | 399 | 15.965 | 6.194 | −34.861 | 1 | 46.7 | C |
| ATOM | 1307 | CB | ASP | A | 399 | 15.479 | 5.566 | −36.177 | 1 | 46.52 | C |
| ATOM | 1308 | CG | ASP | A | 399 | 16.278 | 6.022 | −37.38 | 1 | 46.47 | C |
| ATOM | 1309 | OD1 | ASP | A | 399 | 16.864 | 7.109 | −37.319 | 1 | 46.18 | O |
| ATOM | 1310 | OD2 | ASP | A | 399 | 16.32 | 5.3 | −38.393 | 1 | 47.28 | O |
| ATOM | 1311 | C | ASP | A | 399 | 15.208 | 7.521 | −34.582 | 1 | 47.33 | C |

TABLE V-continued

Atomic Structure Coordinates of Fc/YTE (SEQ ID NO: 11)

| Atom | | A.A. | Type | | | X | Y | Z | Occ | B | |
|---|---|---|---|---|---|---|---|---|---|---|---|
| ATOM | 1312 | O | ASP | A | 399 | 14.619 | 7.722 | −33.499 | 1 | 47.87 | O |
| ATOM | 1313 | N | SER | A | 400 | 15.217 | 8.417 | −35.563 | 1 | 47.4 | N |
| ATOM | 1314 | CA | SER | A | 400 | 14.763 | 9.777 | −35.367 | 1 | 47.85 | C |
| ATOM | 1315 | CB | SER | A | 400 | 15.399 | 10.694 | −36.415 | 1 | 48.57 | C |
| ATOM | 1316 | OG | SER | A | 400 | 15.246 | 10.162 | −37.734 | 1 | 51.47 | O |
| ATOM | 1317 | C | SER | A | 400 | 13.251 | 9.912 | −35.381 | 1 | 47.96 | C |
| ATOM | 1318 | O | SER | A | 400 | 12.707 | 10.85 | −34.8 | 1 | 48.9 | O |
| ATOM | 1319 | N | ASP | A | 401 | 12.568 | 8.97 | −36.022 | 1 | 47.52 | N |
| ATOM | 1320 | CA | ASP | A | 401 | 11.107 | 8.991 | −36.117 | 1 | 46.47 | C |
| ATOM | 1321 | CB | ASP | A | 401 | 10.652 | 8.491 | −37.493 | 1 | 46.48 | C |
| ATOM | 1322 | CG | ASP | A | 401 | 11.023 | 7.032 | −37.742 | 1 | 47.78 | C |
| ATOM | 1323 | OD1 | ASP | A | 401 | 11.537 | 6.365 | −36.814 | 1 | 47.56 | O |
| ATOM | 1324 | OD2 | ASP | A | 401 | 10.822 | 6.548 | −38.877 | 1 | 49.91 | O |
| ATOM | 1325 | C | ASP | A | 401 | 10.469 | 8.117 | −35.059 | 1 | 45.85 | C |
| ATOM | 1326 | O | ASP | A | 401 | 9.291 | 7.789 | −35.193 | 1 | 46.76 | O |
| ATOM | 1327 | N | GLY | A | 402 | 11.236 | 7.689 | −34.053 | 1 | 44.63 | N |
| ATOM | 1328 | CA | GLY | A | 402 | 10.714 | 6.822 | −32.957 | 1 | 43.52 | C |
| ATOM | 1329 | C | GLY | A | 402 | 10.652 | 5.319 | −33.247 | 1 | 42.76 | C |
| ATOM | 1330 | O | GLY | A | 402 | 10.28 | 4.515 | −32.37 | 1 | 42.69 | O |
| ATOM | 1331 | N | SER | A | 403 | 10.988 | 4.94 | −34.486 | 1 | 41.48 | N |
| ATOM | 1332 | CA | SER | A | 403 | 11.139 | 3.568 | −34.876 | 1 | 40.16 | C |
| ATOM | 1333 | CB | SER | A | 403 | 10.937 | 3.436 | −36.384 | 1 | 40.41 | C |
| ATOM | 1334 | OG | SER | A | 403 | 12.137 | 3.743 | −37.069 | 1 | 40.51 | O |
| ATOM | 1335 | C | SER | A | 403 | 12.55 | 3.11 | −34.528 | 1 | 39.29 | C |
| ATOM | 1336 | O | SER | A | 403 | 13.396 | 3.93 | −34.198 | 1 | 38.65 | O |
| ATOM | 1337 | N | PHE | A | 404 | 12.813 | 1.804 | −34.634 | 1 | 38.43 | N |
| ATOM | 1338 | CA | PHE | A | 404 | 14.154 | 1.276 | −34.385 | 1 | 38.1 | C |
| ATOM | 1339 | CB | PHE | A | 404 | 14.106 | 0.147 | −33.335 | 1 | 37.6 | C |
| ATOM | 1340 | CG | PHE | A | 404 | 13.684 | 0.608 | −31.928 | 1 | 37.61 | C |
| ATOM | 1341 | CD1 | PHE | A | 404 | 14.63 | 0.822 | −30.932 | 1 | 36.8 | C |
| ATOM | 1342 | CE1 | PHE | A | 404 | 14.258 | 1.236 | −29.633 | 1 | 36.81 | C |
| ATOM | 1343 | CZ | PHE | A | 404 | 12.925 | 1.431 | −29.309 | 1 | 36.8 | C |
| ATOM | 1344 | CE2 | PHE | A | 404 | 11.946 | 1.202 | −30.278 | 1 | 37.95 | C |
| ATOM | 1345 | CD2 | PHE | A | 404 | 12.327 | 0.789 | −31.599 | 1 | 38.82 | C |
| ATOM | 1346 | C | PHE | A | 404 | 14.841 | 0.791 | −35.685 | 1 | 37.67 | C |
| ATOM | 1347 | O | PHE | A | 404 | 14.194 | 0.471 | −36.702 | 1 | 37.24 | O |
| ATOM | 1348 | N | PHE | A | 405 | 16.162 | 0.79 | −35.657 | 1 | 36.95 | N |
| ATOM | 1349 | CA | PHE | A | 405 | 16.924 | 0.142 | −36.698 | 1 | 36.89 | C |
| ATOM | 1350 | CB | PHE | A | 405 | 17.535 | 1.168 | −37.664 | 1 | 36.74 | C |
| ATOM | 1351 | CG | PHE | A | 405 | 18.722 | 1.895 | −37.108 | 1 | 37.42 | C |
| ATOM | 1352 | CD1 | PHE | A | 405 | 20.012 | 1.445 | −37.356 | 1 | 38.53 | C |
| ATOM | 1353 | CE1 | PHE | A | 405 | 21.122 | 2.114 | −36.823 | 1 | 38 | C |
| ATOM | 1354 | CZ | PHE | A | 405 | 20.927 | 3.227 | −36.032 | 1 | 36.38 | C |
| ATOM | 1355 | CE2 | PHE | A | 405 | 19.66 | 3.669 | −35.791 | 1 | 36.51 | C |
| ATOM | 1356 | CD2 | PHE | A | 405 | 18.559 | 3.008 | −36.319 | 1 | 36.94 | C |
| ATOM | 1357 | C | PHE | A | 405 | 18.016 | −0.694 | −36.041 | 1 | 36.5 | C |
| ATOM | 1358 | O | PHE | A | 405 | 18.376 | −0.443 | −34.892 | 1 | 36.44 | O |
| ATOM | 1359 | N | LEU | A | 406 | 18.487 | −1.709 | −36.769 | 1 | 36.13 | N |
| ATOM | 1360 | CA | LEU | A | 406 | 19.731 | −2.394 | −36.472 | 1 | 35.51 | C |
| ATOM | 1361 | CB | LEU | A | 406 | 19.512 | −3.609 | −35.577 | 1 | 35.05 | C |
| ATOM | 1362 | CG | LEU | A | 406 | 18.684 | −4.837 | −36.028 | 1 | 34.86 | C |
| ATOM | 1363 | CD1 | LEU | A | 406 | 19.13 | −5.442 | −37.337 | 1 | 34.8 | C |
| ATOM | 1364 | CD2 | LEU | A | 406 | 18.719 | −5.909 | −34.95 | 1 | 34.9 | C |
| ATOM | 1365 | C | LEU | A | 406 | 20.424 | −2.813 | −37.763 | 1 | 35.63 | C |
| ATOM | 1366 | O | LEU | A | 406 | 19.855 | −2.742 | −38.851 | 1 | 34.76 | O |
| ATOM | 1367 | N | TYR | A | 407 | 21.675 | −3.254 | −37.604 | 1 | 36.27 | N |
| ATOM | 1368 | CA | TYR | A | 407 | 22.429 | −3.896 | −38.663 | 1 | 36.67 | C |
| ATOM | 1369 | CB | TYR | A | 407 | 23.707 | −3.103 | −39.033 | 1 | 36.64 | C |
| ATOM | 1370 | CG | TYR | A | 407 | 23.506 | −1.796 | −39.762 | 1 | 36.53 | C |
| ATOM | 1371 | CD1 | TYR | A | 407 | 23.281 | −0.61 | −39.056 | 1 | 36.44 | C |
| ATOM | 1372 | CE1 | TYR | A | 407 | 23.103 | 0.602 | −39.727 | 1 | 37.22 | C |
| ATOM | 1373 | CZ | TYR | A | 407 | 23.16 | 0.637 | −41.146 | 1 | 36.41 | C |
| ATOM | 1374 | OH | TYR | A | 407 | 23.003 | 1.85 | −41.818 | 1 | 36.57 | O |
| ATOM | 1375 | CE2 | TYR | A | 407 | 23.371 | −0.523 | −41.853 | 1 | 34.96 | C |
| ATOM | 1376 | CD2 | TYR | A | 407 | 23.553 | −1.736 | −41.16 | 1 | 35.93 | C |
| ATOM | 1377 | C | TYR | A | 407 | 22.887 | −5.233 | −38.141 | 1 | 36.88 | C |
| ATOM | 1378 | O | TYR | A | 407 | 23.214 | −5.371 | −36.944 | 1 | 36.2 | O |
| ATOM | 1379 | N | SER | A | 408 | 23 | −6.184 | −39.064 | 1 | 37.44 | N |
| ATOM | 1380 | CA | SER | A | 408 | 23.614 | −7.464 | −38.789 | 1 | 38.13 | C |
| ATOM | 1381 | CB | SER | A | 408 | 22.556 | −8.573 | −38.884 | 1 | 37.78 | C |
| ATOM | 1382 | OG | SER | A | 408 | 23.063 | −9.834 | −38.463 | 1 | 37.1 | O |
| ATOM | 1383 | C | SER | A | 408 | 24.75 | −7.659 | −39.804 | 1 | 39.26 | C |
| ATOM | 1384 | O | SER | A | 408 | 24.59 | −7.361 | −41.013 | 1 | 40.76 | O |
| ATOM | 1385 | N | LYS | A | 409 | 25.889 | −8.137 | −39.317 | 1 | 39.6 | N |
| ATOM | 1386 | CA | LYS | A | 409 | 27.06 | −8.382 | −40.135 | 1 | 40.23 | C |
| ATOM | 1387 | CB | LYS | A | 409 | 28.286 | −7.617 | −39.561 | 1 | 39.88 | C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 1388 | CG | LYS | A | 409 | 29.563 | −7.668 | −40.445 | 1 | 39.6 C |
| ATOM | 1389 | CD | LYS | A | 409 | 30.677 | −6.705 | −40.018 | 1 | 39.33 C |
| ATOM | 1390 | CE | LYS | A | 409 | 31.16 | −6.896 | −38.571 | 1 | 39.39 C |
| ATOM | 1391 | NZ | LYS | A | 409 | 31.819 | −8.225 | −38.33 | 1 | 39 N |
| ATOM | 1392 | C | LYS | A | 409 | 27.357 | −9.889 | −40.173 | 1 | 41.06 C |
| ATOM | 1393 | O | LYS | A | 409 | 27.637 | −10.495 | −39.149 | 1 | 39.87 O |
| ATOM | 1394 | N | LEU | A | 410 | 27.318 | −10.476 | −41.366 | 1 | 42.87 N |
| ATOM | 1395 | CA | LEU | A | 410 | 27.817 | −11.827 | −41.564 | 1 | 44.52 C |
| ATOM | 1396 | CB | LEU | A | 410 | 26.91 | −12.62 | −42.508 | 1 | 44.73 C |
| ATOM | 1397 | CG | LEU | A | 410 | 27.321 | −14.072 | −42.787 | 1 | 43.75 C |
| ATOM | 1398 | CD1 | LEU | A | 410 | 27.081 | −14.943 | −41.581 | 1 | 41.56 C |
| ATOM | 1399 | CD2 | LEU | A | 410 | 26.555 | −14.596 | −43.98 | 1 | 45.09 C |
| ATOM | 1400 | C | LEU | A | 410 | 29.184 | −11.733 | −42.186 | 1 | 45.89 C |
| ATOM | 1401 | O | LEU | A | 410 | 29.342 | −11.075 | −43.194 | 1 | 46.17 O |
| ATOM | 1402 | N | THR | A | 411 | 30.166 | −12.379 | −41.566 | 1 | 47.98 N |
| ATOM | 1403 | CA | THR | A | 411 | 31.517 | −12.48 | −42.096 | 1 | 49.19 C |
| ATOM | 1404 | CB | THR | A | 411 | 32.548 | −12.426 | −40.952 | 1 | 49.27 C |
| ATOM | 1405 | OG1 | THR | A | 411 | 32.322 | −11.243 | −40.169 | 1 | 49.91 O |
| ATOM | 1406 | CG2 | THR | A | 411 | 33.998 | −12.422 | −41.486 | 1 | 48.7 C |
| ATOM | 1407 | C | THR | A | 411 | 31.659 | −13.796 | −42.873 | 1 | 50.67 C |
| ATOM | 1408 | O | THR | A | 411 | 31.281 | −14.854 | −42.392 | 1 | 50.94 O |
| ATOM | 1409 | N | VAL | A | 412 | 32.162 | −13.719 | −44.094 | 1 | 52.37 N |
| ATOM | 1410 | CA | VAL | A | 412 | 32.434 | −14.91 | −44.886 | 1 | 53.57 C |
| ATOM | 1411 | CB | VAL | A | 412 | 31.414 | −15.059 | −46.041 | 1 | 53.94 C |
| ATOM | 1412 | CG1 | VAL | A | 412 | 29.979 | −15.062 | −45.52 | 1 | 54.13 C |
| ATOM | 1413 | CG2 | VAL | A | 412 | 31.607 | −13.958 | −47.081 | 1 | 53.94 C |
| ATOM | 1414 | C | VAL | A | 412 | 33.824 | −14.806 | −45.499 | 1 | 54.71 C |
| ATOM | 1415 | O | VAL | A | 412 | 34.334 | −13.7 | −45.701 | 1 | 55.07 O |
| ATOM | 1416 | N | ASP | A | 413 | 34.424 | −15.944 | −45.833 | 1 | 56.05 N |
| ATOM | 1417 | CA | ASP | A | 413 | 35.648 | −15.94 | −46.657 | 1 | 57.03 C |
| ATOM | 1418 | CB | ASP | A | 413 | 36.155 | −17.361 | −46.89 | 1 | 57.43 C |
| ATOM | 1419 | CG | ASP | A | 413 | 36.578 | −18.045 | −45.619 | 1 | 59.32 C |
| ATOM | 1420 | OD1 | ASP | A | 413 | 36.388 | −19.285 | −45.539 | 1 | 61.87 O |
| ATOM | 1421 | OD2 | ASP | A | 413 | 37.096 | −17.357 | −44.699 | 1 | 61.43 O |
| ATOM | 1422 | C | ASP | A | 413 | 35.401 | −15.278 | −48.014 | 1 | 57.66 C |
| ATOM | 1423 | O | ASP | A | 413 | 34.329 | −15.407 | −48.584 | 1 | 58.61 O |
| ATOM | 1424 | N | LYS | A | 414 | 36.391 | −14.585 | −48.55 | 1 | 58.42 N |
| ATOM | 1425 | CA | LYS | A | 414 | 36.201 | −13.901 | −49.835 | 1 | 58.77 C |
| ATOM | 1426 | CB | LYS | A | 414 | 37.459 | −13.139 | −50.239 | 1 | 58.99 C |
| ATOM | 1427 | CG | LYS | A | 414 | 37.263 | −12.274 | −51.467 | 1 | 58.97 C |
| ATOM | 1428 | CD | LYS | A | 414 | 38.266 | −11.12 | −51.529 | 1 | 59.38 C |
| ATOM | 1429 | CE | LYS | A | 414 | 39.712 | −11.569 | −51.859 | 1 | 60.04 C |
| ATOM | 1430 | NZ | LYS | A | 414 | 40.608 | −11.757 | −50.667 | 1 | 59.67 N |
| ATOM | 1431 | C | LYS | A | 414 | 35.794 | −14.862 | −50.954 | 1 | 59 C |
| ATOM | 1432 | O | LYS | A | 414 | 34.876 | −14.567 | −51.721 | 1 | 59.19 O |
| ATOM | 1433 | N | SER | A | 415 | 36.457 | −16.013 | −51.029 | 1 | 59.1 N |
| ATOM | 1434 | CA | SER | A | 415 | 36.138 | −17.025 | −52.05 | 1 | 59.26 C |
| ATOM | 1435 | CB | SER | A | 415 | 36.928 | −18.313 | −51.822 | 1 | 59.3 C |
| ATOM | 1436 | OG | SER | A | 415 | 36.906 | −18.68 | −50.454 | 1 | 60.51 O |
| ATOM | 1437 | C | SER | A | 415 | 34.65 | −17.352 | −52.092 | 1 | 59.43 C |
| ATOM | 1438 | O | SER | A | 415 | 34.023 | −17.309 | −53.168 | 1 | 59.57 O |
| ATOM | 1439 | N | ARG | A | 416 | 34.076 | −17.646 | −50.924 | 1 | 59.23 N |
| ATOM | 1440 | CA | ARG | A | 416 | 32.682 | −18.061 | −50.87 | 1 | 58.96 C |
| ATOM | 1441 | CB | ARG | A | 416 | 32.221 | −18.287 | −49.438 | 1 | 58.79 C |
| ATOM | 1442 | CG | ARG | A | 416 | 32.945 | −19.441 | −48.74 | 1 | 58.3 C |
| ATOM | 1443 | CD | ARG | A | 416 | 32.272 | −19.782 | −47.448 | 1 | 57.92 C |
| ATOM | 1444 | NE | ARG | A | 416 | 30.879 | −20.144 | −47.668 | 1 | 58.27 N |
| ATOM | 1445 | CZ | ARG | A | 416 | 29.935 | −20.154 | −46.724 | 1 | 58 C |
| ATOM | 1446 | NH1 | ARG | A | 416 | 30.228 | −19.819 | −45.467 | 1 | 58.91 N |
| ATOM | 1447 | NH2 | ARG | A | 416 | 28.69 | −20.495 | −47.043 | 1 | 56.18 N |
| ATOM | 1448 | C | ARG | A | 416 | 31.834 | −17.013 | −51.536 | 1 | 59.5 C |
| ATOM | 1449 | O | ARG | A | 416 | 30.874 | −17.324 | −52.232 | 1 | 59.66 O |
| ATOM | 1450 | N | TRP | A | 417 | 32.205 | −15.759 | −51.337 | 1 | 60.02 N |
| ATOM | 1451 | CA | TRP | A | 417 | 31.434 | −14.675 | −51.887 | 1 | 60.88 C |
| ATOM | 1452 | CB | TRP | A | 417 | 31.803 | −13.354 | −51.199 | 1 | 59.18 C |
| ATOM | 1453 | CG | TRP | A | 417 | 31.169 | −12.186 | −51.821 | 1 | 57.56 C |
| ATOM | 1454 | CD1 | TRP | A | 417 | 31.778 | −11.253 | −52.6 | 1 | 56 C |
| ATOM | 1455 | NE1 | TRP | A | 417 | 30.864 | −10.318 | −53.025 | 1 | 55.98 N |
| ATOM | 1456 | CE2 | TRP | A | 417 | 29.633 | −10.643 | −52.522 | 1 | 58.09 C |
| ATOM | 1457 | CD2 | TRP | A | 417 | 29.784 | −11.821 | −51.763 | 1 | 58 C |
| ATOM | 1458 | CE3 | TRP | A | 417 | 28.657 | −12.375 | −51.143 | 1 | 57.93 C |
| ATOM | 1459 | CZ3 | TRP | A | 417 | 27.442 | −11.743 | −51.297 | 1 | 58.96 C |
| ATOM | 1460 | CH2 | TRP | A | 417 | 27.328 | −10.57 | −52.061 | 1 | 59.1 C |
| ATOM | 1461 | CZ2 | TRP | A | 417 | 28.415 | −10.004 | −52.67 | 1 | 57.53 C |
| ATOM | 1462 | C | TRP | A | 417 | 31.677 | −14.641 | −53.397 | 1 | 61.78 C |
| ATOM | 1463 | O | TRP | A | 417 | 30.752 | −14.45 | −54.18 | 1 | 61.84 O |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 1464 | N | GLN | A | 418 | 32.927 | −14.853 | −53.796 | 1 | 63.17 N |
| ATOM | 1465 | CA | GLN | A | 418 | 33.311 | −14.758 | −55.202 | 1 | 63.74 C |
| ATOM | 1466 | CB | GLN | A | 418 | 34.833 | −14.638 | −55.333 | 1 | 64.4 C |
| ATOM | 1467 | CG | GLN | A | 418 | 35.397 | −13.262 | −54.913 | 1 | 65.33 C |
| ATOM | 1468 | CD | GLN | A | 418 | 36.929 | −13.225 | −54.917 | 1 | 65.75 C |
| ATOM | 1469 | OE1 | GLN | A | 418 | 37.54 | −12.154 | −54.906 | 1 | 68.05 O |
| ATOM | 1470 | NE2 | GLN | A | 418 | 37.554 | −14.404 | −54.92 | 1 | 68.33 N |
| ATOM | 1471 | C | GLN | A | 418 | 32.786 | −15.914 | −56.054 | 1 | 63.89 C |
| ATOM | 1472 | O | GLN | A | 418 | 32.539 | −15.726 | −57.238 | 1 | 64.36 O |
| ATOM | 1473 | N | GLN | A | 419 | 32.588 | −17.09 | −55.459 | 1 | 63.75 N |
| ATOM | 1474 | CA | GLN | A | 419 | 31.991 | −18.233 | −56.184 | 1 | 63.42 C |
| ATOM | 1475 | CB | GLN | A | 419 | 32.234 | −19.531 | −55.418 | 1 | 63.85 C |
| ATOM | 1476 | CG | GLN | A | 419 | 33.687 | −20.022 | −55.485 | 1 | 64.78 C |
| ATOM | 1477 | CD | GLN | A | 419 | 34.052 | −20.89 | −54.289 | 1 | 65.23 C |
| ATOM | 1478 | OE1 | GLN | A | 419 | 33.169 | −21.456 | −53.614 | 1 | 66.49 O |
| ATOM | 1479 | NE2 | GLN | A | 419 | 35.357 | −20.978 | −54 | 1 | 66.78 N |
| ATOM | 1480 | C | GLN | A | 419 | 30.487 | −18.101 | −56.479 | 1 | 62.8 C |
| ATOM | 1481 | O | GLN | A | 419 | 29.886 | −19.013 | −57.075 | 1 | 62.92 O |
| ATOM | 1482 | N | GLY | A | 420 | 29.878 | −16.988 | −56.057 | 1 | 61.56 N |
| ATOM | 1483 | CA | GLY | A | 420 | 28.471 | −16.702 | −56.349 | 1 | 60.43 C |
| ATOM | 1484 | C | GLY | A | 420 | 27.476 | −17.305 | −55.369 | 1 | 59.25 C |
| ATOM | 1485 | O | GLY | A | 420 | 26.291 | −17.351 | −55.648 | 1 | 58.38 O |
| ATOM | 1486 | N | ASN | A | 421 | 27.948 | −17.771 | −54.218 | 1 | 58.31 N |
| ATOM | 1487 | CA | ASN | A | 421 | 27.041 | −18.277 | −53.192 | 1 | 57.56 C |
| ATOM | 1488 | CB | ASN | A | 421 | 27.837 | −18.711 | −51.97 | 1 | 57.62 C |
| ATOM | 1489 | CG | ASN | A | 421 | 28.561 | −20.02 | −52.186 | 1 | 58.05 C |
| ATOM | 1490 | OD1 | ASN | A | 421 | 29.766 | −20.053 | −52.428 | 1 | 59.07 O |
| ATOM | 1491 | ND2 | ASN | A | 421 | 27.822 | −21.11 | −52.107 | 1 | 58.45 N |
| ATOM | 1492 | C | ASN | A | 421 | 25.98 | −17.246 | −52.786 | 1 | 56.78 C |
| ATOM | 1493 | O | ASN | A | 421 | 26.308 | −16.087 | −52.494 | 1 | 57.2 O |
| ATOM | 1494 | N | VAL | A | 422 | 24.709 | −17.653 | −52.798 | 1 | 55.57 N |
| ATOM | 1495 | CA | VAL | A | 422 | 23.618 | −16.792 | −52.303 | 1 | 54.47 C |
| ATOM | 1496 | CB | VAL | A | 422 | 22.205 | −17.187 | −52.882 | 1 | 54.2 C |
| ATOM | 1497 | CG1 | VAL | A | 422 | 21.068 | −16.603 | −52.035 | 1 | 52.89 C |
| ATOM | 1498 | CG2 | VAL | A | 422 | 22.07 | −16.726 | −54.327 | 1 | 53.61 C |
| ATOM | 1499 | C | VAL | A | 422 | 23.621 | −16.91 | −50.785 | 1 | 53.5 C |
| ATOM | 1500 | O | VAL | A | 422 | 23.794 | −18.011 | −50.258 | 1 | 52.86 O |
| ATOM | 1501 | N | PHE | A | 423 | 23.462 | −15.772 | −50.101 | 1 | 52.74 N |
| ATOM | 1502 | CA | PHE | A | 423 | 23.433 | −15.717 | −48.637 | 1 | 52.05 C |
| ATOM | 1503 | CB | PHE | A | 423 | 24.632 | −14.955 | −48.082 | 1 | 52.23 C |
| ATOM | 1504 | CG | PHE | A | 423 | 25.932 | −15.647 | −48.257 | 1 | 51.89 C |
| ATOM | 1505 | CD1 | PHE | A | 423 | 26.674 | −15.464 | −49.416 | 1 | 51.16 C |
| ATOM | 1506 | CE1 | PHE | A | 423 | 27.893 | −16.093 | −49.583 | 1 | 51.77 C |
| ATOM | 1507 | CZ | PHE | A | 423 | 28.397 | −16.919 | −48.579 | 1 | 52.71 C |
| ATOM | 1508 | CE2 | PHE | A | 423 | 27.662 | −17.107 | −47.41 | 1 | 52.75 C |
| ATOM | 1509 | CD2 | PHE | A | 423 | 26.436 | −16.464 | −47.257 | 1 | 52.31 C |
| ATOM | 1510 | C | PHE | A | 423 | 22.195 | −14.963 | −48.24 | 1 | 51.45 C |
| ATOM | 1511 | O | PHE | A | 423 | 21.784 | −14.05 | −48.957 | 1 | 50.96 O |
| ATOM | 1512 | N | SER | A | 424 | 21.63 | −15.3 | −47.075 | 1 | 50.82 N |
| ATOM | 1513 | CA | SER | A | 424 | 20.316 | −14.78 | −46.715 | 1 | 50.5 C |
| ATOM | 1514 | CB | SER | A | 424 | 19.232 | −15.827 | −46.997 | 1 | 50.78 C |
| ATOM | 1515 | OG | SER | A | 424 | 19.174 | −16.14 | −48.384 | 1 | 52.21 O |
| ATOM | 1516 | C | SER | A | 424 | 20.178 | −14.27 | −45.286 | 1 | 49.33 C |
| ATOM | 1517 | O | SER | A | 424 | 20.448 | −14.951 | −44.287 | 1 | 48.37 O |
| ATOM | 1518 | N | CYS | A | 425 | 19.707 | −13.042 | −45.228 | 1 | 48.48 N |
| ATOM | 1519 | CA | CYS | A | 425 | 19.343 | −12.412 | −43.991 | 1 | 48.21 C |
| ATOM | 1520 | CB | CYS | A | 425 | 19.514 | −10.909 | −44.127 | 1 | 47.98 C |
| ATOM | 1521 | SG | CYS | A | 425 | 19.301 | −10.061 | −42.605 | 1 | 47.89 S |
| ATOM | 1522 | C | CYS | A | 425 | 17.895 | −12.738 | −43.72 | 1 | 47.75 C |
| ATOM | 1523 | O | CYS | A | 425 | 17.046 | −12.518 | −44.574 | 1 | 47.45 O |
| ATOM | 1524 | N | SER | A | 426 | 17.603 | −13.26 | −42.542 | 1 | 47.62 N |
| ATOM | 1525 | CA | SER | A | 426 | 16.215 | −13.567 | −42.213 | 1 | 48.07 C |
| ATOM | 1526 | CB | SER | A | 426 | 15.999 | −15.088 | −42.067 | 1 | 48.14 C |
| ATOM | 1527 | OG | SER | A | 426 | 16.767 | −15.596 | −40.991 | 1 | 49.04 O |
| ATOM | 1528 | C | SER | A | 426 | 15.829 | −12.81 | −40.955 | 1 | 47.77 C |
| ATOM | 1529 | O | SER | A | 426 | 16.533 | −12.864 | −39.944 | 1 | 47.29 O |
| ATOM | 1530 | N | VAL | A | 427 | 14.71 | −12.098 | −41.046 | 1 | 47.88 N |
| ATOM | 1531 | CA | VAL | A | 427 | 14.232 | −11.222 | −39.971 | 1 | 47.75 C |
| ATOM | 1532 | CB | VAL | A | 427 | 14.125 | −9.764 | −40.475 | 1 | 47.55 C |
| ATOM | 1533 | CG1 | VAL | A | 427 | 13.819 | −8.804 | −39.33 | 1 | 46.4 C |
| ATOM | 1534 | CG2 | VAL | A | 427 | 15.411 | −9.372 | −41.193 | 1 | 46.88 C |
| ATOM | 1535 | C | VAL | A | 427 | 12.867 | −11.698 | −39.47 | 1 | 47.82 C |
| ATOM | 1536 | O | VAL | A | 427 | 11.978 | −12.042 | −40.252 | 1 | 48.35 O |
| ATOM | 1537 | N | MET | A | 428 | 12.7 | −11.699 | −38.157 | 1 | 47.95 N |
| ATOM | 1538 | CA | MET | A | 428 | 11.466 | −12.161 | −37.532 | 1 | 47.7 C |
| ATOM | 1539 | CB | MET | A | 428 | 11.776 | −13.4 | −36.712 | 1 | 47.96 C |

TABLE V-continued

Atomic Structure Coordinates of Fc/YTE (SEQ ID NO: 11)

| | | Atom | A.A. | Type | | X | Y | Z | Occ | B | |
|---|---|---|---|---|---|---|---|---|---|---|---|
| ATOM | 1540 | CG | MET | A | 428 | 12.664 | −14.378 | −37.491 | 1 | 48.42 | C |
| ATOM | 1541 | SD | MET | A | 428 | 13.2 | −15.769 | −36.536 | 1 | 49.98 | S |
| ATOM | 1542 | CE | MET | A | 428 | 14.908 | −15.86 | −37.082 | 1 | 49.34 | C |
| ATOM | 1543 | C | MET | A | 428 | 10.93 | −11.048 | −36.666 | 1 | 47.33 | C |
| ATOM | 1544 | O | MET | A | 428 | 11.613 | −10.59 | −35.751 | 1 | 47 | O |
| ATOM | 1545 | N | HIS | A | 429 | 9.719 | −10.587 | −36.991 | 1 | 47.11 | N |
| ATOM | 1546 | CA | HIS | A | 429 | 9.099 | −9.453 | −36.306 | 1 | 46.49 | C |
| ATOM | 1547 | CB | HIS | A | 429 | 9.532 | −8.145 | −36.941 | 1 | 46.2 | C |
| ATOM | 1548 | CG | HIS | A | 429 | 9.283 | −6.976 | −36.057 | 1 | 45.27 | C |
| ATOM | 1549 | ND1 | HIS | A | 429 | 10.076 | −6.711 | −34.965 | 1 | 44 | N |
| ATOM | 1550 | CE1 | HIS | A | 429 | 9.606 | −5.644 | −34.346 | 1 | 43.48 | C |
| ATOM | 1551 | NE2 | HIS | A | 429 | 8.529 | −5.23 | −34.981 | 1 | 42.35 | N |
| ATOM | 1552 | CD2 | HIS | A | 429 | 8.299 | −6.048 | −36.053 | 1 | 43.47 | C |
| ATOM | 1553 | C | HIS | A | 429 | 7.591 | −9.491 | −36.355 | 1 | 46.57 | C |
| ATOM | 1554 | O | HIS | A | 429 | 7.024 | −9.919 | −37.362 | 1 | 47.23 | O |
| ATOM | 1555 | N | GLU | A | 430 | 6.925 | −8.999 | −35.309 | 1 | 46.14 | N |
| ATOM | 1556 | CA | GLU | A | 430 | 5.472 | −9.123 | −35.274 | 1 | 45.83 | C |
| ATOM | 1557 | CB | GLU | A | 430 | 4.881 | −8.679 | −33.935 | 1 | 45.67 | C |
| ATOM | 1558 | CG | GLU | A | 430 | 4.93 | −7.199 | −33.625 | 1 | 45.47 | C |
| ATOM | 1559 | CD | GLU | A | 430 | 3.845 | −6.8 | −32.624 | 1 | 45.89 | C |
| ATOM | 1560 | OE1 | GLU | A | 430 | 4.188 | −6.164 | −31.605 | 1 | 46.51 | O |
| ATOM | 1561 | OE2 | GLU | A | 430 | 2.655 | −7.141 | −32.847 | 1 | 46.12 | O |
| ATOM | 1562 | C | GLU | A | 430 | 4.785 | −8.425 | −36.448 | 1 | 45.32 | C |
| ATOM | 1563 | O | GLU | A | 430 | 3.714 | −8.835 | −36.856 | 1 | 45.35 | O |
| ATOM | 1564 | N | ALA | A | 431 | 5.422 | −7.408 | −37.012 | 1 | 45.35 | N |
| ATOM | 1565 | CA | ALA | A | 431 | 4.804 | −6.577 | −38.087 | 1 | 45.63 | C |
| ATOM | 1566 | CB | ALA | A | 431 | 5.227 | −5.119 | −37.93 | 1 | 44.87 | C |
| ATOM | 1567 | C | ALA | A | 431 | 5.147 | −7.063 | −39.494 | 1 | 45.23 | C |
| ATOM | 1568 | O | ALA | A | 431 | 4.891 | −6.382 | −40.458 | 1 | 44.84 | O |
| ATOM | 1569 | N | LEU | A | 432 | 5.758 | −8.234 | −39.599 | 1 | 45.79 | N |
| ATOM | 1570 | CA | LEU | A | 432 | 6.026 | −8.847 | −40.886 | 1 | 46.51 | C |
| ATOM | 1571 | CB | LEU | A | 432 | 7.406 | −9.509 | −40.892 | 1 | 46.71 | C |
| ATOM | 1572 | CG | LEU | A | 432 | 8.623 | −8.567 | −40.959 | 1 | 47.69 | C |
| ATOM | 1573 | CD1 | LEU | A | 432 | 9.906 | −9.368 | −40.821 | 1 | 48.26 | C |
| ATOM | 1574 | CD2 | LEU | A | 432 | 8.64 | −7.701 | −42.257 | 1 | 47.81 | C |
| ATOM | 1575 | C | LEU | A | 432 | 4.954 | −9.873 | −41.154 | 1 | 46.63 | C |
| ATOM | 1576 | O | LEU | A | 432 | 4.408 | −10.444 | −40.231 | 1 | 45.97 | O |
| ATOM | 1577 | N | HIS | A | 433 | 4.639 | −10.082 | −42.424 | 1 | 47.88 | N |
| ATOM | 1578 | CA | HIS | A | 433 | 3.666 | −11.088 | −42.803 | 1 | 48.33 | C |
| ATOM | 1579 | CB | HIS | A | 433 | 3.396 | −11.052 | −44.302 | 1 | 49.05 | C |
| ATOM | 1580 | CG | HIS | A | 433 | 2.353 | −12.032 | −44.719 | 1 | 50.03 | C |
| ATOM | 1581 | ND1 | HIS | A | 433 | 1.014 | −11.85 | −44.438 | 1 | 53.15 | N |
| ATOM | 1582 | CE1 | HIS | A | 433 | 0.326 | −12.885 | −44.894 | 1 | 52.86 | C |
| ATOM | 1583 | NE2 | HIS | A | 433 | 1.175 | −13.744 | −45.427 | 1 | 53.17 | N |
| ATOM | 1584 | CD2 | HIS | A | 433 | 2.451 | −13.236 | −45.33 | 1 | 52.19 | C |
| ATOM | 1585 | C | HIS | A | 433 | 4.143 | −12.486 | −42.42 | 1 | 48.45 | C |
| ATOM | 1586 | O | HIS | A | 433 | 5.236 | −12.879 | −42.753 | 1 | 48.42 | O |
| ATOM | 1587 | N | ASN | A | 434 | 3.314 | −13.238 | −41.711 | 1 | 49.03 | N |
| ATOM | 1588 | CA | ASN | A | 434 | 3.734 | −14.546 | −41.145 | 1 | 48.8 | C |
| ATOM | 1589 | CB | ASN | A | 434 | 4.099 | −15.562 | −42.238 | 1 | 49.03 | C |
| ATOM | 1590 | CG | ASN | A | 434 | 2.908 | −15.931 | −43.132 | 1 | 49.3 | C |
| ATOM | 1591 | OD1 | ASN | A | 434 | 3.018 | −15.964 | −44.369 | 1 | 50.61 | O |
| ATOM | 1592 | ND2 | ASN | A | 434 | 1.788 | −16.231 | −42.513 | 1 | 48.3 | N |
| ATOM | 1593 | C | ASN | A | 434 | 4.893 | −14.415 | −40.155 | 1 | 48.65 | C |
| ATOM | 1594 | O | ASN | A | 434 | 5.523 | −15.404 | −39.814 | 1 | 49.02 | O |
| ATOM | 1595 | N | HIS | A | 435 | 5.137 | −13.201 | −39.672 | 1 | 48.25 | N |
| ATOM | 1596 | CA | HIS | A | 435 | 6.197 | −12.921 | −38.705 | 1 | 48.08 | C |
| ATOM | 1597 | CB | HIS | A | 435 | 5.99 | −13.727 | −37.419 | 1 | 47.5 | C |
| ATOM | 1598 | CG | HIS | A | 435 | 4.732 | −13.391 | −36.681 | 1 | 47.32 | C |
| ATOM | 1599 | ND1 | HIS | A | 435 | 3.925 | −12.325 | −37.018 | 1 | 46.73 | N |
| ATOM | 1600 | CE1 | HIS | A | 435 | 2.919 | −12.259 | −36.165 | 1 | 47.19 | C |
| ATOM | 1601 | NE2 | HIS | A | 435 | 3.054 | −13.23 | −35.28 | 1 | 45.96 | N |
| ATOM | 1602 | CD2 | HIS | A | 435 | 4.179 | −13.947 | −35.576 | 1 | 46.34 | C |
| ATOM | 1603 | C | HIS | A | 435 | 7.604 | −13.167 | −39.257 | 1 | 48.05 | C |
| ATOM | 1604 | O | HIS | A | 435 | 8.538 | −13.425 | −38.494 | 1 | 47.75 | O |
| ATOM | 1605 | N | TYR | A | 436 | 7.778 | −13.064 | −40.57 | 1 | 48.3 | N |
| ATOM | 1606 | CA | TYR | A | 436 | 9.027 | −13.526 | −41.161 | 1 | 48.77 | C |
| ATOM | 1607 | CB | TYR | A | 436 | 9.017 | −15.062 | −41.245 | 1 | 48.65 | C |
| ATOM | 1608 | CG | TYR | A | 436 | 10.298 | −15.711 | −41.771 | 1 | 48.52 | C |
| ATOM | 1609 | CD1 | TYR | A | 436 | 10.501 | −15.874 | −43.13 | 1 | 48.65 | C |
| ATOM | 1610 | CE1 | TYR | A | 436 | 11.635 | −16.464 | −43.606 | 1 | 48.03 | C |
| ATOM | 1611 | CZ | TYR | A | 436 | 12.582 | −16.907 | −42.727 | 1 | 48.25 | C |
| ATOM | 1612 | OH | TYR | A | 436 | 13.727 | −17.506 | −43.23 | 1 | 49.72 | O |
| ATOM | 1613 | CE2 | TYR | A | 436 | 12.407 | −16.763 | −41.358 | 1 | 47.15 | C |
| ATOM | 1614 | CD2 | TYR | A | 436 | 11.282 | −16.179 | −40.897 | 1 | 47.47 | C |
| ATOM | 1615 | C | TYR | A | 436 | 9.269 | −12.954 | −42.534 | 1 | 49.59 | C |

TABLE V-continued

Atomic Structure Coordinates of Fc/YTE (SEQ ID NO: 11)

| Atom | A.A. Type | | | X | Y | Z | Occ | B | |
|---|---|---|---|---|---|---|---|---|---|
| ATOM | 1616 | O | TYR | A | 436 | 8.373 | −12.938 | −43.376 | 1 | 49.49 | O |
| ATOM | 1617 | N | THR | A | 437 | 10.489 | −12.476 | −42.746 | 1 | 50.32 | N |
| ATOM | 1618 | CA | THR | A | 437 | 10.945 | −12.166 | −44.084 | 1 | 51.13 | C |
| ATOM | 1619 | CB | THR | A | 437 | 10.672 | −10.682 | −44.478 | 1 | 50.83 | C |
| ATOM | 1620 | OG1 | THR | A | 437 | 10.517 | −10.604 | −45.894 | 1 | 51.49 | O |
| ATOM | 1621 | CG2 | THR | A | 437 | 11.792 | −9.753 | −44.059 | 1 | 49.3 | C |
| ATOM | 1622 | C | THR | A | 437 | 12.419 | −12.57 | −44.212 | 1 | 51.61 | C |
| ATOM | 1623 | O | THR | A | 437 | 13.124 | −12.744 | −43.199 | 1 | 52.03 | O |
| ATOM | 1624 | N | GLN | A | 438 | 12.839 | −12.757 | −45.46 | 1 | 52.09 | N |
| ATOM | 1625 | CA | GLN | A | 438 | 14.15 | −13.291 | −45.823 | 1 | 52.64 | C |
| ATOM | 1626 | CB | GLN | A | 438 | 14.031 | −14.747 | −46.345 | 1 | 52.55 | C |
| ATOM | 1627 | CG | GLN | A | 438 | 15.224 | −15.716 | −46.038 | 1 | 52.62 | C |
| ATOM | 1628 | CD | GLN | A | 438 | 14.874 | −17.278 | −46.058 | 1 | 53.23 | C |
| ATOM | 1629 | OE1 | GLN | A | 438 | 15.751 | −18.116 | −45.802 | 1 | 54.27 | O |
| ATOM | 1630 | NE2 | GLN | A | 438 | 13.616 | −17.635 | −46.325 | 1 | 52.67 | N |
| ATOM | 1631 | C | GLN | A | 438 | 14.573 | −12.362 | −46.928 | 1 | 53.07 | C |
| ATOM | 1632 | O | GLN | A | 438 | 13.754 | −12.004 | −47.761 | 1 | 53.07 | O |
| ATOM | 1633 | N | LYS | A | 439 | 15.816 | −11.907 | −46.918 | 1 | 53.54 | N |
| ATOM | 1634 | CA | LYS | A | 439 | 16.31 | −11.121 | −48.032 | 1 | 53.92 | C |
| ATOM | 1635 | CB | LYS | A | 439 | 16.36 | −9.616 | −47.721 | 1 | 54.46 | C |
| ATOM | 1636 | CG | LYS | A | 439 | 15.006 | −8.907 | −47.764 | 1 | 55.83 | C |
| ATOM | 1637 | CD | LYS | A | 439 | 14.58 | −8.528 | −49.181 | 1 | 56.97 | C |
| ATOM | 1638 | CE | LYS | A | 439 | 13.163 | −7.925 | −49.218 | 1 | 57.51 | C |
| ATOM | 1639 | NZ | LYS | A | 439 | 13.071 | −6.825 | −50.263 | 1 | 57.97 | N |
| ATOM | 1640 | C | LYS | A | 439 | 17.668 | −11.665 | −48.322 | 1 | 54.13 | C |
| ATOM | 1641 | O | LYS | A | 439 | 18.424 | −11.96 | −47.397 | 1 | 53.45 | O |
| ATOM | 1642 | N | SER | A | 440 | 17.967 | −11.795 | −49.613 | 1 | 54.8 | N |
| ATOM | 1643 | CA | SER | A | 440 | 19.151 | −12.506 | −50.064 | 1 | 55.48 | C |
| ATOM | 1644 | CB | SER | A | 440 | 18.721 | −13.704 | −50.894 | 1 | 55.76 | C |
| ATOM | 1645 | OG | SER | A | 440 | 18.118 | −14.707 | −50.067 | 1 | 57.03 | O |
| ATOM | 1646 | C | SER | A | 440 | 20.168 | −11.643 | −50.815 | 1 | 55.62 | C |
| ATOM | 1647 | O | SER | A | 440 | 19.917 | −10.491 | −51.161 | 1 | 55.59 | O |
| ATOM | 1648 | N | LEU | A | 441 | 21.332 | −12.232 | −51.057 | 1 | 55.94 | N |
| ATOM | 1649 | CA | LEU | A | 441 | 22.516 | −11.479 | −51.409 | 1 | 56.57 | C |
| ATOM | 1650 | CB | LEU | A | 441 | 23.114 | −10.872 | −50.132 | 1 | 56.28 | C |
| ATOM | 1651 | CG | LEU | A | 441 | 24.322 | −9.95 | −50.227 | 1 | 55.4 | C |
| ATOM | 1652 | CD1 | LEU | A | 441 | 23.963 | −8.647 | −50.841 | 1 | 53.22 | C |
| ATOM | 1653 | CD2 | LEU | A | 441 | 24.892 | −9.739 | −48.839 | 1 | 56.1 | C |
| ATOM | 1654 | C | LEU | A | 441 | 23.539 | −12.396 | −52.069 | 1 | 57.11 | C |
| ATOM | 1655 | O | LEU | A | 441 | 23.857 | −13.476 | −51.548 | 1 | 56.68 | O |
| ATOM | 1656 | N | SER | A | 442 | 24.049 | −11.933 | −53.209 | 1 | 58.26 | N |
| ATOM | 1657 | CA | SER | A | 442 | 25.031 | −12.659 | −54.01 | 1 | 59.34 | C |
| ATOM | 1658 | CB | SER | A | 442 | 24.335 | −13.708 | −54.897 | 1 | 59.22 | C |
| ATOM | 1659 | OG | SER | A | 442 | 23.486 | −13.068 | −55.849 | 1 | 58.85 | O |
| ATOM | 1660 | C | SER | A | 442 | 25.776 | −11.664 | −54.897 | 1 | 60.21 | C |
| ATOM | 1661 | O | SER | A | 442 | 25.418 | −10.487 | −54.956 | 1 | 59.7 | O |
| ATOM | 1662 | N | LEU | A | 443 | 26.783 | −12.168 | −55.61 | 1 | 61.72 | N |
| ATOM | 1663 | CA | LEU | A | 443 | 27.665 | −11.341 | −56.446 | 1 | 62.64 | C |
| ATOM | 1664 | CB | LEU | A | 443 | 28.887 | −12.166 | −56.874 | 1 | 62.85 | C |
| ATOM | 1665 | CG | LEU | A | 443 | 30.183 | −11.467 | −57.307 | 1 | 62.47 | C |
| ATOM | 1666 | CD1 | LEU | A | 443 | 30.494 | −10.247 | −56.464 | 1 | 62.81 | C |
| ATOM | 1667 | CD2 | LEU | A | 443 | 31.331 | −12.47 | −57.233 | 1 | 62.67 | C |
| ATOM | 1668 | C | LEU | A | 443 | 26.946 | −10.781 | −57.683 | 1 | 63.68 | C |
| ATOM | 1669 | O | LEU | A | 443 | 26.441 | −11.536 | −58.519 | 1 | 63.76 | O |
| ATOM | 1670 | N | SER | A | 444 | 26.888 | −9.452 | −57.775 | 1 | 64.8 | N |
| ATOM | 1671 | CA | SER | A | 444 | 26.329 | −8.774 | −58.955 | 1 | 65.13 | C |
| ATOM | 1672 | CB | SER | A | 444 | 26.025 | −7.289 | −58.66 | 1 | 65.41 | C |
| ATOM | 1673 | OG | SER | A | 444 | 24.868 | −7.131 | −57.856 | 1 | 64.82 | O |
| ATOM | 1674 | C | SER | A | 444 | 27.309 | −8.875 | −60.133 | 1 | 65.76 | C |
| ATOM | 1675 | O | SER | A | 444 | 26.988 | −9.463 | −61.169 | 1 | 66.45 | O |
| ATOM | 1676 | C1 | NAG | C | 1 | 25.103 | −13.888 | −4.907 | 1 | 114.98 | C |
| ATOM | 1677 | C2 | NAG | C | 1 | 24.634 | −12.467 | −4.559 | 1 | 114.81 | C |
| ATOM | 1678 | N2 | NAG | C | 1 | 24.328 | −12.351 | −3.138 | 1 | 114.52 | N |
| ATOM | 1679 | C7 | NAG | C | 1 | 24.867 | −11.435 | −2.319 | 1 | 114.45 | C |
| ATOM | 1680 | O7 | NAG | C | 1 | 25.668 | −10.571 | −2.679 | 1 | 114.33 | O |
| ATOM | 1681 | C8 | NAG | C | 1 | 24.445 | −11.488 | −0.875 | 1 | 114.03 | C |
| ATOM | 1682 | C3 | NAG | C | 1 | 23.423 | −12.047 | −5.407 | 1 | 114.79 | C |
| ATOM | 1683 | O3 | NAG | C | 1 | 23.168 | −10.672 | −5.222 | 1 | 115.04 | O |
| ATOM | 1684 | C4 | NAG | C | 1 | 23.613 | −12.334 | −6.899 | 1 | 114.71 | C |
| ATOM | 1685 | O4 | NAG | C | 1 | 22.403 | −12.16 | −7.648 | 1 | 112.13 | O |
| ATOM | 1686 | C5 | NAG | C | 1 | 24.126 | −13.765 | −7.063 | 1 | 116.42 | C |
| ATOM | 1687 | C6 | NAG | C | 1 | 24.353 | −14.088 | −8.539 | 1 | 117.96 | C |
| ATOM | 1688 | O6 | NAG | C | 1 | 25.25 | −15.159 | −8.744 | 1 | 120.05 | O |
| ATOM | 1689 | O5 | NAG | C | 1 | 25.311 | −13.907 | −6.306 | 1 | 115.81 | O |
| ATOM | 1690 | C1 | NAG | C | 2 | 22.553 | −11.275 | −8.787 | 1 | 109.46 | C |
| ATOM | 1691 | C2 | NAG | C | 2 | 21.766 | −11.731 | −10.024 | 1 | 108.06 | C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 1692 | N2 | NAG | C | 2 | 22.135 | −13.053 | −10.503 | 1 | 107.54 N |
| ATOM | 1693 | C7 | NAG | C | 2 | 21.244 | −14.006 | −10.788 | 1 | 107.09 C |
| ATOM | 1694 | O7 | NAG | C | 2 | 20.041 | −13.805 | −10.948 | 1 | 107.1 O |
| ATOM | 1695 | C8 | NAG | C | 2 | 21.791 | −15.396 | −10.923 | 1 | 106.48 C |
| ATOM | 1696 | C3 | NAG | C | 2 | 22.019 | −10.738 | −11.155 | 1 | 106.92 C |
| ATOM | 1697 | O3 | NAG | C | 2 | 21.265 | −11.087 | −12.29 | 1 | 106.43 O |
| ATOM | 1698 | C4 | NAG | C | 2 | 21.642 | −9.347 | −10.675 | 1 | 106.63 C |
| ATOM | 1699 | O4 | NAG | C | 2 | 21.845 | −8.381 | −11.68 | 1 | 105.16 O |
| ATOM | 1700 | C5 | NAG | C | 2 | 22.452 | −9.014 | −9.429 | 1 | 107.59 C |
| ATOM | 1701 | C6 | NAG | C | 2 | 22.135 | −7.625 | −8.884 | 1 | 107.88 C |
| ATOM | 1702 | O6 | NAG | C | 2 | 22.711 | −7.467 | −7.604 | 1 | 107.85 O |
| ATOM | 1703 | O5 | NAG | C | 2 | 22.132 | −9.974 | −8.446 | 1 | 108.7 O |
| ATOM | 1704 | C1 | BMA | C | 3 | 20.706 | −8.242 | −12.549 | 1 | 104.25 C |
| ATOM | 1705 | C2 | BMA | C | 3 | 20.468 | −6.745 | −12.763 | 1 | 103.93 C |
| ATOM | 1706 | O2 | BMA | C | 3 | 21.721 | −6.061 | −12.803 | 1 | 103.98 O |
| ATOM | 1707 | C3 | BMA | C | 3 | 19.683 | −6.424 | −14.027 | 1 | 103.68 C |
| ATOM | 1708 | O3 | BMA | C | 3 | 19.846 | −5.038 | −14.332 | 1 | 104.22 O |
| ATOM | 1709 | C4 | BMA | C | 3 | 20.175 | −7.235 | −15.212 | 1 | 103.64 C |
| ATOM | 1710 | O4 | BMA | C | 3 | 19.409 | −6.918 | −16.384 | 1 | 103.49 O |
| ATOM | 1711 | C5 | BMA | C | 3 | 20.066 | −8.709 | −14.857 | 1 | 103.68 C |
| ATOM | 1712 | C6 | BMA | C | 3 | 20.431 | −9.627 | −16.025 | 1 | 103.36 C |
| ATOM | 1713 | O6 | BMA | C | 3 | 20.313 | −10.981 | −15.57 | 1 | 103.08 O |
| ATOM | 1714 | O5 | BMA | C | 3 | 20.937 | −8.979 | −13.752 | 1 | 104.04 O |
| ATOM | 1715 | C1 | MAN | C | 4 | 18.683 | −4.274 | −13.967 | 1 | 105.08 C |
| ATOM | 1716 | C2 | MAN | C | 4 | 18.647 | −2.989 | −14.775 | 1 | 105.58 C |
| ATOM | 1717 | O2 | MAN | C | 4 | 17.46 | −2.316 | −14.426 | 1 | 106.51 O |
| ATOM | 1718 | C3 | MAN | C | 4 | 19.806 | −2.071 | −14.419 | 1 | 105.07 C |
| ATOM | 1719 | O3 | MAN | C | 4 | 19.674 | −0.86 | −15.134 | 1 | 104.69 O |
| ATOM | 1720 | C4 | MAN | C | 4 | 19.807 | −1.823 | −12.914 | 1 | 104.72 C |
| ATOM | 1721 | O4 | MAN | C | 4 | 21.006 | −1.182 | −12.557 | 1 | 104.24 O |
| ATOM | 1722 | C5 | MAN | C | 4 | 19.699 | −3.134 | −12.137 | 1 | 104.95 C |
| ATOM | 1723 | C6 | MAN | C | 4 | 19.452 | −2.881 | −10.659 | 1 | 105.04 C |
| ATOM | 1724 | O6 | MAN | C | 4 | 19.372 | −4.13 | −10.013 | 1 | 105.09 O |
| ATOM | 1725 | O5 | MAN | C | 4 | 18.635 | −3.943 | −12.595 | 1 | 105.06 O |
| ATOM | 1726 | C1 | NAG | C | 5 | 16.475 | −2.351 | −15.462 | 1 | 107.11 C |
| ATOM | 1727 | C2 | NAG | C | 5 | 15.338 | −1.482 | −14.951 | 1 | 107.13 C |
| ATOM | 1728 | N2 | NAG | C | 5 | 14.797 | −2.031 | −13.712 | 1 | 106.77 N |
| ATOM | 1729 | C7 | NAG | C | 5 | 15.214 | −1.624 | −12.513 | 1 | 106.49 C |
| ATOM | 1730 | O7 | NAG | C | 5 | 15.765 | −2.381 | −11.724 | 1 | 106.49 O |
| ATOM | 1731 | C8 | NAG | C | 5 | 14.996 | −0.186 | −12.133 | 1 | 106.35 C |
| ATOM | 1732 | C3 | NAG | C | 5 | 14.251 | −1.296 | −16.011 | 1 | 107.43 C |
| ATOM | 1733 | O3 | NAG | C | 5 | 14.011 | 0.086 | −16.191 | 1 | 107.27 O |
| ATOM | 1734 | C4 | NAG | C | 5 | 14.584 | −1.944 | −17.366 | 1 | 107.67 C |
| ATOM | 1735 | O4 | NAG | C | 5 | 14.205 | −3.306 | −17.361 | 1 | 107.7 O |
| ATOM | 1736 | C5 | NAG | C | 5 | 16.061 | −1.833 | −17.786 | 1 | 107.53 C |
| ATOM | 1737 | C6 | NAG | C | 5 | 16.323 | −0.565 | −18.6 | 1 | 107.06 C |
| ATOM | 1738 | O6 | NAG | C | 5 | 15.628 | −0.635 | −19.823 | 1 | 106.38 O |
| ATOM | 1739 | O5 | NAG | C | 5 | 16.966 | −1.851 | −16.693 | 1 | 107.71 O |
| ATOM | 1740 | C1 | MAN | C | 7 | 20.54 | −11.941 | −16.618 | 1 | 102.85 C |
| ATOM | 1741 | C2 | MAN | C | 7 | 19.939 | −13.266 | −16.155 | 1 | 102.18 C |
| ATOM | 1742 | O2 | MAN | C | 7 | 19.915 | −14.196 | −17.218 | 1 | 100.59 O |
| ATOM | 1743 | C3 | MAN | C | 7 | 20.711 | −13.809 | −14.959 | 1 | 102.54 C |
| ATOM | 1744 | O3 | MAN | C | 7 | 20.302 | −15.121 | −14.675 | 1 | 103.09 O |
| ATOM | 1745 | C4 | MAN | C | 7 | 22.205 | −13.838 | −15.223 | 1 | 102.93 C |
| ATOM | 1746 | O4 | MAN | C | 7 | 22.87 | −14.108 | −14.008 | 1 | 103.11 O |
| ATOM | 1747 | C5 | MAN | C | 7 | 22.707 | −12.522 | −15.817 | 1 | 103.06 C |
| ATOM | 1748 | C6 | MAN | C | 7 | 24.157 | −12.685 | −16.259 | 1 | 102.85 C |
| ATOM | 1749 | O6 | MAN | C | 7 | 24.576 | −11.532 | −16.945 | 1 | 102.58 O |
| ATOM | 1750 | O5 | MAN | C | 7 | 21.909 | −12.136 | −16.925 | 1 | 103.18 O |
| ATOM | 1751 | C1 | NAG | C | 8 | 18.654 | −14.142 | −17.91 | 1 | 99.43 C |
| ATOM | 1752 | C2 | NAG | C | 8 | 18.893 | −14.406 | −19.396 | 1 | 99.26 C |
| ATOM | 1753 | N2 | NAG | C | 8 | 19.681 | −13.328 | −19.962 | 1 | 99.66 N |
| ATOM | 1754 | C7 | NAG | C | 8 | 20.933 | −13.518 | −20.38 | 1 | 99.86 C |
| ATOM | 1755 | O7 | NAG | C | 8 | 21.896 | −13.466 | −19.612 | 1 | 99.4 O |
| ATOM | 1756 | C8 | NAG | C | 8 | 21.125 | −13.799 | −21.848 | 1 | 99.74 C |
| ATOM | 1757 | C3 | NAG | C | 8 | 17.589 | −14.555 | −20.18 | 1 | 98.62 C |
| ATOM | 1758 | O3 | NAG | C | 8 | 17.881 | −15.073 | −21.454 | 1 | 98.36 O |
| ATOM | 1759 | C4 | NAG | C | 8 | 16.625 | −15.493 | −19.462 | 1 | 98.08 C |
| ATOM | 1760 | O4 | NAG | C | 8 | 15.381 | −15.532 | −20.128 | 1 | 97.67 O |
| ATOM | 1761 | C5 | NAG | C | 8 | 16.472 | −15.04 | −18.014 | 1 | 97.74 C |
| ATOM | 1762 | C6 | NAG | C | 8 | 15.492 | −15.907 | −17.239 | 1 | 97.11 C |
| ATOM | 1763 | O6 | NAG | C | 8 | 16.196 | −16.975 | −16.659 | 1 | 96.14 O |
| ATOM | 1764 | O5 | NAG | C | 8 | 17.738 | −15.074 | −17.374 | 1 | 98.25 O |
| ATOM | 1765 | C1 | FUC | C | 11 | 26.617 | −14.709 | −8.773 | 1 | 121.56 C |
| ATOM | 1766 | C2 | FUC | C | 11 | 27.034 | −14.283 | −10.179 | 1 | 122.07 C |
| ATOM | 1767 | O2 | FUC | C | 11 | 26.209 | −13.259 | −10.689 | 1 | 122.11 O |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 1768 | C3 | FUC | C | 11 | 28.463 | −13.765 | −10.107 | 1 | 122.43 C |
| ATOM | 1769 | O3 | FUC | C | 11 | 28.903 | −13.373 | −11.394 | 1 | 122.32 O |
| ATOM | 1770 | C4 | FUC | C | 11 | 29.358 | −14.848 | −9.495 | 1 | 122.66 C |
| ATOM | 1771 | O4 | FUC | C | 11 | 29.438 | −15.949 | −10.374 | 1 | 122.82 O |
| ATOM | 1772 | C5 | FUC | C | 11 | 28.811 | −15.32 | −8.141 | 1 | 122.54 C |
| ATOM | 1773 | C6 | FUC | C | 11 | 29.62 | −16.472 | −7.545 | 1 | 122.53 C |
| ATOM | 1774 | O5 | FUC | C | 11 | 27.469 | −15.736 | −8.297 | 1 | 122 O |
| ATOM | 1775 | N | GLY | B | 236 | 20.744 | 2.218 | 0.43 | 1 | 86.87 N |
| ATOM | 1776 | CA | GLY | B | 236 | 20.449 | 3.07 | 1.628 | 1 | 86.65 C |
| ATOM | 1777 | C | GLY | B | 236 | 21.249 | 4.368 | 1.671 | 1 | 86.67 C |
| ATOM | 1778 | O | GLY | B | 236 | 20.683 | 5.467 | 1.618 | 1 | 86.79 O |
| ATOM | 1779 | N | GLY | B | 237 | 22.569 | 4.247 | 1.781 | 1 | 86.12 N |
| ATOM | 1780 | CA | GLY | B | 237 | 23.449 | 5.418 | 1.802 | 1 | 85.18 C |
| ATOM | 1781 | C | GLY | B | 237 | 23.599 | 6.076 | 0.434 | 1 | 84.47 C |
| ATOM | 1782 | O | GLY | B | 237 | 22.847 | 5.766 | −0.504 | 1 | 84.55 O |
| ATOM | 1783 | N | PRO | B | 238 | 24.558 | 7.012 | 0.316 | 1 | 83.11 N |
| ATOM | 1784 | CA | PRO | B | 238 | 24.876 | 7.606 | −0.981 | 1 | 82.04 C |
| ATOM | 1785 | CB | PRO | B | 238 | 25.697 | 8.85 | −0.609 | 1 | 82.31 C |
| ATOM | 1786 | CG | PRO | B | 238 | 26.346 | 8.494 | 0.694 | 1 | 82.79 C |
| ATOM | 1787 | CD | PRO | B | 238 | 25.38 | 7.574 | 1.404 | 1 | 83.13 C |
| ATOM | 1788 | C | PRO | B | 238 | 25.688 | 6.652 | −1.87 | 1 | 80.92 C |
| ATOM | 1789 | O | PRO | B | 238 | 26.538 | 5.903 | −1.366 | 1 | 80.95 O |
| ATOM | 1790 | N | SER | B | 239 | 25.415 | 6.686 | −3.178 | 1 | 79.22 N |
| ATOM | 1791 | CA | SER | B | 239 | 26.096 | 5.823 | −4.153 | 1 | 77.51 C |
| ATOM | 1792 | CB | SER | B | 239 | 25.076 | 4.975 | −4.916 | 1 | 77.7 C |
| ATOM | 1793 | OG | SER | B | 239 | 24.609 | 3.903 | −4.118 | 1 | 77.8 O |
| ATOM | 1794 | C | SER | B | 239 | 26.915 | 6.649 | −5.136 | 1 | 75.8 C |
| ATOM | 1795 | O | SER | B | 239 | 26.429 | 7.652 | −5.668 | 1 | 75.49 O |
| ATOM | 1796 | N | VAL | B | 240 | 28.155 | 6.222 | −5.368 | 1 | 73.68 N |
| ATOM | 1797 | CA | VAL | B | 240 | 29.044 | 6.902 | −6.304 | 1 | 72.19 C |
| ATOM | 1798 | CB | VAL | B | 240 | 30.514 | 6.814 | −5.861 | 1 | 71.98 C |
| ATOM | 1799 | CG1 | VAL | B | 240 | 31.39 | 7.625 | −6.801 | 1 | 71.24 C |
| ATOM | 1800 | CG2 | VAL | B | 240 | 30.668 | 7.291 | −4.427 | 1 | 71.91 C |
| ATOM | 1801 | C | VAL | B | 240 | 28.927 | 6.272 | −7.684 | 1 | 70.59 C |
| ATOM | 1802 | O | VAL | B | 240 | 28.558 | 5.115 | −7.798 | 1 | 70.68 O |
| ATOM | 1803 | N | PHE | B | 241 | 29.236 | 7.044 | −8.722 | 1 | 68.74 N |
| ATOM | 1804 | CA | PHE | B | 241 | 29.323 | 6.528 | −10.084 | 1 | 67.34 C |
| ATOM | 1805 | CB | PHE | B | 241 | 27.986 | 6.661 | −10.8 | 1 | 67.61 C |
| ATOM | 1806 | CG | PHE | B | 241 | 26.935 | 5.76 | −10.251 | 1 | 67.64 C |
| ATOM | 1807 | CD1 | PHE | B | 241 | 25.84 | 6.28 | −9.561 | 1 | 68.37 C |
| ATOM | 1808 | CE1 | PHE | B | 241 | 24.872 | 5.448 | −9.049 | 1 | 68.05 C |
| ATOM | 1809 | CZ | PHE | B | 241 | 24.995 | 4.07 | −9.201 | 1 | 68.2 C |
| ATOM | 1810 | CE2 | PHE | B | 241 | 26.087 | 3.54 | −9.874 | 1 | 67.72 C |
| ATOM | 1811 | CD2 | PHE | B | 241 | 27.053 | 4.387 | −10.392 | 1 | 67.09 C |
| ATOM | 1812 | C | PHE | B | 241 | 30.397 | 7.253 | −10.861 | 1 | 65.79 C |
| ATOM | 1813 | O | PHE | B | 241 | 30.375 | 8.481 | −10.94 | 1 | 65.68 O |
| ATOM | 1814 | N | LEU | B | 242 | 31.322 | 6.49 | −11.451 | 1 | 63.74 N |
| ATOM | 1815 | CA | LEU | B | 242 | 32.534 | 7.07 | −12.022 | 1 | 62.45 C |
| ATOM | 1816 | CB | LEU | B | 242 | 33.772 | 6.474 | −11.342 | 1 | 62.37 C |
| ATOM | 1817 | CG | LEU | B | 242 | 35.08 | 7.174 | −11.692 | 1 | 62.79 C |
| ATOM | 1818 | CD1 | LEU | B | 242 | 34.961 | 8.68 | −11.439 | 1 | 62.51 C |
| ATOM | 1819 | CD2 | LEU | B | 242 | 36.235 | 6.57 | −10.912 | 1 | 62.15 C |
| ATOM | 1820 | C | LEU | B | 242 | 32.601 | 6.882 | −13.53 | 1 | 61.02 C |
| ATOM | 1821 | O | LEU | B | 242 | 32.767 | 5.77 | −14.023 | 1 | 61.17 O |
| ATOM | 1822 | N | PHE | B | 243 | 32.502 | 7.982 | −14.26 | 1 | 59.25 N |
| ATOM | 1823 | CA | PHE | B | 243 | 32.461 | 7.93 | −15.707 | 1 | 58 C |
| ATOM | 1824 | CB | PHE | B | 243 | 31.385 | 8.882 | −16.209 | 1 | 58.9 C |
| ATOM | 1825 | CG | PHE | B | 243 | 30.05 | 8.569 | −15.656 | 1 | 59.13 C |
| ATOM | 1826 | CD1 | PHE | B | 243 | 29.214 | 7.67 | −16.309 | 1 | 59.92 C |
| ATOM | 1827 | CE1 | PHE | B | 243 | 27.972 | 7.348 | −15.766 | 1 | 60.38 C |
| ATOM | 1828 | CZ | PHE | B | 243 | 27.582 | 7.915 | −14.552 | 1 | 59.08 C |
| ATOM | 1829 | CE2 | PHE | B | 243 | 28.424 | 8.795 | −13.896 | 1 | 58.4 C |
| ATOM | 1830 | CD2 | PHE | B | 243 | 29.652 | 9.101 | −14.433 | 1 | 58.49 C |
| ATOM | 1831 | C | PHE | B | 243 | 33.789 | 8.246 | −16.368 | 1 | 56.49 C |
| ATOM | 1832 | O | PHE | B | 243 | 34.573 | 9.028 | −15.839 | 1 | 56.79 O |
| ATOM | 1833 | N | PRO | B | 244 | 34.045 | 7.63 | −17.537 | 1 | 54.41 N |
| ATOM | 1834 | CA | PRO | B | 244 | 35.2 | 7.973 | −18.34 | 1 | 53.39 C |
| ATOM | 1835 | CB | PRO | B | 244 | 35.351 | 6.745 | −19.24 | 1 | 53.32 C |
| ATOM | 1836 | CG | PRO | B | 244 | 33.956 | 6.321 | −19.484 | 1 | 53.26 C |
| ATOM | 1837 | CD | PRO | B | 244 | 33.263 | 6.548 | −18.163 | 1 | 54.09 C |
| ATOM | 1838 | C | PRO | B | 244 | 34.954 | 9.228 | −19.192 | 1 | 51.85 C |
| ATOM | 1839 | O | PRO | B | 244 | 33.805 | 9.625 | −19.361 | 1 | 51.84 O |
| ATOM | 1840 | N | PRO | B | 245 | 36.024 | 9.828 | −19.745 | 1 | 50.33 N |
| ATOM | 1841 | CA | PRO | B | 245 | 35.906 | 10.945 | −20.679 | 1 | 49.94 C |
| ATOM | 1842 | CB | PRO | B | 245 | 37.36 | 11.373 | −20.897 | 1 | 49.51 C |
| ATOM | 1843 | CG | PRO | B | 245 | 38.147 | 10.181 | −20.645 | 1 | 49.46 C |

TABLE V-continued

Atomic Structure Coordinates of Fc/YTE (SEQ ID NO: 11)

| Atom |  | A.A. | Type |  | X | Y | Z | Occ | B |  |
|---|---|---|---|---|---|---|---|---|---|---|
| ATOM | 1844 | CD | PRO | B | 245 | 37.433 | 9.434 | −19.555 | 1 | 49.89 | C |
| ATOM | 1845 | C | PRO | B | 245 | 35.358 | 10.493 | −22.012 | 1 | 49.31 | C |
| ATOM | 1846 | O | PRO | B | 245 | 35.379 | 9.306 | −22.315 | 1 | 49.06 | O |
| ATOM | 1847 | N | LYS | B | 246 | 34.908 | 11.435 | −22.824 | 1 | 48.99 | N |
| ATOM | 1848 | CA | LYS | B | 246 | 34.407 | 11.102 | −24.151 | 1 | 48.56 | C |
| ATOM | 1849 | CB | LYS | B | 246 | 33.643 | 12.284 | −24.763 | 1 | 48.76 | C |
| ATOM | 1850 | CG | LYS | B | 246 | 32.348 | 12.652 | −24.024 | 1 | 49.77 | C |
| ATOM | 1851 | CD | LYS | B | 246 | 31.395 | 11.425 | −23.853 | 1 | 50.75 | C |
| ATOM | 1852 | CE | LYS | B | 246 | 29.979 | 11.803 | −23.366 | 1 | 50.17 | C |
| ATOM | 1853 | NZ | LYS | B | 246 | 29.953 | 12.621 | −22.119 | 1 | 49.95 | N |
| ATOM | 1854 | C | LYS | B | 246 | 35.551 | 10.663 | −25.078 | 1 | 47.93 | C |
| ATOM | 1855 | O | LYS | B | 246 | 36.646 | 11.222 | −25.017 | 1 | 46.79 | O |
| ATOM | 1856 | N | PRO | B | 247 | 35.297 | 9.622 | −25.915 | 1 | 47.92 | N |
| ATOM | 1857 | CA | PRO | B | 247 | 36.246 | 9.202 | −26.949 | 1 | 48.07 | C |
| ATOM | 1858 | CB | PRO | B | 247 | 35.363 | 8.385 | −27.91 | 1 | 48.16 | C |
| ATOM | 1859 | CG | PRO | B | 247 | 34.385 | 7.715 | −26.994 | 1 | 47.92 | C |
| ATOM | 1860 | CD | PRO | B | 247 | 34.115 | 8.732 | −25.895 | 1 | 47.67 | C |
| ATOM | 1861 | C | PRO | B | 247 | 36.919 | 10.36 | −27.66 | 1 | 48.02 | C |
| ATOM | 1862 | O | PRO | 8 | 247 | 38.146 | 10.395 | −27.763 | 1 | 48.08 | O |
| ATOM | 1863 | N | LYS | B | 248 | 36.116 | 11.316 | −28.103 | 1 | 48.06 | N |
| ATOM | 1864 | CA | LYS | B | 248 | 36.623 | 12.456 | −28.852 | 1 | 48 | C |
| ATOM | 1865 | CB | LYS | B | 248 | 35.458 | 13.316 | −29.312 | 1 | 48.18 | C |
| ATOM | 1866 | CG | LYS | B | 248 | 35.734 | 14.099 | −30.553 | 1 | 49.25 | C |
| ATOM | 1867 | CD | LYS | B | 248 | 34.469 | 14.872 | −30.948 | 1 | 49.13 | C |
| ATOM | 1868 | CE | LYS | B | 248 | 34.783 | 16.076 | −31.83 | 1 | 49.45 | C |
| ATOM | 1869 | NZ | LYS | B | 248 | 33.572 | 16.457 | −32.63 | 1 | 50.55 | N |
| ATOM | 1870 | C | LYS | B | 248 | 37.601 | 13.303 | −28.028 | 1 | 47.47 | C |
| ATOM | 1871 | O | LYS | B | 248 | 38.617 | 13.769 | −28.54 | 1 | 47.25 | O |
| ATOM | 1872 | N | ASP | B | 249 | 37.296 | 13.492 | −26.754 | 1 | 46.95 | N |
| ATOM | 1873 | CA | ASP | B | 249 | 38.016 | 14.478 | −25.952 | 1 | 46.58 | C |
| ATOM | 1874 | CB | ASP | B | 249 | 37.28 | 14.757 | −24.629 | 1 | 46.76 | C |
| ATOM | 1875 | CG | ASP | B | 249 | 35.965 | 15.504 | −24.807 | 1 | 46.92 | C |
| ATOM | 1876 | OD1 | ASP | B | 249 | 35.649 | 15.951 | −25.929 | 1 | 47.37 | O |
| ATOM | 1877 | OD2 | ASP | B | 249 | 35.249 | 15.644 | −23.794 | 1 | 47.77 | O |
| ATOM | 1878 | C | ASP | B | 249 | 39.474 | 14.066 | −25.646 | 1 | 46.14 | C |
| ATOM | 1879 | O | ASP | B | 249 | 40.322 | 14.929 | −25.396 | 1 | 45.64 | O |
| ATOM | 1880 | N | THR | B | 250 | 39.765 | 12.768 | −25.671 | 1 | 45.76 | N |
| ATOM | 1881 | CA | THR | B | 250 | 41.097 | 12.271 | −25.304 | 1 | 45.67 | C |
| ATOM | 1882 | CB | THR | B | 250 | 41.072 | 10.817 | −24.773 | 1 | 44.83 | C |
| ATOM | 1883 | OG1 | THR | B | 250 | 40.789 | 9.933 | −25.855 | 1 | 43.51 | O |
| ATOM | 1884 | CG2 | THR | B | 250 | 40.048 | 10.622 | −23.664 | 1 | 43.29 | C |
| ATOM | 1885 | C | THR | B | 250 | 42.038 | 12.266 | −26.485 | 1 | 46.21 | C |
| ATOM | 1886 | O | THR | B | 250 | 43.256 | 12.104 | −26.307 | 1 | 46.87 | O |
| ATOM | 1887 | N | LEU | B | 251 | 41.478 | 12.441 | −27.68 | 1 | 46.58 | N |
| ATOM | 1888 | CA | LEU | B | 251 | 42.198 | 12.247 | −28.93 | 1 | 47.33 | C |
| ATOM | 1889 | CB | LEU | B | 251 | 41.291 | 11.561 | −29.945 | 1 | 46.94 | C |
| ATOM | 1890 | CG | LEU | B | 251 | 40.768 | 10.169 | −29.611 | 1 | 47.07 | C |
| ATOM | 1891 | CD1 | LEU | B | 251 | 40.037 | 9.597 | −30.851 | 1 | 47.82 | C |
| ATOM | 1892 | CD2 | LEU | B | 251 | 41.874 | 9.251 | −29.138 | 1 | 45.3 | C |
| ATOM | 1893 | C | LEU | B | 251 | 42.748 | 13.511 | −29.596 | 1 | 48.33 | C |
| ATOM | 1894 | O | LEU | B | 251 | 43.352 | 13.395 | −30.667 | 1 | 47.74 | O |
| ATOM | 1895 | N | TYR | B | 252 | 42.534 | 14.699 | −29.003 | 1 | 49.63 | N |
| ATOM | 1896 | CA | TYR | B | 252 | 43.02 | 15.963 | −29.591 | 1 | 50.37 | C |
| ATOM | 1897 | CB | TYR | B | 252 | 41.955 | 16.559 | −30.51 | 1 | 50.26 | C |
| ATOM | 1898 | CG | TYR | B | 252 | 41.424 | 15.583 | −31.518 | 1 | 50.72 | C |
| ATOM | 1899 | CD1 | TYR | B | 252 | 40.171 | 14.99 | −31.351 | 1 | 49.87 | C |
| ATOM | 1900 | CE1 | TYR | B | 252 | 39.68 | 14.062 | −32.28 | 1 | 49.95 | C |
| ATOM | 1901 | CZ | TYR | B | 252 | 40.451 | 13.711 | −33.368 | 1 | 51.04 | C |
| ATOM | 1902 | OH | TYR | B | 252 | 39.971 | 12.791 | −34.288 | 1 | 50.95 | O |
| ATOM | 1903 | CE2 | TYR | B | 252 | 41.713 | 14.286 | −33.551 | 1 | 50.68 | C |
| ATOM | 1904 | CD2 | TYR | B | 252 | 42.187 | 15.216 | −32.633 | 1 | 50.38 | C |
| ATOM | 1905 | C | TYR | B | 252 | 43.368 | 16.975 | −28.514 | 1 | 51.37 | C |
| ATOM | 1906 | O | TYR | B | 252 | 42.602 | 17.128 | −27.568 | 1 | 51.6 | O |
| ATOM | 1907 | N | ILE | B | 253 | 44.48 | 17.7 | −28.662 | 1 | 52.88 | N |
| ATOM | 1908 | CA | ILE | B | 253 | 44.83 | 18.768 | −27.665 | 1 | 54.26 | C |
| ATOM | 1909 | CB | ILE | B | 253 | 46.213 | 19.477 | −27.88 | 1 | 54.83 | C |
| ATOM | 1910 | CG1 | ILE | B | 253 | 46.897 | 19.066 | −29.191 | 1 | 55.79 | C |
| ATOM | 1911 | CD1 | ILE | B | 253 | 46.172 | 19.572 | −30.439 | 1 | 56.39 | C |
| ATOM | 1912 | CG2 | ILE | B | 253 | 47.122 | 19.3 | −26.608 | 1 | 54.58 | C |
| ATOM | 1913 | C | ILE | B | 253 | 43.781 | 19.889 | −27.586 | 1 | 55.1 | C |
| ATOM | 1914 | O | ILE | B | 253 | 43.535 | 20.46 | −26.519 | 1 | 55.72 | O |
| ATOM | 1915 | N | THR | B | 254 | 43.222 | 20.222 | −28.738 | 1 | 55.97 | N |
| ATOM | 1916 | CA | THR | B | 254 | 41.999 | 21.008 | −28.881 | 1 | 56.63 | C |
| ATOM | 1917 | CB | THR | B | 254 | 41.32 | 20.587 | −30.203 | 1 | 57.17 | C |
| ATOM | 1918 | OG1 | THR | B | 254 | 42.023 | 21.157 | −31.32 | 1 | 58.92 | O |
| ATOM | 1919 | CG2 | THR | B | 254 | 39.87 | 20.987 | −30.243 | 1 | 57.86 | C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 1920 | C | THR | B | 254 | 40.978 | 20.783 | −27.756 | 1 | 57.33 C |
| ATOM | 1921 | O | THR | B | 254 | 40.401 | 21.75 | −27.228 | 1 | 57.41 O |
| ATOM | 1922 | N | ARG | B | 255 | 40.745 | 19.51 | −27.403 | 1 | 57.49 N |
| ATOM | 1923 | CA | ARG | B | 255 | 39.647 | 19.156 | −26.499 | 1 | 57.53 C |
| ATOM | 1924 | CB | ARG | B | 255 | 38.899 | 17.96 | −27.075 | 1 | 57.47 C |
| ATOM | 1925 | CG | ARG | B | 255 | 38.278 | 18.36 | −28.439 | 1 | 57.77 C |
| ATOM | 1926 | CD | ARG | B | 255 | 37.4 | 17.339 | −29.069 | 1 | 56.72 C |
| ATOM | 1927 | NE | ARG | B | 255 | 36.16 | 17.093 | −28.339 | 1 | 56.67 N |
| ATOM | 1928 | CZ | ARG | B | 255 | 35.08 | 17.877 | −28.363 | 1 | 55.9 C |
| ATOM | 1929 | NH1 | ARG | B | 255 | 35.054 | 18.999 | −29.068 | 1 | 55.4 N |
| ATOM | 1930 | NH2 | ARG | B | 255 | 34.003 | 17.523 | −27.671 | 1 | 55.74 N |
| ATOM | 1931 | C | ARG | B | 255 | 40.073 | 18.958 | −25.047 | 1 | 57.77 C |
| ATOM | 1932 | O | ARG | B | 255 | 41.248 | 18.767 | −24.77 | 1 | 57.17 O |
| ATOM | 1933 | N | GLU | B | 256 | 39.108 | 19.054 | −24.131 | 1 | 58.68 N |
| ATOM | 1934 | CA | GLU | B | 256 | 39.366 | 18.996 | −22.674 | 1 | 59.52 C |
| ATOM | 1935 | CB | GLU | B | 256 | 38.915 | 20.294 | −21.984 | 1 | 59.48 C |
| ATOM | 1936 | CG | GLU | B | 256 | 39.694 | 21.545 | −22.407 | 1 | 61.1 C |
| ATOM | 1937 | CD | GLU | B | 256 | 38.95 | 22.85 | −22.1 | 1 | 62.07 C |
| ATOM | 1938 | OE1 | GLU | B | 256 | 38.931 | 23.255 | −20.919 | 1 | 64.89 O |
| ATOM | 1939 | OE2 | GLU | B | 256 | 38.382 | 23.472 | −23.04 | 1 | 65.02 O |
| ATOM | 1940 | C | GLU | B | 256 | 38.665 | 17.77 | −22.037 | 1 | 59.67 C |
| ATOM | 1941 | O | GLU | B | 256 | 37.556 | 17.888 | −21.471 | 1 | 59.39 O |
| ATOM | 1942 | N | PRO | B | 257 | 39.325 | 16.593 | −22.102 | 1 | 59.91 N |
| ATOM | 1943 | CA | PRO | B | 257 | 38.734 | 15.351 | −21.577 | 1 | 60.07 C |
| ATOM | 1944 | CB | PRO | B | 257 | 39.677 | 14.257 | −22.088 | 1 | 59.74 C |
| ATOM | 1945 | CG | PRO | B | 257 | 40.98 | 14.941 | −22.288 | 1 | 59.9 C |
| ATOM | 1946 | CD | PRO | B | 257 | 40.693 | 16.384 | −22.617 | 1 | 59.79 C |
| ATOM | 1947 | C | PRO | B | 257 | 38.692 | 15.364 | −20.066 | 1 | 60.15 C |
| ATOM | 1948 | O | PRO | B | 257 | 39.549 | 15.972 | −19.445 | 1 | 60.33 O |
| ATOM | 1949 | N | GLU | B | 258 | 37.688 | 14.714 | −19.492 | 1 | 60.65 N |
| ATOM | 1950 | CA | GLU | B | 258 | 37.495 | 14.709 | −18.048 | 1 | 61.38 C |
| ATOM | 1951 | CB | GLU | B | 258 | 36.463 | 15.76 | −17.651 | 1 | 61.38 C |
| ATOM | 1952 | CG | GLU | B | 258 | 36.412 | 16.97 | −18.532 | 1 | 62.34 C |
| ATOM | 1953 | CD | GLU | B | 258 | 35.278 | 17.88 | −18.159 | 1 | 62.76 C |
| ATOM | 1954 | OE1 | GLU | B | 258 | 35.571 | 18.981 | −17.643 | 1 | 65.82 O |
| ATOM | 1955 | OE2 | GLU | B | 258 | 34.102 | 17.489 | −18.36 | 1 | 63.02 O |
| ATOM | 1956 | C | GLU | B | 258 | 36.957 | 13.368 | −17.576 | 1 | 61.62 C |
| ATOM | 1957 | O | GLU | B | 258 | 36.153 | 12.739 | −18.278 | 1 | 61.81 O |
| ATOM | 1958 | N | VAL | B | 259 | 37.363 | 12.957 | −16.375 | 1 | 61.75 N |
| ATOM | 1959 | CA | VAL | B | 259 | 36.688 | 11.873 | −15.656 | 1 | 62.15 C |
| ATOM | 1960 | CB | VAL | B | 259 | 37.7 | 10.996 | −14.875 | 1 | 62.43 C |
| ATOM | 1961 | CG1 | VAL | B | 259 | 36.993 | 9.913 | −14.046 | 1 | 62.8 C |
| ATOM | 1962 | CG2 | VAL | B | 259 | 38.682 | 10.359 | −15.834 | 1 | 62.67 C |
| ATOM | 1963 | C | VAL | B | 259 | 35.694 | 12.549 | −14.71 | 1 | 62.19 C |
| ATOM | 1964 | O | VAL | B | 259 | 35.917 | 13.673 | −14.295 | 1 | 62.47 O |
| ATOM | 1965 | N | THR | B | 260 | 34.613 | 11.865 | −14.355 | 1 | 62.25 N |
| ATOM | 1966 | CA | THR | B | 260 | 33.525 | 12.489 | −13.602 | 1 | 62.66 C |
| ATOM | 1967 | CB | THR | B | 260 | 32.399 | 12.85 | −14.566 | 1 | 62.25 C |
| ATOM | 1968 | OG1 | THR | B | 260 | 32.933 | 13.67 | −15.614 | 1 | 61.3 O |
| ATOM | 1969 | CG2 | THR | B | 260 | 31.28 | 13.569 | −13.842 | 1 | 61.81 C |
| ATOM | 1970 | C | THR | B | 260 | 32.948 | 11.616 | −12.477 | 1 | 63.2 C |
| ATOM | 1971 | O | THR | B | 260 | 32.375 | 10.553 | −12.737 | 1 | 63.49 O |
| ATOM | 1972 | N | CYS | B | 261 | 33.075 | 12.078 | −11.233 | 1 | 63.79 N |
| ATOM | 1973 | CA | CYS | B | 261 | 32.538 | 11.351 | −10.076 | 1 | 64.34 C |
| ATOM | 1974 | CB | CYS | B | 261 | 33.504 | 11.478 | −8.904 | 1 | 64.12 C |
| ATOM | 1975 | SG | CYS | B | 261 | 33.26 | 10.29 | −7.614 | 1 | 63.82 S |
| ATOM | 1976 | C | CYS | B | 261 | 31.158 | 11.894 | −9.693 | 1 | 65.22 C |
| ATOM | 1977 | O | CYS | B | 261 | 31.049 | 13.021 | −9.218 | 1 | 65.48 O |
| ATOM | 1978 | N | VAL | B | 262 | 30.107 | 11.104 | −9.917 | 1 | 66.1 N |
| ATOM | 1979 | CA | VAL | B | 262 | 28.731 | 11.513 | −9.611 | 1 | 66.87 C |
| ATOM | 1980 | CB | VAL | B | 262 | 27.75 | 11.174 | −10.768 | 1 | 66.5 C |
| ATOM | 1981 | CG1 | VAL | B | 262 | 26.329 | 11.527 | −10.397 | 1 | 66.3 C |
| ATOM | 1982 | CG2 | VAL | B | 262 | 28.142 | 11.879 | −12.021 | 1 | 66.37 C |
| ATOM | 1983 | C | VAL | B | 262 | 28.26 | 10.769 | −8.368 | 1 | 68.04 C |
| ATOM | 1984 | O | VAL | B | 262 | 28.222 | 9.546 | −8.369 | 1 | 68.1 O |
| ATOM | 1985 | N | VAL | B | 263 | 27.912 | 11.501 | −7.309 | 1 | 69.55 N |
| ATOM | 1986 | CA | VAL | B | 263 | 27.307 | 10.9 | −6.124 | 1 | 70.61 C |
| ATOM | 1987 | CB | VAL | B | 263 | 27.845 | 11.495 | −4.817 | 1 | 70.39 C |
| ATOM | 1988 | CG1 | VAL | B | 263 | 27.267 | 10.74 | −3.637 | 1 | 70.03 C |
| ATOM | 1989 | CG2 | VAL | B | 263 | 29.366 | 11.46 | −4.792 | 1 | 70.22 C |
| ATOM | 1990 | C | VAL | B | 263 | 25.831 | 11.186 | −6.188 | 1 | 71.89 C |
| ATOM | 1991 | O | VAL | B | 263 | 25.43 | 12.306 | −6.468 | 1 | 71.83 O |
| ATOM | 1992 | N | VAL | B | 264 | 25.023 | 10.164 | −5.96 | 1 | 73.85 N |
| ATOM | 1993 | CA | VAL | B | 264 | 23.583 | 10.342 | −5.817 | 1 | 75.54 C |
| ATOM | 1994 | CB | VAL | B | 264 | 22.76 | 9.619 | −6.944 | 1 | 75.55 C |
| ATOM | 1995 | CG1 | VAL | B | 264 | 22.928 | 10.341 | −8.27 | 1 | 75.67 C |

TABLE V-continued

Atomic Structure Coordinates of Fc/YTE (SEQ ID NO: 11)

| | Atom | A.A. | Type | | X | Y | Z | Occ | B | |
|---|---|---|---|---|---|---|---|---|---|---|
| ATOM | 1996 | CG2 | VAL | B | 264 | 23.146 | 8.15 | −7.076 | 1 | 75.3 | C |
| ATOM | 1997 | C | VAL | B | 264 | 23.19 | 9.859 | −4.418 | 1 | 77.21 | C |
| ATOM | 1998 | O | VAL | B | 264 | 24.049 | 9.402 | −3.64 | 1 | 77 | O |
| ATOM | 1999 | N | ASP | B | 265 | 21.902 | 10.004 | −4.099 | 1 | 79.42 | N |
| ATOM | 2000 | CA | ASP | B | 265 | 21.349 | 9.699 | −2.768 | 1 | 81.17 | C |
| ATOM | 2001 | CB | ASP | B | 265 | 21.115 | 8.193 | −2.607 | 1 | 80.94 | C |
| ATOM | 2002 | CG | ASP | B | 265 | 20.085 | 7.646 | −3.596 | 1 | 80.41 | C |
| ATOM | 2003 | OD1 | ASP | B | 265 | 19.726 | 6.462 | −3.45 | 1 | 79.48 | O |
| ATOM | 2004 | OD2 | ASP | B | 265 | 19.632 | 8.384 | −4.511 | 1 | 79.68 | O |
| ATOM | 2005 | C | ASP | B | 265 | 22.207 | 10.279 | −1.628 | 1 | 83.17 | C |
| ATOM | 2006 | O | ASP | B | 265 | 22.462 | 9.618 | −0.616 | 1 | 83.46 | O |
| ATOM | 2007 | N | VAL | B | 266 | 22.647 | 11.525 | −1.827 | 1 | 85.44 | N |
| ATOM | 2008 | CA | VAL | B | 266 | 23.266 | 12.344 | −0.782 | 1 | 87.05 | C |
| ATOM | 2009 | CB | VAL | B | 266 | 23.925 | 13.611 | −1.4 | 1 | 87.16 | C |
| ATOM | 2010 | CG1 | VAL | B | 266 | 24.456 | 14.55 | −0.323 | 1 | 87.11 | C |
| ATOM | 2011 | CG2 | VAL | B | 266 | 25.035 | 13.207 | −2.37 | 1 | 86.95 | C |
| ATOM | 2012 | C | VAL | B | 266 | 22.157 | 12.742 | 0.193 | 1 | 88.76 | C |
| ATOM | 2013 | O | VAL | B | 266 | 21.108 | 13.239 | −0.244 | 1 | 88.85 | O |
| ATOM | 2014 | N | SER | B | 267 | 22.373 | 12.508 | 1.493 | 1 | 90.67 | N |
| ATOM | 2015 | CA | SER | 8 | 267 | 21.317 | 12.708 | 2.514 | 1 | 92.15 | C |
| ATOM | 2016 | CB | SER | /3 | 267 | 21.744 | 12.145 | 3.885 | 1 | 92.46 | C |
| ATOM | 2017 | OG | SER | B | 267 | 22.773 | 12.912 | 4.503 | 1 | 92.68 | O |
| ATOM | 2018 | C | SER | B | 267 | 20.911 | 14.174 | 2.666 | 1 | 93.65 | C |
| ATOM | 2019 | O | SER | B | 267 | 21.728 | 15.086 | 2.471 | 1 | 94.13 | O |
| ATOM | 2020 | N | HIS | B | 268 | 19.651 | 14.408 | 3.016 | 1 | 95.04 | N |
| ATOM | 2021 | CA | HIS | B | 268 | 19.19 | 15.784 | 3.209 | 1 | 95.94 | C |
| ATOM | 2022 | CB | HIS | B | 268 | 17.672 | 15.867 | 3.234 | 1 | 96.59 | C |
| ATOM | 2023 | CG | HIS | B | 268 | 17.142 | 17.024 | 2.462 | 1 | 97.66 | C |
| ATOM | 2024 | ND1 | HIS | B | 268 | 16.667 | 16.9 | 1.173 | 1 | 98.72 | N |
| ATOM | 2025 | CE1 | HIS | B | 268 | 16.282 | 18.084 | 0.733 | 1 | 99.24 | C |
| ATOM | 2026 | NE2 | HIS | B | 268 | 16.503 | 18.974 | 1.685 | 1 | 99.68 | N |
| ATOM | 2027 | CD2 | HIS | B | 268 | 17.051 | 18.338 | 2.774 | 1 | 98.98 | C |
| ATOM | 2028 | C | HIS | B | 268 | 19.762 | 16.393 | 4.488 | 1 | 96.71 | C |
| ATOM | 2029 | O | HIS | B | 268 | 20.19 | 17.551 | 4.492 | 1 | 96.92 | O |
| ATOM | 2030 | N | GLU | B | 269 | 19.782 | 15.595 | 5.555 | 1 | 97.28 | N |
| ATOM | 2031 | CA | GLU | B | 269 | 20.244 | 16.045 | 6.869 | 1 | 97.54 | C |
| ATOM | 2032 | CB | GLU | B | 269 | 19.834 | 15.037 | 7.951 | 1 | 97.69 | C |
| ATOM | 2033 | CG | GLU | B | 269 | 18.31 | 14.903 | 8.128 | 1 | 97.69 | C |
| ATOM | 2034 | CD | GLU | B | 269 | 17.907 | 13.784 | 9.084 | 1 | 97.68 | C |
| ATOM | 2035 | OE1 | GLU | B | 269 | 18.609 | 12.755 | 9.152 | 1 | 97.56 | O |
| ATOM | 2036 | OE2 | GLU | B | 269 | 16.874 | 13.929 | 9.767 | 1 | 98.08 | O |
| ATOM | 2037 | C | GLU | B | 269 | 21.755 | 16.3 | 6.905 | 1 | 97.82 | C |
| ATOM | 2038 | O | GLU | B | 269 | 22.205 | 17.24 | 7.559 | 1 | 97.86 | O |
| ATOM | 2039 | N | ASP | B | 270 | 22.528 | 15.468 | 6.207 | 1 | 98.08 | N |
| ATOM | 2040 | CA | ASP | B | 270 | 23.976 | 15.701 | 6.03 | 1 | 98.08 | C |
| ATOM | 2041 | CB | ASP | B | 270 | 24.798 | 14.557 | 6.656 | 1 | 98.27 | C |
| ATOM | 2042 | CG | ASP | B | 270 | 25.489 | 14.969 | 7.949 | 1 | 98.36 | C |
| ATOM | 2043 | OD1 | ASP | B | 270 | 26.255 | 15.963 | 7.918 | 1 | 98.36 | O |
| ATOM | 2044 | OD2 | ASP | B | 270 | 25.281 | 14.294 | 8.983 | 1 | 98.18 | O |
| ATOM | 2045 | C | ASP | B | 270 | 24.338 | 15.91 | 4.533 | 1 | 98.11 | C |
| ATOM | 2046 | O | ASP | B | 270 | 24.358 | 14.95 | 3.746 | 1 | 98.14 | O |
| ATOM | 2047 | N | PRO | B | 271 | 24.649 | 17.166 | 4.143 | 1 | 97.84 | N |
| ATOM | 2048 | CA | PRO | B | 271 | 24.8 | 17.517 | 2.725 | 1 | 97.28 | C |
| ATOM | 2049 | CB | PRO | B | 271 | 24.291 | 18.955 | 2.707 | 1 | 97.55 | C |
| ATOM | 2050 | CG | PRO | B | 271 | 24.894 | 19.524 | 4.026 | 1 | 97.81 | C |
| ATOM | 2051 | CD | PRO | B | 271 | 24.898 | 18.345 | 5.009 | 1 | 97.85 | C |
| ATOM | 2052 | C | PRO | B | 271 | 26.259 | 17.511 | 2.242 | 1 | 96.77 | C |
| ATOM | 2053 | O | PRO | B | 271 | 26.506 | 17.575 | 1.037 | 1 | 96.7 | O |
| ATOM | 2054 | N | GLU | B | 272 | 27.198 | 17.426 | 3.188 | 1 | 96.1 | N |
| ATOM | 2055 | CA | GLU | B | 272 | 28.615 | 17.734 | 2.954 | 1 | 95.31 | C |
| ATOM | 2056 | CB | GLU | B | 272 | 29.308 | 18.183 | 4.269 | 1 | 95.4 | C |
| ATOM | 2057 | CG | GLU | B | 272 | 29.019 | 17.309 | 5.542 | 1 | 95.45 | C |
| ATOM | 2058 | CD | GLU | B | 272 | 29.761 | 17.777 | 6.81 | 1 | 95.16 | C |
| ATOM | 2059 | OE1 | GLU | B | 272 | 30.924 | 18.225 | 6.703 | 1 | 94.63 | O |
| ATOM | 2060 | OE2 | GLU | B | 272 | 29.177 | 17.687 | 7.917 | 1 | 94.24 | O |
| ATOM | 2061 | C | GLU | B | 272 | 29.342 | 16.536 | 2.342 | 1 | 94.73 | C |
| ATOM | 2062 | O | GLU | B | 272 | 29.541 | 15.517 | 3.016 | 1 | 94.97 | O |
| ATOM | 2063 | N | VAL | B | 273 | 29.727 | 16.655 | 1.066 | 1 | 93.7 | N |
| ATOM | 2064 | CA | VAL | B | 273 | 30.485 | 15.598 | 0.376 | 1 | 92.62 | C |
| ATOM | 2065 | CB | VAL | B | 273 | 29.837 | 15.19 | −0.954 | 1 | 92.69 | C |
| ATOM | 2066 | CG1 | VAL | B | 273 | 30.502 | 13.923 | −1.478 | 1 | 92.86 | C |
| ATOM | 2067 | CG2 | VAL | B | 273 | 28.339 | 14.991 | −0.789 | 1 | 92.78 | C |
| ATOM | 2068 | C | VAL | B | 273 | 31.909 | 16.038 | 0.064 | 1 | 91.59 | C |
| ATOM | 2069 | O | VAL | B | 273 | 32.114 | 17.1 | −0.533 | 1 | 91.31 | O |
| ATOM | 2070 | N | LYS | B | 274 | 32.884 | 15.219 | 0.464 | 1 | 90.43 | N |
| ATOM | 2071 | CA | LYS | B | 274 | 34.288 | 15.48 | 0.137 | 1 | 89.68 | C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2072 | CB | LYS | B | 274 | 35.18 | 15.57 | 1.385 | 1 | 89.74 C |
| ATOM | 2073 | CG | LYS | B | 274 | 36.603 | 16.064 | 1.037 | 1 | 90.17 C |
| ATOM | 2074 | CD | LYS | B | 274 | 37.412 | 16.511 | 2.252 | 1 | 90.07 C |
| ATOM | 2075 | CE | LYS | B | 274 | 38.59 | 15.6 | 2.529 | 1 | 90.04 C |
| ATOM | 2076 | NZ | LYS | B | 274 | 39.16 | 15.88 | 3.877 | 1 | 90.19 N |
| ATOM | 2077 | C | LYS | B | 274 | 34.868 | 14.44 | −0.829 | 1 | 88.72 C |
| ATOM | 2078 | O | LYS | B | 274 | 34.877 | 13.234 | −0.547 | 1 | 88.62 O |
| ATOM | 2079 | N | PHE | B | 275 | 35.385 | 14.955 | −1.944 | 1 | 87.39 N |
| ATOM | 2080 | CA | PHE | B | 275 | 35.952 | 14.168 | −3.013 | 1 | 86.38 C |
| ATOM | 2081 | CB | PHE | B | 275 | 35.582 | 14.794 | −4.368 | 1 | 86.01 C |
| ATOM | 2082 | CG | PHE | B | 275 | 34.113 | 14.749 | −4.69 | 1 | 85.6 C |
| ATOM | 2083 | CD1 | PHE | B | 275 | 33.242 | 15.684 | −4.152 | 1 | 86.14 C |
| ATOM | 2084 | CE1 | PHE | B | 275 | 31.885 | 15.648 | −4.452 | 1 | 86.24 C |
| ATOM | 2085 | CZ | PHE | B | 275 | 31.388 | 14.672 | −5.305 | 1 | 85.5 C |
| ATOM | 2086 | CE2 | PHE | B | 275 | 32.249 | 13.732 | −5.852 | 1 | 84.89 C |
| ATOM | 2087 | CD2 | PHE | B | 275 | 33.601 | 13.777 | −5.548 | 1 | 84.69 C |
| ATOM | 2088 | C | PHE | B | 275 | 37.466 | 14.172 | −2.886 | 1 | 85.54 C |
| ATOM | 2089 | O | PHE | B | 275 | 38.059 | 15.226 | −2.669 | 1 | 85.56 O |
| ATOM | 2090 | N | ASN | B | 276 | 38.087 | 13.003 | −3.036 | 1 | 84.58 N |
| ATOM | 2091 | CA | ASN | B | 276 | 39.532 | 12.917 | −3.251 | 1 | 83.89 C |
| ATOM | 2092 | CB | ASN | B | 276 | 40.226 | 12.199 | −2.091 | 1 | 83.93 C |
| ATOM | 2093 | CG | ASN | B | 276 | 40.087 | 12.936 | −0.779 | 1 | 83.61 C |
| ATOM | 2094 | OD1 | ASN | B | 276 | 40.98 | 13.687 | −0.388 | 1 | 83.49 O |
| ATOM | 2095 | ND2 | ASN | B | 276 | 38.964 | 12.728 | −0.091 | 1 | 82.67 N |
| ATOM | 2096 | C | ASN | B | 276 | 39.851 | 12.195 | −4.562 | 1 | 83.09 C |
| ATOM | 2097 | O | ASN | B | 276 | 39.224 | 11.194 | −4.89 | 1 | 82.74 O |
| ATOM | 2098 | N | TRP | B | 277 | 40.838 | 12.707 | −5.294 | 1 | 82.47 N |
| ATOM | 2099 | CA | TRP | B | 277 | 41.232 | 12.143 | −6.582 | 1 | 82.04 C |
| ATOM | 2100 | CB | TRP | B | 277 | 40.982 | 13.152 | −7.693 | 1 | 80.3 C |
| ATOM | 2101 | CG | TRP | B | 277 | 39.538 | 13.326 | −7.981 | 1 | 77.29 C |
| ATOM | 2102 | CD1 | TRP | B | 277 | 38.636 | 14.051 | −7.253 | 1 | 76.8 C |
| ATOM | 2103 | NE1 | TRP | B | 277 | 37.392 | 13.974 | −7.83 | 1 | 75.91 N |
| ATOM | 2104 | CE2 | TRP | B | 277 | 37.471 | 13.179 | −8.946 | 1 | 80.47 C |
| ATOM | 2105 | CD2 | TRP | B | 277 | 38.809 | 12.752 | −9.068 | 1 | 80.71 C |
| ATOM | 2106 | CE3 | TRP | B | 277 | 39.157 | 11.923 | −10.139 | 1 | 80.67 C |
| ATOM | 2107 | CZ3 | TRP | B | 277 | 38.181 | 1.558 | −11.039 | 1 | 83.55 C |
| ATOM | 2108 | CH2 | TRP | B | 277 | 36.856 | 11.995 | −10.89 | 1 | 83.46 C |
| ATOM | 2109 | CZ2 | TRP | B | 277 | 36.484 | 12.808 | −9.855 | 1 | 80.76 C |
| ATOM | 2110 | C | TRP | B | 277 | 42.691 | 11.692 | −6.61 | 1 | 81.61 C |
| ATOM | 2111 | O | TRP | B | 277 | 43.588 | 12.411 | −6.162 | 1 | 81.21 O |
| ATOM | 2112 | N | TYR | B | 278 | 42.906 | 10.494 | −7.152 | 1 | 81.32 N |
| ATOM | 2113 | CA | TYR | B | 278 | 44.23 | 9.912 | −7.279 | 1 | 81.29 C |
| ATOM | 2114 | CB | TYR | B | 278 | 44.391 | 8.776 | −6.274 | 1 | 81.57 C |
| ATOM | 2115 | CG | TYR | B | 278 | 44.026 | 9.146 | −4.855 | 1 | 81.56 C |
| ATOM | 2116 | CD1 | TYR | B | 278 | 42.754 | 8.88 | −4.352 | 1 | 81.13 C |
| ATOM | 2117 | CE1 | TYR | B | 278 | 42.409 | 9.222 | −3.049 | 1 | 81.58 C |
| ATOM | 2118 | CZ | TYR | B | 278 | 43.353 | 9.844 | −2.233 | 1 | 82.3 C |
| ATOM | 2119 | OH | TYR | B | 278 | 43.039 | 10.191 | −0.93 | 1 | 82.3 O |
| ATOM | 2120 | CE2 | TYR | B | 278 | 44.621 | 10.12 | −2.72 | 1 | 81.94 C |
| ATOM | 2121 | CD2 | TYR | B | 278 | 44.949 | 9.766 | −4.021 | 1 | 81.58 C |
| ATOM | 2122 | C | TYR | B | 278 | 44.484 | 9.376 | −8.688 | 1 | 81.06 C |
| ATOM | 2123 | O | TYR | B | 278 | 43.639 | 8.698 | −9.263 | 1 | 80.99 O |
| ATOM | 2124 | N | VAL | B | 279 | 45.657 | 9.697 | −9.227 | 1 | 81.03 N |
| ATOM | 2125 | CA | VAL | B | 279 | 46.18 | 9.096 | −10.457 | 1 | 81 C |
| ATOM | 2126 | CB | VAL | B | 279 | 46.816 | 10.162 | −11.38 | 1 | 80.73 C |
| ATOM | 2127 | CG1 | VAL | B | 279 | 47.139 | 9.561 | −12.742 | 1 | 80.44 C |
| ATOM | 2128 | CG2 | VAL | B | 279 | 45.892 | 11.363 | −11.526 | 1 | 80.25 C |
| ATOM | 2129 | C | VAL | B | 279 | 47.245 | 8.048 | −10.087 | 1 | 81.05 C |
| ATOM | 2130 | O | VAL | B | 279 | 48.329 | 8.397 | −9.62 | 1 | 80.84 O |
| ATOM | 2131 | N | ASP | B | 280 | 46.927 | 6.768 | −10.283 | 1 | 81.24 N |
| ATOM | 2132 | CA | ASP | B | 280 | 47.824 | 5.67 | −9.905 | 1 | 81.47 C |
| ATOM | 2133 | CB | ASP | B | 280 | 49.112 | 5.691 | −10.748 | 1 | 81.27 C |
| ATOM | 2134 | CG | ASP | B | 280 | 48.863 | 5.39 | −12.213 | 1 | 81.04 C |
| ATOM | 2135 | OD1 | ASP | B | 280 | 47.738 | 4.986 | −12.564 | 1 | 80.89 O |
| ATOM | 2136 | OD2 | ASP | B | 280 | 49.805 | 5.55 | −13.016 | 1 | 80.8 O |
| ATOM | 2137 | C | ASP | B | 280 | 48.174 | 5.709 | −8.416 | 1 | 81.67 C |
| ATOM | 2138 | O | ASP | B | 280 | 49.32 | 5.48 | −8.034 | 1 | 81.39 O |
| ATOM | 2139 | N | GLY | B | 281 | 47.184 | 6.004 | −7.579 | 1 | 82.2 N |
| ATOM | 2140 | CA | GLY | B | 281 | 47.407 | 6.151 | −6.138 | 1 | 82.67 C |
| ATOM | 2141 | C | GLY | B | 281 | 47.904 | 7.532 | −5.715 | 1 | 83.03 C |
| ATOM | 2142 | O | GLY | B | 281 | 47.49 | 8.044 | −4.677 | 1 | 83.23 O |
| ATOM | 2143 | N | VAL | B | 282 | 48.793 | 8.127 | −6.508 | 1 | 83.41 N |
| ATOM | 2144 | CA | VAL | B | 282 | 49.332 | 9.463 | −6.232 | 1 | 83.81 C |
| ATOM | 2145 | CB | VAL | B | 282 | 50.479 | 9.843 | −7.222 | 1 | 83.72 C |
| ATOM | 2146 | CG1 | VAL | B | 282 | 51.088 | 11.197 | −6.872 | 1 | 83.32 C |
| ATOM | 2147 | CG2 | VAL | B | 282 | 51.549 | 8.756 | −7.264 | 1 | 83.44 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2148 | C | VAL | B | 282 | 48.219 | 10.508 | −6.352 | 1 | 84.39 C |
| ATOM | 2149 | O | VAL | B | 282 | 47.613 | 10.662 | −7.412 | 1 | 84.74 O |
| ATOM | 2150 | N | GLU | B | 283 | 47.949 | 11.223 | −5.268 | 1 | 84.83 N |
| ATOM | 2151 | CA | GLU | B | 283 | 46.919 | 12.263 | −5.268 | 1 | 84.92 C |
| ATOM | 2152 | CB | GLU | B | 283 | 46.737 | 12.808 | −3.846 | 1 | 84.93 C |
| ATOM | 2153 | CG | GLU | B | 283 | 45.495 | 13.658 | −3.647 | 1 | 85.04 C |
| ATOM | 2154 | CD | GLU | B | 283 | 45.093 | 13.771 | −2.187 | 1 | 84.92 C |
| ATOM | 2155 | OE1 | GLU | B | 283 | 46.005 | 13.806 | −1.337 | 1 | 84.4 O |
| ATOM | 2156 | OE2 | GLU | B | 283 | 43.873 | 13.81 | −1.893 | 1 | 84.6 O |
| ATOM | 2157 | C | GLU | B | 283 | 47.253 | 13.412 | −6.232 | 1 | 85.1 C |
| ATOM | 2158 | O | GLU | B | 283 | 48.407 | 13.836 | −6.34 | 1 | 84.97 O |
| ATOM | 2159 | N | VAL | B | 284 | 46.235 | 13.868 | −6.96 | 1 | 85.31 N |
| ATOM | 2160 | CA | VAL | B | 284 | 46.266 | 15.151 | −7.667 | 1 | 85.41 C |
| ATOM | 2161 | CB | VAL | B | 284 | 46.037 | 15.012 | −9.2 | 1 | 85.14 C |
| ATOM | 2162 | CG1 | VAL | B | 284 | 47.222 | 14.329 | −9.857 | 1 | 84.43 C |
| ATOM | 2163 | CG2 | VAL | B | 284 | 44.732 | 14.276 | −9.505 | 1 | 84.78 C |
| ATOM | 2164 | C | VAL | B | 284 | 45.171 | 15.984 | −7.003 | 1 | 85.7 C |
| ATOM | 2165 | O | VAL | B | 284 | 44.48 | 15.468 | −6.116 | 1 | 85.48 O |
| ATOM | 2166 | N | HIS | B | 285 | 45.009 | 17.248 | −7.408 | 1 | 86.16 N |
| ATOM | 2167 | CA | HIS | B | 285 | 44.15 | 18.187 | −6.659 | 1 | 86.64 C |
| ATOM | 2168 | CB | HIS | B | 285 | 45.029 | 19.111 | −5.799 | 1 | 86.59 C |
| ATOM | 2169 | CG | HIS | B | 285 | 45.724 | 18.395 | −4.687 | 1 | 86.56 C |
| ATOM | 2170 | ND1 | HIS | B | 285 | 45.08 | 18.026 | −3.525 | 1 | 86.3 N |
| ATOM | 2171 | CE1 | HIS | B | 285 | 45.929 | 17.384 | −2.741 | 1 | 86.66 C |
| ATOM | 2172 | NE2 | HIS | B | 285 | 47.096 | 17.315 | −3.358 | 1 | 86.79 N |
| ATOM | 2173 | CD2 | HIS | B | 285 | 46.993 | 17.932 | −4.581 | 1 | 86.42 C |
| ATOM | 2174 | C | HIS | B | 285 | 43.156 | 19.04 | −7.446 | 1 | 87.04 C |
| ATOM | 2175 | O | HIS | B | 285 | 42.35 | 19.745 | −6.833 | 1 | 86.98 O |
| ATOM | 2176 | N | ASN | B | 286 | 43.178 | 18.967 | −8.776 | 1 | 87.58 N |
| ATOM | 2177 | CA | ASN | B | 286 | 42.409 | 19.913 | −9.599 | 1 | 88 C |
| ATOM | 2178 | CB | ASN | B | 286 | 43.157 | 20.241 | −10.902 | 1 | 88.08 C |
| ATOM | 2179 | CG | ASN | B | 286 | 43.355 | 19.037 | −11.789 | 1 | 88.39 C |
| ATOM | 2180 | OD1 | ASN | B | 286 | 43.98 | 18.052 | −11.392 | 1 | 88.75 O |
| ATOM | 2181 | ND2 | ASN | B | 286 | 42.839 | 19.114 | −13.008 | 1 | 88.77 N |
| ATOM | 2182 | C | ASN | B | 286 | 40.945 | 19.547 | −9.892 | 1 | 88.27 C |
| ATOM | 2183 | O | ASN | B | 286 | 40.312 | 20.193 | −10.721 | 1 | 88.17 O |
| ATOM | 2184 | N | ALA | B | 287 | 40.394 | 18.552 | −9.198 | 1 | 88.88 N |
| ATOM | 2185 | CA | ALA | B | 287 | 38.96 | 18.258 | −9.305 | 1 | 89.63 C |
| ATOM | 2186 | CB | ALA | B | 287 | 38.558 | 17.143 | −8.362 | 1 | 89.7 C |
| ATOM | 2187 | C | ALA | B | 287 | 38.165 | 19.506 | −8.978 | 1 | 90.22 C |
| ATOM | 2188 | O | ALA | B | 287 | 38.559 | 20.272 | −8.107 | 1 | 90.32 O |
| ATOM | 2189 | N | LYS | B | 288 | 37.056 | 19.71 | −9.681 | 1 | 90.93 N |
| ATOM | 2190 | CA | LYS | B | 288 | 36.225 | 20.892 | −9.491 | 1 | 91.57 C |
| ATOM | 2191 | CB | LYS | B | 288 | 36.138 | 21.735 | −10.758 | 1 | 91.69 C |
| ATOM | 2192 | CG | LYS | B | 288 | 37.472 | 22.19 | −11.324 | 1 | 91.9 C |
| ATOM | 2193 | CD | LYS | B | 288 | 37.31 | 22.96 | −12.63 | 1 | 91.83 C |
| ATOM | 2194 | CE | LYS | B | 288 | 38.674 | 23.386 | −13.178 | 1 | 92.26 C |
| ATOM | 2195 | NZ | LYS | B | 288 | 38.536 | 24.211 | −14.412 | 1 | 92.6 N |
| ATOM | 2196 | C | LYS | B | 288 | 34.829 | 20.473 | −9.078 | 1 | 92.18 C |
| ATOM | 2197 | O | LYS | B | 288 | 33.987 | 20.183 | −9.941 | 1 | 92.16 O |
| ATOM | 2198 | N | THR | B | 289 | 34.571 | 20.433 | −7.772 | 1 | 92.82 N |
| ATOM | 2199 | CA | THR | B | 289 | 33.226 | 20.082 | −7.304 | 1 | 93.47 C |
| ATOM | 2200 | CB | THR | B | 289 | 33.179 | 19.857 | −5.797 | 1 | 93.34 C |
| ATOM | 2201 | OG1 | THR | B | 289 | 34.199 | 18.92 | −5.411 | 1 | 93.23 O |
| ATOM | 2202 | CG2 | THR | B | 289 | 31.803 | 19.339 | −5.378 | 1 | 93.09 C |
| ATOM | 2203 | C | THR | B | 289 | 32.246 | 21.185 | −7.708 | 1 | 94.13 C |
| ATOM | 2204 | O | THR | B | 289 | 32.507 | 22.364 | −7.57 | 1 | 94.06 O |
| ATOM | 2205 | N | LYS | B | 290 | 31.145 | 20.686 | −8.206 | 1 | 95.17 N |
| ATOM | 2206 | CA | LYS | B | 290 | 30.058 | 21.493 | −8.663 | 1 | 96.26 C |
| ATOM | 2207 | CB | LYS | B | 290 | 29.801 | 21.205 | −10.16 | 1 | 96.16 C |
| ATOM | 2208 | CG | LYS | B | 290 | 30.702 | 21.985 | −11.091 | 1 | 96.18 C |
| ATOM | 2209 | CD | LYS | B | 290 | 31.671 | 21.091 | −11.847 | 1 | 96.22 C |
| ATOM | 2210 | CE | LYS | B | 290 | 32.518 | 21.885 | −12.83 | 1 | 96.01 C |
| ATOM | 2211 | NZ | LYS | B | 290 | 33.441 | 21.01 | −13.604 | 1 | 95.72 N |
| ATOM | 2212 | C | LYS | B | 290 | 28.795 | 21.324 | −7.81 | 1 | 97.33 C |
| ATOM | 2213 | O | LYS | B | 290 | 28.328 | 20.232 | −7.476 | 1 | 97.63 O |
| ATOM | 2214 | N | PRO | B | 291 | 28.273 | 22.543 | −7.473 | 1 | 98.47 N |
| ATOM | 2215 | CA | PRO | B | 291 | 27.109 | 22.914 | −6.627 | 1 | 99.12 C |
| ATOM | 2216 | CB | PRO | B | 291 | 26.147 | 23.656 | −7.546 | 1 | 99.13 C |
| ATOM | 2217 | CG | PRO | B | 291 | 26.9 | 23.817 | −8.815 | 1 | 98.94 C |
| ATOM | 2218 | CD | PRO | B | 291 | 28.318 | 23.717 | −8.376 | 1 | 98.61 C |
| ATOM | 2219 | C | PRO | B | 291 | 26.357 | 21.766 | −5.988 | 1 | 99.93 C |
| ATOM | 2220 | O | PRO | B | 291 | 26.837 | 21.119 | −5.056 | 1 | 100.04 O |
| ATOM | 2221 | N | ARG | B | 292 | 25.195 | 21.522 | −6.464 | 1 | 100.64 N |
| ATOM | 2222 | CA | ARG | B | 292 | 24.44 | 20.451 | −5.912 | 1 | 101.37 C |
| ATOM | 2223 | C | ARG | B | 292 | 23.147 | 20.449 | −6.63 | 1 | 102.12 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2224 | O | ARG | B | 292 | 22.412 | 21.437 | −6.625 | 1 | 102.33 O |
| ATOM | 2225 | CB | ARG | B | 292 | 24.291 | 20.607 | −4.403 | 1 | 101.43 C |
| ATOM | 2226 | CG | ARG | B | 292 | 25.621 | 20.69 | −3.67 | 1 | 101.48 C |
| ATOM | 2227 | CD | ARG | B | 292 | 25.421 | 20.698 | −2.164 | 1 | 101.4 C |
| ATOM | 2228 | NE | ARG | B | 292 | 26.691 | 20.688 | −1.444 | 1 | 101.29 N |
| ATOM | 2229 | CZ | ARG | B | 292 | 26.798 | 20.667 | −0.12 | 1 | 100.92 C |
| ATOM | 2230 | NH1 | ARG | B | 292 | 25.708 | 20.654 | 0.633 | 1 | 100.57 N |
| ATOM | 2231 | NH2 | ARG | B | 292 | 27.995 | 20.66 | 0.448 | 1 | 101.04 N |
| ATOM | 2232 | N | GLU | B | 293 | 22.822 | 19.362 | −7.219 | 1 | 103 N |
| ATOM | 2233 | CA | GLU | B | 293 | 21.557 | 19.473 | −7.864 | 1 | 103.57 C |
| ATOM | 2234 | CB | GLU | B | 293 | 21.703 | 19.119 | −9.335 | 1 | 103.62 C |
| ATOM | 2235 | CG | GLU | B | 293 | 22.798 | 19.942 | −9.982 | 1 | 103.77 C |
| ATOM | 2236 | CD | GLU | B | 293 | 23.443 | 19.261 | −11.176 | 1 | 103.88 C |
| ATOM | 2237 | OE1 | GLU | B | 293 | 22.906 | 19.399 | −12.307 | 1 | 104.3 O |
| ATOM | 2238 | OE2 | GLU | B | 293 | 24.487 | 18.585 | −10.983 | 1 | 103.91 O |
| ATOM | 2239 | C | GLU | B | 293 | 20.537 | 18.68 | −7.092 | 1 | 104.1 C |
| ATOM | 2240 | O | GLU | B | 293 | 20.578 | 17.451 | −7.075 | 1 | 103.95 O |
| ATOM | 2241 | N | GLU | B | 294 | 19.603 | 19.387 | −6.427 | 1 | 104.82 N |
| ATOM | 2242 | CA | GLU | B | 294 | 18.533 | 18.73 | −5.649 | 1 | 105.26 C |
| ATOM | 2243 | CB | GLU | B | 294 | 17.769 | 19.749 | −4.793 | 1 | 105.51 C |
| ATOM | 2244 | CG | GLU | B | 294 | 16.983 | 20.784 | −5.587 | 1 | 105.91 C |
| ATOM | 2245 | CD | GLU | B | 294 | 16.709 | 22.078 | −4.813 | 1 | 106.01 C |
| ATOM | 2246 | OE1 | GLU | B | 294 | 16.829 | 22.055 | −3.569 | 1 | 107.11 O |
| ATOM | 2247 | OE2 | GLU | B | 294 | 16.392 | 23.093 | −5.455 | 1 | 106.42 O |
| ATOM | 2248 | C | GLU | B | 294 | 17.576 | 18 | −6.587 | 1 | 105.5 C |
| ATOM | 2249 | O | GLU | B | 294 | 17.085 | 18.56 | −7.56 | 1 | 105.53 O |
| ATOM | 2250 | N | GLN | B | 295 | 17.319 | 16.747 | −6.276 | 1 | 105.65 N |
| ATOM | 2251 | CA | GLN | B | 295 | 16.493 | 15.869 | −7.09 | 1 | 105.72 C |
| ATOM | 2252 | CB | GLN | B | 295 | 17.131 | 14.48 | −7.16 | 1 | 105.86 C |
| ATOM | 2253 | CG | GLN | B | 295 | 18.618 | 14.478 | −7.496 | 1 | 106.03 C |
| ATOM | 2254 | CD | GLN | B | 295 | 18.882 | 15.023 | −8.892 | 1 | 106.18 C |
| ATOM | 2255 | OE1 | GLN | B | 295 | 18.168 | 14.702 | −9.844 | 1 | 106.14 O |
| ATOM | 2256 | NE2 | GLN | B | 295 | 19.913 | 15.849 | −9.019 | 1 | 106.39 N |
| ATOM | 2257 | C | GLN | B | 295 | 15.069 | 15.766 | −6.565 | 1 | 105.8 C |
| ATOM | 2258 | O | GLN | B | 295 | 14.831 | 15.867 | −5.361 | 1 | 105.87 O |
| ATOM | 2259 | N | TYR | B | 296 | 14.122 | 15.566 | −7.469 | 1 | 105.83 N |
| ATOM | 2260 | CA | TYR | B | 296 | 12.709 | 15.451 | −7.1 | 1 | 105.61 C |
| ATOM | 2261 | CB | TYR | B | 296 | 11.816 | 15.67 | −8.335 | 1 | 106.61 C |
| ATOM | 2262 | CG | TYR | B | 296 | 11.994 | 17.014 | −9.045 | 1 | 107.27 C |
| ATOM | 2263 | CD1 | TYR | B | 296 | 12.165 | 17.073 | −10.437 | 1 | 107.6 C |
| ATOM | 2264 | CE1 | TYR | B | 296 | 12.321 | 18.297 | −11.098 | 1 | 107.39 C |
| ATOM | 2265 | CZ | TYR | B | 296 | 12.304 | 19.479 | −10.372 | 1 | 107.58 C |
| ATOM | 2266 | OH | TYR | B | 296 | 12.455 | 20.676 | −11.036 | 1 | 107.66 O |
| ATOM | 2267 | CE2 | TYR | B | 296 | 12.133 | 19.455 | −8.99 | 1 | 107.59 C |
| ATOM | 2268 | CD2 | TYR | B | 296 | 11.975 | 18.225 | −8.333 | 1 | 107.68 C |
| ATOM | 2269 | C | TYR | B | 296 | 12.372 | 14.108 | −6.425 | 1 | 105.14 C |
| ATOM | 2270 | O | TYR | B | 296 | 11.391 | 13.45 | −6.783 | 1 | 105.12 O |
| ATOM | 2271 | N | ASN | B | 297 | 13.175 | 13.734 | −5.437 | 1 | 104.29 N |
| ATOM | 2272 | CA | ASN | B | 297 | 12.921 | 12.568 | −4.586 | 1 | 103.53 C |
| ATOM | 2273 | CB | ASN | B | 297 | 13.348 | 11.265 | −5.254 | 1 | 103.78 C |
| ATOM | 2274 | CG | ASN | B | 297 | 14.733 | 11.246 | −5.843 | 1 | 104.86 C |
| ATOM | 2275 | OD1 | ASN | B | 297 | 15.609 | 11.952 | −5.352 | 1 | 104.49 O |
| ATOM | 2276 | ND2 | ASN | B | 297 | 14.948 | 10.45 | −6.883 | 1 | 106.68 N |
| ATOM | 2277 | C | ASN | B | 297 | 13.582 | 12.781 | −3.201 | 1 | 102.67 C |
| ATOM | 2278 | O | ASN | B | 297 | 13.847 | 11.815 | −2.479 | 1 | 102.43 O |
| ATOM | 2279 | N | SER | B | 298 | 13.871 | 14.04 | −2.82 | 1 | 101.51 N |
| ATOM | 2280 | CA | SER | B | 298 | 14.458 | 14.295 | −1.499 | 1 | 100.51 C |
| ATOM | 2281 | CB | SER | B | 298 | 14.012 | 13.229 | −0.501 | 1 | 100.62 C |
| ATOM | 2282 | OG | SER | B | 298 | 12.632 | 13.357 | −0.204 | 1 | 100.43 O |
| ATOM | 2283 | C | SER | B | 298 | 15.979 | 14.28 | −1.465 | 1 | 99.48 C |
| ATOM | 2284 | O | SER | 8 | 298 | 16.556 | 14.827 | −0.528 | 1 | 99.31 O |
| ATOM | 2285 | N | THR | B | 299 | 16.678 | 13.673 | −2.412 | 1 | 98.24 N |
| ATOM | 2286 | CA | THR | B | 299 | 18.119 | 13.674 | −2.22 | 1 | 97.06 C |
| ATOM | 2287 | CB | THR | B | 299 | 18.66 | 12.25 | −2.394 | 1 | 96.9 C |
| ATOM | 2288 | OG1 | THR | B | 299 | 17.879 | 11.54 | −3.372 | 1 | 96.19 O |
| ATOM | 2289 | CG2 | THR | B | 299 | 18.62 | 11.526 | −1.054 | 1 | 96.89 C |
| ATOM | 2290 | C | THR | B | 299 | 18.836 | 14.621 | −3.171 | 1 | 95.99 C |
| ATOM | 2291 | O | THR | B | 299 | 18.278 | 15.033 | −4.178 | 1 | 95.81 O |
| ATOM | 2292 | N | TYR | B | 300 | 20.089 | 14.953 | −2.83 | 1 | 94.66 N |
| ATOM | 2293 | CA | TYR | B | 300 | 20.911 | 15.811 | −3.686 | 1 | 93.51 C |
| ATOM | 2294 | CB | TYR | B | 300 | 21.732 | 16.788 | −2.836 | 1 | 95.03 C |
| ATOM | 2295 | CG | TYR | B | 300 | 20.904 | 17.735 | −1.991 | 1 | 96.06 C |
| ATOM | 2296 | CD1 | TYR | B | 300 | 20.686 | 17.478 | −0.634 | 1 | 94.82 C |
| ATOM | 2297 | CE1 | TYR | B | 300 | 19.929 | 18.333 | 0.144 | 1 | 95.64 C |
| ATOM | 2298 | CZ | TYR | B | 300 | 19.378 | 19.472 | −0.427 | 1 | 96.99 C |
| ATOM | 2299 | OH | TYR | B | 300 | 18.631 | 20.33 | 0.357 | 1 | 94.13 O |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2300 | CE2 | TYR | B | 300 | 19.581 | 19.756 | −1.772 | 1 | 95.97 C |
| ATOM | 2301 | CD2 | TYR | B | 300 | 20.342 | 18.891 | −2.544 | 1 | 95.78 C |
| ATOM | 2302 | C | TYR | B | 300 | 21.861 | 14.986 | −4.562 | 1 | 91.98 C |
| ATOM | 2303 | O | TYR | B | 300 | 22.03 | 13.786 | −4.357 | 1 | 92.13 O |
| ATOM | 2304 | N | ARG | B | 301 | 22.46 | 15.653 | −5.549 | 1 | 89.57 N |
| ATOM | 2305 | CA | ARG | B | 301 | 23.367 | 15.02 | −6.516 | 1 | 87.78 C |
| ATOM | 2306 | CB | ARG | B | 301 | 22.624 | 14.794 | −7.841 | 1 | 88 C |
| ATOM | 2307 | CG | ARG | B | 301 | 23.42 | 14.016 | −8.868 | 1 | 88.73 C |
| ATOM | 2308 | CD | ARG | B | 301 | 22.611 | 13.851 | −10.148 | 1 | 88.96 C |
| ATOM | 2309 | NE | ARG | B | 301 | 23.35 | 13.062 | −11.135 | 1 | 89.59 N |
| ATOM | 2310 | CZ | ARG | B | 301 | 24.126 | 13.565 | −12.086 | 1 | 90.33 C |
| ATOM | 2311 | NH1 | ARG | B | 301 | 24.276 | 14.887 | −12.194 | 1 | 90.37 N |
| ATOM | 2312 | NH2 | ARG | B | 301 | 24.749 | 12.754 | −12.94 | 1 | 90.64 N |
| ATOM | 2313 | C | ARG | B | 301 | 24.631 | 15.872 | −6.737 | 1 | 85.39 C |
| ATOM | 2314 | O | ARG | B | 301 | 24.577 | 16.903 | −7.414 | 1 | 84.71 O |
| ATOM | 2315 | N | VAL | B | 302 | 25.756 | 15.423 | −6.167 | 1 | 82.91 N |
| ATOM | 2316 | CA | VAL | B | 302 | 27.043 | 16.155 | −6.204 | 1 | 81.04 C |
| ATOM | 2317 | CB | VAL | B | 302 | 27.777 | 16.134 | −4.817 | 1 | 80.97 C |
| ATOM | 2318 | CG1 | VAL | B | 302 | 28.877 | 17.194 | −4.771 | 1 | 80.68 C |
| ATOM | 2319 | CG2 | VAL | B | 302 | 26.801 | 16.328 | −3.664 | 1 | 80.81 C |
| ATOM | 2320 | C | VAL | B | 302 | 28.012 | 15.572 | −7.247 | 1 | 79.03 C |
| ATOM | 2321 | O | VAL | B | 302 | 28.385 | 14.405 | −7.176 | 1 | 79.05 O |
| ATOM | 2322 | N | VAL | B | 303 | 28.446 | 16.41 | −8.181 | 1 | 76.74 N |
| ATOM | 2323 | CA | VAL | B | 303 | 29.29 | 16.009 | −9.299 | 1 | 75.03 C |
| ATOM | 2324 | CB | VAL | B | 303 | 28.622 | 16.43 | −10.627 | 1 | 74.8 C |
| ATOM | 2325 | CG1 | VAL | B | 303 | 29.504 | 16.096 | −11.81 | 1 | 74.58 C |
| ATOM | 2326 | CG2 | VAL | B | 303 | 27.242 | 15.787 | −10.766 | 1 | 74.49 C |
| ATOM | 2327 | C | VAL | B | 303 | 30.665 | 16.686 | −9.223 | 1 | 73.41 C |
| ATOM | 2328 | O | VAL | B | 303 | 30.736 | 17.913 | −9.227 | 1 | 73.23 O |
| ATOM | 2329 | N | SER | B | 304 | 31.738 | 15.888 | −9.159 | 1 | 71.55 N |
| ATOM | 2330 | CA | SER | B | 304 | 33.118 | 16.382 | −9.262 | 1 | 70.43 C |
| ATOM | 2331 | CB | SER | B | 304 | 33.974 | 15.859 | −8.105 | 1 | 70.11 C |
| ATOM | 2332 | OG | SER | B | 304 | 35.337 | 16.224 | −8.28 | 1 | 69.21 O |
| ATOM | 2333 | C | SER | B | 304 | 33.779 | 15.969 | −10.586 | 1 | 69.53 C |
| ATOM | 2334 | O | SER | B | 304 | 33.694 | 14.802 | −10.999 | 1 | 69.36 O |
| ATOM | 2335 | N | VAL | B | 305 | 34.48 | 16.921 | −11.212 | 1 | 68.51 N |
| ATOM | 2336 | CA | VAL | B | 305 | 35.083 | 16.744 | −12.54 | 1 | 67.53 C |
| ATOM | 2337 | CB | VAL | B | 305 | 34.545 | 17.79 | −13.563 | 1 | 67.32 C |
| ATOM | 2338 | CG1 | VAL | B | 305 | 35.375 | 17.79 | −14.833 | 1 | 67.49 C |
| ATOM | 2339 | CG2 | VAL | B | 305 | 33.091 | 17.519 | −13.9 | 1 | 66.97 C |
| ATOM | 2340 | C | VAL | B | 305 | 36.584 | 16.89 | −12.441 | 1 | 66.63 C |
| ATOM | 2341 | O | VAL | B | 305 | 37.082 | 17.966 | −12.16 | 1 | 66.75 O |
| ATOM | 2342 | N | LEU | B | 306 | 37.302 | 15.797 | −12.663 | 1 | 65.96 N |
| ATOM | 2343 | CA | LEU | B | 306 | 38.748 | 15.839 | −12.761 | 1 | 65.69 C |
| ATOM | 2344 | CB | LEU | B | 306 | 39.374 | 14.603 | −12.127 | 1 | 65.62 C |
| ATOM | 2345 | CG | LEU | B | 306 | 40.898 | 14.514 | −12.266 | 1 | 65.63 C |
| ATOM | 2346 | CD1 | LEU | B | 306 | 41.582 | 15.508 | −11.317 | 1 | 65.87 C |
| ATOM | 2347 | CD2 | LEU | B | 306 | 41.411 | 13.117 | −12.021 | 1 | 65.24 C |
| ATOM | 2348 | C | LEU | B | 306 | 39.15 | 15.918 | −14.231 | 1 | 65.36 C |
| ATOM | 2349 | O | LEU | B | 306 | 38.755 | 15.079 | −15.037 | 1 | 65.58 O |
| ATOM | 2350 | N | THR | B | 307 | 39.927 | 16.943 | −14.561 | 1 | 64.96 N |
| ATOM | 2351 | CA | THR | B | 307 | 40.605 | 17.049 | −15.842 | 1 | 64.83 C |
| ATOM | 2352 | CB | THR | B | 307 | 41.173 | 18.477 | −16.087 | 1 | 65.06 C |
| ATOM | 2353 | OG1 | THR | B | 307 | 40.187 | 19.271 | −16.766 | 1 | 65.79 O |
| ATOM | 2354 | CG2 | THR | B | 307 | 42.445 | 18.438 | −16.913 | 1 | 64.56 C |
| ATOM | 2355 | C | THR | B | 307 | 41.749 | 16.062 | −15.824 | 1 | 64.71 C |
| ATOM | 2356 | O | THR | B | 307 | 42.271 | 15.725 | −14.753 | 1 | 65.18 O |
| ATOM | 2357 | N | VAL | B | 308 | 42.132 | 15.585 | −17.003 | 1 | 63.75 N |
| ATOM | 2358 | CA | VAL | B | 308 | 43.165 | 14.575 | −17.1 | 1 | 63.16 C |
| ATOM | 2359 | CB | VAL | B | 308 | 42.551 | 13.153 | −17.14 | 1 | 63.17 C |
| ATOM | 2360 | CG1 | VAL | B | 308 | 41.8 | 12.848 | −15.846 | 1 | 62.4 C |
| ATOM | 2361 | CG2 | VAL | B | 308 | 41.619 | 12.991 | −18.361 | 1 | 63.25 C |
| ATOM | 2362 | C | VAL | B | 308 | 43.964 | 14.818 | −18.358 | 1 | 62.14 C |
| ATOM | 2363 | O | VAL | B | 308 | 43.447 | 15.354 | −19.345 | 1 | 62.43 O |
| ATOM | 2364 | N | LEU | B | 309 | 45.227 | 14.43 | −18.33 | 1 | 60.94 N |
| ATOM | 2365 | CA | LEU | B | 309 | 46.032 | 14.521 | −19.52 | 1 | 60.02 C |
| ATOM | 2366 | CB | LEU | B | 309 | 47.53 | 14.494 | −19.199 | 1 | 60.24 C |
| ATOM | 2367 | CG | LEU | B | 309 | 48.1 | 15.723 | −18.474 | 1 | 60.19 C |
| ATOM | 2368 | CD1 | LEU | B | 309 | 49.446 | 16.058 | −19.089 | 1 | 59.29 C |
| ATOM | 2369 | CD2 | LEU | B | 309 | 47.146 | 16.943 | −18.526 | 1 | 59.48 C |
| ATOM | 2370 | C | LEU | B | 309 | 45.66 | 13.404 | −20.484 | 1 | 59.44 C |
| ATOM | 2371 | O | LEU | B | 309 | 45.45 | 12.258 | −20.081 | 1 | 58.75 O |
| ATOM | 2372 | N | HIS | B | 310 | 45.597 | 13.793 | −21.756 | 1 | 58.83 N |
| ATOM | 2373 | CA | HIS | B | 310 | 45.278 | 12.932 | −22.887 | 1 | 58.46 C |
| ATOM | 2374 | CB | HIS | B | 310 | 45.544 | 13.672 | −24.21 | 1 | 57.96 C |
| ATOM | 2375 | CG | HIS | B | 310 | 44.728 | 14.922 | −24.388 | 1 | 57.57 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2376 | ND1 | HIS | B | 310 | 44.901 | 16.048 | −23.609 | 1 | 57.18 N |
| ATOM | 2377 | CE1 | HIS | B | 310 | 44.041 | 16.978 | −23.985 | 1 | 57.48 C |
| ATOM | 2378 | NE2 | HIS | B | 310 | 43.322 | 16.504 | −24.987 | 1 | 56.2 N |
| ATOM | 2379 | CD2 | HIS | B | 310 | 43.726 | 15.219 | −25.252 | 1 | 57.04 C |
| ATOM | 2380 | C | HIS | B | 310 | 46.101 | 11.657 | −22.831 | 1 | 58.5 C |
| ATOM | 2381 | O | HIS | B | 310 | 45.542 | 10.555 | −22.859 | 1 | 58.88 O |
| ATOM | 2382 | N | GLN | B | 311 | 47.427 | 11.794 | −22.725 | 1 | 58.2 N |
| ATOM | 2383 | CA | GLN | B | 311 | 48.297 | 10.619 | −22.794 | 1 | 57.51 C |
| ATOM | 2384 | CB | GLN | B | 311 | 49.75 | 10.978 | −23.135 | 1 | 58.03 C |
| ATOM | 2385 | CG | GLN | B | 311 | 50.033 | 11.114 | −24.645 | 1 | 59.44 C |
| ATOM | 2386 | CD | GLN | B | 311 | 49.726 | 9.832 | −25.463 | 1 | 62.17 C |
| ATOM | 2387 | OE1 | GLN | B | 311 | 50.028 | 8.709 | −25.039 | 1 | 64.45 O |
| ATOM | 2388 | NE2 | GLN | B | 311 | 49.127 | 10.011 | −26.643 | 1 | 64.01 N |
| ATOM | 2389 | C | GLN | B | 311 | 48.231 | 9.752 | −21.546 | 1 | 56.95 C |
| ATOM | 2390 | O | GLN | B | 311 | 48.513 | 8.565 | −21.648 | 1 | 56.96 O |
| ATOM | 2391 | N | ASP | B | 312 | 47.858 | 10.319 | −20.391 | 1 | 55.97 N |
| ATOM | 2392 | CA | ASP | B | 312 | 47.669 | 9.522 | −19.162 | 1 | 54.83 C |
| ATOM | 2393 | CB | ASP | B | 312 | 47.389 | 10.419 | −17.947 | 1 | 55.54 C |
| ATOM | 2394 | CG | ASP | B | 312 | 48.59 | 11.247 | −17.512 | 1 | 57.57 C |
| ATOM | 2395 | OD1 | ASP | B | 312 | 49.71 | 11.066 | −18.069 | 1 | 58.66 O |
| ATOM | 2396 | OD2 | ASP | B | 312 | 48.388 | 12.095 | −16.591 | 1 | 60.18 O |
| ATOM | 2397 | C | ASP | B | 312 | 46.498 | 8.526 | −19.29 | 1 | 53.68 C |
| ATOM | 2398 | O | ASP | B | 312 | 46.574 | 7.385 | −18.823 | 1 | 53.97 O |
| ATOM | 2399 | N | TRP | B | 313 | 45.393 | 8.986 | −19.871 | 1 | 52.33 N |
| ATOM | 2400 | CA | TRP | B | 313 | 44.256 | 8.129 | −20.146 | 1 | 50.71 C |
| ATOM | 2401 | CB | TRP | B | 313 | 43.048 | 8.964 | −20.558 | 1 | 46.57 C |
| ATOM | 2402 | CG | TRP | B | 313 | 41.915 | 8.114 | −20.974 | 1 | 45.33 C |
| ATOM | 2403 | CD1 | TRP | B | 313 | 41.599 | 7.755 | −22.244 | 1 | 41.69 C |
| ATOM | 2404 | NE1 | TRP | B | 313 | 40.51 | 6.927 | −22.232 | 1 | 42.52 N |
| ATOM | 2405 | CE2 | TRP | B | 313 | 40.107 | 6.745 | −20.94 | 1 | 43.68 C |
| ATOM | 2406 | CD2 | TRP | B | 313 | 40.982 | 7.464 | −20.123 | 1 | 44.85 C |
| ATOM | 2407 | CE3 | TRP | B | 313 | 40.788 | 7.446 | −18.742 | 1 | 44.99 C |
| ATOM | 2408 | CZ3 | TRP | B | 313 | 39.761 | 6.698 | −18.23 | 1 | 48.24 C |
| ATOM | 2409 | CH2 | TRP | B | 313 | 38.906 | 5.981 | −19.07 | 1 | 48.93 C |
| ATOM | 2410 | CZ2 | TRP | B | 313 | 39.061 | 6 | −20.434 | 1 | 46.14 C |
| ATOM | 2411 | C | TRP | B | 313 | 44.619 | 7.118 | −21.247 | 1 | 50.28 C |
| ATOM | 2412 | O | TRP | B | 313 | 44.363 | 5.922 | −21.111 | 1 | 50.27 O |
| ATOM | 2413 | N | LEU | B | 314 | 45.234 | 7.598 | −22.321 | 1 | 50.27 N |
| ATOM | 2414 | CA | LEU | B | 314 | 45.62 | 6.725 | −23.416 | 1 | 50.73 C |
| ATOM | 2415 | CB | LEU | B | 314 | 46.126 | 7.531 | −24.626 | 1 | 49.91 C |
| ATOM | 2416 | CG | LEU | B | 314 | 45.05 | 8.209 | −25.502 | 1 | 47.82 C |
| ATOM | 2417 | CD1 | LEU | B | 314 | 45.7 | 8.796 | −26.747 | 1 | 45.45 C |
| ATOM | 2418 | CD2 | LEU | B | 314 | 43.893 | 7.26 | −25.872 | 1 | 43.04 C |
| ATOM | 2419 | C | LEU | B | 314 | 46.649 | 5.69 | −22.975 | 1 | 51.59 C |
| ATOM | 2420 | O | LEU | B | 314 | 46.633 | 4.575 | −23.465 | 1 | 51.93 O |
| ATOM | 2421 | N | ASN | B | 315 | 47.516 | 6.056 | −22.032 | 1 | 52.91 N |
| ATOM | 2422 | CA | ASN | B | 315 | 48.491 | 5.134 | −21.431 | 1 | 53.52 C |
| ATOM | 2423 | CB | ASN | B | 315 | 49.734 | 5.886 | −20.942 | 1 | 53.55 C |
| ATOM | 2424 | CG | ASN | B | 315 | 50.582 | 6.394 | −22.095 | 1 | 55.55 C |
| ATOM | 2425 | OD1 | ASN | B | 315 | 50.699 | 5.722 | −23.127 | 1 | 58.33 O |
| ATOM | 2426 | ND2 | ASN | B | 315 | 51.157 | 7.59 | −21.944 | 1 | 57.11 N |
| ATOM | 2427 | C | ASN | B | 315 | 47.906 | 4.333 | −20.305 | 1 | 53.9 C |
| ATOM | 2428 | O | ASN | B | 315 | 48.599 | 3.527 | −19.701 | 1 | 53.79 O |
| ATOM | 2429 | N | GLY | B | 316 | 46.637 | 4.559 | −20.015 | 1 | 54.84 N |
| ATOM | 2430 | CA | GLY | B | 316 | 45.865 | 3.646 | −19.184 | 1 | 56.27 C |
| ATOM | 2431 | C | GLY | B | 316 | 45.977 | 3.887 | −17.694 | 1 | 57.5 C |
| ATOM | 2432 | O | GLY | B | 316 | 45.549 | 3.061 | −16.878 | 1 | 58.13 O |
| ATOM | 2433 | N | LYS | B | 317 | 46.528 | 5.034 | −17.328 | 1 | 58.67 N |
| ATOM | 2434 | CA | LYS | B | 317 | 46.692 | 5.37 | −15.933 | 1 | 59.38 C |
| ATOM | 2435 | CB | LYS | B | 317 | 47.292 | 6.762 | −15.817 | 1 | 59.43 C |
| ATOM | 2436 | CG | LYS | B | 317 | 48.689 | 6.875 | −16.439 | 1 | 59.68 C |
| ATOM | 2437 | CD | LYS | B | 317 | 49.513 | 7.907 | −15.665 | 1 | 60.1 C |
| ATOM | 2438 | CE | LYS | B | 317 | 50.854 | 8.193 | −16.325 | 1 | 60.09 C |
| ATOM | 2439 | NZ | LYS | B | 317 | 51.46 | 9.393 | −15.708 | 1 | 60.33 N |
| ATOM | 2440 | C | LYS | B | 317 | 45.366 | 5.271 | −15.186 | 1 | 59.97 C |
| ATOM | 2441 | O | LYS | B | 317 | 44.306 | 5.525 | −15.738 | 1 | 59.66 O |
| ATOM | 2442 | N | GLU | B | 318 | 45.451 | 4.901 | −13.918 | 1 | 61.41 N |
| ATOM | 2443 | CA | GLU | B | 318 | 44.289 | 4.535 | −13.119 | 1 | 62.47 C |
| ATOM | 2444 | CB | GLU | B | 318 | 44.704 | 3.401 | −12.189 | 1 | 62.52 C |
| ATOM | 2445 | CG | GLU | B | 318 | 43.57 | 2.528 | −11.684 | 1 | 62.46 C |
| ATOM | 2446 | CD | GLU | B | 318 | 43.89 | 1.031 | −11.75 | 1 | 63.25 C |
| ATOM | 2447 | OE1 | GLU | B | 318 | 43.032 | 0.222 | −11.324 | 1 | 65.68 O |
| ATOM | 2448 | OE2 | GLU | B | 318 | 44.98 | 0.658 | −12.237 | 1 | 62.97 O |
| ATOM | 2449 | C | GLU | B | 318 | 43.757 | 5.722 | −12.306 | 1 | 63.68 C |
| ATOM | 2450 | O | GLU | B | 318 | 44.513 | 6.365 | −11.558 | 1 | 64.33 O |
| ATOM | 2451 | N | TYR | B | 319 | 42.464 | 6.01 | −12.439 | 1 | 64.49 N |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2452 | CA | TYR | B | 319 | 41.868 | 7.175 | −11.793 | 1 | 65.23 C |
| ATOM | 2453 | CB | TYR | B | 319 | 41.124 | 8.012 | −12.819 | 1 | 64.97 C |
| ATOM | 2454 | CG | TYR | B | 319 | 42.044 | 8.655 | −13.788 | 1 | 64.59 C |
| ATOM | 2455 | CD1 | TYR | B | 319 | 42.429 | 7.993 | −14.939 | 1 | 65.15 C |
| ATOM | 2456 | CE1 | TYR | B | 319 | 43.29 | 8.574 | −15.843 | 1 | 65.06 C |
| ATOM | 2457 | CZ | TYR | B | 319 | 43.79 | 9.835 | −15.587 | 1 | 64.67 C |
| ATOM | 2458 | OH | TYR | B | 319 | 44.649 | 10.421 | −16.485 | 1 | 65.31 O |
| ATOM | 2459 | CE2 | TYR | B | 319 | 43.419 | 10.511 | −14.442 | 1 | 64.83 C |
| ATOM | 2460 | CD2 | TYR | B | 319 | 42.554 | 9.913 | −13.548 | 1 | 64.5 C |
| ATOM | 2461 | C | TYR | B | 319 | 40.906 | 6.79 | −10.698 | 1 | 66.15 C |
| ATOM | 2462 | O | TYR | B | 319 | 39.897 | 6.141 | −10.971 | 1 | 65.8 O |
| ATOM | 2463 | N | LYS | B | 320 | 41.193 | 7.234 | −9.472 | 1 | 67.75 N |
| ATOM | 2464 | CA | LYS | B | 320 | 40.355 | 6.896 | −8.309 | 1 | 68.89 C |
| ATOM | 2465 | CB | LYS | B | 320 | 41.219 | 6.302 | −7.187 | 1 | 68.93 C |
| ATOM | 2466 | CG | LYS | B | 320 | 40.431 | 5.83 | −5.957 | 1 | 68.72 C |
| ATOM | 2467 | CD | LYS | B | 320 | 41.13 | 4.69 | −5.195 | 1 | 68.93 C |
| ATOM | 2468 | CE | LYS | B | 320 | 42.587 | 4.986 | −4.864 | 1 | 69.27 C |
| ATOM | 2469 | NZ | LYS | B | 320 | 43.332 | 3.72 | −4.619 | 1 | 70.01 N |
| ATOM | 2470 | C | LYS | B | 320 | 39.563 | 8.093 | −7.774 | 1 | 69.95 C |
| ATOM | 2471 | O | LYS | B | 320 | 40.104 | 9.186 | −7.629 | 1 | 70.32 O |
| ATOM | 2472 | N | CYS | B | 321 | 38.283 | 7.88 | −7.5 | 1 | 71.06 N |
| ATOM | 2473 | CA | CYS | B | 321 | 37.476 | 8.848 | −6.782 | 1 | 72.47 C |
| ATOM | 2474 | CB | CYS | B | 321 | 36.152 | 9.109 | −7.522 | 1 | 71.91 C |
| ATOM | 2475 | SG | CYS | B | 321 | 35.033 | 10.254 | −6.643 | 1 | 70.24 S |
| ATOM | 2476 | C | CYS | B | 321 | 37.207 | 8.247 | −5.407 | 1 | 74.19 C |
| ATOM | 2477 | O | CYS | B | 321 | 36.596 | 7.184 | −5.317 | 1 | 74.55 O |
| ATOM | 2478 | N | LYS | B | 322 | 37.706 | 8.892 | −4.351 | 1 | 76.39 N |
| ATOM | 2479 | CA | LYS | B | 322 | 37.263 | 8.622 | −2.97 | 1 | 77.77 C |
| ATOM | 2480 | CB | LYS | B | 322 | 38.442 | 8.667 | −1.994 | 1 | 77.73 C |
| ATOM | 2481 | CG | LYS | B | 322 | 38.112 | 8.212 | −0.563 | 1 | 77.4 C |
| ATOM | 2482 | CD | LYS | B | 322 | 39.269 | 8.498 | 0.412 | 1 | 78.06 C |
| ATOM | 2483 | CE | LYS | B | 322 | 40.517 | 7.635 | 0.121 | 1 | 78.83 C |
| ATOM | 2484 | NZ | LYS | B | 322 | 41.701 | 7.965 | 0.977 | 1 | 78.92 N |
| ATOM | 2485 | C | LYS | B | 322 | 36.236 | 9.675 | −2.552 | 1 | 79.45 C |
| ATOM | 2486 | O | LYS | B | 322 | 36.549 | 10.871 | −2.528 | 1 | 79.85 O |
| ATOM | 2487 | N | VAL | B | 323 | 35.024 | 9.236 | −2.229 | 1 | 81.11 N |
| ATOM | 2488 | CA | VAL | B | 323 | 33.963 | 10.143 | −1.792 | 1 | 82.59 C |
| ATOM | 2489 | CB | VAL | B | 323 | 32.654 | 9.924 | −2.608 | 1 | 82.5 C |
| ATOM | 2490 | CG1 | VAL | B | 323 | 31.43 | 10.448 | −1.857 | 1 | 81.63 C |
| ATOM | 2491 | CG2 | VAL | B | 323 | 32.777 | 10.581 | −3.988 | 1 | 81.84 C |
| ATOM | 2492 | C | VAL | B | 323 | 33.71 | 9.957 | −0.298 | 1 | 84.31 C |
| ATOM | 2493 | O | VAL | B | 323 | 33.653 | 8.819 | 0.187 | 1 | 84.52 O |
| ATOM | 2494 | N | SER | B | 324 | 33.569 | 11.08 | 0.419 | 1 | 86.14 N |
| ATOM | 2495 | CA | SER | B | 324 | 33.29 | 11.084 | 1.867 | 1 | 87.3 C |
| ATOM | 2496 | CB | SER | B | 324 | 34.463 | 11.71 | 2.622 | 1 | 87.26 C |
| ATOM | 2497 | OG | SER | B | 324 | 35.553 | 10.806 | 2.703 | 1 | 87.13 O |
| ATOM | 2498 | C | SER | B | 324 | 31.968 | 11.802 | 2.217 | 1 | 88.69 C |
| ATOM | 2499 | O | SER | B | 324 | 31.561 | 12.741 | 1.526 | 1 | 88.64 O |
| ATOM | 2500 | N | ASN | B | 325 | 31.322 | 11.332 | 3.293 | 1 | 90.35 N |
| ATOM | 2501 | CA | ASN | B | 325 | 30.004 | 11.811 | 3.773 | 1 | 91.16 C |
| ATOM | 2502 | CB | ASN | B | 325 | 28.896 | 11.572 | 2.722 | 1 | 91.29 C |
| ATOM | 2503 | CG | ASN | B | 325 | 27.499 | 12.059 | 3.182 | 1 | 91.21 C |
| ATOM | 2504 | OD1 | ASN | B | 325 | 27.308 | 12.476 | 4.323 | 1 | 92.84 O |
| ATOM | 2505 | ND2 | ASN | B | 325 | 26.526 | 12 | 2.281 | 1 | 91.31 N |
| ATOM | 2506 | C | ASN | B | 325 | 29.64 | 11.089 | 5.084 | 1 | 92.26 C |
| ATOM | 2507 | O | ASN | B | 325 | 29.942 | 9.905 | 5.259 | 1 | 92.38 O |
| ATOM | 2508 | N | LYS | B | 326 | 28.975 | 11.799 | 5.992 | 1 | 93.32 N |
| ATOM | 2509 | CA | LYS | B | 326 | 28.577 | 11.23 | 7.286 | 1 | 93.9 C |
| ATOM | 2510 | CB | LYS | B | 326 | 28.121 | 12.338 | 8.241 | 1 | 94.29 C |
| ATOM | 2511 | CG | LYS | B | 326 | 29.251 | 13.12 | 8.907 | 1 | 94.48 C |
| ATOM | 2512 | CD | LYS | B | 326 | 28.659 | 14.09 | 9.931 | 1 | 94.57 C |
| ATOM | 2513 | CE | LYS | B | 326 | 29.727 | 14.835 | 10.711 | 1 | 94.83 C |
| ATOM | 2514 | NZ | LYS | B | 326 | 29.161 | 16.027 | 11.405 | 1 | 94.73 N |
| ATOM | 2515 | C | LYS | B | 326 | 27.481 | 10.153 | 7.181 | 1 | 94.34 C |
| ATOM | 2516 | O | LYS | B | 326 | 27.328 | 9.335 | 8.096 | 1 | 94.45 O |
| ATOM | 2517 | N | ALA | B | 327 | 26.726 | 10.154 | 6.08 | 1 | 94.57 N |
| ATOM | 2518 | CA | ALA | B | 327 | 25.723 | 9.107 | 5.813 | 1 | 94.49 C |
| ATOM | 2519 | CB | ALA | B | 327 | 24.72 | 9.585 | 4.758 | 1 | 94.43 C |
| ATOM | 2520 | C | ALA | B | 327 | 26.338 | 7.748 | 5.398 | 1 | 94.65 C |
| ATOM | 2521 | O | ALA | B | 327 | 25.592 | 6.791 | 5.143 | 1 | 94.8 O |
| ATOM | 2522 | N | LEU | B | 328 | 27.677 | 7.671 | 5.311 | 1 | 94.51 N |
| ATOM | 2523 | CA | LEU | B | 328 | 28.402 | 6.39 | 5.18 | 1 | 94.22 C |
| ATOM | 2524 | CB | LEU | B | 328 | 29.315 | 6.37 | 3.941 | 1 | 94.44 C |
| ATOM | 2525 | CG | LEU | B | 328 | 28.725 | 6.45 | 2.527 | 1 | 94.74 C |
| ATOM | 2526 | CD1 | LEU | B | 328 | 29.791 | 6.96 | 1.571 | 1 | 94.95 C |
| ATOM | 2527 | CD2 | LEU | B | 328 | 28.156 | 5.111 | 2.048 | 1 | 94.62 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2528 | C | LEU | B | 328 | 29.279 | 6.153 | 6.409 | 1 | 93.92 C |
| ATOM | 2529 | O | LEU | B | 328 | 29.774 | 7.112 | 6.998 | 1 | 93.9 O |
| ATOM | 2530 | N | PRO | B | 329 | 29.488 | 4.873 | 6.787 | 1 | 93.51 N |
| ATOM | 2531 | CA | PRO | B | 329 | 30.463 | 4.53 | 7.834 | 1 | 92.86 C |
| ATOM | 2532 | CB | PRO | B | 329 | 30.088 | 3.088 | 8.205 | 1 | 93.05 C |
| ATOM | 2533 | CG | PRO | B | 329 | 29.464 | 2.524 | 6.979 | 1 | 93.38 C |
| ATOM | 2534 | CD | PRO | B | 329 | 28.804 | 3.674 | 6.256 | 1 | 93.53 C |
| ATOM | 2535 | C | PRO | B | 329 | 31.919 | 4.615 | 7.347 | 1 | 92.24 C |
| ATOM | 2536 | O | PRO | B | 329 | 32.788 | 5.096 | 8.083 | 1 | 92.18 O |
| ATOM | 2537 | N | ALA | B | 330 | 32.176 | 4.14 | 6.126 | 1 | 91.33 N |
| ATOM | 2538 | CA | ALA | B | 330 | 33.49 | 4.27 | 5.493 | 1 | 90.52 C |
| ATOM | 2539 | CB | ALA | B | 330 | 34.051 | 2.899 | 5.151 | 1 | 90.53 C |
| ATOM | 2540 | C | ALA | B | 330 | 33.382 | 5.126 | 4.227 | 1 | 89.77 C |
| ATOM | 2541 | O | ALA | B | 330 | 32.292 | 5.273 | 3.668 | 1 | 89.76 O |
| ATOM | 2542 | N | PRO | B | 331 | 34.508 | 5.719 | 3.781 | 1 | 88.68 N |
| ATOM | 2543 | CA | PRO | B | 331 | 34.48 | 6.404 | 2.482 | 1 | 87.67 C |
| ATOM | 2544 | CB | PRO | B | 331 | 35.832 | 7.142 | 2.435 | 1 | 87.83 C |
| ATOM | 2545 | CG | PRO | B | 331 | 36.387 | 7.077 | 3.839 | 1 | 88.17 C |
| ATOM | 2546 | CD | PRO | B | 331 | 35.827 | 5.828 | 4.434 | 1 | 88.63 C |
| ATOM | 2547 | C | PRO | B | 331 | 34.352 | 5.41 | 1.316 | 1 | 86.64 C |
| ATOM | 2548 | O | PRO | B | 331 | 35.001 | 4.37 | 1.34 | 1 | 86.79 O |
| ATOM | 2549 | N | ILE | B | 332 | 33.508 | 5.723 | 0.328 | 1 | 85.18 N |
| ATOM | 2550 | CA | ILE | B | 332 | 33.388 | 4.911 | −0.892 | 1 | 83.99 C |
| ATOM | 2551 | CB | ILE | B | 332 | 32 | 5.061 | −1.572 | 1 | 84.14 C |
| ATOM | 2552 | CG1 | ILE | B | 332 | 30.871 | 4.69 | −0.613 | 1 | 84.34 C |
| ATOM | 2553 | CD1 | ILE | B | 332 | 29.488 | 5.159 | −1.081 | 1 | 84.16 C |
| ATOM | 2554 | CG2 | ILE | B | 332 | 31.898 | 4.172 | −2.809 | 1 | 84.68 C |
| ATOM | 2555 | C | ILE | B | 332 | 34.463 | 5.326 | −1.902 | 1 | 82.56 C |
| ATOM | 2556 | O | ILE | B | 332 | 34.743 | 6.507 | −2.077 | 1 | 82.15 O |
| ATOM | 2557 | N | GLU | B | 333 | 35.056 | 4.332 | −2.556 | 1 | 81.08 N |
| ATOM | 2558 | CA | GLU | B | 333 | 36.029 | 4.548 | −3.626 | 1 | 79.67 C |
| ATOM | 2559 | CB | GLU | B | 333 | 37.354 | 3.89 | −3.269 | 1 | 79.8 C |
| ATOM | 2560 | CG | GLU | B | 333 | 38.008 | 4.435 | −2.02 | 1 | 80.18 C |
| ATOM | 2561 | CD | GLU | B | 333 | 39.345 | 3.781 | −1.765 | 1 | 80.34 C |
| ATOM | 2562 | OE1 | GLU | B | 333 | 40.301 | 4.48 | −1.357 | 1 | 79.97 O |
| ATOM | 2563 | OE2 | GLU | B | 333 | 39.437 | 2.556 | −2.001 | 1 | 82.15 O |
| ATOM | 2564 | C | GLU | B | 333 | 35.541 | 3.957 | −4.954 | 1 | 78.16 C |
| ATOM | 2565 | O | GLU | B | 333 | 34.762 | 3.001 | −4.979 | 1 | 78.36 O |
| ATOM | 2566 | N | LYS | B | 334 | 35.995 | 4.544 | −6.056 | 1 | 76.04 N |
| ATOM | 2567 | CA | LYS | B | 334 | 35.79 | 3.964 | −7.379 | 1 | 74.09 C |
| ATOM | 2568 | CB | LYS | B | 334 | 34.56 | 4.541 | −8.076 | 1 | 73.79 C |
| ATOM | 2569 | CG | LYS | B | 334 | 33.233 | 4.22 | −7.405 | 1 | 73.69 C |
| ATOM | 2570 | CD | LYS | B | 334 | 32.857 | 2.749 | −7.472 | 1 | 73.25 C |
| ATOM | 2571 | CE | LYS | B | 334 | 31.484 | 2.515 | −6.855 | 1 | 73.33 C |
| ATOM | 2572 | NZ | LYS | B | 334 | 31.077 | 1.077 | −6.828 | 1 | 73.19 N |
| ATOM | 2573 | C | LYS | B | 334 | 37.026 | 4.257 | −8.197 | 1 | 72.4 C |
| ATOM | 2574 | O | LYS | B | 334 | 37.595 | 5.339 | −8.1 | 1 | 72.32 O |
| ATOM | 2575 | N | THR | B | 335 | 37.438 | 3.272 | −8.986 | 1 | 70.45 N |
| ATOM | 2576 | CA | THR | B | 335 | 38.604 | 3.386 | −9.848 | 1 | 68.66 C |
| ATOM | 2577 | CB | THR | B | 335 | 39.727 | 2.423 | −9.41 | 1 | 68.76 C |
| ATOM | 2578 | OG1 | THR | B | 335 | 39.676 | 2.251 | −7.99 | 1 | 69.38 O |
| ATOM | 2579 | CG2 | THR | B | 335 | 41.078 | 2.979 | −9.786 | 1 | 68.56 C |
| ATOM | 2580 | C | THR | B | 335 | 38.171 | 3.088 | −11.279 | 1 | 66.98 C |
| ATOM | 2581 | O | THR | B | 335 | 37.289 | 2.257 | −11.506 | 1 | 67.54 O |
| ATOM | 2582 | N | ILE | B | 336 | 38.777 | 3.792 | −12.232 | 1 | 64.5 N |
| ATOM | 2583 | CA | ILE | B | 336 | 38.39 | 3.717 | −13.635 | 1 | 62.13 C |
| ATOM | 2584 | CB | ILE | B | 336 | 37.422 | 4.852 | −14.019 | 1 | 62.16 C |
| ATOM | 2585 | CG1 | ILE | B | 336 | 36.408 | 4.394 | −15.053 | 1 | 62.26 C |
| ATOM | 2586 | CD1 | ILE | B | 336 | 35.803 | 5.553 | −15.833 | 1 | 62.25 C |
| ATOM | 2587 | CG2 | ILE | B | 336 | 38.181 | 6.045 | −14.593 | 1 | 62.56 C |
| ATOM | 2588 | C | ILE | B | 336 | 39.647 | 3.868 | −14.461 | 1 | 59.89 C |
| ATOM | 2589 | O | ILE | B | 336 | 40.609 | 4.502 | −14.035 | 1 | 59.53 O |
| ATOM | 2590 | N | SER | B | 337 | 39.639 | 3.268 | −15.641 | 1 | 57.51 N |
| ATOM | 2591 | CA | SER | B | 337 | 40.773 | 3.344 | −16.555 | 1 | 55.44 C |
| ATOM | 2592 | CB | SER | B | 337 | 41.936 | 2.487 | −16.055 | 1 | 55.45 C |
| ATOM | 2593 | OG | SER | B | 337 | 41.882 | 1.19 | −16.639 | 1 | 56.48 O |
| ATOM | 2594 | C | SER | B | 337 | 40.356 | 2.842 | −17.918 | 1 | 52.9 C |
| ATOM | 2595 | O | SER | B | 337 | 39.428 | 2.063 | −18.034 | 1 | 52.04 O |
| ATOM | 2596 | N | LYS | B | 338 | 41.068 | 3.287 | −18.943 | 1 | 50.79 N |
| ATOM | 2597 | CA | LYS | B | 338 | 40.918 | 2.756 | −20.291 | 1 | 49.85 C |
| ATOM | 2598 | CB | LYS | B | 338 | 41.989 | 3.34 | −21.201 | 1 | 49.14 C |
| ATOM | 2599 | CG | LYS | B | 338 | 41.74 | 3.028 | −22.647 | 1 | 49.41 C |
| ATOM | 2600 | CD | LYS | B | 338 | 42.805 | 3.612 | −23.54 | 1 | 49.67 C |
| ATOM | 2601 | CE | LYS | B | 338 | 43.988 | 2.678 | −23.723 | 1 | 49.11 C |
| ATOM | 2602 | NZ | LYS | B | 338 | 44.739 | 3.064 | −24.94 | 1 | 48.06 N |
| ATOM | 2603 | C | LYS | B | 338 | 41.008 | 1.217 | −20.339 | 1 | 48.42 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2604 | O | LYS | B | 338 | 41.781 | 0.624 | −19.624 | 1 | 48.19 O |
| ATOM | 2605 | N | ALA | B | 339 | 40.193 | 0.596 | −21.181 | 1 | 47.46 N |
| ATOM | 2606 | CA | ALA | B | 339 | 40.324 | −0.818 | −21.509 | 1 | 47.24 C |
| ATOM | 2607 | CB | ALA | B | 339 | 39.376 | −1.2 | −22.645 | 1 | 46.7 C |
| ATOM | 2608 | C | ALA | B | 339 | 41.762 | −1.141 | −21.899 | 1 | 46.65 C |
| ATOM | 2609 | O | ALA | B | 339 | 42.404 | −0.377 | −22.626 | 1 | 46.07 O |
| ATOM | 2610 | N | LYS | B | 340 | 42.253 | −2.274 | −21.395 | 1 | 46.53 N |
| ATOM | 2611 | CA | LYS | B | 340 | 43.655 | −2.686 | −21.547 | 1 | 46.19 C |
| ATOM | 2612 | CB | LYS | B | 340 | 44.083 | −3.555 | −20.368 | 1 | 46.71 C |
| ATOM | 2613 | CG | LYS | B | 340 | 44.175 | −2.803 | −19.054 | 1 | 47.59 C |
| ATOM | 2614 | CD | LYS | B | 340 | 44.437 | −3.747 | −17.861 | 1 | 47.78 C |
| ATOM | 2615 | CE | LYS | B | 340 | 44.848 | −2.962 | −16.605 | 1 | 49.07 C |
| ATOM | 2616 | NZ | LYS | B | 340 | 44.01 | −1.7 | −16.386 | 1 | 50.13 N |
| ATOM | 2617 | C | LYS | B | 340 | 43.813 | −3.493 | −22.806 | 1 | 45.34 C |
| ATOM | 2618 | O | LYS | B | 340 | 42.885 | −4.213 | −23.189 | 1 | 44.98 O |
| ATOM | 2619 | N | GLY | B | 341 | 44.971 | −3.351 | −23.453 | 1 | 44.68 N |
| ATOM | 2620 | CA | GLY | B | 341 | 45.277 | −4.108 | −24.652 | 1 | 44.78 C |
| ATOM | 2621 | C | GLY | B | 341 | 45.764 | −3.336 | −25.869 | 1 | 44.86 C |
| ATOM | 2622 | O | GLY | B | 341 | 45.365 | −2.212 | −26.132 | 1 | 45.3 O |
| ATOM | 2623 | N | GLN | B | 342 | 46.645 | −3.968 | −26.628 | 1 | 44.94 N |
| ATOM | 2624 | CA | GLN | B | 342 | 47.081 | −3.456 | −27.912 | 1 | 44.65 C |
| ATOM | 2625 | CB | GLN | B | 342 | 47.709 | −4.599 | −28.714 | 1 | 44.56 C |
| ATOM | 2626 | CG | GLN | B | 342 | 48.263 | −4.189 | −30.047 | 1 | 45.06 C |
| ATOM | 2627 | CD | GLN | B | 342 | 49.39 | −3.189 | −29.905 | 1 | 46.32 C |
| ATOM | 2628 | OE1 | GLN | B | 342 | 49.286 | −2.052 | −30.364 | 1 | 47.17 O |
| ATOM | 2629 | NE2 | GLN | B | 342 | 50.473 | −3.603 | −29.249 | 1 | 46.61 N |
| ATOM | 2630 | C | GLN | B | 342 | 45.904 | −2.845 | −28.684 | 1 | 44.5 C |
| ATOM | 2631 | O | GLN | B | 342 | 44.95 | −3.548 | −29.032 | 1 | 44.47 O |
| ATOM | 2632 | N | PRO | B | 343 | 45.942 | −1.53 | −28.919 | 1 | 44.36 N |
| ATOM | 2633 | CA | PRO | B | 343 | 44.974 | −0.924 | −29.802 | 1 | 44.8 C |
| ATOM | 2634 | CB | PRO | B | 343 | 45.312 | 0.559 | −29.719 | 1 | 44.61 C |
| ATOM | 2635 | CG | PRO | B | 343 | 45.953 | 0.708 | −28.4 | 1 | 44.7 C |
| ATOM | 2636 | CD | PRO | B | 343 | 46.809 | −0.51 | −28.33 | 1 | 44.53 C |
| ATOM | 2637 | C | PRO | B | 343 | 45.063 | −1.4 | −31.242 | 1 | 45.21 C |
| ATOM | 2638 | O | PRO | B | 343 | 46.152 | −1.722 | −31.757 | 1 | 45.12 O |
| ATOM | 2639 | N | ARG | B | 344 | 43.907 | −1.422 | −31.883 | 1 | 45.81 N |
| ATOM | 2640 | CA | ARG | B | 344 | 43.796 | −1.902 | −33.245 | 1 | 46.46 C |
| ATOM | 2641 | CB | ARG | B | 344 | 43.01 | −3.235 | −33.295 | 1 | 47.76 C |
| ATOM | 2642 | CG | ARG | B | 344 | 43.579 | −4.351 | −32.412 | 1 | 49.87 C |
| ATOM | 2643 | CD | ARG | B | 344 | 44.891 | −4.954 | −32.962 | 1 | 53.64 C |
| ATOM | 2644 | NE | ARG | B | 344 | 45.581 | −5.764 | −31.948 | 1 | 53.27 N |
| ATOM | 2645 | CZ | ARG | B | 344 | 46.635 | −6.565 | −32.153 | 1 | 54.63 C |
| ATOM | 2646 | NH1 | ARG | B | 344 | 47.191 | −6.7 | −33.36 | 1 | 56.11 N |
| ATOM | 2647 | NH2 | ARG | B | 344 | 47.14 | −7.249 | −31.125 | 1 | 55.8 N |
| ATOM | 2648 | C | ARG | B | 344 | 43.104 | −0.838 | −34.089 | 1 | 46.07 C |
| ATOM | 2649 | O | ARG | B | 344 | 42.077 | −0.262 | −33.71 | 1 | 45.43 O |
| ATOM | 2650 | N | GLU | B | 345 | 43.675 | −0.623 | −35.255 | 1 | 46.16 N |
| ATOM | 2651 | CA | GLU | B | 345 | 43.217 | 0.373 | −36.195 | 1 | 46.7 C |
| ATOM | 2652 | CB | GLU | B | 345 | 44.234 | 0.452 | −37.314 | 1 | 46.48 C |
| ATOM | 2653 | CG | GLU | B | 345 | 44.074 | 1.628 | −38.202 | 1 | 47.76 C |
| ATOM | 2654 | CD | GLU | B | 345 | 45.234 | 1.745 | −39.166 | 1 | 48.41 C |
| ATOM | 2655 | OE1 | GLU | B | 345 | 46.358 | 2.077 | −38.701 | 1 | 50.28 O |
| ATOM | 2656 | OE2 | GLU | B | 345 | 45.01 | 1.502 | −40.373 | 1 | 50.93 O |
| ATOM | 2657 | C | GLU | B | 345 | 41.868 | 0.002 | −36.781 | 1 | 46.44 C |
| ATOM | 2658 | O | GLU | B | 345 | 41.716 | −1.078 | −37.295 | 1 | 47.22 O |
| ATOM | 2659 | N | PRO | B | 346 | 40.882 | 0.897 | −36.72 | 1 | 46.36 N |
| ATOM | 2660 | CA | PRO | B | 346 | 39.608 | 0.591 | −37.351 | 1 | 46.7 C |
| ATOM | 2661 | CB | PRO | B | 346 | 38.687 | 1.714 | −36.84 | 1 | 45.99 C |
| ATOM | 2662 | CG | PRO | B | 346 | 39.554 | 2.784 | −36.558 | 1 | 46.29 C |
| ATOM | 2663 | CD | PRO | B | 346 | 40.841 | 2.202 | −36.058 | 1 | 46.34 C |
| ATOM | 2664 | C | PRO | B | 346 | 39.69 | 0.616 | −38.886 | 1 | 46.9 C |
| ATOM | 2665 | O | PRO | B | 346 | 40.482 | 1.345 | −39.439 | 1 | 46.86 O |
| ATOM | 2666 | N | GLN | B | 347 | 38.876 | −0.196 | −39.549 | 1 | 47.38 N |
| ATOM | 2667 | CA | GLN | B | 347 | 38.765 | −0.158 | −41.001 | 1 | 47.91 C |
| ATOM | 2668 | CB | GLN | B | 347 | 38.905 | −1.551 | −41.608 | 1 | 48.91 C |
| ATOM | 2669 | CG | GLN | B | 347 | 40.178 | −2.274 | −41.231 | 1 | 52.12 C |
| ATOM | 2670 | CD | GLN | B | 347 | 39.89 | −3.725 | −40.906 | 1 | 57.2 C |
| ATOM | 2671 | OE1 | GLN | B | 347 | 39.144 | −4.413 | −41.639 | 1 | 60.47 O |
| ATOM | 2672 | NE2 | GLN | B | 347 | 40.466 | −4.209 | −39.799 | 1 | 59.78 N |
| ATOM | 2673 | C | GLN | B | 347 | 37.386 | 0.372 | −41.318 | 1 | 47.34 C |
| ATOM | 2674 | O | GLN | B | 347 | 36.38 | −0.141 | −40.801 | 1 | 47.64 O |
| ATOM | 2675 | N | VAL | B | 348 | 37.352 | 1.384 | −42.177 | 1 | 46.31 N |
| ATOM | 2676 | CA | VAL | B | 348 | 36.17 | 2.155 | −42.42 | 1 | 45.81 C |
| ATOM | 2677 | CB | VAL | B | 348 | 36.465 | 3.61 | −42.222 | 1 | 45.01 C |
| ATOM | 2678 | CG1 | VAL | B | 348 | 35.263 | 4.41 | −42.597 | 1 | 44.15 C |
| ATOM | 2679 | CG2 | VAL | B | 348 | 36.87 | 3.865 | −40.766 | 1 | 43.91 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2680 | C | VAL | 8 | 348 | 35.757 | 1.924 | −43.849 | 1 | 46.54 | C |
| ATOM | 2681 | O | VAL | B | 348 | 36.551 | 2.189 | −44.756 | 1 | 47.01 | O |
| ATOM | 2682 | N | TYR | B | 349 | 34.548 | 1.394 | −44.057 | 1 | 46.76 | N |
| ATOM | 2683 | CA | TYR | B | 349 | 34.031 | 1.184 | −45.419 | 1 | 47.17 | C |
| ATOM | 2684 | CB | TYR | B | 349 | 33.949 | −0.294 | −45.815 | 1 | 47.77 | C |
| ATOM | 2685 | CG | TYR | B | 349 | 35.148 | −1.132 | −45.451 | 1 | 48.71 | C |
| ATOM | 2686 | CD1 | TYR | B | 349 | 36.297 | −1.114 | −46.229 | 1 | 47.61 | C |
| ATOM | 2687 | CE1 | TYR | B | 349 | 37.425 | −1.874 | −45.891 | 1 | 47.71 | C |
| ATOM | 2688 | CZ | TYR | B | 349 | 37.386 | −2.688 | −44.77 | 1 | 49.68 | C |
| ATOM | 2689 | OH | TYR | B | 349 | 38.471 | −3.481 | −44.435 | 1 | 48.78 | O |
| ATOM | 2690 | CE2 | TYR | B | 349 | 36.232 | −2.746 | −43.988 | 1 | 49.97 | C |
| ATOM | 2691 | CD2 | TYR | B | 349 | 35.126 | −1.96 | −44.326 | 1 | 49.2 | C |
| ATOM | 2692 | C | TYR | B | 349 | 32.648 | 1.762 | −45.505 | 1 | 47.29 | C |
| ATOM | 2693 | O | TYR | B | 349 | 31.828 | 1.566 | −44.601 | 1 | 47.66 | O |
| ATOM | 2694 | N | THR | B | 350 | 32.382 | 2.47 | −46.589 | 1 | 46.93 | N |
| ATOM | 2695 | CA | THR | B | 350 | 31.11 | 3.109 | −46.751 | 1 | 46.88 | C |
| ATOM | 2696 | CB | THR | B | 350 | 31.249 | 4.589 | −47.071 | 1 | 46.8 | C |
| ATOM | 2697 | OG1 | THR | B | 350 | 31.999 | 4.778 | −48.277 | 1 | 47.24 | O |
| ATOM | 2698 | CG2 | THR | B | 350 | 31.98 | 5.263 | −45.946 | 1 | 47.03 | C |
| ATOM | 2699 | C | THR | B | 350 | 30.382 | 2.351 | −47.817 | 1 | 47.08 | C |
| ATOM | 2700 | O | THR | B | 350 | 30.98 | 1.819 | −48.734 | 1 | 47.38 | O |
| ATOM | 2701 | N | LEU | B | 351 | 29.07 | 2.28 | −47.647 | 1 | 47.34 | N |
| ATOM | 2702 | CA | LEU | B | 351 | 28.224 | 1.417 | −48.42 | 1 | 46.62 | C |
| ATOM | 2703 | CB | LEU | B | 351 | 27.773 | 0.239 | −47.55 | 1 | 46.54 | C |
| ATOM | 2704 | CG | LEU | B | 351 | 28.862 | −0.519 | −46.763 | 1 | 45.38 | C |
| ATOM | 2705 | CD1 | LEU | B | 351 | 28.206 | −1.366 | −45.689 | 1 | 44.14 | C |
| ATOM | 2706 | CD2 | LEU | B | 351 | 29.733 | −1.37 | −47.681 | 1 | 43.22 | C |
| ATOM | 2707 | C | LEU | B | 351 | 27.039 | 2.25 | −48.862 | 1 | 46.44 | C |
| ATOM | 2708 | O | LEU | B | 351 | 26.361 | 2.849 | −48.027 | 1 | 45.19 | O |
| ATOM | 2709 | N | PRO | B | 352 | 26.805 | 2.315 | −50.189 | 1 | 47.08 | N |
| ATOM | 2710 | CA | PRO | B | 352 | 25.716 | 3.108 | −50.758 | 1 | 47.95 | C |
| ATOM | 2711 | CB | PRO | B | 352 | 25.999 | 3.032 | −52.257 | 1 | 47.5 | C |
| ATOM | 2712 | CG | PRO | B | 352 | 26.651 | 1.723 | −52.438 | 1 | 46.37 | C |
| ATOM | 2713 | CD | PRO | B | 352 | 27.55 | 1.594 | −51.24 | 1 | 46.47 | C |
| ATOM | 2714 | C | PRO | B | 352 | 24.345 | 2.489 | −50.453 | 1 | 49.07 | C |
| ATOM | 2715 | O | PRO | B | 352 | 24.281 | 1.354 | −49.965 | 1 | 48.36 | O |
| ATOM | 2716 | N | PRO | B | 353 | 23.243 | 3.212 | −50.761 | 1 | 50.68 | N |
| ATOM | 2717 | CA | PRO | B | 353 | 21.942 | 2.647 | −50.481 | 1 | 51.87 | C |
| ATOM | 2718 | CB | PRO | B | 353 | 20.982 | 3.777 | −50.833 | 1 | 51.86 | C |
| ATOM | 2719 | CG | PRO | B | 353 | 21.797 | 5.001 | −50.821 | 1 | 51.16 | C |
| ATOM | 2720 | CD | PRO | B | 353 | 23.109 | 4.544 | −51.353 | 1 | 50.79 | C |
| ATOM | 2721 | C | PRO | B | 353 | 21.663 | 1.439 | −51.341 | 1 | 53.39 | C |
| ATOM | 2722 | O | PRO | B | 353 | 22.154 | 1.351 | −52.461 | 1 | 53.63 | O |
| ATOM | 2723 | N | SER | B | 354 | 20.907 | 0.506 | −50.767 | 1 | 55.37 | N |
| ATOM | 2724 | CA | SER | B | 354 | 20.331 | −0.657 | −51.455 | 1 | 56.38 | C |
| ATOM | 2725 | CB | SER | B | 354 | 19.564 | −1.5 | −50.419 | 1 | 56.25 | C |
| ATOM | 2726 | OG | SER | B | 354 | 18.658 | −2.418 | −51 | 1 | 56.79 | O |
| ATOM | 2727 | C | SER | B | 354 | 19.403 | −0.223 | −52.6 | 1 | 57.8 | C |
| ATOM | 2728 | O | SER | B | 354 | 18.699 | 0.788 | −52.494 | 1 | 57.93 | O |
| ATOM | 2729 | N | ARG | B | 355 | 19.409 | −0.982 | −53.696 | 1 | 59.95 | N |
| ATOM | 2730 | CA | ARG | B | 355 | 18.5 | −0.719 | −54.83 | 1 | 60.35 | C |
| ATOM | 2731 | CB | ARG | B | 355 | 18.78 | −1.692 | −55.995 | 1 | 61.75 | C |
| ATOM | 2732 | CG | ARG | B | 355 | 17.623 | −1.939 | −56.97 | 1 | 62.87 | C |
| ATOM | 2733 | CD | ARG | B | 355 | 17.208 | −0.707 | −57.807 | 1 | 68.42 | C |
| ATOM | 2734 | NE | ARG | B | 355 | 16.039 | −1.015 | −58.666 | 1 | 68.89 | N |
| ATOM | 2735 | CZ | ARG | B | 355 | 15.776 | −0.471 | −59.865 | 1 | 70.77 | C |
| ATOM | 2736 | NH1 | ARG | B | 355 | 16.589 | 0.434 | −60.403 | 1 | 71.4 | N |
| ATOM | 2737 | NH2 | ARG | B | 355 | 14.687 | −0.836 | −60.54 | 1 | 70.93 | N |
| ATOM | 2738 | C | ARG | B | 355 | 17.054 | −0.791 | −54.344 | 1 | 60.77 | C |
| ATOM | 2739 | O | ARG | B | 355 | 16.232 | 0.059 | −54.697 | 1 | 60.27 | O |
| ATOM | 2740 | N | ASP | B | 356 | 16.761 | −1.782 | −53.501 | 1 | 61.25 | N |
| ATOM | 2741 | CA | ASP | B | 356 | 15.465 | −1.842 | −52.833 | 1 | 61.85 | C |
| ATOM | 2742 | CB | ASP | B | 356 | 15.494 | −2.796 | −51.631 | 1 | 62.37 | C |
| ATOM | 2743 | CG | ASP | B | 356 | 15.384 | −4.28 | −52.006 | 1 | 63.75 | C |
| ATOM | 2744 | OD1 | ASP | B | 356 | 15.355 | −5.118 | −51.053 | 1 | 63.81 | O |
| ATOM | 2745 | OD2 | ASP | B | 356 | 15.332 | −4.608 | −53.221 | 1 | 65.8 | O |
| ATOM | 2746 | C | ASP | B | 356 | 15.055 | −0.459 | −52.331 | 1 | 61.93 | C |
| ATOM | 2747 | O | ASP | B | 356 | 13.975 | 0.006 | −52.657 | 1 | 61.79 | O |
| ATOM | 2748 | N | GLU | B | 357 | 15.93 | 0.188 | −51.557 | 1 | 62.29 | N |
| ATOM | 2749 | CA | GLU | B | 357 | 15.593 | 1.438 | −50.83 | 1 | 62.99 | C |
| ATOM | 2750 | CB | GLU | B | 357 | 16.628 | 1.746 | −49.712 | 1 | 62.68 | C |
| ATOM | 2751 | CG | GLU | B | 357 | 16.204 | 2.864 | −48.715 | 1 | 61.58 | C |
| ATOM | 2752 | CD | GLU | B | 357 | 17.214 | 3.114 | −47.591 | 1 | 60.3 | C |
| ATOM | 2753 | OE1 | GLU | B | 357 | 18.421 | 2.919 | −47.79 | 1 | 56.88 | O |
| ATOM | 2754 | OE2 | GLU | B | 357 | 16.805 | 3.533 | −46.503 | 1 | 56.76 | O |
| ATOM | 2755 | C | GLU | B | 357 | 15.455 | 2.67 | −51.718 | 1 | 63.96 | C |

TABLE V-continued

Atomic Structure Coordinates of Fc/YTE (SEQ ID NO: 11)

| | Atom | A.A. | Type | | X | Y | Z | Occ | B | |
|---|---|---|---|---|---|---|---|---|---|---|
| ATOM | 2756 | O | GLU | B | 357 | 14.823 | 3.652 | −51.31 | 1 | 63.64 | O |
| ATOM | 2757 | N | LEU | B | 358 | 16.037 | 2.629 | −52.92 | 1 | 65.46 | N |
| ATOM | 2758 | CA | LEU | B | 358 | 15.93 | 3.769 | −53.856 | 1 | 66.57 | C |
| ATOM | 2759 | CB | LEU | B | 358 | 16.909 | 3.625 | −55.037 | 1 | 66.87 | C |
| ATOM | 2760 | CG | LEU | B | 358 | 18.378 | 3.903 | −54.632 | 1 | 67.53 | C |
| ATOM | 2761 | CD1 | LEU | B | 358 | 19.343 | 3.514 | −55.759 | 1 | 68.7 | C |
| ATOM | 2762 | CD2 | LEU | B | 358 | 18.598 | 5.362 | −54.204 | 1 | 66.43 | C |
| ATOM | 2763 | C | LEU | B | 358 | 14.491 | 4.044 | −54.333 | 1 | 67.6 | C |
| ATOM | 2764 | O | LEU | B | 358 | 14.249 | 5.014 | −55.051 | 1 | 68.24 | O |
| ATOM | 2765 | N | THR | B | 359 | 13.546 | 3.208 | −53.897 | 1 | 68.42 | N |
| ATOM | 2766 | CA | THR | B | 359 | 12.113 | 3.455 | −54.047 | 1 | 68.57 | C |
| ATOM | 2767 | CB | THR | B | 359 | 11.301 | 2.112 | −53.984 | 1 | 68.89 | C |
| ATOM | 2768 | OG1 | THR | B | 359 | 12.077 | 1.018 | −54.505 | 1 | 69.06 | O |
| ATOM | 2769 | CG2 | THR | B | 359 | 10.018 | 2.228 | −54.789 | 1 | 68.78 | C |
| ATOM | 2770 | C | THR | B | 359 | 11.516 | 4.422 | −53.003 | 1 | 68.91 | C |
| ATOM | 2771 | O | THR | B | 359 | 10.317 | 4.67 | −53.039 | 1 | 69.51 | O |
| ATOM | 2772 | N | LYS | B | 360 | 12.312 | 4.979 | −52.087 | 1 | 69.02 | N |
| ATOM | 2773 | CA | LYS | B | 360 | 11.759 | 5.892 | −51.045 | 1 | 68.98 | C |
| ATOM | 2774 | CB | LYS | B | 360 | 12.092 | 5.399 | −49.629 | 1 | 69.67 | C |
| ATOM | 2775 | CG | LYS | B | 360 | 11.905 | 3.898 | −49.405 | 1 | 70.64 | C |
| ATOM | 2776 | CD | LYS | B | 360 | 10.464 | 3.528 | −49.063 | 1 | 71.9 | C |
| ATOM | 2777 | CE | LYS | B | 360 | 10.288 | 2.001 | −48.955 | 1 | 72.37 | C |
| ATOM | 2778 | NZ | LYS | B | 360 | 9.432 | 1.586 | −47.783 | 1 | 73.04 | N |
| ATOM | 2779 | C | LYS | B | 360 | 12.248 | 7.325 | −51.192 | 1 | 68.48 | C |
| ATOM | 2780 | O | LYS | B | 360 | 13.162 | 7.592 | −51.944 | 1 | 68.54 | O |
| ATOM | 2781 | N | ASN | B | 361 | 11.635 | 8.246 | −50.455 | 1 | 68.2 | N |
| ATOM | 2782 | CA | ASN | B | 361 | 12.034 | 9.665 | −50.489 | 1 | 67.66 | C |
| ATOM | 2783 | CB | ASN | B | 361 | 10.833 | 10.575 | −50.19 | 1 | 68.36 | C |
| ATOM | 2784 | CG | ASN | B | 361 | 10.27 | 10.396 | −48.762 | 1 | 69.54 | C |
| ATOM | 2785 | OD1 | ASN | B | 361 | 10.975 | 10.58 | −47.765 | 1 | 70.76 | O |
| ATOM | 2786 | ND2 | ASN | B | 361 | 8.978 | 10.081 | −48.675 | 1 | 70.9 | N |
| ATOM | 2787 | C | ASN | B | 361 | 13.201 | 10 | −49.548 | 1 | 66.9 | C |
| ATOM | 2788 | O | ASN | B | 361 | 13.617 | 11.158 | −49.433 | 1 | 66.98 | O |
| ATOM | 2789 | N | GLN | B | 362 | 13.697 | 8.983 | −48.854 | 1 | 65.63 | N |
| ATOM | 2790 | CA | GLN | B | 362 | 14.894 | 9.1 | −48.04 | 1 | 64.43 | C |
| ATOM | 2791 | CB | GLN | B | 362 | 14.516 | 9.171 | −46.565 | 1 | 64.87 | C |
| ATOM | 2792 | CG | GLN | B | 362 | 13.734 | 10.443 | −46.141 | 1 | 65.74 | C |
| ATOM | 2793 | CD | GLN | B | 362 | 14.543 | 11.357 | −45.223 | 1 | 67.13 | C |
| ATOM | 2794 | OE1 | GLN | B | 362 | 14.096 | 11.735 | −44.132 | 1 | 66.15 | O |
| ATOM | 2795 | NE2 | GLN | B | 362 | 15.756 | 11.699 | −45.656 | 1 | 69.46 | N |
| ATOM | 2796 | C | GLN | B | 362 | 15.734 | 7.856 | −48.331 | 1 | 63.27 | C |
| ATOM | 2797 | O | GLN | B | 362 | 15.185 | 6.824 | −48.727 | 1 | 63.67 | O |
| ATOM | 2798 | N | VAL | B | 363 | 17.053 | 7.962 | −48.188 | 1 | 61.09 | N |
| ATOM | 2799 | CA | VAL | B | 363 | 17.945 | 6.81 | −48.354 | 1 | 59.19 | C |
| ATOM | 2800 | CB | VAL | B | 363 | 18.728 | 6.861 | −49.706 | 1 | 59.4 | C |
| ATOM | 2801 | CG1 | VAL | B | 363 | 17.861 | 6.364 | −50.868 | 1 | 59.43 | C |
| ATOM | 2802 | CG2 | VAL | B | 363 | 19.262 | 8.265 | −49.981 | 1 | 58.35 | C |
| ATOM | 2803 | C | VAL | B | 363 | 18.926 | 6.737 | −47.177 | 1 | 57.52 | C |
| ATOM | 2804 | O | VAL | B | 363 | 19.158 | 7.733 | −46.487 | 1 | 57.15 | O |
| ATOM | 2805 | N | SER | B | 364 | 19.49 | 5.552 | −46.956 | 1 | 55.52 | N |
| ATOM | 2806 | CA | SER | B | 364 | 20.43 | 5.323 | −45.875 | 1 | 54.04 | C |
| ATOM | 2807 | CB | SER | B | 364 | 20.078 | 4.048 | −45.105 | 1 | 53.79 | C |
| ATOM | 2808 | OG | SER | B | 364 | 18.797 | 4.118 | −44.505 | 1 | 53.94 | O |
| ATOM | 2809 | C | SER | B | 364 | 21.827 | 5.193 | −46.452 | 1 | 52.51 | C |
| ATOM | 2810 | O | SER | B | 364 | 22.098 | 4.294 | −47.227 | 1 | 51.95 | O |
| ATOM | 2811 | N | LEU | B | 365 | 22.707 | 6.119 | −46.094 | 1 | 51.32 | N |
| ATOM | 2812 | CA | LEU | B | 365 | 24.122 | 5.952 | −46.363 | 1 | 50.54 | C |
| ATOM | 2813 | CB | LEU | B | 365 | 24.775 | 7.297 | −46.68 | 1 | 50.74 | C |
| ATOM | 2814 | CG | LEU | B | 365 | 24.091 | 8.134 | −47.773 | 1 | 51.72 | C |
| ATOM | 2815 | CD1 | LEU | B | 365 | 24.913 | 9.38 | −48.099 | 1 | 51.9 | C |
| ATOM | 2816 | CD2 | LEU | B | 365 | 23.828 | 7.331 | −49.038 | 1 | 51.53 | C |
| ATOM | 2817 | C | LEU | B | 365 | 24.752 | 5.296 | −45.13 | 1 | 49.29 | C |
| ATOM | 2818 | O | LEU | B | 365 | 24.512 | 5.745 | −43.993 | 1 | 49.06 | O |
| ATOM | 2819 | N | THR | B | 366 | 25.526 | 4.231 | −45.355 | 1 | 47.52 | N |
| ATOM | 2820 | CA | THR | B | 366 | 26.001 | 3.389 | −44.261 | 1 | 47.07 | C |
| ATOM | 2821 | CB | THR | B | 366 | 25.558 | 1.891 | −44.434 | 1 | 46.68 | C |
| ATOM | 2822 | OG1 | THR | B | 366 | 24.129 | 1.773 | −44.327 | 1 | 45.23 | O |
| ATOM | 2823 | CG2 | THR | B | 366 | 26.186 | 1.02 | −43.357 | 1 | 46.71 | C |
| ATOM | 2824 | C | THR | B | 366 | 27.502 | 3.432 | −44.138 | 1 | 46.32 | C |
| ATOM | 2825 | O | THR | B | 366 | 28.223 | 3.315 | −45.125 | 1 | 46.64 | O |
| ATOM | 2826 | N | CYS | B | 367 | 27.984 | 3.551 | −42.915 | 1 | 45.72 | N |
| ATOM | 2827 | CA | CYS | B | 367 | 29.418 | 3.494 | −42.68 | 1 | 45.18 | C |
| ATOM | 2828 | CB | CYS | B | 367 | 29.87 | 4.808 | −42.085 | 1 | 45.78 | C |
| ATOM | 2829 | SG | CYS | B | 367 | 31.604 | 4.968 | −41.872 | 1 | 47.09 | S |
| ATOM | 2830 | C | CYS | B | 367 | 29.733 | 2.372 | −41.723 | 1 | 44.42 | C |
| ATOM | 2831 | O | CYS | B | 367 | 29.163 | 2.331 | −40.633 | 1 | 45.17 | O |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2832 | N | LEU | B | 368 | 30.634 | 1.474 | −42.116 | 1 | 42.94 N |
| ATOM | 2833 | CA | LEU | B | 368 | 30.995 | 0.331 | −41.297 | 1 | 42.4 C |
| ATOM | 2834 | CB | LEU | B | 368 | 30.953 | −0.953 | −42.109 | 1 | 42.32 C |
| ATOM | 2835 | CG | LEU | B | 368 | 31.515 | −2.256 | −41.538 | 1 | 42.48 C |
| ATOM | 2836 | CD1 | LEU | B | 368 | 30.739 | −2.779 | −40.333 | 1 | 42.17 C |
| ATOM | 2837 | CD2 | LEU | B | 368 | 31.529 | −3.31 | −42.648 | 1 | 42.45 C |
| ATOM | 2838 | C | LEU | B | 368 | 32.384 | 0.529 | −40.737 | 1 | 41.72 C |
| ATOM | 2839 | O | LEU | B | 368 | 33.341 | 0.796 | −41.458 | 1 | 41.65 O |
| ATOM | 2840 | N | VAL | B | 369 | 32.491 | 0.395 | −39.419 | 1 | 41.04 N |
| ATOM | 2841 | CA | VAL | B | 369 | 33.746 | 0.564 | −38.759 | 1 | 39.79 C |
| ATOM | 2842 | CB | VAL | B | 369 | 33.682 | 1.799 | −37.831 | 1 | 39.79 C |
| ATOM | 2843 | CG1 | VAL | B | 369 | 35.055 | 2.113 | −37.304 | 1 | 40.08 C |
| ATOM | 2844 | CG2 | VAL | B | 369 | 33.124 | 3.007 | −38.581 | 1 | 37.78 C |
| ATOM | 2845 | C | VAL | B | 369 | 33.944 | −0.734 | −38.005 | 1 | 39.59 C |
| ATOM | 2846 | O | VAL | B | 369 | 33.166 | −1.011 | −37.117 | 1 | 40.54 O |
| ATOM | 2847 | N | LYS | B | 370 | 34.934 | −1.538 | −38.399 | 1 | 38.84 N |
| ATOM | 2848 | CA | LYS | B | 370 | 35.248 | −2.811 | −37.771 | 1 | 38.65 C |
| ATOM | 2849 | CB | LYS | B | 370 | 34.808 | −3.976 | −38.648 | 1 | 38.95 C |
| ATOM | 2850 | CG | LYS | B | 370 | 35.509 | −4.061 | −40.014 | 1 | 39.34 C |
| ATOM | 2851 | CD | LYS | B | 370 | 35.352 | −5.428 | −40.68 | 1 | 39.04 C |
| ATOM | 2852 | CE | LYS | B | 370 | 36.375 | −6.44 | −40.227 | 1 | 40.63 C |
| ATOM | 2853 | NZ | LYS | B | 370 | 36.684 | −7.479 | −41.298 | 1 | 41.67 N |
| ATOM | 2854 | C | LYS | B | 370 | 36.735 | −2.947 | −37.522 | 1 | 38.61 C |
| ATOM | 2855 | O | LYS | B | 370 | 37.547 | −2.171 | −38.016 | 1 | 39.24 O |
| ATOM | 2856 | N | GLY | B | 371 | 37.082 | −3.948 | −36.739 | 1 | 38.72 N |
| ATOM | 2857 | CA | GLY | B | 371 | 38.472 | −4.294 | −36.45 | 1 | 38.78 C |
| ATOM | 2858 | C | GLY | B | 371 | 39.108 | −3.518 | −35.323 | 1 | 39.24 C |
| ATOM | 2859 | O | GLY | B | 371 | 40.309 | −3.703 | −35.075 | 1 | 39.79 O |
| ATOM | 2860 | N | PHE | B | 372 | 38.343 | −2.65 | −34.637 | 1 | 39.23 N |
| ATOM | 2861 | CA | PHE | B | 372 | 38.952 | −1.676 | −33.687 | 1 | 39.27 C |
| ATOM | 2862 | CB | PHE | B | 372 | 38.358 | −0.259 | −33.833 | 1 | 39.89 C |
| ATOM | 2863 | CG | PHE | B | 372 | 36.876 | −0.138 | −33.473 | 1 | 39.73 C |
| ATOM | 2864 | CD1 | PHE | B | 372 | 36.481 | 0.123 | −32.176 | 1 | 39.29 C |
| ATOM | 2865 | CE1 | PHE | B | 372 | 35.114 | 0.254 | −31.839 | 1 | 40.09 C |
| ATOM | 2866 | CZ | PHE | B | 372 | 34.157 | 0.156 | −32.818 | 1 | 40.57 C |
| ATOM | 2867 | CE2 | PHE | B | 372 | 34.547 | −0.085 | −34.145 | 1 | 40.85 C |
| ATOM | 2868 | CD2 | PHE | B | 372 | 35.895 | −0.235 | −34.458 | 1 | 40.59 C |
| ATOM | 2869 | C | PHE | B | 372 | 38.964 | −2.062 | −32.216 | 1 | 39.29 C |
| ATOM | 2870 | O | PHE | B | 372 | 38.148 | −2.835 | −31.763 | 1 | 39.68 O |
| ATOM | 2871 | N | TYR | B | 373 | 39.919 | −1.501 | −31.488 | 1 | 39.16 N |
| ATOM | 2872 | CA | TYR | B | 373 | 40.116 | −1.792 | −30.073 | 1 | 39.24 C |
| ATOM | 2873 | CB | TYR | B | 373 | 40.807 | −3.172 | −29.83 | 1 | 39.01 C |
| ATOM | 2874 | CG | TYR | B | 373 | 40.776 | −3.551 | −28.352 | 1 | 38.41 C |
| ATOM | 2875 | CD1 | TYR | B | 373 | 39.713 | −4.263 | −27.832 | 1 | 38.41 C |
| ATOM | 2876 | CE1 | TYR | B | 373 | 39.631 | −4.559 | −26.5 | 1 | 38.21 C |
| ATOM | 2877 | CZ | TYR | B | 373 | 40.6 | −4.123 | −25.654 | 1 | 37.64 C |
| ATOM | 2878 | OH | TYR | B | 373 | 40.491 | −4.425 | −24.328 | 1 | 37.44 O |
| ATOM | 2879 | CE2 | TYR | B | 373 | 41.673 | −3.399 | −26.136 | 1 | 37.98 C |
| ATOM | 2880 | CD2 | TYR | B | 373 | 41.755 | −3.115 | −27.482 | 1 | 36.86 C |
| ATOM | 2881 | C | TYR | B | 373 | 40.996 | −0.653 | −29.541 | 1 | 39.53 C |
| ATOM | 2882 | O | TYR | B | 373 | 41.953 | −0.231 | −30.232 | 1 | 39.28 O |
| ATOM | 2883 | N | PRO | B | 374 | 40.649 | −0.1 | −28.359 | 1 | 39.95 N |
| ATOM | 2884 | CA | PRO | B | 374 | 39.491 | −0.343 | −27.481 | 1 | 40.35 C |
| ATOM | 2885 | CB | PRO | B | 374 | 39.784 | 0.535 | −26.243 | 1 | 40.65 C |
| ATOM | 2886 | CG | PRO | B | 374 | 41.177 | 1.027 | −26.387 | 1 | 40.29 C |
| ATOM | 2887 | CD | PRO | B | 374 | 41.534 | 0.952 | −27.825 | 1 | 40.12 C |
| ATOM | 2888 | C | PRO | B | 374 | 38.138 | 0.063 | −28.09 | 1 | 40.49 C |
| ATOM | 2889 | O | PRO | B | 374 | 38.072 | 0.434 | −29.258 | 1 | 41.14 O |
| ATOM | 2890 | N | SER | B | 375 | 37.055 | −0.01 | −27.319 | 1 | 40.36 N |
| ATOM | 2891 | CA | SER | B | 375 | 35.722 | 0.264 | −27.892 | 1 | 40.59 C |
| ATOM | 2892 | CB | SER | B | 375 | 34.627 | −0.37 | −27.048 | 1 | 40.97 C |
| ATOM | 2893 | OG | SER | B | 375 | 34.403 | 0.409 | −25.885 | 1 | 42.24 O |
| ATOM | 2894 | C | SER | B | 375 | 35.428 | 1.752 | −28.022 | 1 | 40.55 C |
| ATOM | 2895 | O | SER | B | 375 | 34.404 | 2.133 | −28.575 | 1 | 41.17 O |
| ATOM | 2896 | N | ASP | B | 376 | 36.326 | 2.574 | −27.485 | 1 | 40.46 N |
| ATOM | 2897 | CA | ASP | B | 376 | 36.192 | 4.022 | −27.427 | 1 | 39.74 C |
| ATOM | 2898 | CB | ASP | B | 376 | 37.225 | 4.579 | −26.444 | 1 | 39.63 C |
| ATOM | 2899 | CG | ASP | B | 376 | 37.047 | 4.02 | −25.008 | 1 | 39.74 C |
| ATOM | 2900 | OD1 | ASP | B | 376 | 38.038 | 3.582 | −24.419 | 1 | 41.63 O |
| ATOM | 2901 | OD2 | ASP | B | 376 | 35.933 | 3.996 | −24.458 | 1 | 39.21 O |
| ATOM | 2902 | C | ASP | B | 376 | 36.404 | 4.614 | −28.822 | 1 | 39.36 C |
| ATOM | 2903 | O | ASP | B | 376 | 37.496 | 4.544 | −29.383 | 1 | 38.6 O |
| ATOM | 2904 | N | ILE | B | 377 | 35.349 | 5.2 | −29.374 | 1 | 38.87 N |
| ATOM | 2905 | CA | ILE | B | 377 | 35.402 | 5.708 | −30.727 | 1 | 38.8 C |
| ATOM | 2906 | CB | ILE | B | 377 | 35.108 | 4.554 | −31.699 | 1 | 38.85 C |
| ATOM | 2907 | CG1 | ILE | B | 377 | 35.609 | 4.861 | −33.1 | 1 | 38.26 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2908 | CD1 | ILE | B | 377 | 35.772 | 3.644 | −33.934 | 1 | 38.22 C |
| ATOM | 2909 | CG2 | ILE | B | 377 | 33.621 | 4.23 | −31.701 | 1 | 38.6 C |
| ATOM | 2910 | C | ILE | B | 377 | 34.387 | 6.849 | −30.909 | 1 | 38.8 C |
| ATOM | 2911 | O | ILE | B | 377 | 33.449 | 6.977 | −30.134 | 1 | 39.4 O |
| ATOM | 2912 | N | ALA | B | 378 | 34.616 | 7.7 | −31.897 | 1 | 38.43 N |
| ATOM | 2913 | CA | ALA | B | 378 | 33.634 | 8.689 | −32.306 | 1 | 38.31 C |
| ATOM | 2914 | CB | ALA | B | 378 | 34.038 | 10.086 | −31.874 | 1 | 37.89 C |
| ATOM | 2915 | C | ALA | B | 378 | 33.497 | 8.621 | −33.815 | 1 | 38.24 C |
| ATOM | 2916 | O | ALA | B | 378 | 34.471 | 8.371 | −34.515 | 1 | 38.35 O |
| ATOM | 2917 | N | VAL | B | 379 | 32.27 | 8.804 | −34.292 | 1 | 38.05 N |
| ATOM | 2918 | CA | VAL | B | 379 | 31.958 | 8.809 | −35.701 | 1 | 38.46 C |
| ATOM | 2919 | CB | VAL | B | 379 | 31.23 | 7.52 | −36.069 | 1 | 38.35 C |
| ATOM | 2920 | CG1 | VAL | B | 379 | 31.019 | 7.423 | −37.582 | 1 | 38.41 C |
| ATOM | 2921 | CG2 | VAL | B | 379 | 31.987 | 6.31 | −35.503 | 1 | 37.28 C |
| ATOM | 2922 | C | VAL | B | 379 | 31.061 | 10.035 | −36.015 | 1 | 39.09 C |
| ATOM | 2923 | O | VAL | B | 379 | 30.249 | 10.462 | −35.188 | 1 | 38.4 O |
| ATOM | 2924 | N | GLU | B | 380 | 31.231 | 10.608 | −37.2 | 1 | 39.42 N |
| ATOM | 2925 | CA | GLU | B | 380 | 30.506 | 11.807 | −37.582 | 1 | 40.12 C |
| ATOM | 2926 | CB | GLU | B | 380 | 31.191 | 13.079 | −37.089 | 1 | 40.05 C |
| ATOM | 2927 | CG | GLU | B | 380 | 30.886 | 13.432 | −35.648 | 1 | 40.87 C |
| ATOM | 2928 | CD | GLU | B | 380 | 31.869 | 14.437 | −35.079 | 1 | 42.63 C |
| ATOM | 2929 | OE1 | GLU | B | 380 | 32.608 | 15.028 | −35.902 | 1 | 46.3 O |
| ATOM | 2930 | OE2 | GLU | B | 380 | 31.911 | 14.626 | −33.825 | 1 | 45.46 O |
| ATOM | 2931 | C | GLU | B | 380 | 30.405 | 11.85 | −39.076 | 1 | 40.53 C |
| ATOM | 2932 | O | GLU | B | 380 | 31.088 | 11.12 | −39.78 | 1 | 39.49 O |
| ATOM | 2933 | N | TRP | B | 381 | 29.528 | 12.713 | −39.55 | 1 | 41.79 N |
| ATOM | 2934 | CA | TRP | B | 381 | 29.265 | 12.789 | −40.96 | 1 | 43.41 C |
| ATOM | 2935 | CB | TRP | B | 381 | 27.917 | 12.154 | −41.274 | 1 | 43.68 C |
| ATOM | 2936 | CG | TRP | B | 381 | 27.817 | 10.631 | −41.28 | 1 | 44.25 C |
| ATOM | 2937 | CD1 | TRP | B | 381 | 27.512 | 9.829 | −40.221 | 1 | 45.54 C |
| ATOM | 2938 | NE1 | TRP | B | 381 | 27.444 | 8.52 | −40.62 | 1 | 44.29 N |
| ATOM | 2939 | CE2 | TRP | B | 381 | 27.681 | 8.46 | −41.966 | 1 | 42.07 C |
| ATOM | 2940 | CD2 | TRP | B | 381 | 27.913 | 9.767 | −42.415 | 1 | 42.2 C |
| ATOM | 2941 | CE3 | TRP | B | 381 | 28.186 | 9.973 | −43.771 | 1 | 44.18 C |
| ATOM | 2942 | CZ3 | TRP | B | 381 | 28.235 | 8.877 | −44.624 | 1 | 42.93 C |
| ATOM | 2943 | CH2 | TRP | B | 381 | 27.995 | 7.587 | −44.14 | 1 | 42.84 C |
| ATOM | 2944 | CZ2 | TRP | B | 381 | 27.713 | 7.363 | −42.817 | 1 | 43.09 C |
| ATOM | 2945 | C | TRP | B | 381 | 29.252 | 14.241 | −41.416 | 1 | 45.02 C |
| ATOM | 2946 | O | TRP | B | 381 | 28.981 | 15.162 | −40.643 | 1 | 44.23 O |
| ATOM | 2947 | N | GLU | B | 382 | 29.53 | 14.419 | −42.696 | 1 | 47.8 N |
| ATOM | 2948 | CA | GLU | B | 382 | 29.478 | 15.721 | −43.299 | 1 | 50.5 C |
| ATOM | 2949 | CB | GLU | B | 382 | 30.738 | 16.493 | −42.933 | 1 | 50.34 C |
| ATOM | 2950 | CG | GLU | B | 382 | 32.018 | 15.934 | −43.514 | 1 | 50.48 C |
| ATOM | 2951 | CD | GLU | B | 382 | 33.19 | 16.817 | −43.184 | 1 | 51.28 C |
| ATOM | 2952 | OE1 | GLU | B | 382 | 33.384 | 17.092 | −41.978 | 1 | 53.54 O |
| ATOM | 2953 | OE2 | GLU | B | 382 | 33.901 | 17.248 | −44.116 | 1 | 52.26 O |
| ATOM | 2954 | C | GLU | B | 382 | 29.364 | 15.67 | −44.811 | 1 | 51.56 C |
| ATOM | 2955 | O | GLU | B | 382 | 29.657 | 14.655 | −45.453 | 1 | 51.57 O |
| ATOM | 2956 | N | SER | B | 383 | 28.925 | 16.792 | −45.368 | 1 | 53.3 N |
| ATOM | 2957 | CA | SER | B | 383 | 29.038 | 17.038 | −46.799 | 1 | 54.31 C |
| ATOM | 2958 | CB | SER | B | 383 | 27.721 | 16.773 | −47.508 | 1 | 54.5 C |
| ATOM | 2959 | OG | SER | B | 383 | 27.941 | 16.803 | −48.903 | 1 | 55.88 O |
| ATOM | 2960 | C | SER | B | 383 | 29.493 | 18.479 | −47.039 | 1 | 55.1 C |
| ATOM | 2961 | O | SER | B | 383 | 29.138 | 19.385 | −46.284 | 1 | 54.86 O |
| ATOM | 2962 | N | ASN | B | 384 | 30.311 | 18.664 | −48.074 | 1 | 56.59 N |
| ATOM | 2963 | CA | ASN | B | 384 | 30.833 | 19.982 | −48.448 | 1 | 56.84 C |
| ATOM | 2964 | CB | ASN | B | 384 | 29.772 | 20.765 | −49.238 | 1 | 57.42 C |
| ATOM | 2965 | CG | ASN | B | 384 | 30.385 | 21.837 | −50.138 | 1 | 58.35 C |
| ATOM | 2966 | OD1 | ASN | B | 384 | 30.158 | 23.036 | −49.943 | 1 | 62.68 O |
| ATOM | 2967 | ND2 | ASN | B | 384 | 31.18 | 21.409 | −51.117 | 1 | 60.03 N |
| ATOM | 2968 | C | ASN | B | 384 | 31.316 | 20.802 | −47.249 | 1 | 57.23 C |
| ATOM | 2969 | O | ASN | B | 384 | 30.941 | 21.964 | −47.077 | 1 | 57.65 O |
| ATOM | 2970 | N | GLY | B | 385 | 32.115 | 20.172 | −46.399 | 1 | 57.04 N |
| ATOM | 2971 | CA | GLY | B | 385 | 32.659 | 20.831 | −45.22 | 1 | 56.92 C |
| ATOM | 2972 | C | GLY | B | 385 | 31.701 | 20.926 | −44.062 | 1 | 56.94 C |
| ATOM | 2973 | O | GLY | B | 385 | 32.125 | 21.146 | −42.926 | 1 | 57.47 O |
| ATOM | 2974 | N | GLN | B | 386 | 30.412 | 20.746 | −44.323 | 1 | 56.86 N |
| ATOM | 2975 | CA | GLN | B | 386 | 29.4 | 20.988 | −43.304 | 1 | 56.47 C |
| ATOM | 2976 | CB | GLN | B | 386 | 28.168 | 21.644 | −43.939 | 1 | 57.11 C |
| ATOM | 2977 | CG | GLN | B | 386 | 27.3 | 22.429 | −42.953 | 1 | 58.38 C |
| ATOM | 2978 | CD | GLN | B | 386 | 28.005 | 23.674 | −42.426 | 1 | 61.98 C |
| ATOM | 2979 | OE1 | GLN | B | 386 | 28.799 | 24.297 | −43.139 | 1 | 63.94 O |
| ATOM | 2980 | NE2 | GLN | B | 386 | 27.729 | 24.032 | −41.167 | 1 | 64.14 N |
| ATOM | 2981 | C | GLN | 8 | 386 | 28.961 | 19.704 | −42.585 | 1 | 55.84 C |
| ATOM | 2982 | O | GLN | B | 386 | 28.663 | 18.704 | −43.236 | 1 | 55.23 O |
| ATOM | 2983 | N | PRO | B | 387 | 28.922 | 19.735 | −41.237 | 1 | 55.2 N |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 2984 | CA | PRO | B | 387 | 28.324 | 18.64 | −40.475 | 1 | 54.89 C |
| ATOM | 2985 | CB | PRO | B | 387 | 28.32 | 19.19 | −39.036 | 1 | 54.73 C |
| ATOM | 2986 | CG | PRO | B | 387 | 29.51 | 20.051 | −38.999 | 1 | 54.49 C |
| ATOM | 2987 | CD | PRO | B | 387 | 29.5 | 20.749 | −40.331 | 1 | 54.83 C |
| ATOM | 2988 | C | PRO | B | 387 | 26.914 | 18.283 | −40.936 | 1 | 54.46 C |
| ATOM | 2989 | O | PRO | B | 387 | 26.097 | 19.173 | −41.147 | 1 | 54.51 O |
| ATOM | 2990 | N | GLU | B | 388 | 26.664 | 16.982 | −41.1 | 1 | 54.23 N |
| ATOM | 2991 | CA | GLU | B | 388 | 25.35 | 16.452 | −41.453 | 1 | 53.65 C |
| ATOM | 2992 | CB | GLU | B | 388 | 25.467 | 15.208 | −42.295 | 1 | 53.77 C |
| ATOM | 2993 | CG | GLU | B | 388 | 25.786 | 15.489 | −43.717 | 1 | 55.26 C |
| ATOM | 2994 | CD | GLU | B | 388 | 24.62 | 16.067 | −44.472 | 1 | 56.4 C |
| ATOM | 2995 | OE1 | GLU | B | 388 | 23.537 | 16.256 | −43.873 | 1 | 56.08 O |
| ATOM | 2996 | OE2 | GLU | B | 388 | 24.797 | 16.327 | −45.676 | 1 | 57.8 O |
| ATOM | 2997 | C | GLU | B | 388 | 24.568 | 16.088 | −40.227 | 1 | 52.97 C |
| ATOM | 2998 | O | GLU | B | 388 | 25.021 | 15.346 | −39.382 | 1 | 53.09 O |
| ATOM | 2999 | N | ASN | B | 389 | 23.351 | 16.588 | −40.195 | 1 | 52.77 N |
| ATOM | 3000 | CA | ASN | B | 389 | 22.445 | 16.491 | −39.065 | 1 | 52.48 C |
| ATOM | 3001 | CB | ASN | B | 389 | 21.183 | 17.343 | −39.377 | 1 | 52.73 C |
| ATOM | 3002 | CG | ASN | B | 389 | 21.519 | 18.821 | −39.724 | 1 | 52.99 C |
| ATOM | 3003 | OD1 | ASN | B | 389 | 22.683 | 19.191 | −39.92 | 1 | 52.04 O |
| ATOM | 3004 | ND2 | ASN | B | 389 | 20.486 | 19.657 | −39.784 | 1 | 53.05 N |
| ATOM | 3005 | C | ASN | B | 389 | 22.024 | 15.057 | −38.716 | 1 | 52.06 C |
| ATOM | 3006 | O | ASN | B | 389 | 22.215 | 14.61 | −37.579 | 1 | 52.17 O |
| ATOM | 3007 | N | ASN | B | 390 | 21.505 | 14.336 | −39.715 | 1 | 51.23 N |
| ATOM | 3008 | CA | ASN | B | 390 | 20.554 | 13.241 | −39.474 | 1 | 49.95 C |
| ATOM | 3009 | CB | ASN | B | 390 | 19.338 | 13.489 | −40.351 | 1 | 50.46 C |
| ATOM | 3010 | CG | ASN | B | 390 | 18.233 | 12.496 | −40.144 | 1 | 52.15 C |
| ATOM | 3011 | OD1 | ASN | B | 390 | 17.477 | 12.248 | −41.078 | 1 | 54.93 O |
| ATOM | 3012 | ND2 | ASN | B | 390 | 18.116 | 11.917 | −38.932 | 1 | 55.35 N |
| ATOM | 3013 | C | ASN | B | 390 | 21.139 | 11.831 | −39.651 | 1 | 48.79 C |
| ATOM | 3014 | O | ASN | B | 390 | 20.952 | 11.165 | −40.667 | 1 | 48.88 O |
| ATOM | 3015 | N | TYR | B | 391 | 21.871 | 11.414 | −38.622 | 1 | 47.2 N |
| ATOM | 3016 | CA | TYR | B | 391 | 22.497 | 10.113 | −38.558 | 1 | 45.87 C |
| ATOM | 3017 | CB | TYR | 13 | 391 | 23.973 | 10.186 | −38.984 | 1 | 45.97 C |
| ATOM | 3018 | CG | TYR | B | 391 | 24.853 | 10.95 | −38.035 | 1 | 46.05 C |
| ATOM | 3019 | CD1 | TYR | B | 391 | 25.218 | 12.273 | −38.293 | 1 | 45.21 C |
| ATOM | 3020 | CE1 | TYR | B | 391 | 26.029 | 12.983 | −37.392 | 1 | 45.84 C |
| ATOM | 3021 | CZ | TYR | B | 391 | 26.492 | 12.344 | −36.234 | 1 | 46.86 C |
| ATOM | 3022 | OH | TYR | B | 391 | 27.297 | 12.997 | −35.336 | 1 | 46.34 O |
| ATOM | 3023 | CE2 | TYR | B | 391 | 26.126 | 11.035 | −35.962 | 1 | 46.48 C |
| ATOM | 3024 | CD2 | TYR | B | 391 | 25.324 | 10.348 | −36.86 | 1 | 46.55 C |
| ATOM | 3025 | C | TYR | B | 391 | 22.402 | 9.552 | −37.137 | 1 | 44.59 C |
| ATOM | 3026 | O | TYR | B | 391 | 22.259 | 10.293 | −36.154 | 1 | 43.53 O |
| ATOM | 3027 | N | LYS | B | 392 | 22.49 | 8.224 | −37.068 | 1 | 43.49 N |
| ATOM | 3028 | CA | LYS | B | 392 | 22.564 | 7.484 | −35.818 | 1 | 42.71 C |
| ATOM | 3029 | CB | LYS | B | 392 | 21.253 | 6.765 | −35.519 | 1 | 42.51 C |
| ATOM | 3030 | CG | LYS | B | 392 | 20.027 | 7.696 | −35.369 | 1 | 43.03 C |
| ATOM | 3031 | CD | LYS | B | 392 | 20.055 | 8.466 | −34.022 | 1 | 42.83 C |
| ATOM | 3032 | CE | LYS | B | 392 | 18.879 | 9.458 | −33.868 | 1 | 42.91 C |
| ATOM | 3033 | NZ | LYS | B | 392 | 18.691 | 9.903 | −32.423 | 1 | 43.51 N |
| ATOM | 3034 | C | LYS | B | 392 | 23.632 | 6.46 | −36.023 | 1 | 41.41 C |
| ATOM | 3035 | O | LYS | B | 392 | 23.821 | 5.965 | −37.137 | 1 | 41.58 O |
| ATOM | 3036 | N | THR | B | 393 | 24.326 | 6.153 | −34.938 | 1 | 40.33 N |
| ATOM | 3037 | CA | THR | B | 393 | 25.411 | 5.198 | −34.923 | 1 | 39.33 C |
| ATOM | 3038 | CB | THR | B | 393 | 26.737 | 5.941 | −34.643 | 1 | 39.64 C |
| ATOM | 3039 | OG1 | THR | B | 393 | 26.915 | 6.983 | −35.619 | 1 | 40.21 O |
| ATOM | 3040 | CG2 | THR | B | 393 | 27.928 | 4.998 | −34.715 | 1 | 39.58 C |
| ATOM | 3041 | C | THR | B | 393 | 25.156 | 4.149 | −33.834 | 1 | 38.85 C |
| ATOM | 3042 | O | THR | B | 393 | 24.79 | 4.47 | −32.705 | 1 | 37.91 O |
| ATOM | 3043 | N | THR | B | 394 | 25.373 | 2.885 | −34.173 | 1 | 38.52 N |
| ATOM | 3044 | CA | THR | B | 394 | 25.148 | 1.829 | −33.215 | 1 | 38.22 C |
| ATOM | 3045 | CB | THR | B | 394 | 25.18 | 0.464 | −33.864 | 1 | 37.57 C |
| ATOM | 3046 | OG1 | THR | B | 394 | 26.528 | 0.147 | −34.225 | 1 | 34.8 O |
| ATOM | 3047 | CG2 | THR | B | 394 | 24.261 | 0.441 | −35.069 | 1 | 37.03 C |
| ATOM | 3048 | C | THR | B | 394 | 26.235 | 1.875 | −32.147 | 1 | 38.39 C |
| ATOM | 3049 | O | THR | B | 394 | 27.323 | 2.362 | −32.394 | 1 | 38.4 O |
| ATOM | 3050 | N | PRO | B | 395 | 25.955 | 1.322 | −30.962 | 1 | 38.76 N |
| ATOM | 3051 | CA | PRO | B | 395 | 27.072 | 1.2 | −30.011 | 1 | 38.71 C |
| ATOM | 3052 | CB | PRO | B | 395 | 26.433 | 0.666 | −28.733 | 1 | 38.27 C |
| ATOM | 3053 | CG | PRO | B | 395 | 24.971 | 0.531 | −29 | 1 | 38.98 C |
| ATOM | 3054 | CD | PRO | B | 395 | 24.69 | 0.764 | −30.457 | 1 | 38.83 C |
| ATOM | 3055 | C | PRO | B | 395 | 28.095 | 0.194 | −30.556 | 1 | 38.86 C |
| ATOM | 3056 | O | PRO | B | 395 | 27.78 | −0.576 | −31.473 | 1 | 38.01 O |
| ATOM | 3057 | N | PRO | B | 396 | 29.307 | 0.198 | −30.003 | 1 | 39.05 N |
| ATOM | 3058 | CA | PRO | B | 396 | 30.279 | −0.806 | −30.435 | 1 | 39.58 C |
| ATOM | 3059 | CB | PRO | B | 396 | 31.537 | −0.421 | −29.684 | 1 | 39.42 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 3060 | CG | PRO | B | 396 | 31.289 | 1.052 | −29.28 | 1 | 39.8 | C |
| ATOM | 3061 | CD | PRO | B | 396 | 29.855 | 1.092 | −28.984 | 1 | 39.03 | C |
| ATOM | 3062 | C | PRO | B | 396 | 29.819 | −2.189 | −30.02 | 1 | 39.96 | C |
| ATOM | 3063 | O | PRO | B | 396 | 29.331 | −2.344 | −28.898 | 1 | 39.61 | O |
| ATOM | 3064 | N | VAL | B | 397 | 29.948 | −3.154 | −30.938 | 1 | 40.11 | N |
| ATOM | 3065 | CA | VAL | B | 397 | 29.549 | −4.513 | −30.708 | 1 | 40.72 | C |
| ATOM | 3066 | CB | VAL | B | 397 | 28.582 | −5.027 | −31.801 | 1 | 40.65 | C |
| ATOM | 3067 | CG1 | VAL | B | 397 | 28.167 | −6.457 | −31.511 | 1 | 40.19 | C |
| ATOM | 3068 | CG2 | VAL | B | 397 | 27.347 | −4.124 | −31.939 | 1 | 39.28 | C |
| ATOM | 3069 | C | VAL | B | 397 | 30.822 | −5.322 | −30.744 | 1 | 41.74 | C |
| ATOM | 3070 | O | VAL | B | 397 | 31.615 | −5.168 | −31.666 | 1 | 42.05 | O |
| ATOM | 3071 | N | LEU | B | 398 | 31.015 | −6.166 | −29.724 | 1 | 42.73 | N |
| ATOM | 3072 | CA | LEU | B | 398 | 32.141 | −7.113 | −29.646 | 1 | 43.16 | C |
| ATOM | 3073 | CB | LEU | B | 398 | 32.162 | −7.78 | −28.263 | 1 | 43.19 | C |
| ATOM | 3074 | CG | LEU | B | 398 | 33.354 | −8.657 | −27.914 | 1 | 43.07 | C |
| ATOM | 3075 | CD1 | LEU | B | 398 | 34.624 | −7.808 | −27.831 | 1 | 42.49 | C |
| ATOM | 3076 | CD2 | LEU | B | 398 | 33.087 | −9.378 | −26.607 | 1 | 42.79 | C |
| ATOM | 3077 | C | LEU | B | 398 | 32.043 | −8.188 | −30.723 | 1 | 43.87 | C |
| ATOM | 3078 | O | LEU | B | 398 | 31.037 | −8.896 | −30.82 | 1 | 43.63 | O |
| ATOM | 3079 | N | ASP | B | 399 | 33.083 | −8.297 | −31.545 | 1 | 45.02 | N |
| ATOM | 3080 | CA | ASP | B | 399 | 33.087 | −9.236 | −32.679 | 1 | 45.43 | C |
| ATOM | 3081 | CB | ASP | B | 399 | 33.825 | −8.604 | −33.867 | 1 | 45.45 | C |
| ATOM | 3082 | CG | ASP | B | 399 | 33.32 | −9.102 | −35.241 | 1 | 44.93 | C |
| ATOM | 3083 | OD1 | ASP | B | 399 | 32.869 | −10.276 | −35.332 | 1 | 44.25 | O |
| ATOM | 3084 | OD2 | ASP | B | 399 | 33.395 | −8.312 | −36.222 | 1 | 40.66 | O |
| ATOM | 3085 | C | ASP | B | 399 | 33.744 | −10.562 | −32.267 | 1 | 46.33 | C |
| ATOM | 3086 | O | ASP | B | 399 | 34.415 | −10.647 | −31.236 | 1 | 47.05 | O |
| ATOM | 3087 | N | SER | B | 400 | 33.563 | −11.59 | −33.082 | 1 | 47 | N |
| ATOM | 3088 | CA | SER | B | 400 | 34.12 | −12.902 | −32.792 | 1 | 47.63 | C |
| ATOM | 3089 | CB | SER | B | 400 | 33.827 | −13.843 | −33.96 | 1 | 48.6 | C |
| ATOM | 3090 | OG | SER | B | 400 | 34.408 | −13.359 | −35.157 | 1 | 50.83 | O |
| ATOM | 3091 | C | SER | B | 400 | 35.62 | −12.945 | −32.468 | 1 | 48.01 | C |
| ATOM | 3092 | O | SER | B | 400 | 36.059 | −13.83 | −31.731 | 1 | 49.02 | O |
| ATOM | 3093 | N | ASP | B | 401 | 36.413 | −12.016 | −33.001 | 1 | 47.76 | N |
| ATOM | 3094 | CA | ASP | B | 401 | 37.85 | −11.995 | −32.701 | 1 | 46.8 | C |
| ATOM | 3095 | CB | ASP | B | 401 | 38.688 | −11.681 | −33.958 | 1 | 47.1 | C |
| ATOM | 3096 | CG | ASP | B | 401 | 38.718 | −10.195 | −34.334 | 1 | 49.24 | C |
| ATOM | 3097 | OD1 | ASP | B | 401 | 37.812 | −9.416 | −33.946 | 1 | 49.84 | O |
| ATOM | 3098 | OD2 | ASP | B | 401 | 39.67 | −9.805 | −35.062 | 1 | 51.78 | O |
| ATOM | 3099 | C | ASP | B | 401 | 38.223 | −11.076 | −31.554 | 1 | 45.9 | C |
| ATOM | 3100 | O | ASP | B | 401 | 39.383 | −10.743 | −31.401 | 1 | 46.37 | O |
| ATOM | 3101 | N | GLY | B | 402 | 37.26 | −10.637 | −30.755 | 1 | 44.89 | N |
| ATOM | 3102 | CA | GLY | B | 402 | 37.589 | −9.796 | −29.583 | 1 | 44.29 | C |
| ATOM | 3103 | C | GLY | B | 402 | 37.879 | −8.316 | −29.873 | 1 | 43.64 | C |
| ATOM | 3104 | O | GLY | B | 402 | 38.081 | −7.514 | −28.906 | 1 | 42.62 | O |
| ATOM | 3105 | N | SER | B | 403 | 37.915 | −7.967 | −31.182 | 1 | 42.25 | N |
| ATOM | 3106 | CA | SER | B | 403 | 37.92 | −6.583 | −31.656 | 1 | 41.7 | C |
| ATOM | 3107 | CB | SER | B | 403 | 38.538 | −6.484 | −33.049 | 1 | 41.99 | C |
| ATOM | 3108 | OG | SER | B | 403 | 37.624 | −6.876 | −34.066 | 1 | 41.84 | O |
| ATOM | 3109 | C | SER | B | 403 | 36.487 | −6.081 | −31.745 | 1 | 41.11 | C |
| ATOM | 3110 | O | SER | B | 403 | 35.564 | −6.858 | −31.482 | 1 | 40.66 | O |
| ATOM | 3111 | N | PHE | B | 404 | 36.296 | −4.814 | −32.161 | 1 | 40.35 | N |
| ATOM | 3112 | CA | PHE | B | 404 | 34.948 | −4.187 | −32.177 | 1 | 40.15 | C |
| ATOM | 3113 | CB | PHE | B | 404 | 34.846 | −3.036 | −31.171 | 1 | 39.68 | C |
| ATOM | 3114 | CG | PHE | B | 404 | 34.785 | −3.484 | −29.735 | 1 | 39.56 | C |
| ATOM | 3115 | CD1 | PHE | B | 404 | 33.558 | −3.661 | −29.098 | 1 | 39.13 | C |
| ATOM | 3116 | CE1 | PHE | B | 404 | 33.483 | −4.065 | −27.733 | 1 | 38.89 | C |
| ATOM | 3117 | CZ | PHE | B | 404 | 34.641 | −4.294 | −27.008 | 1 | 38.76 | C |
| ATOM | 3118 | CE2 | PHE | B | 404 | 35.885 | −4.103 | −27.629 | 1 | 40.27 | C |
| ATOM | 3119 | CD2 | PHE | B | 404 | 35.944 | −3.704 | −29.015 | 1 | 39.98 | C |
| ATOM | 3120 | C | PHE | B | 404 | 34.493 | −3.684 | −33.528 | 1 | 39.56 | C |
| ATOM | 3121 | O | PHE | B | 404 | 35.299 | −3.428 | −34.432 | 1 | 39.34 | O |
| ATOM | 3122 | N | PHE | B | 405 | 33.182 | −3.557 | −33.663 | 1 | 39.23 | N |
| ATOM | 3123 | CA | PHE | B | 405 | 32.624 | −2.99 | −34.879 | 1 | 39.55 | C |
| ATOM | 3124 | CB | PHE | B | 405 | 32.364 | −4.056 | −35.949 | 1 | 39.9 | C |
| ATOM | 3125 | CG | PHE | B | 405 | 31.074 | −4.805 | −35.765 | 1 | 40.98 | C |
| ATOM | 3126 | CD1 | PHE | B | 405 | 29.907 | −4.389 | −36.42 | 1 | 42.15 | C |
| ATOM | 3127 | CE1 | PHE | B | 405 | 28.675 | −5.102 | −36.24 | 1 | 42.59 | C |
| ATOM | 3128 | CZ | PHE | B | 405 | 28.653 | −6.221 | −35.403 | 1 | 40.68 | C |
| ATOM | 3129 | CE2 | PHE | B | 405 | 29.814 | −6.638 | −34.774 | 1 | 39.57 | C |
| ATOM | 3130 | CD2 | PHE | B | 405 | 31.015 | −5.933 | −34.946 | 1 | 39.95 | C |
| ATOM | 3131 | C | PHE | B | 405 | 31.365 | −2.203 | −34.585 | 1 | 39.29 | C |
| ATOM | 3132 | O | PHE | B | 405 | 30.735 | −2.377 | −33.548 | 1 | 38.57 | O |
| ATOM | 3133 | N | LEU | B | 406 | 31.055 | −1.289 | −35.5 | 1 | 39.32 | N |
| ATOM | 3134 | CA | LEU | B | 406 | 29.799 | −0.551 | −35.478 | 1 | 39.05 | C |
| ATOM | 3135 | CB | LEU | B | 406 | 29.881 | 0.714 | −34.619 | 1 | 38.67 | C |

TABLE V-continued

Atomic Structure Coordinates of Fc/YTE (SEQ ID NO: 11)

| | Atom | A.A. | Type | | X | Y | Z | Occ | B | |
|---|---|---|---|---|---|---|---|---|---|---|
| ATOM | 3136 | CG | LEU | B | 406 | 30.856 | 1.884 | −34.851 | 1 | 37.89 C |
| ATOM | 3137 | CD1 | LEU | B | 406 | 30.663 | 2.661 | −36.132 | 1 | 36.08 C |
| ATOM | 3138 | CD2 | LEU | B | 406 | 30.733 | 2.869 | −33.657 | 1 | 38.23 C |
| ATOM | 3139 | C | LEU | B | 406 | 29.363 | −0.224 | −36.896 | 1 | 39.58 C |
| ATOM | 3140 | O | LEU | B | 406 | 30.134 | −0.404 | −37.873 | 1 | 39.41 O |
| ATOM | 3141 | N | TYR | B | 407 | 28.109 | 0.207 | −36.996 | 1 | 39.59 N |
| ATOM | 3142 | CA | TYR | B | 407 | 27.586 | 0.775 | −38.204 | 1 | 39.82 C |
| ATOM | 3143 | CB | TYR | B | 407 | 26.496 | −0.106 | −38.79 | 1 | 39.88 C |
| ATOM | 3144 | CG | TYR | B | 407 | 26.934 | −1.364 | −39.509 | 1 | 39.86 C |
| ATOM | 3145 | CD1 | TYR | B | 407 | 27.015 | −2.579 | −38.835 | 1 | 40.3 C |
| ATOM | 3146 | CE1 | TYR | B | 407 | 27.39 | −3.758 | −39.494 | 1 | 39.91 C |
| ATOM | 3147 | CZ | TYR | B | 407 | 27.659 | −3.729 | −40.854 | 1 | 40.26 C |
| ATOM | 3148 | OH | TYR | B | 407 | 28.003 | −4.877 | −41.488 | 1 | 40.65 O |
| ATOM | 3149 | CE2 | TYR | B | 407 | 27.575 | −2.544 | −41.565 | 1 | 40.05 C |
| ATOM | 3150 | CD2 | TYR | B | 407 | 27.197 | −1.36 | −40.881 | 1 | 40.57 C |
| ATOM | 3151 | C | TYR | B | 407 | 26.978 | 2.121 | −37.839 | 1 | 40.2 C |
| ATOM | 3152 | O | TYR | B | 407 | 26.295 | 2.231 | −36.814 | 1 | 40.16 O |
| ATOM | 3153 | N | SER | B | 408 | 27.225 | 3.129 | −38.687 | 1 | 40.35 N |
| ATOM | 3154 | CA | SER | B | 408 | 26.57 | 4.424 | −38.599 | 1 | 40.04 C |
| ATOM | 3155 | CB | SER | B | 408 | 27.598 | 5.538 | −38.434 | 1 | 40.11 C |
| ATOM | 3156 | OG | SER | B | 408 | 26.951 | 6.77 | −38.19 | 1 | 40.29 O |
| ATOM | 3157 | C | SER | B | 408 | 25.767 | 4.656 | −39.874 | 1 | 40.31 C |
| ATOM | 3158 | O | SER | B | 408 | 26.261 | 4.425 | −40.987 | 1 | 40.5 O |
| ATOM | 3159 | N | LYS | B | 409 | 24.536 | 5.138 | −39.688 | 1 | 40.44 N |
| ATOM | 3160 | CA | LYS | B | 409 | 23.566 | 5.371 | −40.762 | 1 | 40.32 C |
| ATOM | 3161 | CB | LYS | B | 409 | 22.275 | 4.582 | −40.446 | 1 | 39.7 C |
| ATOM | 3162 | CG | LYS | B | 409 | 21.156 | 4.69 | −41.505 | 1 | 40.08 C |
| ATOM | 3163 | CD | LYS | B | 409 | 20.068 | 3.593 | −41.39 | 1 | 39.47 C |
| ATOM | 3164 | CE | LYS | B | 409 | 19.211 | 3.69 | −40.128 | 1 | 38.19 C |
| ATOM | 3165 | NZ | LYS | B | 409 | 18.398 | 4.953 | −40.066 | 1 | 37.74 N |
| ATOM | 3166 | C | LYS | B | 409 | 23.268 | 6.879 | −40.906 | 1 | 40.85 C |
| ATOM | 3167 | O | LYS | B | 409 | 22.82 | 7.507 | −39.953 | 1 | 40.99 O |
| ATOM | 3168 | N | LEU | B | 410 | 23.534 | 7.451 | −42.083 | 1 | 41.81 N |
| ATOM | 3169 | CA | LEU | B | 410 | 23.154 | 8.829 | −42.388 | 1 | 42.2 C |
| ATOM | 3170 | CB | LEU | B | 410 | 24.267 | 9.564 | −43.126 | 1 | 42.88 C |
| ATOM | 3171 | CG | LEU | B | 410 | 24.015 | 11.022 | −43.547 | 1 | 42.27 C |
| ATOM | 3172 | CD1 | LEU | B | 410 | 24.018 | 11.961 | −42.306 | 1 | 41.21 C |
| ATOM | 3173 | CD2 | LEU | B | 410 | 25.068 | 11.439 | −44.544 | 1 | 41.6 C |
| ATOM | 3174 | C | LEU | B | 410 | 21.981 | 8.781 | −43.298 | 1 | 44.25 C |
| ATOM | 3175 | O | LEU | B | 410 | 22.033 | 8.135 | −44.354 | 1 | 44.23 O |
| ATOM | 3176 | N | THR | B | 411 | 20.918 | 9.462 | −42.888 | 1 | 46.34 N |
| ATOM | 3177 | CA | THR | B | 411 | 19.711 | 9.573 | −43.692 | 1 | 47.81 C |
| ATOM | 3178 | CB | THR | B | 411 | 18.47 | 9.405 | −42.822 | 1 | 47.47 C |
| ATOM | 3179 | OG1 | THR | B | 411 | 18.43 | 8.048 | −42.394 | 1 | 47.6 O |
| ATOM | 3180 | CG2 | THR | B | 411 | 17.198 | 9.709 | −43.616 | 1 | 46.87 C |
| ATOM | 3181 | C | THR | B | 411 | 19.676 | 10.904 | −44.432 | 1 | 48.41 C |
| ATOM | 3182 | O | THR | B | 411 | 19.834 | 11.952 | −43.827 | 1 | 48.91 O |
| ATOM | 3183 | N | VAL | B | 412 | 19.476 | 10.833 | −45.742 | 1 | 49.76 N |
| ATOM | 3184 | CA | VAL | B | 412 | 19.42 | 12.003 | −46.63 | 1 | 50.74 C |
| ATOM | 3185 | CB | VAL | B | 412 | 20.698 | 12.15 | −47.482 | 1 | 50.34 C |
| ATOM | 3186 | CG1 | VAL | B | 412 | 21.929 | 12.181 | −46.607 | 1 | 50.04 C |
| ATOM | 3187 | CG2 | VAL | B | 412 | 20.787 | 11.027 | −48.498 | 1 | 50.06 C |
| ATOM | 3188 | C | VAL | B | 412 | 18.267 | 11.882 | −47.616 | 1 | 51.86 C |
| ATOM | 3189 | O | VAL | B | 412 | 17.783 | 10.78 | −47.89 | 1 | 51.99 O |
| ATOM | 3190 | N | ASP | B | 413 | 17.849 | 13.022 | −48.161 | 1 | 53.5 N |
| ATOM | 3191 | CA | ASP | B | 413 | 16.863 | 13.05 | −49.242 | 1 | 54.2 C |
| ATOM | 3192 | CB | ASP | B | 413 | 16.622 | 14.485 | −49.713 | 1 | 54.63 C |
| ATOM | 3193 | CG | ASP | B | 413 | 15.768 | 15.279 | −48.753 | 1 | 55.38 C |
| ATOM | 3194 | OD1 | ASP | B | 413 | 16.171 | 16.414 | −48.388 | 1 | 57.24 O |
| ATOM | 3195 | OD2 | ASP | B | 413 | 14.696 | 14.77 | −48.365 | 1 | 55.71 O |
| ATOM | 3196 | C | ASP | B | 413 | 17.47 | 12.293 | −50.389 | 1 | 55.07 C |
| ATOM | 3197 | O | ASP | B | 413 | 18.637 | 12.531 | −50.713 | 1 | 55.56 O |
| ATOM | 3198 | N | LYS | B | 414 | 16.704 | 11.392 | −50.996 | 1 | 55.6 N |
| ATOM | 3199 | CA | LYS | B | 414 | 17.158 | 10.671 | −52.175 | 1 | 56.11 C |
| ATOM | 3200 | CB | LYS | B | 414 | 16.014 | 9.84 | −52.766 | 1 | 56.43 C |
| ATOM | 3201 | CG | LYS | B | 414 | 16.394 | 9.03 | −54.012 | 1 | 56.63 C |
| ATOM | 3202 | CD | LYS | B | 414 | 15.469 | 7.824 | −54.256 | 1 | 57.05 C |
| ATOM | 3203 | CE | LYS | B | 414 | 14.106 | 8.245 | −54.815 | 1 | 58.25 C |
| ATOM | 3204 | NZ | LYS | B | 414 | 13.365 | 7.106 | −55.444 | 1 | 58.43 N |
| ATOM | 3205 | C | LYS | B | 414 | 17.733 | 11.614 | −53.242 | 1 | 56.73 C |
| ATOM | 3206 | O | LYS | B | 414 | 18.757 | 11.3 | −53.857 | 1 | 56.85 O |
| ATOM | 3207 | N | SER | B | 415 | 17.104 | 12.775 | −53.443 | 1 | 57.25 N |
| ATOM | 3208 | CA | SER | B | 415 | 17.535 | 13.701 | −54.508 | 1 | 57.46 C |
| ATOM | 3209 | CB | SER | B | 415 | 16.674 | 14.962 | −54.545 | 1 | 57.38 C |
| ATOM | 3210 | OG | SER | B | 415 | 16.988 | 15.836 | −53.484 | 1 | 57.57 O |
| ATOM | 3211 | C | SER | B | 415 | 18.986 | 14.08 | −54.31 | 1 | 58.03 C |

TABLE V-continued

Atomic Structure Coordinates of Fc/YTE (SEQ ID NO: 11)

| Atom | A.A. | Type | | | X | Y | Z | Occ | B | |
|---|---|---|---|---|---|---|---|---|---|---|
| ATOM | 3212 | O | SER | B | 415 | 19.789 | 14.031 | −55.259 | 1 | 58.56 | O |
| ATOM | 3213 | N | ARG | B | 416 | 19.314 | 14.437 | −53.064 | 1 | 58.05 | N |
| ATOM | 3214 | CA | ARG | B | 416 | 20.689 | 14.738 | −52.675 | 1 | 57.74 | C |
| ATOM | 3215 | CB | ARG | B | 416 | 20.783 | 14.987 | −51.174 | 1 | 57.27 | C |
| ATOM | 3216 | CG | ARG | B | 416 | 20.222 | 16.329 | −50.745 | 1 | 55.7 | C |
| ATOM | 3217 | CD | ARG | B | 416 | 21.219 | 17.08 | −49.884 | 1 | 53.15 | C |
| ATOM | 3218 | NE | ARG | B | 416 | 21.151 | 16.736 | −48.468 | 1 | 52.29 | N |
| ATOM | 3219 | CZ | ARG | B | 416 | 22.16 | 16.895 | −47.605 | 1 | 51.84 | C |
| ATOM | 3220 | NH1 | ARG | B | 416 | 23.341 | 17.373 | −48.004 | 1 | 49.18 | N |
| ATOM | 3221 | NH2 | ARG | B | 416 | 21.987 | 16.561 | −46.326 | 1 | 52.03 | N |
| ATOM | 3222 | C | ARG | B | 416 | 21.65 | 13.626 | −53.064 | 1 | 57.81 | C |
| ATOM | 3223 | O | ARG | B | 416 | 22.743 | 13.884 | −53.535 | 1 | 58.66 | O |
| ATOM | 3224 | N | TRP | B | 417 | 21.246 | 12.39 | −52.862 | 1 | 57.82 | N |
| ATOM | 3225 | CA | TRP | B | 417 | 22.064 | 11.267 | −53.276 | 1 | 58.29 | C |
| ATOM | 3226 | CB | TRP | B | 417 | 21.548 | 9.949 | −52.653 | 1 | 57.92 | C |
| ATOM | 3227 | CG | TRP | B | 417 | 22.286 | 8.726 | −53.091 | 1 | 57.64 | C |
| ATOM | 3228 | CD1 | TRP | B | 417 | 21.83 | 7.755 | −53.928 | 1 | 59.28 | C |
| ATOM | 3229 | NE1 | TRP | B | 417 | 22.788 | 6.789 | −54.111 | 1 | 57.73 | N |
| ATOM | 3230 | CE2 | TRP | B | 417 | 23.898 | 7.13 | −53.386 | 1 | 56.67 | C |
| ATOM | 3231 | CD2 | TRP | B | 417 | 23.614 | 8.344 | −52.722 | 1 | 56.99 | C |
| ATOM | 3232 | CE3 | TRP | B | 417 | 24.592 | 8.909 | −51.896 | 1 | 56.8 | C |
| ATOM | 3233 | CZ3 | TRP | B | 417 | 25.806 | 8.253 | −51.755 | 1 | 56.25 | C |
| ATOM | 3234 | CH2 | TRP | B | 417 | 26.056 | 7.044 | −52.429 | 1 | 56.55 | C |
| ATOM | 3235 | CZ2 | TRP | B | 417 | 25.115 | 6.468 | −53.245 | 1 | 57.55 | C |
| ATOM | 3236 | C | TRP | B | 417 | 22.07 | 11.213 | −54.804 | 1 | 58.76 | C |
| ATOM | 3237 | O | TRP | B | 417 | 23.14 | 11.079 | −55.399 | 1 | 58.94 | O |
| ATOM | 3238 | N | GLN | B | 418 | 20.888 | 11.334 | −55.431 | 1 | 59.38 | N |
| ATOM | 3239 | CA | GLN | B | 418 | 20.76 | 11.215 | −56.901 | 1 | 59.74 | C |
| ATOM | 3240 | CB | GLN | B | 418 | 19.282 | 11.25 | −57.357 | 1 | 59.83 | C |
| ATOM | 3241 | CG | GLN | B | 418 | 18.516 | 9.915 | −57.103 | 1 | 60.09 | C |
| ATOM | 3242 | CD | GLN | B | 418 | 16.99 | 9.956 | −57.403 | 1 | 60.45 | C |
| ATOM | 3243 | OE1 | GLN | B | 418 | 16.402 | 8.942 | −57.787 | 1 | 60.31 | O |
| ATOM | 3244 | NE2 | GLN | B | 418 | 16.355 | 11.115 | −57.203 | 1 | 62.14 | N |
| ATOM | 3245 | C | GLN | B | 418 | 21.624 | 12.274 | −57.615 | 1 | 59.99 | C |
| ATOM | 3246 | O | GLN | B | 418 | 22.383 | 11.946 | −58.531 | 1 | 60.24 | O |
| ATOM | 3247 | N | GLN | B | 419 | 21.564 | 13.511 | −57.132 | 1 | 59.85 | N |
| ATOM | 3248 | CA | GLN | B | 419 | 22.366 | 14.612 | −57.661 | 1 | 60.12 | C |
| ATOM | 3249 | CB | GLN | B | 419 | 21.855 | 15.931 | −57.055 | 1 | 60.47 | C |
| ATOM | 3250 | CG | GLN | B | 419 | 20.48 | 16.337 | −57.569 | 1 | 61.32 | C |
| ATOM | 3251 | CD | GLN | B | 419 | 19.918 | 17.556 | −56.857 | 1 | 61.73 | C |
| ATOM | 3252 | OE1 | GLN | B | 419 | 20.63 | 18.239 | −56.113 | 1 | 64.18 | O |
| ATOM | 3253 | NE2 | GLN | B | 419 | 18.629 | 17.839 | −57.084 | 1 | 63.3 | N |
| ATOM | 3254 | C | GLN | B | 419 | 23.91 | 14.552 | −57.466 | 1 | 60.07 | C |
| ATOM | 3255 | O | GLN | B | 419 | 24.598 | 15.548 | −57.737 | 1 | 60.55 | O |
| ATOM | 3256 | N | GLY | B | 420 | 24.465 | 13.447 | −56.969 | 1 | 59.44 | N |
| ATOM | 3257 | CA | GLY | B | 420 | 25.93 | 13.285 | −56.904 | 1 | 58.53 | C |
| ATOM | 3258 | C | GLY | B | 420 | 26.721 | 13.925 | −55.758 | 1 | 57.99 | C |
| ATOM | 3259 | O | GLY | B | 420 | 27.94 | 13.746 | −55.697 | 1 | 57.85 | O |
| ATOM | 3260 | N | ASN | B | 421 | 26.056 | 14.662 | −54.858 | 1 | 57.26 | N |
| ATOM | 3261 | CA | ASN | B | 421 | 26.696 | 15.209 | −53.636 | 1 | 56.4 | C |
| ATOM | 3262 | CB | ASN | B | 421 | 25.644 | 15.718 | −52.636 | 1 | 56.77 | C |
| ATOM | 3263 | CG | ASN | B | 421 | 24.918 | 16.991 | −53.104 | 1 | 57.57 | C |
| ATOM | 3264 | OD1 | ASN | B | 421 | 23.692 | 16.992 | −53.27 | 1 | 58.81 | O |
| ATOM | 3265 | ND2 | ASN | B | 421 | 25.669 | 18.079 | −53.288 | 1 | 57.51 | N |
| ATOM | 3266 | C | ASN | B | 421 | 27.561 | 14.178 | −52.91 | 1 | 55.47 | C |
| ATOM | 3267 | O | ASN | B | 421 | 27.197 | 13.014 | −52.811 | 1 | 55.4 | O |
| ATOM | 3268 | N | VAL | B | 422 | 28.7 | 14.619 | −52.391 | 1 | 54.75 | N |
| ATOM | 3269 | CA | VAL | B | 422 | 29.666 | 13.731 | −51.74 | 1 | 53.86 | C |
| ATOM | 3270 | CB | VAL | B | 422 | 31.121 | 14.107 | −52.128 | 1 | 53.87 | C |
| ATOM | 3271 | CG1 | VAL | B | 422 | 32.134 | 13.319 | −51.287 | 1 | 52.43 | C |
| ATOM | 3272 | CG2 | VAL | B | 422 | 31.333 | 13.852 | −53.65 | 1 | 52.98 | C |
| ATOM | 3273 | C | VAL | B | 422 | 29.498 | 13.788 | −50.223 | 1 | 53.22 | C |
| ATOM | 3274 | O | VAL | B | 422 | 29.547 | 14.869 | −49.634 | 1 | 53.39 | O |
| ATOM | 3275 | N | PHE | B | 423 | 29.269 | 12.622 | −49.607 | 1 | 52.32 | N |
| ATOM | 3276 | CA | PHE | B | 423 | 29.114 | 12.519 | −48.148 | 1 | 51.43 | C |
| ATOM | 3277 | CB | PHE | B | 423 | 27.809 | 11.816 | −47.78 | 1 | 50.94 | C |
| ATOM | 3278 | CG | PHE | B | 423 | 26.597 | 12.579 | −48.17 | 1 | 49.68 | C |
| ATOM | 3279 | CD1 | PHE | B | 423 | 26.092 | 12.481 | −49.463 | 1 | 48.82 | C |
| ATOM | 3280 | CE1 | PHE | B | 423 | 24.957 | 13.193 | −49.854 | 1 | 48.88 | C |
| ATOM | 3281 | CZ | PHE | B | 423 | 24.332 | 14.027 | −48.958 | 1 | 50.21 | C |
| ATOM | 3282 | CE2 | PHE | B | 423 | 24.835 | 14.142 | −47.656 | 1 | 50.91 | C |
| ATOM | 3283 | CD2 | PHE | B | 423 | 25.967 | 13.406 | −47.271 | 1 | 49.67 | C |
| ATOM | 3284 | C | PHE | B | 423 | 30.292 | 11.793 | −47.522 | 1 | 51.15 | C |
| ATOM | 3285 | O | PHE | B | 423 | 30.881 | 10.862 | −48.134 | 1 | 51.19 | O |
| ATOM | 3286 | N | SER | B | 424 | 30.619 | 12.193 | −46.292 | 1 | 50.47 | N |
| ATOM | 3287 | CA | SER | B | 424 | 31.812 | 11.671 | −45.658 | 1 | 50.15 | C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 3288 | CB | SER | B | 424 | 32.928 | 12.714 | −45.698 | 1 | 50.56 C |
| ATOM | 3289 | OG | SER | B | 424 | 33.552 | 12.685 | −46.972 | 1 | 52.25 O |
| ATOM | 3290 | C | SER | B | 424 | 31.602 | 11.19 | −44.239 | 1 | 49.67 C |
| ATOM | 3291 | O | SER | B | 424 | 30.932 | 11.86 | −43.426 | 1 | 49.31 O |
| ATOM | 3292 | N | CYS | B | 425 | 32.217 | 10.032 | −43.972 | 1 | 48.76 N |
| ATOM | 3293 | CA | CYS | B | 425 | 32.212 | 9.37 | −42.678 | 1 | 48.15 C |
| ATOM | 3294 | CB | CYS | B | 425 | 32.005 | 7.855 | −42.864 | 1 | 48.32 C |
| ATOM | 3295 | SG | CYS | B | 425 | 31.756 | 6.95 | −41.323 | 1 | 48.71 S |
| ATOM | 3296 | C | CYS | B | 425 | 33.532 | 9.629 | −41.965 | 1 | 47.62 C |
| ATOM | 3297 | O | CYS | B | 425 | 34.583 | 9.181 | −42.425 | 1 | 47.41 O |
| ATOM | 3298 | N | SER | B | 426 | 33.461 | 10.331 | −40.834 | 1 | 47.04 N |
| ATOM | 3299 | CA | SER | B | 426 | 34.627 | 10.706 | −40.046 | 1 | 46.75 C |
| ATOM | 3300 | CB | SER | B | 426 | 34.525 | 12.175 | −39.587 | 1 | 46.81 C |
| ATOM | 3301 | OG | SER | B | 426 | 34.142 | 13.019 | −40.662 | 1 | 48.7 O |
| ATOM | 3302 | C | SER | B | 426 | 34.734 | 9.814 | −38.815 | 1 | 46.07 C |
| ATOM | 3303 | O | SER | B | 426 | 33.862 | 9.866 | −37.941 | 1 | 45.92 O |
| ATOM | 3304 | N | VAL | B | 427 | 35.81 | 9.025 | −38.744 | 1 | 45.32 N |
| ATOM | 3305 | CA | VAL | B | 427 | 36.052 | 8.107 | −37.635 | 1 | 45.01 C |
| ATOM | 3306 | CB | VAL | B | 427 | 36.219 | 6.684 | −38.156 | 1 | 45.04 C |
| ATOM | 3307 | CG1 | VAL | B | 427 | 36.22 | 5.651 | −36.998 | 1 | 45.52 C |
| ATOM | 3308 | CG2 | VAL | B | 427 | 35.128 | 6.361 | −39.178 | 1 | 45.03 C |
| ATOM | 3309 | C | VAL | B | 427 | 37.296 | 8.5 | −36.809 | 1 | 44.55 C |
| ATOM | 3310 | O | VAL | B | 427 | 38.399 | 8.679 | −37.345 | 1 | 43.96 O |
| ATOM | 3311 | N | MET | B | 428 | 37.103 | 8.595 | −35.498 | 1 | 44.4 N |
| ATOM | 3312 | CA | MET | B | 428 | 38.117 | 9.093 | −34.579 | 1 | 44.81 C |
| ATOM | 3313 | CB | MET | B | 428 | 37.619 | 10.342 | −33.845 | 1 | 45.07 C |
| ATOM | 3314 | CG | MET | B | 428 | 37.302 | 11.549 | −34.748 | 1 | 46.33 C |
| ATOM | 3315 | SD | MET | B | 428 | 36.012 | 12.643 | −34.094 | 1 | 46.9 S |
| ATOM | 3316 | CE | MET | B | 428 | 34.788 | 12.479 | −35.407 | 1 | 47.87 C |
| ATOM | 3317 | C | MET | B | 428 | 38.469 | 8.022 | −33.555 | 1 | 44.56 C |
| ATOM | 3318 | O | MET | B | 428 | 37.68 | 7.727 | −32.669 | 1 | 44.14 O |
| ATOM | 3319 | N | HIS | B | 429 | 39.675 | 7.469 | −33.675 | 1 | 44.47 N |
| ATOM | 3320 | CA | HIS | B | 429 | 40.15 | 6.399 | −32.786 | 1 | 44.47 C |
| ATOM | 3321 | CB | HIS | B | 429 | 39.839 | 5.025 | −33.412 | 1 | 44.06 C |
| ATOM | 3322 | CG | HIS | B | 429 | 40.203 | 3.864 | −32.549 | 1 | 43.91 C |
| ATOM | 3323 | ND1 | HIS | B | 429 | 39.359 | 3.356 | −31.582 | 1 | 44.28 N |
| ATOM | 3324 | CE1 | HIS | B | 429 | 39.936 | 2.328 | −30.989 | 1 | 42.95 C |
| ATOM | 3325 | NE2 | HIS | B | 429 | 41.127 | 2.153 | −31.528 | 1 | 43.81 N |
| ATOM | 3326 | CD2 | HIS | B | 429 | 41.31 | 3.094 | −32.518 | 1 | 43.72 C |
| ATOM | 3327 | C | HIS | B | 429 | 41.67 | 6.53 | −32.518 | 1 | 44.49 C |
| ATOM | 3328 | O | HIS | B | 429 | 42.459 | 6.897 | −33.417 | 1 | 44 O |
| ATOM | 3329 | N | GLU | B | 430 | 42.042 | 6.215 | −31.28 | 1 | 44.31 N |
| ATOM | 3330 | CA | GLU | B | 430 | 43.433 | 6.127 | −30.827 | 1 | 44.52 C |
| ATOM | 3331 | CB | GLU | B | 430 | 43.53 | 5.211 | −29.595 | 1 | 44.34 C |
| ATOM | 3332 | CG | GLU | B | 430 | 44.962 | 5.115 | −29.065 | 1 | 45.18 C |
| ATOM | 3333 | CD | GLU | B | 430 | 45.077 | 4.346 | −27.773 | 1 | 44.89 C |
| ATOM | 3334 | OE1 | GLU | B | 430 | 44.046 | 3.866 | −27.252 | 1 | 41.91 O |
| ATOM | 3335 | OE2 | GLU | B | 430 | 46.225 | 4.244 | −27.289 | 1 | 48.19 O |
| ATOM | 3336 | C | GLU | B | 430 | 44.446 | 5.6 | −31.848 | 1 | 44.19 C |
| ATOM | 3337 | O | GLU | B | 430 | 45.493 | 6.162 | −32.023 | 1 | 43.31 O |
| ATOM | 3338 | N | ALA | B | 431 | 44.11 | 4.497 | −32.487 | 1 | 44.75 N |
| ATOM | 3339 | CA | ALA | B | 431 | 45.041 | 3.686 | −33.226 | 1 | 45.41 C |
| ATOM | 3340 | CB | ALA | B | 431 | 44.654 | 2.228 | −33.064 | 1 | 44.41 C |
| ATOM | 3341 | C | ALA | B | 431 | 45.088 | 4.099 | −34.711 | 1 | 46.53 C |
| ATOM | 3342 | O | ALA | B | 431 | 45.713 | 3.417 | −35.542 | 1 | 47.62 O |
| ATOM | 3343 | N | LEU | B | 432 | 44.438 | 5.213 | −35.038 | 1 | 47.21 N |
| ATOM | 3344 | CA | LEU | B | 432 | 44.539 | 5.818 | −36.367 | 1 | 47.74 C |
| ATOM | 3345 | CB | LEU | B | 432 | 43.207 | 6.468 | −36.732 | 1 | 47.75 C |
| ATOM | 3346 | CG | LEU | B | 432 | 42.065 | 5.503 | −37.048 | 1 | 48.04 C |
| ATOM | 3347 | CD1 | LEU | B | 432 | 40.725 | 6.237 | −36.999 | 1 | 47.05 C |
| ATOM | 3348 | CD2 | LEU | B | 432 | 42.299 | 4.787 | −38.42 | 1 | 47.32 C |
| ATOM | 3349 | C | LEU | B | 432 | 45.651 | 6.891 | −36.44 | 1 | 48.3 C |
| ATOM | 3350 | O | LEU | B | 432 | 45.937 | 7.586 | −35.47 | 1 | 48.35 O |
| ATOM | 3351 | N | HIS | B | 433 | 46.266 | 7.027 | −37.606 | 1 | 49.31 N |
| ATOM | 3352 | CA | HIS | B | 433 | 47.218 | 8.091 | −37.829 | 1 | 49.28 C |
| ATOM | 3353 | CB | HIS | B | 433 | 47.851 | 8.019 | −39.216 | 1 | 49.65 C |
| ATOM | 3354 | CG | HIS | B | 433 | 48.92 | 9.044 | −39.423 | 1 | 51.03 C |
| ATOM | 3355 | ND1 | HIS | B | 433 | 50.084 | 9.06 | −38.678 | 1 | 52.81 N |
| ATOM | 3356 | CE1 | HIS | B | 433 | 50.822 | 10.096 | −39.05 | 1 | 53.59 C |
| ATOM | 3357 | NE2 | HIS | B | 433 | 50.185 | 10.744 | −40.013 | 1 | 52.77 N |
| ATOM | 3358 | CD2 | HIS | B | 433 | 48.987 | 10.115 | −40.258 | 1 | 52.59 C |
| ATOM | 3359 | C | HIS | B | 433 | 46.489 | 9.415 | −37.65 | 1 | 49.61 C |
| ATOM | 3360 | O | HIS | B | 433 | 45.437 | 9.646 | −38.247 | 1 | 49.99 O |
| ATOM | 3361 | N | ASN | B | 434 | 47.06 | 10.265 | −36.801 | 1 | 49.58 N |
| ATOM | 3362 | CA | ASN | B | 434 | 46.431 | 11.51 | −36.345 | 1 | 48.85 C |
| ATOM | 3363 | CB | ASN | B | 434 | 46.369 | 12.575 | −37.45 | 1 | 49.24 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 3364 | CG | ASN | B | 434 | 47.738 | 12.973 | −37.983 | 1 | 49.93 C |
| ATOM | 3365 | OD1 | ASN | B | 434 | 47.921 | 13.082 | −39.205 | 1 | 52.92 O |
| ATOM | 3366 | ND2 | ASN | B | 434 | 48.683 | 13.232 | −37.092 | 1 | 48.59 N |
| ATOM | 3367 | C | ASN | B | 434 | 45.047 | 11.283 | −35.764 | 1 | 48.17 C |
| ATOM | 3368 | O | ASN | B | 434 | 44.215 | 12.177 | −35.792 | 1 | 48.03 O |
| ATOM | 3369 | N | HIS | B | 435 | 44.811 | 10.108 | −35.194 | 1 | 47.34 N |
| ATOM | 3370 | CA | HIS | B | 435 | 43.558 | 9.846 | −34.511 | 1 | 46.97 C |
| ATOM | 3371 | CB | HIS | B | 435 | 43.502 | 10.688 | −33.234 | 1 | 46.56 C |
| ATOM | 3372 | CG | HIS | B | 435 | 44.486 | 10.276 | −32.197 | 1 | 46.37 C |
| ATOM | 3373 | ND1 | HIS | B | 435 | 44.656 | 10.968 | −31.017 | 1 | 46.43 N |
| ATOM | 3374 | CE1 | HIS | B | 435 | 45.568 | 10.357 | −30.284 | 1 | 45.23 C |
| ATOM | 3375 | NE2 | HIS | B | 435 | 45.999 | 9.299 | −30.948 | 1 | 45.02 N |
| ATOM | 3376 | CD2 | HIS | B | 435 | 45.345 | 9.231 | −32.15 | 1 | 45.55 C |
| ATOM | 3377 | C | HIS | B | 435 | 42.297 | 10.132 | −35.35 | 1 | 46.9 C |
| ATOM | 3378 | O | HIS | B | 435 | 41.238 | 10.432 | −34.777 | 1 | 47.11 O |
| ATOM | 3379 | N | TYR | B | 436 | 42.4 | 10.022 | −36.679 | 1 | 46.65 N |
| ATOM | 3380 | CA | TYR | B | 436 | 41.359 | 10.496 | −37.589 | 1 | 46.91 C |
| ATOM | 3381 | CB | TYR | B | 436 | 41.527 | 11.976 | −37.854 | 1 | 47.28 C |
| ATOM | 3382 | CG | TYR | B | 436 | 40.345 | 12.641 | −38.521 | 1 | 47.04 C |
| ATOM | 3383 | CD1 | TYR | B | 436 | 40.308 | 12.884 | −39.905 | 1 | 46.84 C |
| ATOM | 3384 | CE1 | TYR | B | 436 | 39.185 | 13.518 | −40.503 | 1 | 47.16 C |
| ATOM | 3385 | CZ | TYR | B | 436 | 38.13 | 13.909 | −39.693 | 1 | 48.11 C |
| ATOM | 3386 | OH | TYR | B | 436 | 36.989 | 14.524 | −40.16 | 1 | 48.14 O |
| ATOM | 3387 | CE2 | TYR | B | 436 | 38.178 | 13.686 | −38.331 | 1 | 48.44 C |
| ATOM | 3388 | CD2 | TYR | B | 436 | 39.272 | 13.058 | −37.761 | 1 | 47.72 C |
| ATOM | 3389 | C | TYR | B | 436 | 41.44 | 9.827 | −38.936 | 1 | 47.89 C |
| ATOM | 3390 | O | TYR | B | 436 | 42.535 | 9.616 | −39.473 | 1 | 48.27 O |
| ATOM | 3391 | N | THR | B | 437 | 40.28 | 9.492 | −39.481 | 1 | 48.44 N |
| ATOM | 3392 | CA | THR | B | 437 | 40.178 | 9.125 | −40.88 | 1 | 49.1 C |
| ATOM | 3393 | CB | THR | B | 437 | 40.465 | 7.65 | −41.124 | 1 | 48.98 C |
| ATOM | 3394 | OG1 | THR | B | 437 | 40.793 | 7.471 | −42.498 | 1 | 48.96 O |
| ATOM | 3395 | CG2 | THR | B | 437 | 39.232 | 6.761 | −40.772 | 1 | 48.24 C |
| ATOM | 3396 | C | THR | B | 437 | 38.777 | 9.462 | −41.349 | 1 | 49.52 O |
| ATOM | 3397 | O | THR | B | 437 | 37.85 | 9.567 | −40.536 | 1 | 49.25 O |
| ATOM | 3398 | N | GLN | B | 438 | 38.645 | 9.632 | −42.657 | 1 | 50.33 N |
| ATOM | 3399 | CA | GLN | B | 438 | 37.453 | 10.188 | −43.264 | 1 | 51.11 C |
| ATOM | 3400 | CB | GLN | B | 438 | 37.689 | 11.664 | −43.582 | 1 | 51.22 C |
| ATOM | 3401 | CG | GLN | B | 438 | 36.456 | 12.495 | −44.05 | 1 | 51.82 C |
| ATOM | 3402 | CD | GLN | B | 438 | 36.747 | 14.041 | −44.181 | 1 | 52.99 C |
| ATOM | 3403 | OE1 | GLN | B | 438 | 36.157 | 14.736 | −45.029 | 1 | 54.56 O |
| ATOM | 3404 | NE2 | GLN | B | 438 | 37.67 | 14.556 | −43.346 | 1 | 54.31 N |
| ATOM | 3405 | C | GLN | B | 438 | 37.278 | 9.384 | −44.526 | 1 | 51.79 C |
| ATOM | 3406 | O | GLN | B | 438 | 38.228 | 9.23 | −45297 | 1 | 51.71 O |
| ATOM | 3407 | N | LYS | B | 439 | 36.1 | 8.807 | −44.723 | 1 | 52.44 N |
| ATOM | 3408 | CA | LYS | B | 439 | 35.855 | 8.03 | −45.938 | 1 | 52.86 C |
| ATOM | 3409 | CB | LYS | B | 439 | 35.672 | 6.538 | −45.65 | 1 | 52.99 C |
| ATOM | 3410 | CG | LYS | B | 439 | 36.925 | 5.838 | −45.182 | 1 | 53.42 C |
| ATOM | 3411 | CD | LYS | 8 | 439 | 37.842 | 5.458 | −46.305 | 1 | 53.77 C |
| ATOM | 3412 | CE | LYS | B | 439 | 39.057 | 4.681 | −45.776 | 1 | 54.13 C |
| ATOM | 3413 | NZ | LYS | B | 439 | 40.12 | 4.588 | −46.821 | 1 | 54.07 N |
| ATOM | 3414 | C | LYS | B | 439 | 34.631 | 8.579 | −46.637 | 1 | 53.7 C |
| ATOM | 3415 | O | LYS | B | 439 | 33.604 | 8.852 | −46.009 | 1 | 52.98 O |
| ATOM | 3416 | N | SER | B | 440 | 34.759 | 8.72 | −47.949 | 1 | 54.92 N |
| ATOM | 3417 | CA | SER | B | 440 | 33.765 | 9.406 | −48.738 | 1 | 56.11 C |
| ATOM | 3418 | CB | SER | B | 440 | 34.427 | 10.521 | −49.506 | 1 | 55.75 C |
| ATOM | 3419 | OG | SER | B | 440 | 35.1 | 11.33 | −48.555 | 1 | 55.83 O |
| ATOM | 3420 | C | SER | B | 440 | 33 | 8.469 | −49.637 | 1 | 56.63 C |
| ATOM | 3421 | O | SER | B | 440 | 33.487 | 7.412 | −50.02 | 1 | 56.61 O |
| ATOM | 3422 | N | LEU | B | 441 | 31.76 | 8.864 | −49.899 | 1 | 57.93 N |
| ATOM | 3423 | CA | LEU | B | 441 | 30.782 | 8.066 | −50.622 | 1 | 58.78 C |
| ATOM | 3424 | CB | LEU | B | 441 | 29.896 | 7.335 | −49.61 | 1 | 58.67 C |
| ATOM | 3425 | CG | LEU | B | 441 | 28.587 | 6.641 | −49.998 | 1 | 58.04 C |
| ATOM | 3426 | CD1 | LEU | B | 441 | 28.809 | 5.219 | −50.471 | 1 | 57.15 C |
| ATOM | 3427 | CD2 | LEU | B | 441 | 27.658 | 6.655 | −48.793 | 1 | 58.21 C |
| ATOM | 3428 | C | LEU | B | 441 | 29.976 | 9.046 | −51.466 | 1 | 59.47 C |
| ATOM | 3429 | O | LEU | B | 441 | 29.658 | 10.132 | −51.004 | 1 | 58.92 O |
| ATOM | 3430 | N | SER | B | 442 | 29.709 | 8.671 | −52.71 | 1 | 61.05 N |
| ATOM | 3431 | CA | SER | B | 442 | 28.88 | 9.464 | −53.612 | 1 | 62.62 C |
| ATOM | 3432 | CB | SER | B | 442 | 29.686 | 10.603 | −54.237 | 1 | 62.46 C |
| ATOM | 3433 | OG | SER | B | 442 | 30.123 | 10.264 | −55.539 | 1 | 61.79 O |
| ATOM | 3434 | C | SER | B | 442 | 28.295 | 8.572 | −54.71 | 1 | 64.17 C |
| ATOM | 3435 | O | SER | B | 442 | 28.732 | 7.436 | −54.896 | 1 | 64.32 O |
| ATOM | 3436 | N | LEU | B | 443 | 27.325 | 9.09 | −55.456 | 1 | 66.21 N |
| ATOM | 3437 | CA | LEU | B | 443 | 26.663 | 8.279 | −56.486 | 1 | 67.17 C |
| ATOM | 3438 | CB | LEU | B | 443 | 25.49 | 9.039 | −57.098 | 1 | 67.46 C |
| ATOM | 3439 | CG | LEU | B | 443 | 24.495 | 8.245 | −57.954 | 1 | 67.46 C |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 3440 | CD1 | LEU | B | 443 | 23.893 | 7.038 | −57.21 | 1 | 68.17 C |
| ATOM | 3441 | CD2 | LEU | B | 443 | 23.404 | 9.199 | −58.439 | 1 | 67.51 C |
| ATOM | 3442 | C | LEU | B | 443 | 27.646 | 7.817 | −57.565 | 1 | 68.39 C |
| ATOM | 3443 | O | LEU | B | 443 | 28.555 | 8.553 | −57.952 | 1 | 68.65 O |
| ATOM | 3444 | N | SER | B | 444 | 27.47 | 6.584 | −58.036 | 1 | 69.66 N |
| ATOM | 3445 | CA | SER | B | 444 | 28.446 | 5.976 | −58.952 | 1 | 70.08 C |
| ATOM | 3446 | CB | SER | B | 444 | 28.318 | 4.438 | −58.987 | 1 | 70.59 C |
| ATOM | 3447 | OG | SER | B | 444 | 29.362 | 3.821 | −58.233 | 1 | 70.36 O |
| ATOM | 3448 | C | SER | B | 444 | 28.35 | 6.57 | −60.357 | 1 | 70.97 C |
| ATOM | 3449 | O | SER | B | 444 | 29.232 | 7.342 | −60.761 | 1 | 71.8 O |
| ATOM | 3450 | C1 | NAG | D | 1 | 16.343 | 10.156 | −7.176 | 1 | 108.48 C |
| ATOM | 3451 | C2 | NAG | D | 1 | 16.371 | 8.663 | −7.495 | 1 | 108.81 C |
| ATOM | 3452 | N2 | NAG | D | 1 | 15.701 | 7.85 | −6.486 | 1 | 108.41 N |
| ATOM | 3453 | C7 | NAG | D | 1 | 14.521 | 7.272 | −6.743 | 1 | 107.79 C |
| ATOM | 3454 | O7 | NAG | D | 1 | 13.463 | 7.903 | −6.765 | 1 | 107.17 O |
| ATOM | 3455 | C8 | NAG | D | 1 | 14.522 | 5.796 | −7.024 | 1 | 107.11 C |
| ATOM | 3456 | C3 | NAG | D | 1 | 17.825 | 8.256 | −7.734 | 1 | 109.21 C |
| ATOM | 3457 | O3 | NAG | D | 1 | 17.913 | 6.866 | −7.962 | 1 | 109.04 O |
| ATOM | 3458 | C4 | NAG | D | 1 | 18.343 | 9.044 | −8.94 | 1 | 109.36 C |
| ATOM | 3459 | O4 | NAG | D | 1 | 19.732 | 8.851 | −9.169 | 1 | 107.86 O |
| ATOM | 3460 | C5 | NAG | D | 1 | 18.092 | 10.543 | −8.778 | 1 | 110.88 C |
| ATOM | 3461 | C6 | NAG | D | 1 | 18.458 | 11.259 | −10.084 | 1 | 112.82 C |
| ATOM | 3462 | O6 | NAG | D | 1 | 17.402 | 11.889 | −10.792 | 1 | 115.62 O |
| ATOM | 3463 | O5 | NAG | D | 1 | 16.762 | 10.827 | −8.355 | 1 | 109.74 O |
| ATOM | 3464 | C1 | NAG | D | 2 | 20.019 | 7.748 | −10.068 | 1 | 106.04 C |
| ATOM | 3465 | C2 | NAG | D | 2 | 21.008 | 8.157 | −11.171 | 1 | 105.12 C |
| ATOM | 3466 | N2 | NAG | D | 2 | 20.548 | 9.253 | −12.015 | 1 | 104.81 N |
| ATOM | 3467 | C7 | NAG | D | 2 | 21.363 | 10.246 | −12.398 | 1 | 104.29 C |
| ATOM | 3468 | O7 | NAG | D | 2 | 22.386 | 10.563 | −11.79 | 1 | 103.53 O |
| ATOM | 3469 | C8 | NAG | D | 2 | 20.968 | 10.99 | −13.642 | 1 | 103.63 C |
| ATOM | 3470 | C3 | NAG | D | 2 | 21.307 | 6.958 | −12.071 | 1 | 104.27 C |
| ATOM | 3471 | O3 | NAG | D | 2 | 22.312 | 7.297 | −13.007 | 1 | 104.47 O |
| ATOM | 3472 | C4 | NAG | D | 2 | 21.737 | 5.743 | −11.249 | 1 | 102.95 C |
| ATOM | 3473 | O4 | NAG | D | 2 | 21.759 | 4.604 | −12.08 | 1 | 100.26 O |
| ATOM | 3474 | C5 | NAG | D | 2 | 20.762 | 5.479 | −10.106 | 1 | 103.58 C |
| ATOM | 3475 | C6 | NAG | D | 2 | 21.269 | 4.373 | −9.19 | 1 | 103.23 C |
| ATOM | 3476 | O6 | NAG | D | 2 | 20.189 | 3.922 | −8.409 | 1 | 103.03 O |
| ATOM | 3477 | O5 | NAG | D | 2 | 20.558 | 6.654 | −9.343 | 1 | 105.07 O |
| ATOM | 3478 | C1 | BMA | D | 3 | 23.053 | 4.331 | −12.638 | 1 | 97.6 C |
| ATOM | 3479 | C2 | BMA | D | 3 | 23.172 | 2.829 | −12.809 | 1 | 96.88 C |
| ATOM | 3480 | O2 | BMA | D | 3 | 22.139 | 2.375 | −13.689 | 1 | 96.54 O |
| ATOM | 3481 | C3 | BMA | D | 3 | 24.529 | 2.478 | −13.393 | 1 | 96.21 C |
| ATOM | 3482 | O3 | BMA | D | 3 | 24.567 | 1.073 | −13.649 | 1 | 96.94 O |
| ATOM | 3483 | C4 | BMA | D | 3 | 24.752 | 3.245 | −14.69 | 1 | 94.95 C |
| ATOM | 3484 | O4 | BMA | D | 3 | 26.075 | 2.983 | −15.152 | 1 | 94.69 O |
| ATOM | 3485 | C5 | BMA | D | 3 | 24.547 | 4.737 | −14.458 | 1 | 93.98 C |
| ATOM | 3486 | C6 | BMA | D | 3 | 24.675 | 5.528 | −15.751 | 1 | 91.75 C |
| ATOM | 3487 | O6 | BMA | D | 3 | 24.576 | 6.943 | −15.489 | 1 | 88.63 O |
| ATOM | 3488 | O5 | BMA | D | 3 | 23.247 | 4.959 | −13.904 | 1 | 95.82 O |
| ATOM | 3489 | C1 | MAN | D | 4 | 25.602 | 0.418 | −12.898 | 1 | 97.16 C |
| ATOM | 3490 | C2 | MAN | D | 4 | 25.796 | −0.956 | −13.521 | 1 | 97.49 C |
| ATOM | 3491 | O2 | MAN | D | 4 | 26.919 | −1.569 | −12.923 | 1 | 98.3 O |
| ATOM | 3492 | C3 | MAN | D | 4 | 24.566 | −1.823 | −13.299 | 1 | 96.78 C |
| ATOM | 3493 | O3 | MAN | D | 4 | 24.799 | −3.121 | −13.782 | 1 | 96.2 O |
| ATOM | 3494 | C4 | MAN | D | 4 | 24.292 | −1.887 | −11.807 | 1 | 96.9 C |
| ATOM | 3495 | O4 | MAN | D | 4 | 23.161 | −2.699 | −11.575 | 1 | 96.95 O |
| ATOM | 3496 | C5 | MAN | D | 4 | 24.133 | −0.465 | −11.253 | 1 | 96.94 C |
| ATOM | 3497 | C6 | MAN | D | 4 | 23.853 | −0.454 | −9.751 | 1 | 96.68 C |
| ATOM | 3498 | O6 | MAN | D | 4 | 24.479 | 0.657 | −9.149 | 1 | 96.59 O |
| ATOM | 3499 | O5 | MAN | D | 4 | 25.316 | 0.274 | −11.52 | 1 | 97.03 O |
| ATOM | 3500 | C1 | NAG | D | 5 | 28.108 | −1.288 | −13.673 | 1 | 99.08 C |
| ATOM | 3501 | O2 | NAG | D | 5 | 29.286 | −1.812 | −12.87 | 1 | 99.18 C |
| ATOM | 3502 | N2 | NAG | D | 5 | 29.416 | −1.013 | −11.655 | 1 | 98.98 N |
| ATOM | 3503 | C7 | NAG | D | 5 | 29.077 | −1.436 | −10.434 | 1 | 98.47 C |
| ATOM | 3504 | O7 | NAG | D | 5 | 27.939 | −1.78 | −10.122 | 1 | 97.9 O |
| ATOM | 3505 | C8 | NAG | D | 5 | 30.174 | −1.449 | −9.408 | 1 | 98.47 C |
| ATOM | 3506 | C3 | NAG | D | 5 | 30.591 | −1.763 | −13.675 | 1 | 99.69 C |
| ATOM | 3507 | O3 | NAG | D | 5 | 31.356 | −2.905 | −13.341 | 1 | 100 O |
| ATOM | 3508 | C4 | NAG | D | 5 | 30.467 | −1.718 | −15.213 | 1 | 99.88 C |
| ATOM | 3509 | O4 | NAG | D | 5 | 31.401 | −0.785 | −15.713 | 1 | 100.13 O |
| ATOM | 3510 | C5 | NAG | D | 5 | 29.091 | −1.375 | −15.8 | 1 | 99.72 C |
| ATOM | 3511 | C6 | NAG | D | 5 | 28.892 | −1.964 | −17.204 | 1 | 99.65 C |
| ATOM | 3512 | O6 | NAG | D | 5 | 30.047 | −1.818 | −18.009 | 1 | 98.86 O |
| ATOM | 3513 | O5 | NAG | D | 5 | 28.077 | −1.872 | −14.958 | 1 | 99.47 O |
| ATOM | 3514 | C1 | MAN | D | 7 | 24.587 | 7.682 | −16.729 | 1 | 85.4 C |
| ATOM | 3515 | C2 | MAN | D | 7 | 24.643 | 9.176 | −16.399 | 1 | 83.69 C |

TABLE V-continued

Atomic Structure Coordinates of Fc/YTE (SEQ ID NO: 11)

| | Atom | A.A. | Type | | X | Y | Z | Occ | B | |
|---|---|---|---|---|---|---|---|---|---|---|
| ATOM | 3516 | O2 | MAN | D | 7 | 24.898 | 9.953 | −17.567 | 1 | 81.08 | O |
| ATOM | 3517 | C3 | MAN | D | 7 | 23.305 | 9.596 | −15.801 | 1 | 83.83 | C |
| ATOM | 3518 | O3 | MAN | D | 7 | 23.344 | 10.965 | −15.46 | 1 | 84.37 | O |
| ATOM | 3519 | C4 | MAN | D | 7 | 22.219 | 9.3 | −16.839 | 1 | 83.76 | C |
| ATOM | 3520 | O4 | MAN | D | 7 | 20.953 | 9.766 | −16.428 | 1 | 83.28 | O |
| ATOM | 3521 | C5 | MAN | D | 7 | 22.206 | 7.804 | −17.154 | 1 | 83.78 | C |
| ATOM | 3522 | C6 | MAN | D | 7 | 21.221 | 7.495 | −18.275 | 1 | 83.42 | C |
| ATOM | 3523 | O6 | MAN | D | 7 | 21.142 | 6.101 | −18.458 | 1 | 82.39 | O |
| ATOM | 3524 | O5 | MAN | D | 7 | 23.487 | 7.368 | −17.578 | 1 | 84.51 | O |
| ATOM | 3525 | C1 | NAG | D | 8 | 26.306 | 10.088 | −17.862 | 1 | 78.17 | C |
| ATOM | 3526 | C2 | NAG | D | 8 | 26.482 | 10.339 | −19.366 | 1 | 77.47 | C |
| ATOM | 3527 | N2 | NAG | D | 8 | 25.987 | 9.169 | −20.075 | 1 | 78.37 | N |
| ATOM | 3528 | C7 | NAG | D | 8 | 25.022 | 9.179 | −20.999 | 1 | 79.15 | C |
| ATOM | 3529 | O7 | NAG | D | 8 | 23.97 | 8.547 | −20.857 | 1 | 78.81 | O |
| ATOM | 3530 | C8 | NAG | D | 8 | 25.292 | 9.965 | −22.259 | 1 | 79.94 | C |
| ATOM | 3531 | C3 | NAG | D | 8 | 27.947 | 10.646 | −19.736 | 1 | 75.11 | C |
| ATOM | 3532 | O3 | NAG | D | 8 | 28.012 | 11.059 | −21.084 | 1 | 74.58 | O |
| ATOM | 3533 | C4 | NAG | D | 8 | 28.503 | 11.723 | −18.796 | 1 | 73.84 | C |
| ATOM | 3534 | O4 | NAG | D | 8 | 29.848 | 12.083 | −19.052 | 1 | 69.73 | O |
| ATOM | 3535 | C5 | NAG | D | 8 | 28.31 | 11.204 | −17.369 | 1 | 75.3 | C |
| ATOM | 3536 | C6 | NAG | D | 8 | 28.982 | 12.05 | −16.285 | 1 | 75.43 | C |
| ATOM | 3537 | O6 | NAG | D | 8 | 28.429 | 13.345 | −16.285 | 1 | 75.67 | O |
| ATOM | 3538 | O5 | NAG | D | 8 | 26.917 | 11.119 | −17.118 | 1 | 76.26 | O |
| ATOM | 3539 | C1 | FUC | D | 11 | 16.272 | 11.072 | −11.182 | 1 | 117.36 | C |
| ATOM | 3540 | C2 | FUC | D | 11 | 16.509 | 10.31 | −12.481 | 1 | 117.85 | C |
| ATOM | 3541 | O2 | FUC | D | 11 | 17.505 | 9.339 | −12.291 | 1 | 117.49 | O |
| ATOM | 3542 | C3 | FUC | O | 11 | 15.227 | 9.575 | −12.87 | 1 | 118.69 | C |
| ATOM | 3543 | O3 | FUC | D | 11 | 15.369 | 8.876 | −14.091 | 1 | 118.97 | O |
| ATOM | 3544 | C4 | FUC | D | 11 | 14.069 | 10.563 | −12.949 | 1 | 118.92 | C |
| ATOM | 3545 | O4 | FUC | D | 11 | 14.334 | 11.518 | −13.955 | 1 | 119.07 | O |
| ATOM | 3546 | C5 | FUC | D | 11 | 13.933 | 11.259 | −11.6 | 1 | 118.72 | C |
| ATOM | 3547 | C6 | FUC | D | 11 | 12.782 | 12.263 | −11.573 | 1 | 118.62 | C |
| ATOM | 3548 | O5 | FUC | D | 11 | 15.148 | 11.924 | −11.328 | 1 | 118.2 | O |
| ATOM | 3549 | OW | HOH | W | 1 | 14.816 | −13.97 | −29.756 | 1 | 53.6 | O |
| ATOM | 3550 | OW | HOH | W | 2 | 10.753 | −17.126 | −24.181 | 1 | 39.98 | O |
| ATOM | 3551 | OW | HOH | W | 3 | −2.469 | −17.274 | −28.224 | 1 | 64.47 | O |
| ATOM | 3552 | OW | HOH | W | 4 | 11.67 | −4.259 | −17.645 | 1 | 59.92 | O |
| ATOM | 3553 | OW | HOH | W | 5 | 7.035 | −3.289 | −21.146 | 1 | 61.29 | O |
| ATOM | 3554 | OW | HOH | W | 6 | 15.037 | −7.228 | −30.234 | 1 | 43.98 | O |
| ATOM | 3555 | OW | HOH | W | 7 | 4.922 | 3.173 | −33.426 | 1 | 45.24 | O |
| ATOM | 3556 | OW | HOH | W | 8 | 13.157 | 1.662 | −45.482 | 1 | 36.43 | O |
| ATOM | 3557 | OW | HOH | W | 9 | 28.971 | −5.064 | −46.169 | 1 | 45.09 | O |
| ATOM | 3558 | OW | HOH | W | 10 | 18.494 | −12.652 | −32.901 | 1 | 44.65 | O |
| ATOM | 3559 | OW | HOH | W | 11 | 21.337 | −11.846 | −34.652 | 1 | 45.66 | O |
| ATOM | 3560 | OW | HOH | W | 12 | 25.361 | −2.162 | −26.939 | 1 | 41.07 | O |
| ATOM | 3561 | OW | HOH | W | 13 | 21.473 | 0.443 | −29.098 | 1 | 33.65 | O |
| ATOM | 3562 | OW | HOH | W | 14 | 10.164 | 5.199 | −29.847 | 1 | 37.84 | O |
| ATOM | 3563 | OW | HOH | W | 15 | 11.232 | 7.819 | −28.608 | 1 | 56.47 | O |
| ATOM | 3564 | OW | HOH | W | 16 | 30.469 | −10.847 | −38.536 | 1 | 50.88 | O |
| ATOM | 3565 | OW | HOH | W | 17 | 8.153 | −8.676 | −32.937 | 1 | 40.03 | O |
| ATOM | 3566 | OW | HOH | W | 18 | 0.919 | −12.821 | −39.773 | 1 | 56.71 | O |
| ATOM | 3567 | OW | HOH | W | 19 | 31.666 | 21.776 | −3.605 | 1 | 61.81 | O |
| ATOM | 3568 | OW | HOH | W | 20 | 48.818 | 14.014 | −22.677 | 1 | 54.71 | O |
| ATOM | 3569 | OW | HOH | W | 21 | 26.287 | −0.315 | −7.443 | 1 | 78.2 | O |
| ATOM | 3570 | OW | HOH | W | 22 | 40.802 | −3.65 | −19.69 | 1 | 47.53 | O |
| ATOM | 3571 | OW | HOH | W | 23 | 42.014 | −7.961 | −30.809 | 1 | 55.35 | O |
| ATOM | 3572 | OW | HOH | W | 24 | 42.014 | −3.847 | −37.611 | 1 | 47.47 | O |
| ATOM | 3573 | OW | HOH | W | 25 | 39.909 | 1.613 | −43.663 | 1 | 59.8 | O |
| ATOM | 3574 | OW | HOH | W | 26 | 23.295 | 2.05 | −47.13 | 1 | 41.71 | O |
| ATOM | 3575 | OW | HOH | W | 27 | 21.896 | −3.378 | −52.758 | 1 | 56.7 | O |
| ATOM | 3576 | OW | HOH | W | 28 | 15.614 | −4.196 | −55.883 | 1 | 57.41 | O |
| ATOM | 3577 | OW | HOH | W | 29 | 20.409 | 1.067 | −47.649 | 1 | 51.29 | O |
| ATOM | 3578 | OW | HOH | W | 30 | 17.908 | 5.693 | −43.023 | 1 | 39.09 | O |
| ATOM | 3579 | OW | HOH | W | 31 | 32.817 | 4.278 | −28.114 | 1 | 41.49 | O |
| ATOM | 3580 | OW | HOH | W | 32 | 39.213 | 7.54 | −26.92 | 1 | 42.19 | O |
| ATOM | 3581 | OW | HOH | W | 33 | 33.219 | 19.128 | −40.673 | 1 | 48.98 | O |
| ATOM | 3582 | OW | HOH | W | 34 | 23.478 | 4.478 | −30.305 | 1 | 31.17 | O |
| ATOM | 3583 | OW | HOH | W | 35 | 29.827 | −1.928 | −26.324 | 1 | 45.84 | O |
| ATOM | 3584 | OW | HOH | W | 36 | 38.414 | −7.858 | −26.061 | 1 | 39.91 | O |
| ATOM | 3585 | OW | HOH | W | 37 | 20.143 | 19.728 | −45.345 | 1 | 66.79 | O |
| ATOM | 3586 | OW | HOH | W | 38 | 27.164 | 20.197 | −57.878 | 1 | 67.05 | O |
| ATOM | 3587 | OW | HOH | W | 39 | 50.441 | 9.225 | −35.954 | 1 | 62.2 | O |
| ATOM | 3588 | OW | HOH | W | 40 | 48.823 | 10.133 | −32.666 | 1 | 46.95 | O |
| ATOM | 3589 | OW | HOH | W | 41 | 45.757 | 12.029 | −27.654 | 1 | 42.83 | O |
| ATOM | 3590 | OW | HOH | W | 42 | 43.645 | 8.718 | −42.072 | 1 | 51.11 | O |
| ATOM | 3591 | OW | HOH | W | 43 | 38.105 | −5.807 | −42.772 | 1 | 65.07 | O |

TABLE V-continued

Atomic Structure Coordinates of Fc/YTE (SEQ ID NO: 11)

| Atom | | A.A. | Type | | X | Y | Z | Occ | B | |
|---|---|---|---|---|---|---|---|---|---|---|
| ATOM | 3592 | OW | HOH | W | 44 | 38.528 | 11.692 | −50.854 | 1 | 55.16 O |
| ATOM | 3593 | OW | HOH | W | 45 | 3.576 | −19.778 | −35.64 | 1 | 48.53 O |
| ATOM | 3594 | OW | HOH | W | 46 | 5.808 | −21.917 | −37.326 | 1 | 52.75 O |
| ATOM | 3595 | OW | HOH | W | 47 | 6.079 | −21.239 | −39.51 | 1 | 48.05 O |
| ATOM | 3596 | OW | HOH | W | 48 | 10.349 | −21.529 | −37.691 | 1 | 56.87 O |
| ATOM | 3597 | OW | HOH | W | 49 | 10.835 | −20.741 | −40.267 | 1 | 52.49 O |
| ATOM | 3598 | OW | HOH | W | 50 | −4.09 | −20.285 | −14.059 | 1 | 55.15 O |
| ATOM | 3599 | OW | HOH | W | 51 | −0.358 | −15.622 | −21.694 | 1 | 46.2 O |
| ATOM | 3600 | OW | HOH | W | 52 | 10.95 | −9.297 | 9.159 | 1 | 62.7 O |
| ATOM | 3601 | OW | HOH | W | 53 | 21.505 | 3.014 | −28.64 | 1 | 32.02 O |
| ATOM | 3602 | OW | HOH | W | 54 | 21.901 | −1.081 | −26.855 | 1 | 44.31 O |
| ATOM | 3603 | OW | HOH | W | 55 | 19.07 | 6.947 | −31.087 | 1 | 46.22 O |
| ATOM | 3604 | OW | HOH | W | 56 | 35.867 | −16.856 | −59.509 | 1 | 73.09 O |
| ATOM | 3605 | OW | HOH | W | 57 | 27.407 | −20.912 | −58.016 | 1 | 60.78 O |
| ATOM | 3606 | OW | HOH | W | 58 | 25.981 | −22.938 | −56.629 | 1 | 57.77 O |
| ATOM | 3607 | OW | HOH | W | 59 | 28.512 | 3.614 | −4.818 | 1 | 64.54 O |
| ATOM | 3608 | OW | HOH | W | 60 | 51.974 | 8.012 | −28.189 | 1 | 56.95 O |
| ATOM | 3609 | OW | HOH | W | 61 | 36.799 | −1.425 | −24.893 | 1 | 51.12 O |
| ATOM | 3610 | OW | HOH | W | 62 | 33.014 | 5.693 | −23.377 | 1 | 55.83 O |
| ATOM | 3611 | OW | HOH | W | 63 | 29.991 | 7.437 | −26.373 | 1 | 58.66 O |
| ATOM | 3612 | OW | HOH | W | 64 | 29.337 | 17.764 | −51.744 | 1 | 56.83 O |
| ATOM | 3613 | OW | HOH | W | 65 | 23.046 | 11.096 | −33.762 | 1 | 46.89 O |
| ATOM | 3614 | OW | HOH | W | 66 | 23.85 | 7.757 | −32.616 | 1 | 51.69 O |
| ATOM | 3615 | OW | HOH | W | 67 | 12.901 | −5.079 | −25.459 | 1 | 53.38 O |
| ATOM | 3616 | OW | HOH | W | 68 | 17.517 | −15.7 | −33.094 | 1 | 48.94 O |

What is claimed is:

1. A method of identifying a compound that binds a human IgG or a human IgG Fc region, comprising
   (a) computationally screening a candidate compound for an ability to bind the human IgG or the human IgG Fc region using a three-dimensional structural representation of a human IgG Fc variant comprising SEQ ID NO:7 or SEQ ID NO:11, and having amino acid residue mutations M252Y, S254T and T256E, as numbered by the EU index as set forth in Kabat, wherein the three-dimensional structural representation of a human IgG Fc variant is generated from the coordinates provided in Table V;
   (b) contacting the compound with a human IgG or human IgG Fc region; and
   (c) determining the binding affinity of the compound for human IgG or human IgG Fc region.

2. The method of claim 1, wherein the three-dimensional structural representation of the human IgG Fc variant is visually inspected to identify a candidate compound.

3. The method of claim 1 further comprising synthesizing the candidate compound.

4. A method of identifying a modification of a human IgG Fc region that would result in an altered binding affinity of the human IgG Fc region for a neonatal Fc Receptor (FcRn), or an altered half-life of the human IgG Fc region in serum, compared to the comparable human IgG Fc region not comprising the modification, the method comprising:
   (a) computationally screening a modification of a human IgG Fc region for an altered binding affinity for a FcRn using a three-dimensional structural representation of a human IgG Fc variant comprising SEQ ID NO:7 or SEQ ID NO:11, and having amino acid residue mutations M252Y, S254T and T256E, as numbered by the EU index as set forth in Kabat, wherein the three-dimensional structural representation of a human IgG Fc variant is generated from the coordinates provided in Table V;
   (b) synthesizing a compound comprising the modified human IgG Fc region; and
   (c) determining the binding affinity of the synthesized compound for FcRn or the half-life of the compound in serum.

5. The method of claim 4, wherein the modification results in additional hydrogen bonds, increase in surface of contact, or both, with FcRn compared to the comparable human IgG Fc region not comprising the modification.

6. The method of claim 4, wherein the modification results in fewer hydrogen bonds, decrease in surface of contact, or both, with FcRn compared to the comparable human IgG Fc region not comprising the modification.

7. The method of claim 4, wherein the modification results in:
   (a) an additional hydrogen bond between the Oη atom of Y252 in the human IgG Fc variant and Oϵ1 or Oϵ2 atom of E133 in the human FcRn α chain than that between M252 in the wild type human IgG Fc region and Oϵ1 or Oϵ2 atom of E133 in the human FcRn α chain;
   (b) an additional hydrogen bond between the Oγ1 atom of T254 in the human IgG Fc variant and Oϵ1 or Oϵ2 atom of E133 in the human FcRn α chain than that between the Oγ1 atom of S254 in the wild type human IgG Fc region and Oϵ1 or Oϵ2 atom of E133 in the human FcRn α chain; or
   (c) an additional hydrogen bond between the Oϵ1 or Oϵ2 atom of E256 in the human IgG Fc variant and Q2/Oϵ1 or Q2/Nϵ2 in human FcRn β2 microglobulin than that between the Oϵ1 or Oϵ2 atom of T256 in the human wild type IgG Fc region and Q2/Oϵ1 or Q2/Nϵ2 in human FcRn β2 microglobulin.

8. The method of claim 4, wherein the modification results in an about 30 Å$^2$ increase in the surface of contact between the human IgG Fc variant and human FcRn α chain or about 20 Å$^2$ increase in the surface of contact between the human IgG Fc variant and human FcRn β2 microglobulin.

9. A method of designing a compound that binds a human IgG or a human IgG Fc region, comprising
  (a) computationally designing a synthesizable candidate compound for an ability to bind the human IgG or the human IgG Fc region using a three-dimensional structural representation of a human IgG Fc variant comprising SEQ ID NO:7 or SEQ ID NO:11, and having amino acid residue mutations M252Y, S254T and T256E, as numbered by the EU index as set forth in Kabat, wherein the three-dimensional structural representation of a human IgG Fc variant is generated from the coordinates provided in Table V;
  (b) synthesizing the compound;
  (c) contacting the compound with a human IgG or human IgG Fc region; and
  (d) determining the binding affinity of the compound for human IgG or human IgG Fc region.

10. A method of designing a modification of a human IgG Fc region that would result in an altered binding affinity of the human IgG Fc region for a neonatal Fc Receptor (FcRn), or an altered half-life of the human IgG Fc region in serum, compared to the comparable human IgG Fc region not comprising the modification, the method comprising:
  (a) computationally screening a modification of a human IgG Fc region for an altered binding affinity for a FcRn using a three-dimensional structural representation of a human IgG Fc variant comprising SEQ ID NO:7 or SEQ ID NO:11, and having amino acid residue mutations M252Y, S254T and T256E, as numbered by the EU index as set forth in Kabat, wherein the three-dimensional structural representation of a human IgG Fc variant is generated from the coordinates provided in Table V;
  (b) synthesizing a compound comprising the modified human IgG Fc region; and
  (c) determining the binding affinity of the compound for FcRn or the half-life of the compound in serum.

11. The method of claim 10, wherein the modification results in additional hydrogen bonds, increase in surface of contact, or both, with FcRn compared to the comparable human IgG Fc region not comprising the modification.

12. The method of claim 10, wherein the modification results in fewer hydrogen bonds, decrease in surface of contact, or both, with FcRn compared to the comparable human IgG Fc region not comprising the modification.

13. The method of claim 10, wherein the modification results in:
  (a) an additional hydrogen bond between the Oη atom of Y252 in the human IgG Fc variant and Oε1 or Oε2 atom of E133 in the human FcRn α chain than that between M252 in the wild type human IgG Fc region and Oε1 or Oε2 atom of E133 in the human FcRn α chain;
  (b) an additional hydrogen bond between the Oγ1 atom of T254 in the human IgG Fc variant and Oε1 or Oε2 atom of E133 in the human FcRn α chain than that between the Oγ1 atom of 5254 in the wild type human IgG Fc region and Oε1 or Oε2 atom of E133 in the human FcRn α chain; or
  (c) an additional hydrogen bond between the Oε1 or Oε2 atom of E256 in the human IgG Fc variant and Q2/Oε1 or Q2/Nε2 in human FcRn β2 microglobulin than that between the Oε1 or Oε2 atom of T256 in the human wild type IgG Fc region and Q2/Oε1 or Q2/Nε2 in human FcRn β2 microglobulin.

14. The method of claim 10, wherein the modification results in an about 30 Å$^2$ increase in the surface of contact between the human IgG Fc variant and human FcRn α chain or about 20 Å$^2$ increase in the surface of contact between the human IgG Fc variant and human FcRn β2 microglobulin.

* * * * *

SEQUENCE LISTING

<160> NUMBER OF SEQ ID NOS: 11

<210> SEQ ID NO 1
<211> LENGTH: 212
<212> TYPE: PRT
<213> ORGANISM: Artificial Sequence
<220> FEATURE:
<223> OTHER INFORMATION: human Fc/YTE sequence fragment

<400> SEQUENCE: 1

```
Gly Gly Pro Ser Val Phe Leu Phe Pro Pro Lys Pro Lys Asp Thr Leu
1               5                   10                  15

Tyr Ile Thr Arg Glu Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175
```

```
Val Asp Lys Ser Arg Trp Gln Gln Gly Asn Val Phe Ser Cys Ser Val
                180                 185                 190

Met His Glu Ala Leu His Asn His Tyr Thr Gln Lys Ser Leu Ser Leu
            195                 200                 205

Ser Pro Gly Lys
        210

<210> SEQ ID NO 2
<211> LENGTH: 211
<212> TYPE: PRT
<213> ORGANISM: Rattus
<220> FEATURE:
<221> NAME/KEY: misc_feature
<223> OTHER INFORMATION: rat Fc sequence

<400> SEQUENCE: 2

Val Ser Ser Val Phe Ile Phe Pro Pro Lys Thr Lys Asp Val Leu Thr
1               5                   10                  15

Ile Thr Leu Thr Pro Lys Val Thr Cys Val Val Val Asp Ile Ser Gln
            20                  25                  30

Asn Asp Pro Glu Val Arg Phe Ser Trp Phe Ile Asp Asp Val Glu Val
        35                  40                  45

His Thr Ala Gln Thr His Ala Pro Glu Lys Gln Ser Asn Ser Thr Leu
    50                  55                  60

Arg Ser Val Ser Glu Leu Pro Ile Val His Arg Asp Trp Leu Asn Gly
65                  70                  75                  80

Lys Thr Phe Lys Cys Lys Val Asn Ser Gly Ala Phe Pro Ala Pro Ile
                85                  90                  95

Glu Lys Ser Ile Ser Lys Pro Glu Gly Thr Pro Arg Gly Pro Gln Val
            100                 105                 110

Tyr Thr Met Ala Pro Pro Lys Glu Glu Met Thr Gln Ser Gln Val Ser
        115                 120                 125

Ile Thr Cys Met Val Lys Gly Phe Tyr Pro Pro Asp Ile Tyr Thr Glu
    130                 135                 140

Trp Lys Met Asn Gly Gln Pro Gln Glu Asn Tyr Lys Asn Thr Pro Pro
145                 150                 155                 160

Thr Met Asp Thr Asp Gly Ser Tyr Phe Leu Tyr Ser Lys Leu Asn Val
                165                 170                 175

Lys Lys Glu Thr Trp Gln Gln Gly Asn Thr Phe Thr Cys Ser Val Leu
            180                 185                 190

His Glu Gly Leu His Asn His His Thr Glu Lys Ser Leu Ser His Ser
        195                 200                 205

Pro Gly Lys
    210

<210> SEQ ID NO 3
<211> LENGTH: 99
<212> TYPE: PRT
<213> ORGANISM: Homo sapiens
<220> FEATURE:
<221> NAME/KEY: misc_feature
<223> OTHER INFORMATION: Beta-2 microglobulin chain of FcRn

<400> SEQUENCE: 3

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30
```

```
Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
 50                  55                  60

Leu Tyr Tyr Thr Glu Phe Thr Pro Thr Glu Lys Asp Glu Tyr Ala Cys
 65                  70                  75                  80

Arg Val Asn His Val Thr Leu Ser Gln Pro Lys Ile Val Lys Trp Asp
                 85                  90                  95

Arg Asp Met

<210> SEQ ID NO 4
<211> LENGTH: 99
<212> TYPE: PRT
<213> ORGANISM: Rattus
<220> FEATURE:
<221> NAME/KEY: misc_feature
<223> OTHER INFORMATION: Beta-2 microglobulin chain of FcRn

<400> SEQUENCE: 4

Ile Gln Lys Thr Pro Gln Ile Gln Val Tyr Ser Arg His Pro Pro Glu
 1               5                  10                  15

Asn Gly Lys Pro Asn Phe Leu Asn Cys Tyr Val Ser Gln Phe His Pro
                20                  25                  30

Pro Gln Ile Glu Ile Glu Leu Leu Lys Asn Gly Lys Lys Ile Pro Asn
        35                  40                  45

Ile Glu Met Ser Asp Leu Ser Phe Ser Lys Asp Trp Ser Phe Tyr Ile
 50                  55                  60

Leu Ala His Thr Glu Phe Thr Pro Thr Glu Thr Asp Val Tyr Ala Cys
 65                  70                  75                  80

Arg Val Lys His Val Thr Leu Lys Glu Pro Lys Thr Val Thr Trp Asp
                 85                  90                  95

Arg Asp Met

<210> SEQ ID NO 5
<211> LENGTH: 267
<212> TYPE: PRT
<213> ORGANISM: Homo sapiens
<220> FEATURE:
<221> NAME/KEY: misc_feature
<223> OTHER INFORMATION: alpha chain of FcRn

<400> SEQUENCE: 5

Ala Glu Ser His Leu Ser Leu Leu Tyr His Leu Thr Ala Val Ser Ser
 1               5                  10                  15

Pro Ala Pro Gly Thr Pro Ala Phe Trp Val Ser Gly Trp Leu Gly Pro
                20                  25                  30

Gln Gln Tyr Leu Ser Tyr Asn Ser Leu Arg Gly Glu Ala Glu Pro Cys
        35                  40                  45

Gly Ala Trp Val Trp Glu Asn Gln Val Ser Trp Tyr Trp Glu Lys Glu
 50                  55                  60

Thr Thr Asp Leu Arg Ile Lys Glu Lys Leu Phe Leu Glu Ala Phe Lys
 65                  70                  75                  80

Ala Leu Gly Gly Lys Gly Pro Tyr Thr Leu Gln Gly Leu Leu Gly Cys
                 85                  90                  95

Glu Leu Gly Pro Asp Asn Thr Ser Val Pro Thr Ala Lys Phe Ala Leu
                100                 105                 110

Asn Gly Glu Glu Phe Met Asn Phe Asp Leu Lys Gln Gly Thr Trp Gly
        115                 120                 125
```

```
Gly Asp Trp Pro Glu Ala Leu Ala Ile Ser Gln Arg Trp Gln Gln Gln
        130                 135                 140

Asp Lys Ala Ala Asn Lys Glu Leu Thr Phe Leu Leu Phe Ser Cys Pro
145                 150                 155                 160

His Arg Leu Arg Glu His Leu Glu Arg Gly Arg Gly Asn Leu Glu Trp
                165                 170                 175

Lys Glu Pro Pro Ser Met Arg Leu Lys Ala Arg Pro Ser Ser Pro Gly
                180                 185                 190

Phe Ser Val Leu Thr Cys Ser Ala Phe Ser Phe Tyr Pro Pro Glu Leu
                195                 200                 205

Gln Leu Arg Phe Leu Arg Asn Gly Leu Ala Ala Gly Thr Gly Gln Gly
        210                 215                 220

Asp Phe Gly Pro Asn Ser Asp Gly Ser Phe His Ala Ser Ser Ser Leu
225                 230                 235                 240

Thr Val Lys Ser Gly Asp Glu His His Tyr Cys Cys Ile Val Gln His
                245                 250                 255

Ala Gly Leu Ala Gln Pro Leu Arg Val Glu Leu
        260                 265

<210> SEQ ID NO 6
<211> LENGTH: 269
<212> TYPE: PRT
<213> ORGANISM: Rattus
<220> FEATURE:
<221> NAME/KEY: misc_feature
<223> OTHER INFORMATION: alpha chain of FcRn

<400> SEQUENCE: 6

Ala Glu Pro Arg Leu Pro Leu Met Tyr His Leu Ala Ala Val Ser Asp
1               5                   10                  15

Leu Ser Thr Gly Leu Pro Ser Phe Trp Ala Thr Gly Trp Leu Gly Ala
                20                  25                  30

Gln Gln Tyr Leu Thr Tyr Asn Asn Leu Arg Gln Glu Ala Asp Pro Cys
        35                  40                  45

Gly Ala Trp Ile Trp Glu Asn Gln Val Ser Trp Tyr Trp Glu Lys Glu
50                  55                  60

Thr Thr Asp Leu Lys Ser Lys Glu Gln Leu Phe Leu Glu Ala Ile Arg
65                  70                  75                  80

Thr Leu Glu Asn Gln Ile Asn Gly Thr Phe Thr Leu Gln Gly Leu Leu
                85                  90                  95

Gly Cys Glu Leu Ala Pro Asp Asn Ser Ser Leu Pro Thr Ala Val Phe
            100                 105                 110

Ala Leu Asn Gly Glu Glu Phe Met Arg Phe Asn Pro Arg Thr Gly Asn
        115                 120                 125

Trp Ser Gly Glu Trp Pro Glu Thr Asp Ile Val Gly Asn Leu Trp Met
130                 135                 140

Lys Gln Pro Glu Ala Ala Arg Lys Glu Ser Glu Phe Leu Leu Thr Ser
145                 150                 155                 160

Cys Pro Glu Arg Leu Leu Gly His Leu Glu Arg Gly Arg Gln Asn Leu
                165                 170                 175

Glu Trp Lys Glu Pro Pro Ser Met Arg Leu Lys Ala Arg Pro Gly Asn
                180                 185                 190

Ser Gly Ser Ser Val Leu Thr Cys Ala Ala Phe Ser Phe Tyr Pro Pro
        195                 200                 205

Glu Leu Lys Phe Arg Phe Leu Arg Asn Gly Leu Ala Ser Gly Ser Gly
        210                 215                 220
```

```
Asn Cys Ser Thr Gly Pro Asn Gly Asp Gly Ser Phe His Ala Trp Ser
225                 230                 235                 240

Leu Leu Glu Val Lys Arg Gly Asp Glu His His Tyr Gln Cys Gln Val
                245                 250                 255

Glu His Glu Gly Leu Ala Gln Pro Leu Thr Val Asp Leu
            260                 265

<210> SEQ ID NO 7
<211> LENGTH: 209
<212> TYPE: PRT
<213> ORGANISM: Artificial Sequence
<220> FEATURE:
<223> OTHER INFORMATION: Fc/YTE sequence Crystallized in Examples

<400> SEQUENCE: 7

Gly Gly Pro Ser Val Phe Leu Phe Pro Pro Lys Pro Lys Asp Thr Leu
1               5                   10                  15

Tyr Ile Thr Arg Glu Pro Glu Val Thr Cys Val Val Val Asp Val Ser
                20                  25                  30

His Glu Asp Pro Glu Val Lys Phe Asn Trp Tyr Val Asp Gly Val Glu
            35                  40                  45

Val His Asn Ala Lys Thr Lys Pro Arg Glu Glu Gln Tyr Asn Ser Thr
        50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser

<210> SEQ ID NO 8
<211> LENGTH: 225
<212> TYPE: PRT
<213> ORGANISM: Homo sapiens
<220> FEATURE:
<221> NAME/KEY: misc_feature
<223> OTHER INFORMATION: Wild-type IgG Heavy Chain

<400> SEQUENCE: 8

Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
                20                  25                  30

Arg Thr Pro Glu Val Thr Cys Val Val Val Asp Val Ser His Glu Asp
            35                  40                  45
```

-continued

```
Pro Glu Val Lys Phe Asn Trp Tyr Val Asp Gly Val Glu Val His Asn
 50                  55                  60
Ala Lys Thr Lys Pro Arg Glu Glu Gln Tyr Asn Ser Thr Tyr Arg Val
 65                  70                  75                  80
Val Ser Val Leu Thr Val Leu His Gln Asp Trp Leu Asn Gly Lys Glu
                 85                  90                  95
Tyr Lys Cys Lys Val Ser Asn Lys Ala Leu Pro Ala Pro Ile Glu Lys
            100                 105                 110
Thr Ile Ser Lys Ala Lys Gly Gln Pro Arg Glu Pro Gln Val Tyr Thr
        115                 120                 125
Leu Pro Pro Ser Arg Glu Glu Met Thr Lys Asn Gln Val Ser Leu Thr
130                 135                 140
Cys Leu Val Lys Gly Phe Tyr Pro Ser Asp Ile Ala Val Glu Trp Glu
145                 150                 155                 160
Ser Asn Gly Gln Pro Glu Asn Asn Tyr Lys Thr Thr Pro Pro Val Leu
                165                 170                 175
Asp Ser Asp Gly Ser Phe Phe Leu Tyr Ser Lys Leu Thr Val Asp Lys
            180                 185                 190
Ser Arg Trp Gln Gln Gly Asn Val Phe Ser Cys Ser Val Met His Glu
        195                 200                 205
Ala Leu His Asn His Tyr Thr Gln Lys Ser Leu Ser Leu Ser Pro Gly
    210                 215                 220
Lys
225

<210> SEQ ID NO 9
<211> LENGTH: 45
<212> TYPE: DNA
<213> ORGANISM: Artificial Sequence
<220> FEATURE:
<223> OTHER INFORMATION: primer used for introducing mutation in
      MEDI-524 (to generate MEDI-524-YTE)

<400> SEQUENCE: 9
gcatgtgacc tcaggttccc gagtgatata gagggtgtcc ttggg              45

<210> SEQ ID NO 10
<211> LENGTH: 45
<212> TYPE: DNA
<213> ORGANISM: Artificial Sequence
<220> FEATURE:
<223> OTHER INFORMATION: primer used for introducing mutation in
      MEDI-524 (to generate MEDI-524-YTE)

<400> SEQUENCE: 10
cccaaggaca ccctctatat cactcgggaa cctgaggtca catgc              45

<210> SEQ ID NO 11
<211> LENGTH: 209
<212> TYPE: PRT
<213> ORGANISM: Artificial Sequence
<220> FEATURE:
<223> OTHER INFORMATION: Fc/YTE sequence Crystallized in Examples

<400> SEQUENCE: 11

Gly Gly Pro Ser Val Phe Leu Phe Pro Pro Lys Pro Lys Asp Thr Leu
1               5                   10                  15
Tyr Ile Thr Arg Glu Pro Glu Val Thr Cys Val Val Val Asp Val Ser
            20                  25                  30
```

```
His Glu Asp Pro Glu Val Lys Phe Asn Trp Tyr Val Asp Gly Val Glu
        35                  40                  45
Val His Asn Ala Lys Thr Lys Pro Arg Glu Glu Gln Tyr Asn Ser Thr
 50                  55                  60
Tyr Arg Val Val Ser Val Leu Thr Val Leu His Gln Asp Trp Leu Asn
 65                  70                  75                  80
Gly Lys Glu Tyr Lys Cys Lys Val Ser Asn Lys Ala Leu Pro Ala Pro
                 85                  90                  95
Ile Glu Lys Thr Ile Ser Lys Ala Lys Gly Gln Pro Arg Glu Pro Gln
                100                 105                 110
Val Tyr Thr Leu Pro Pro Ser Arg Asp Glu Leu Thr Lys Asn Gln Val
                115                 120                 125
Ser Leu Thr Cys Leu Val Lys Gly Phe Tyr Pro Ser Asp Ile Ala Val
                130                 135                 140
Glu Trp Glu Ser Asn Gly Gln Pro Glu Asn Asn Tyr Lys Thr Thr Pro
145                 150                 155                 160
Pro Val Leu Asp Ser Asp Gly Ser Phe Phe Leu Tyr Ser Lys Leu Thr
                165                 170                 175
Val Asp Lys Ser Arg Trp Gln Gln Gly Asn Val Phe Ser Cys Ser Val
                180                 185                 190
Met His Glu Ala Leu His Asn His Tyr Thr Gln Lys Ser Leu Ser Leu
                195                 200                 205
Ser
```